United States Patent
Straubinger et al.

(10) Patent No.: US 9,510,947 B2
(45) Date of Patent: Dec. 6, 2016

(54) CATHETER SYSTEM FOR INTRODUCING AN EXPANDABLE HEART VALVE STENT INTO THE BODY OF A PATIENT

(75) Inventors: Helmut Straubinger, Achheim (DE); Michael Litzenburger, Munich (DE); Thomas Töllner, Berlin (DE)

(73) Assignee: JenaValve Technology, Inc., Irvine, CA (US)

( * ) Notice: Subject to any disclaimer, the term of this patent is extended or adjusted under 35 U.S.C. 154(b) by 139 days.

(21) Appl. No.: 14/352,117

(22) PCT Filed: Sep. 11, 2012

(86) PCT No.: PCT/EP2012/067714
§ 371 (c)(1),
(2), (4) Date: Jul. 15, 2014

(87) PCT Pub. No.: WO2013/056898
PCT Pub. Date: Apr. 25, 2013

(65) Prior Publication Data
US 2015/0127092 A1    May 7, 2015

(30) Foreign Application Priority Data

Oct. 21, 2011  (EP) ..................................... 11186156

(51) Int. Cl.
*A61F 2/24*     (2006.01)
*A61F 2/95*     (2013.01)

(52) U.S. Cl.
CPC ............ *A61F 2/2436* (2013.01); *A61F 2/2418* (2013.01); *A61F 2002/9517* (2013.01)

(58) Field of Classification Search
CPC ............ A61F 2/2436; A61F 2002/9517; A61F 2/2427; A61F 2/243
(Continued)

(56) References Cited

U.S. PATENT DOCUMENTS 3,755,823 A    9/1973   Hancock
4,485,816 A    12/1984  Krumme
(Continued)

FOREIGN PATENT DOCUMENTS

AU    2006308187 A1    5/2007
AU    2006310681 A1    5/2007
(Continued)

OTHER PUBLICATIONS

International Search Report for PCT/EP2012/067714 dated Dec. 18, 2012 (2 pages).
(Continued)

*Primary Examiner* — Katherine M Shi
(74) *Attorney, Agent, or Firm* — Bookoff McAndrews, PLLC

(57) ABSTRACT

The invention relates to catheter system for introducing an expandable heart valve stent (150) into the body of a patient, the catheter system comprising: a catheter tip (10) having a seat portion for accommodating the stent (150) in its collapsed state and a stent holder (15) for releasably fixing the stent (150), wherein the seat portion is constituted by a first sleeve-shaped member (11) and a second sleeve-shaped member (21), said sleeve-shaped members (11, 21) being moveable relative to each other and relative to the stent holder (15), and a catheter shaft (30) for connecting the catheter tip (10) to a handle (70). The catheter shaft (30) comprising: first force transmitting means (31) connected to the first sleeve-shaped member (11), second force transmitting means (41) connected to the second sleeve-shaped member (21) and a distal end section connectable to second operating means (81) of the handle (70), and guiding means (51) having a passageway extending there between, wherein the first and second force trans mining means (31, 41) are at least partly received within the passageway such as to be (Continued)

Figure 1:
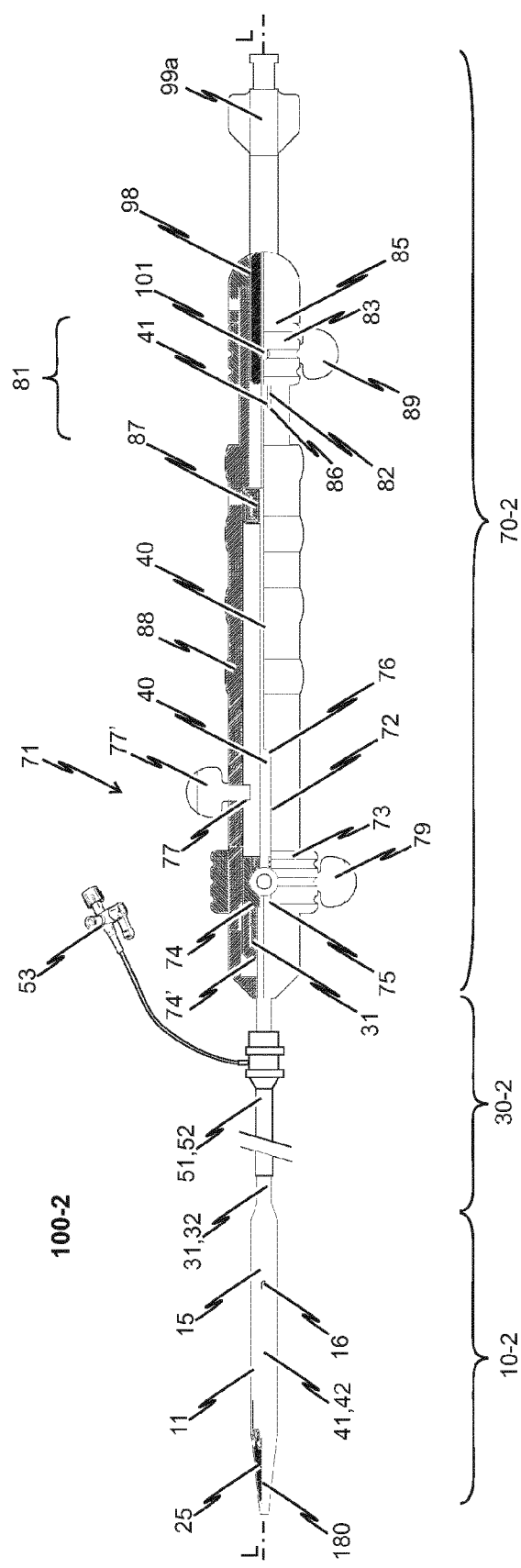

moveable relative to the guiding means (51), and wherein the proximal end of the guiding means (51) terminates distal to the catheter tip (10).

18 Claims, 39 Drawing Sheets

(58) Field of Classification Search
USPC .............................................. 623/1.11, 2.11
See application file for complete search history.

(56) References Cited

U.S. PATENT DOCUMENTS

| | | |
|---|---|---|
| 4,502,488 A | 3/1985 | Degironimo et al. |
| 4,922,905 A | 5/1990 | Strecker |
| 4,994,077 A | 2/1991 | Dobben |
| 5,002,566 A | 3/1991 | Carpentier et al. |
| 5,026,377 A | 6/1991 | Burton et al. |
| 5,035,706 A | 7/1991 | Giantureo et al. |
| 5,053,008 A | 10/1991 | Bajaj |
| 5,061,277 A | 10/1991 | Carpentier et al. |
| 5,094,661 A | 3/1992 | Levy et al. |
| 5,104,407 A | 4/1992 | Lam et al. |
| 5,163,953 A | 11/1992 | Vince |
| 5,197,979 A | 3/1993 | Quintero et al. |
| 5,211,183 A | 5/1993 | Wilson |
| 5,234,447 A | 8/1993 | Kaster et al. |
| 5,279,612 A | 1/1994 | Eberhardt |
| 5,332,402 A | 7/1994 | Teitelbaum |
| 5,336,258 A | 8/1994 | Quintero et al. |
| 5,350,399 A | 9/1994 | Erlebacher et al. |
| 5,352,240 A | 10/1994 | Ross |
| 5,368,608 A | 11/1994 | Levy et al. |
| 5,411,552 A | 5/1995 | Andersen et al. |
| 5,429,144 A | 7/1995 | Wilk |
| 5,456,713 A | 10/1995 | Chuter |
| 5,509,930 A | 4/1996 | Love |
| 5,540,712 A | 7/1996 | Kleshinski et al. |
| 5,549,666 A | 8/1996 | Hata et al. |
| 5,595,571 A | 1/1997 | Jaffe et al. |
| 5,609,626 A | 3/1997 | Quijano et al. |
| 5,613,982 A | 3/1997 | Goldstein |
| 5,632,778 A | 5/1997 | Goldstein |
| 5,643,278 A | 7/1997 | Wijay |
| 5,655,548 A | 8/1997 | Nelson et al. |
| 5,674,298 A | 10/1997 | Levy et al. |
| 5,679,112 A | 10/1997 | Levy et al. |
| 5,683,451 A | 11/1997 | Lenker et al. |
| 5,697,972 A | 12/1997 | Kim et al. |
| 5,713,953 A | 2/1998 | Vallana et al. |
| 5,733,325 A | 3/1998 | Robinson et al. |
| 5,746,775 A | 5/1998 | Levy et al. |
| 5,755,777 A | 5/1998 | Chuter |
| 5,817,113 A | 10/1998 | Gifford, III et al. |
| 5,824,041 A | 10/1998 | Lenker et al. |
| 5,824,080 A | 10/1998 | Lamuraglia |
| 5,840,081 A | 11/1998 | Andersen et al. |
| 5,841,382 A | 11/1998 | Walden et al. |
| 5,843,181 A | 12/1998 | Jaffe et al. |
| 5,855,601 A | 1/1999 | Bessler et al. |
| 5,876,434 A | 3/1999 | Flomenblit et al. |
| 5,880,242 A | 3/1999 | Hu et al. |
| 5,885,238 A | 3/1999 | Stevens et al. |
| 5,891,160 A | 4/1999 | Williamson, IV et al. |
| 5,899,936 A | 5/1999 | Goldstein |
| 5,928,281 A | 7/1999 | Huynh et al. |
| 5,935,163 A | 8/1999 | Gabbay |
| 5,104,407 B1 | 9/1999 | Lam et al. |
| 5,957,949 A | 9/1999 | Leonhardt et al. |
| 5,987,344 A | 11/1999 | West |
| 6,001,126 A | 12/1999 | Nguyen-Thien-Nhon |
| 5,061,277 B1 | 2/2000 | Carpentier et al. |
| 6,077,297 A | 6/2000 | Robinson et al. |
| 6,093,530 A | 7/2000 | McIlroy et al. |
| 6,102,944 A | 8/2000 | Huynh et al. |
| 6,117,169 A | 9/2000 | Moe |
| 6,126,685 A | 10/2000 | Lenker et al. |
| 6,168,614 B1 | 1/2001 | Andersen et al. |
| 6,177,514 B1 | 1/2001 | Pathak et al. |
| 6,183,481 B1 | 2/2001 | Lee et al. |
| 6,200,336 B1 | 3/2001 | Pavcnik et al. |
| 6,214,055 B1 | 4/2001 | Simionescu et al. |
| 6,231,602 B1 | 5/2001 | Carpentier et al. |
| 6,241,738 B1 | 6/2001 | Dereume |
| 6,254,564 B1 | 7/2001 | Wilk et al. |
| 6,254,636 B1 | 7/2001 | Peredo |
| 6,273,876 B1 | 8/2001 | Klima et al. |
| 6,283,995 B1 | 9/2001 | Moe et al. |
| 6,287,338 B1 | 9/2001 | Sarnowski et al. |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,278 B1 | 2/2002 | Lenker et al. |
| 6,352,547 B1 | 3/2002 | Brown et al. |
| 6,379,740 B1 | 4/2002 | Rinaldi et al. |
| 6,391,538 B1 | 5/2002 | Vyavahare et al. |
| 6,425,916 B1 | 7/2002 | Garrison et al. |
| 6,454,799 B1 | 9/2002 | Schreck |
| 6,471,723 B1 | 10/2002 | Ashworth et al. |
| 6,478,819 B2 | 11/2002 | Moe |
| 6,508,833 B2 | 1/2003 | Pavcnik et al. |
| 6,509,145 B1 | 1/2003 | Torrianni |
| 6,521,179 B1 | 2/2003 | Girardot et al. |
| 6,540,782 B1 | 4/2003 | Snyders |
| 6,558,417 B2 | 5/2003 | Peredo |
| 6,558,418 B2 | 5/2003 | Carpentier et al. |
| 6,572,642 B2 | 6/2003 | Rinaldi et al. |
| 6,582,462 B1 | 6/2003 | Andersen et al. |
| 6,585,766 B1 | 7/2003 | Huynh et al. |
| 6,613,086 B1 | 9/2003 | Moe et al. |
| 6,682,559 B2 | 1/2004 | Myers et al. |
| 6,730,118 B2 | 5/2004 | Spenser et al. |
| 6,736,845 B2 | 5/2004 | Marquez et al. |
| 6,767,362 B2 | 7/2004 | Schreck |
| 6,776,791 B1 | 8/2004 | Stallings et al. |
| 6,790,230 B2 | 9/2004 | Beyersdorf et al. |
| 6,808,529 B2 | 10/2004 | Fulkerson |
| 6,821,211 B2 | 11/2004 | Otten et al. |
| 6,821,297 B2 | 11/2004 | Snyders |
| 6,824,970 B2 | 11/2004 | Vyavahare et al. |
| 6,830,584 B1 | 12/2004 | Seguin |
| 6,861,211 B2 | 3/2005 | Levy et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,945,997 B2 | 9/2005 | Huynh et al. |
| 6,974,474 B2 | 12/2005 | Pavcnik et al. |
| 7,014,655 B2 | 3/2006 | Barbarash et al. |
| 7,018,406 B2 | 3/2006 | Seguin et al. |
| 7,037,333 B2 | 5/2006 | Myers et al. |
| 7,050,276 B2 | 5/2006 | Nishiyama |
| 7,078,163 B2 | 7/2006 | Torrianni |
| 7,081,132 B2 | 7/2006 | Cook et al. |
| 7,101,396 B2 | 9/2006 | Artof et al. |
| 7,137,184 B2 | 11/2006 | Schreck et al. |
| 7,141,064 B2 | 11/2006 | Scott et al. |
| 7,163,556 B2 | 1/2007 | Xie et al. |
| 7,189,259 B2 | 3/2007 | Simionescu et al. |
| 7,198,646 B2 | 4/2007 | Figulla et al. |
| 7,201,772 B2 | 4/2007 | Schwammenthal et al. |
| 7,238,200 B2 | 7/2007 | Lee et al. |
| 7,252,682 B2 | 8/2007 | Seguin |
| 7,318,278 B2 | 1/2008 | Zhang et al. |
| 7,318,998 B2 | 1/2008 | Goldstein et al. |
| 7,322,932 B2 | 1/2008 | Xie et al. |
| 7,329,278 B2 | 2/2008 | Seguin et al. |
| 7,381,218 B2 | 6/2008 | Schreck |
| 7,393,360 B2 | 7/2008 | Spenser et al. |
| 7,399,315 B2 | 7/2008 | Iobbi |
| 7,452,371 B2 | 11/2008 | Pavcnik et al. |
| 7,473,275 B2 | 1/2009 | Marquez |
| 7,896,915 B2 | 3/2011 | Guyenot et al. |

(56) References Cited

U.S. PATENT DOCUMENTS

| | | |
|---|---|---|
| 7,914,575 B2 | 3/2011 | Guyenot et al. |
| 2001/0011187 A1 | 8/2001 | Pavcnik et al. |
| 2001/0021872 A1 | 9/2001 | Bailey et al. |
| 2001/0039450 A1 | 11/2001 | Pavcnik et al. |
| 2002/0010489 A1 | 1/2002 | Grayzel et al. |
| 2002/0032481 A1 | 3/2002 | Gabbay |
| 2002/0035390 A1 | 3/2002 | Schaldach et al. |
| 2002/0045846 A1 | 4/2002 | Kaplon et al. |
| 2002/0045929 A1 | 4/2002 | Diaz |
| 2002/0055775 A1 | 5/2002 | Carpentier et al. |
| 2002/0120322 A1 | 8/2002 | Thompson et al. |
| 2002/0120323 A1 | 8/2002 | Thompson et al. |
| 2002/0123790 A1 | 9/2002 | White et al. |
| 2002/0133226 A1 | 9/2002 | Marquez et al. |
| 2002/0143387 A1 | 10/2002 | Soetikno et al. |
| 2002/0151970 A1 | 10/2002 | Garrison et al. |
| 2002/0161426 A1 | 10/2002 | Iancea |
| 2002/0177840 A1 | 11/2002 | Farnholtz |
| 2002/0198594 A1 | 12/2002 | Schreck |
| 2003/0027332 A1 | 2/2003 | Lafrance et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0114913 A1 | 6/2003 | Spenser et al. |
| 2003/0125795 A1 | 7/2003 | Pavcnik et al. |
| 2003/0139796 A1 | 7/2003 | Sequin et al. |
| 2003/0139803 A1 | 7/2003 | Sequin et al. |
| 2003/0149476 A1 | 8/2003 | Damm et al. |
| 2003/0153974 A1 | 8/2003 | Spenser et al. |
| 2003/0195620 A1 | 10/2003 | Huynh et al. |
| 2003/0236570 A1 | 12/2003 | Cook et al. |
| 2004/0006380 A1 | 1/2004 | Buck et al. |
| 2004/0039436 A1 | 2/2004 | Spenser et al. |
| 2004/0049262 A1 | 3/2004 | Obermiller et al. |
| 2004/0073289 A1 | 4/2004 | Hartley |
| 2004/0078950 A1 | 4/2004 | Schreck et al. |
| 2004/0093060 A1 | 5/2004 | Seguin et al. |
| 2004/0093063 A1 | 5/2004 | Wright et al. |
| 2004/0117004 A1 | 6/2004 | Osborne et al. |
| 2004/0117009 A1 | 6/2004 | Cali et al. |
| 2004/0148018 A1 | 7/2004 | Carpentier et al. |
| 2004/0153145 A1 | 8/2004 | Simionescu et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0193244 A1 | 9/2004 | Hartley et al. |
| 2004/0206363 A1 | 10/2004 | McCarthy et al. |
| 2004/0210301 A1 | 10/2004 | Obermiller et al. |
| 2004/0210304 A1 | 10/2004 | Seguin et al. |
| 2004/0210306 A1 | 10/2004 | Quijano et al. |
| 2004/0243143 A1 | 12/2004 | Corcoran et al. |
| 2004/0249343 A1 | 12/2004 | Cioanta |
| 2004/0260389 A1 | 12/2004 | Case et al. |
| 2005/0009000 A1 | 1/2005 | Wilhelm et al. |
| 2005/0033220 A1 | 2/2005 | Wilk et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0060018 A1 | 3/2005 | Dittman |
| 2005/0075725 A1 | 4/2005 | Rowe |
| 2005/0075776 A1 | 4/2005 | Cho |
| 2005/0096726 A1 | 5/2005 | Sequin et al. |
| 2005/0096736 A1 | 5/2005 | Osse et al. |
| 2005/0098547 A1 | 5/2005 | Cali et al. |
| 2005/0113902 A1 | 5/2005 | Geiser et al. |
| 2005/0113910 A1 | 5/2005 | Paniagua et al. |
| 2005/0119728 A1 | 6/2005 | Sarac |
| 2005/0119736 A1 | 6/2005 | Zilla et al. |
| 2005/0125075 A1 | 6/2005 | Meade et al. |
| 2005/0137499 A1 | 6/2005 | Sheets et al. |
| 2005/0137609 A1 | 6/2005 | Guiraudon |
| 2005/0137682 A1 | 6/2005 | Justino |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137697 A1 | 6/2005 | Salahieh et al. |
| 2005/0137698 A1 | 6/2005 | Salahieh et al. |
| 2005/0137702 A1 | 6/2005 | Haug et al. |
| 2005/0143804 A1 | 6/2005 | Haverkost |
| 2005/0143807 A1 | 6/2005 | Pavcnik et al. |
| 2005/0149166 A1 | 7/2005 | Schaeffer et al. |
| 2005/0150775 A1 | 7/2005 | Zhang et al. |
| 2005/0171597 A1 | 8/2005 | Boatman et al. |
| 2005/0171598 A1 | 8/2005 | Schaeffer |
| 2005/0192665 A1 | 9/2005 | Spenser et al. |
| 2005/0197695 A1 | 9/2005 | Stacchino et al. |
| 2005/0222668 A1 | 10/2005 | Schaeffer et al. |
| 2005/0234546 A1 | 10/2005 | Nugent et al. |
| 2005/0267560 A1 | 12/2005 | Bates |
| 2006/0009842 A1 | 1/2006 | Huynh et al. |
| 2006/0025857 A1 | 2/2006 | Bergheim et al. |
| 2006/0047343 A1 | 3/2006 | Oviatt et al. |
| 2006/0058864 A1 | 3/2006 | Schaeffer et al. |
| 2006/0074484 A1 | 4/2006 | Huber |
| 2006/0111770 A1 | 5/2006 | Pavcnik et al. |
| 2006/0136034 A1 | 6/2006 | Modesitt et al. |
| 2006/0142846 A1 | 6/2006 | Pavcnik et al. |
| 2006/0149360 A1 | 7/2006 | Schwammenthal et al. |
| 2006/0155366 A1 | 7/2006 | LaDuca et al. |
| 2006/0167543 A1 | 7/2006 | Bailey et al. |
| 2006/0193885 A1 | 8/2006 | Leonard Neethling et al. |
| 2006/0210597 A1 | 9/2006 | Hiles |
| 2006/0224183 A1 | 10/2006 | Freudenthal |
| 2006/0229561 A1 | 10/2006 | Huszar |
| 2006/0229718 A1 | 10/2006 | Marquez |
| 2006/0229719 A1 | 10/2006 | Marquez et al. |
| 2006/0246584 A1 | 11/2006 | Covelli |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265043 A1* | 11/2006 | Mandrusov ........ A61B 5/02007 623/1.11 |
| 2006/0265056 A1 | 11/2006 | Nguyen et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0020248 A1 | 1/2007 | Everaerts et al. |
| 2007/0021826 A1 | 1/2007 | Case et al. |
| 2007/0027535 A1 | 2/2007 | Purdy, Jr. et al. |
| 2007/0038291 A1 | 2/2007 | Case et al. |
| 2007/0038295 A1 | 2/2007 | Case et al. |
| 2007/0043435 A1 | 2/2007 | Seguin et al. |
| 2007/0050014 A1 | 3/2007 | Johnson |
| 2007/0056346 A1 | 3/2007 | Spenser et al. |
| 2007/0088431 A1 | 4/2007 | Bourang et al. |
| 2007/0093887 A1 | 4/2007 | Case et al. |
| 2007/0100435 A1 | 5/2007 | Case et al. |
| 2007/0100440 A1 | 5/2007 | Figulla et al. |
| 2007/0112422 A1 | 5/2007 | Dehdashtian |
| 2007/0123700 A1 | 5/2007 | Ueda et al. |
| 2007/0123979 A1 | 5/2007 | Perier et al. |
| 2007/0142906 A1 | 6/2007 | Figulla et al. |
| 2007/0162103 A1 | 7/2007 | Case et al. |
| 2007/0173932 A1 | 7/2007 | Cali et al. |
| 2007/0179592 A1 | 8/2007 | Schaeffer |
| 2007/0185565 A1 | 8/2007 | Schwammenthal et al. |
| 2007/0203576 A1 | 8/2007 | Lee et al. |
| 2007/0213813 A1 | 9/2007 | Von Segesser et al. |
| 2007/0239271 A1 | 10/2007 | Nguyen |
| 2007/0244551 A1 | 10/2007 | Stobie |
| 2007/0260327 A1 | 11/2007 | Case et al. |
| 2007/0288087 A1 | 12/2007 | Fearnot et al. |
| 2008/0004688 A1 | 1/2008 | Spenser et al. |
| 2008/0021546 A1 | 1/2008 | Patz et al. |
| 2008/0022504 A1 | 1/2008 | Melsheimer |
| 2008/0033534 A1 | 2/2008 | Cook et al. |
| 2008/0065011 A1 | 3/2008 | Marchand et al. |

(56) References Cited

U.S. PATENT DOCUMENTS

| | | |
|---|---|---|
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077236 A1 | 3/2008 | Letac et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0127707 A1 | 6/2008 | Kokish et al. |
| 2008/0133003 A1 | 6/2008 | Seguin et al. |
| 2008/0140189 A1 | 6/2008 | Nguyen et al. |
| 2008/0147182 A1 | 6/2008 | Righini et al. |
| 2008/0154355 A1 | 6/2008 | Benichou et al. |
| 2008/0200977 A1 | 8/2008 | Paul et al. |
| 2008/0215143 A1 | 9/2008 | Seguin |
| 2008/0221703 A1 | 9/2008 | Que et al. |
| 2008/0255660 A1 | 10/2008 | Guyenot et al. |
| 2008/0255661 A1 | 10/2008 | Straubinger et al. |
| 2008/0262602 A1 | 10/2008 | Wilk et al. |
| 2008/0269878 A1 | 10/2008 | Iobbi |
| 2008/0275549 A1 | 11/2008 | Rowe |
| 2009/0093876 A1 | 4/2009 | Nitzan et al. |
| 2009/0216312 A1 | 8/2009 | Straubinger et al. |
| 2009/0222076 A1 | 9/2009 | Figulla et al. |
| 2010/0100167 A1 | 4/2010 | Bortlein et al. |
| 2010/0160725 A1 | 6/2010 | Kiser et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0262231 A1 | 10/2010 | Tuval et al. |
| 2011/0015616 A1* | 1/2011 | Straubinger .......... A61F 2/2436 604/528 |
| 2011/0093007 A1 | 4/2011 | Abbott et al. |
| 2011/0208290 A1 | 8/2011 | Straubinger et al. |
| 2011/0208297 A1 | 8/2011 | Tuval et al. |
| 2011/0319989 A1 | 12/2011 | Lane et al. |

FOREIGN PATENT DOCUMENTS

| | | |
|---|---|---|
| CA | 2436258 A1 | 1/2005 |
| CA | 2595233 A1 | 7/2006 |
| CA | 2627555 | 5/2007 |
| CN | 1745727 A | 3/2006 |
| CN | 2762776 Y | 3/2006 |
| CN | 1897892 A | 1/2007 |
| CN | 2933337 Y | 8/2007 |
| CN | 101431963 A | 5/2009 |
| CN | 101605509 A | 12/2009 |
| CN | 101623217 A | 1/2010 |
| CN | 101700199 A | 5/2010 |
| CN | 101720211 A | 6/2010 |
| CN | 102271626 A | 12/2011 |
| DE | 4316971 A1 | 11/1994 |
| DE | 19532846 A1 | 3/1997 |
| DE | 19546692 A1 | 6/1997 |
| DE | 19633901 A1 | 2/1998 |
| DE | 20003874 U1 | 6/2000 |
| DE | 19857887 A1 | 7/2000 |
| DE | 10010073 A1 | 9/2001 |
| DE | 10010074 A1 | 10/2001 |
| DE | 10034105 C1 | 4/2002 |
| DE | 101 21 210 A1 | 11/2002 |
| DE | 19546692 C2 | 11/2002 |
| DE | 10301026 A1 | 2/2004 |
| DE | 10302447 A1 | 7/2004 |
| DE | 10335948 B3 | 2/2005 |
| DE | 10010074 B4 | 4/2005 |
| DE | 19857887 B4 | 5/2005 |
| DE | 10010073 B4 | 12/2005 |
| DE | 10 2005 051 849 | 5/2007 |
| DE | 10 2005 052628 A1 | 5/2007 |
| DE | 20 2007 005 491 U1 | 7/2007 |
| DE | 20221871 U1 | 10/2008 |
| EP | 0084395 A1 | 7/1983 |
| EP | 0402036 B1 | 12/1990 |
| EP | 0402176 B1 | 12/1990 |
| EP | 0411118 A1 | 2/1991 |
| EP | 0458877 B1 | 4/1991 |
| EP | 0515324 A1 | 11/1992 |
| EP | 0547135 B1 | 6/1993 |
| EP | 0657147 A2 | 6/1995 |
| EP | 0 592 410 B1 | 10/1995 |
| EP | 0 592 410 B1 | 11/1995 |
| EP | 0729364 B1 | 9/1996 |
| EP | 0756498 B1 | 5/1997 |
| EP | 0778775 B1 | 6/1997 |
| EP | 0826346 A1 | 3/1998 |
| EP | 0896813 A2 | 2/1999 |
| EP | 0903122 A2 | 3/1999 |
| EP | 0928615 A1 | 7/1999 |
| EP | 0938877 A2 | 9/1999 |
| EP | 0986348 B1 | 3/2000 |
| EP | 1 251 805 B1 | 10/2000 |
| EP | 1041942 B1 | 10/2000 |
| EP | 1041943 B1 | 10/2000 |
| EP | 1117446 B1 | 7/2001 |
| EP | 1 233 731 B1 | 5/2002 |
| EP | 1206179 B1 | 5/2002 |
| EP | 1251804 B1 | 10/2002 |
| EP | 0 971 649 B1 | 12/2002 |
| EP | 1281357 A2 | 2/2003 |
| EP | 1281375 A2 | 2/2003 |
| EP | 1 017 868 B1 | 9/2003 |
| EP | 1354569 A1 | 10/2003 |
| EP | 1452153 A1 | 9/2004 |
| EP | 0987998 B1 | 10/2004 |
| EP | 1 087 727 B1 | 11/2004 |
| EP | 1499366 B1 | 1/2005 |
| EP | 1518518 A2 | 3/2005 |
| EP | 1 253 875 B1 | 4/2005 |
| EP | 1 251 803 B1 | 6/2005 |
| EP | 1469797 B1 | 11/2005 |
| EP | 1 690 515 A1 | 8/2006 |
| EP | 1 255 510 B1 | 3/2007 |
| EP | 1112042 B1 | 11/2007 |
| EP | 1878407 A1 | 1/2008 |
| EP | 1886649 A2 | 2/2008 |
| EP | 1 900 343 A2 | 3/2008 |
| EP | 1259195 B1 | 10/2008 |
| EP | 1980220 A1 | 10/2008 |
| EP | 1994913 A2 | 11/2008 |
| EP | 2 000 115 A2 | 12/2008 |
| EP | 2474287 A1 | 7/2012 |
| FR | 2788217 A1 | 7/2000 |
| FR | 2815844 A1 | 5/2002 |
| FR | 2828263 A1 | 2/2003 |
| GB | 2433700 A | 7/2007 |
| GB | 2440809 A | 2/2008 |
| JP | 52-86296 | 7/1977 |
| JP | 62-227352 | 10/1987 |
| JP | 1049571 A | 2/1989 |
| JP | 7-504091 | 5/1995 |
| JP | 2001-526574 A | 12/2001 |
| JP | 2004-504111 A | 2/2002 |
| JP | 2002-525168 A | 8/2002 |
| JP | 2002-525169 A | 8/2002 |
| JP | 2002-536115 A | 10/2002 |
| JP | 2003-515386 A | 5/2003 |
| JP | 2003-523262 | 8/2003 |
| JP | 2003-524504 | 8/2003 |
| JP | 2004-283461 A | 10/2004 |
| JP | 2005-118585 | 5/2005 |
| JP | 2007-521125 A | 8/2007 |
| JP | 2007-296375 | 11/2007 |
| JP | 2008-539985 A | 11/2008 |
| JP | 2009-131397 A | 6/2009 |
| JP | 2009-534157 A | 9/2009 |
| JP | 2010-526609 A | 8/2010 |
| WO | WO-90/09102 | 8/1990 |
| WO | WO 91/17720 A1 | 11/1991 |

(56) References Cited

FOREIGN PATENT DOCUMENTS

| | | |
|---|---|---|
| WO | WO 92/12690 | 8/1992 |
| WO | WO 95/11055 A1 | 4/1995 |
| WO | WO-95/24873 | 9/1995 |
| WO | WO-95/28183 | 10/1995 |
| WO | WO 95/29713 A1 | 11/1995 |
| WO | WO-96/13227 | 5/1996 |
| WO | WO 97/27893 A1 | 8/1997 |
| WO | WO 97/27898 A1 | 8/1997 |
| WO | WO-97/32615 | 9/1997 |
| WO | WO 98/08456 A1 | 3/1998 |
| WO | WO 98/11846 A1 | 3/1998 |
| WO | WO 98/19633 A1 | 5/1998 |
| WO | WO-98/43556 | 10/1998 |
| WO | WO-98/46165 | 10/1998 |
| WO | WO 98/53761 A1 | 12/1998 |
| WO | WO 99/36001 A1 | 7/1999 |
| WO | WO-99/37337 | 7/1999 |
| WO | WO 99/42058 A1 | 8/1999 |
| WO | WO 99/53987 A1 | 10/1999 |
| WO | WO-99/66863 | 12/1999 |
| WO | WO 00/02503 A1 | 1/2000 |
| WO | WO 00/15148 | 3/2000 |
| WO | WO 00/18330 | 4/2000 |
| WO | WO 00/18333 A1 | 4/2000 |
| WO | WO-00/18445 | 4/2000 |
| WO | WO 00/21464 A1 | 4/2000 |
| WO | WO 00/25702 A1 | 5/2000 |
| WO | WO 00/47139 A1 | 8/2000 |
| WO | WO-00/53125 | 9/2000 |
| WO | WO-00/62714 | 10/2000 |
| WO | WO 00/69367 A1 | 11/2000 |
| WO | WO 00/78226 A1 | 12/2000 |
| WO | WO-01/10209 A1 | 2/2001 |
| WO | WO 01/35870 A1 | 5/2001 |
| WO | WO 01/39700 A1 | 6/2001 |
| WO | WO-01/41679 A1 | 6/2001 |
| WO | WO 01/49213 A2 | 7/2001 |
| WO | WO-01/51104 A1 | 7/2001 |
| WO | WO 01/54625 A1 | 8/2001 |
| WO | WO 01/58503 A1 | 8/2001 |
| WO | WO 01/62189 A1 | 8/2001 |
| WO | WO 01/64137 A1 | 9/2001 |
| WO | WO 02/22054 A1 | 3/2002 |
| WO | WO 02/36048 A1 | 5/2002 |
| WO | WO-02/058745 A1 | 8/2002 |
| WO | WO-02/100301 A1 | 12/2002 |
| WO | WO-02/102286 A1 | 12/2002 |
| WO | WO 03/003949 A2 | 1/2003 |
| WO | WO-03/007795 A2 | 1/2003 |
| WO | WO-03/009785 A1 | 2/2003 |
| WO | WO 03/011195 A2 | 2/2003 |
| WO | WO 03/013239 | 2/2003 |
| WO | WO 03/028592 A1 | 4/2003 |
| WO | WO 03/047468 A1 | 6/2003 |
| WO | WO 03/051231 A2 | 6/2003 |
| WO | WO-03/079928 A2 | 10/2003 |
| WO | WO 03/079933 A1 | 10/2003 |
| WO | WO 03/092554 A1 | 11/2003 |
| WO | WO 03/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO 2004/019825 A1 | 3/2004 |
| WO | WO-2004/026117 A2 | 4/2004 |
| WO | WO 2004/026173 A2 | 4/2004 |
| WO | WO 2004/028399 A2 | 4/2004 |
| WO | WO 2004/030515 A2 | 4/2004 |
| WO | WO 2004/043301 A1 | 5/2004 |
| WO | WO 2004/064671 A2 | 8/2004 |
| WO | WO 2004/082527 A2 | 9/2004 |
| WO | WO 2004/082528 A2 | 9/2004 |
| WO | WO 2004/096100 A1 | 11/2004 |
| WO | WO 2005/011534 A1 | 2/2005 |
| WO | WO 2005/021063 A2 | 3/2005 |
| WO | WO 2005/034812 A1 | 4/2005 |
| WO | WO 2005/062980 A2 | 7/2005 |
| WO | WO 2005/063980 A1 | 7/2005 |
| WO | WO 2005/070343 A1 | 8/2005 |
| WO | WO-2005/072654 A1 | 8/2005 |
| WO | WO 2005/102015 A2 | 11/2005 |
| WO | WO 2006/066327 | 6/2006 |
| WO | WO-2006/066327 A1 | 6/2006 |
| WO | WO 2006/070372 A2 | 7/2006 |
| WO | WO 2006/076890 | 7/2006 |
| WO | WO 2006/089517 A1 | 8/2006 |
| WO | WO-2006/102063 A2 | 9/2006 |
| WO | WO 2006/108090 A2 | 10/2006 |
| WO | WO 2006/124649 A2 | 11/2006 |
| WO | WO-2006/124649 A2 | 11/2006 |
| WO | WO 2006/127756 A2 | 11/2006 |
| WO | WO 2006/127765 A1 | 11/2006 |
| WO | WO 2006/129441 A1 | 12/2006 |
| WO | WO-2006/132948 A1 | 12/2006 |
| WO | WO 2006/133959 A1 | 12/2006 |
| WO | WO 2007/047488 A2 | 4/2007 |
| WO | WO 2007/047945 A2 | 4/2007 |
| WO | WO 2007/048529 A1 | 5/2007 |
| WO | WO-2007/048529 A1 | 5/2007 |
| WO | WO 2007/051620 A1 | 5/2007 |
| WO | WO 2007/059252 A1 | 5/2007 |
| WO | WO-2007/071436 A2 | 6/2007 |
| WO | WO 2007/098232 A2 | 8/2007 |
| WO | WO 2007/120543 A1 | 10/2007 |
| WO | WO 2007/123956 | 11/2007 |
| WO | WO-2008/028569 A1 | 3/2008 |
| WO | WO 2008/031103 A2 | 3/2008 |
| WO | WO 2008/035337 A2 | 3/2008 |
| WO | WO 2008/045949 | 4/2008 |
| WO | WO 2008/051554 A2 | 5/2008 |
| WO | WO 2008/070797 A2 | 6/2008 |
| WO | WO 2008/079962 A1 | 7/2008 |
| WO | WO 2008/098191 A2 | 8/2008 |
| WO | WO 2008/101083 A2 | 8/2008 |
| WO | WO 2008/125153 A1 | 10/2008 |
| WO | WO 2008/138584 A1 | 11/2008 |
| WO | WO 2008/150529 A1 | 12/2008 |
| WO | WO 2009/053497 A1 | 4/2009 |
| WO | WO 2009/094188 A2 | 7/2009 |
| WO | WO 2009/106545 A1 | 9/2009 |
| WO | WO 2009/149462 A2 | 12/2009 |
| WO | WO 2011/008812 A2 | 1/2011 |
| WO | WO 2011/060386 A2 | 5/2011 |
| WO | WO 2011/104269 A1 | 9/2011 |
| WO | WO 2011/120050 A1 | 9/2011 |
| WO | WO 2011/144351 A2 | 11/2011 |
| WO | WO 2011/147849 A1 | 12/2011 |
| WO | WO 2012/023980 A1 | 2/2012 |
| WO | WO 2012/036742 A2 | 3/2012 |
| WO | WO 2012/038550 A1 | 3/2012 |
| WO | WO 2012/039748 A2 | 3/2012 |
| WO | WO 2012/082952 A2 | 6/2012 |
| WO | WO 2012/106491 A1 | 8/2012 |
| WO | WO 2012/142189 A1 | 10/2012 |

OTHER PUBLICATIONS

English translation of WO 2006/089517 A1 (description and claims) retrieved from the Espacenet database, http://worldwide.espacenet.com/ (22 pages).
Aortenklappenbioprothese erfolgreich in der Entwicklung, May 16, 2003 (1 page).
English translation of Aortenklappenbioprothese erfolgreich in der Entwicklung (2 pages).
Screen shots from http://www.fraunhofer.de/presse/filme/2006/index.jsp, 2006 (2 pages).
Liang, Ma, et al., "Double-crowned valved stents for off-pump mitral valve replacement," Eur. J. Cardio-Thoracic Surgery, vol. 28, pp. 194-198 (2005) (5 pages).
Huber, Christoph H., et al. "Direct Access Valve Replacement (DAVR)—are we entering a new era in cardiac surgery?" Eur. J. Cardio-Thoracic Surgery, vol. 29, pp. 380-385 (2006) (6 pages).
File history for German Patent DE 195 46 692 filed Dec. 14, 1995 and patented Jul. 11, 2002 (111 pages).

(56) References Cited

OTHER PUBLICATIONS

Klein, Allan L. et al., "Age-related Prevalence of Valvular Regurgitation in Normal Subjects: A Comprehensive Color Flow Examination of 118 Volunteers," *J. Am. Soc. Echocardiography*, vol. 3, No. 1, pp. 54-63 (1990) (10 pages).

Gummert, J.F. et al., "Cardiac Surgery in Germany During 2007: A Report on Behalf of the German Society for Thoracic and Cardiovascular Surgery," *Thorac. Cardiov. Surg.*, vol. 56, pp. 328-336 (2008) (9 pages).

Gummert, J.F. et al., "Cardiac Surgery in Germany During 2006: A Report on Behalf of the German Society for Thoracic and Cardiovascular Surgery," *Thorac. Cardiov. Surg.*, vol. 55, pp. 343-350 (2007) (8 pages).

Ferrari, M.W. et al., "Transarterial Aortic Valve Replacement with a Self expanding Stent in Pigs," *Heart*, vol. 90, No. 11, pp. 1326-1331 (2004).

Ferrari, "Entwicklung eines Verfahrens zum transvaskulären Aortenklappenersatz," Habilitationsschrift, Medizinische Fakultät der Friedrich-Schiller-Universität Jena, pp. 49-52, dated Sep. 2003.

Ferrari, "Entwicklung eines Verfahrens zum transvaskulären Aortenklappenersatz," Habilitationsschrift, Medizinische Fakultät der Friedrich-Schiller-Universität Jena, pp. 1-159, dated Sep. 2003.

German National Library, bibliographic information for Ferrari, M., "Entwicklung eines Verfahrens zum transvaskulären Aortenklappenersatz," available at https://www.deutsche-digitale-bibliothek.de/item/U2RQV45RMES4YP6AHEPGN4QPJWAMGROI.

\* cited by examiner

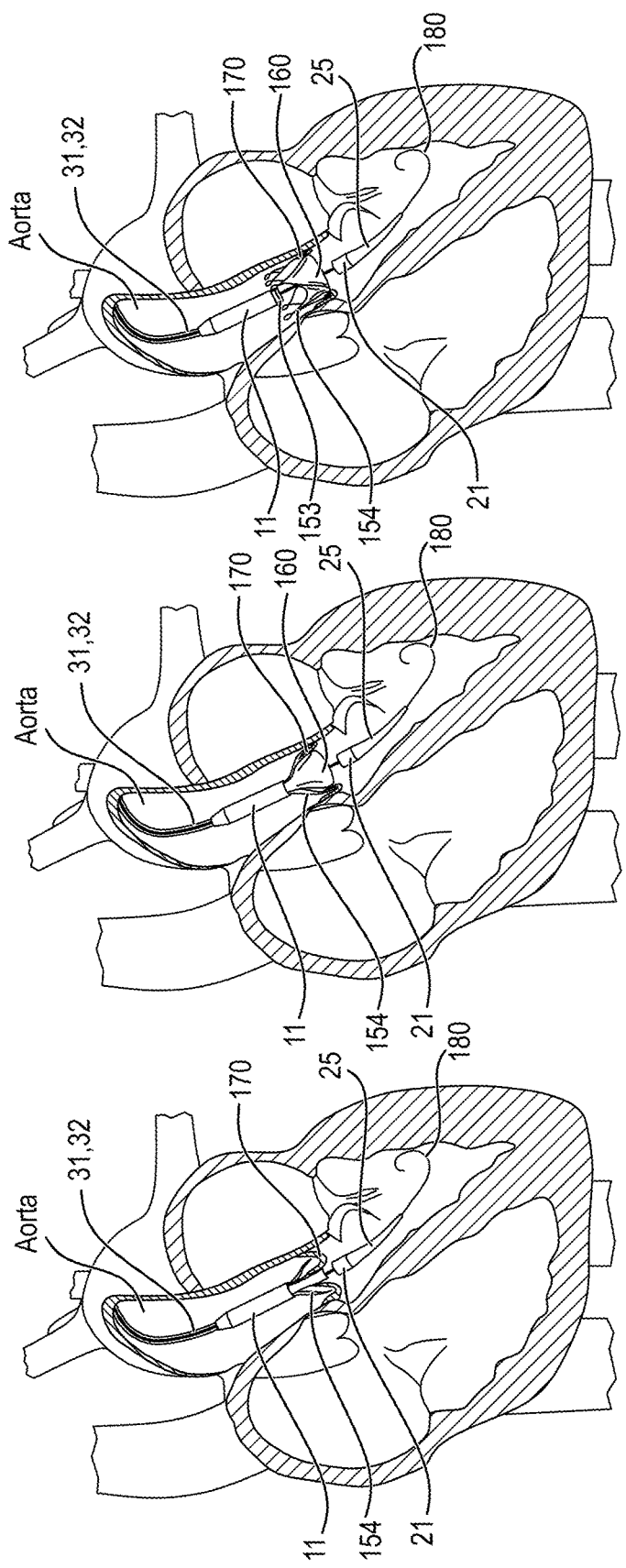

CATHETER SYSTEM FOR INTRODUCING AN EXPANDABLE HEART VALVE STENT INTO THE BODY OF A PATIENT

The present disclosure concerns a catheter system for introducing an expandable heart valve stent into the body of a patient. The disclosure further concerns an insertion system comprising a catheter system and a handle for inserting an expandable heart valve stent into the body of a patient, as well as a medical device for treatment of a heart valve defect, in particular a heart valve failure or a heart valve stenosis in a patient, wherein the medical device has an insertion system and an expandable heart valve stent accommodated in the catheter tip of the insertion system.

In medical technology, there has been an endeavour over a long period to close a heart valve defect, such as an aortic valve insufficiency or an aortic valve stenosis, non-surgically by means of a transarterial interventional access by catheter, thus technically without an operation. Various insertion systems and stent systems have been proposed, with different advantages and disadvantages, which in part can be introduced into the body of a patient transarterially by means of a catheter insertion system, though a specific system has not prevailed up to the present.

The term used here "heart valve stenosis and/or heart valve insufficiency" shall generally be understood here as a congenital or acquired functional disorder of one or several heart valves. A valve defect of this type can affect each of the four heart valves, whereby the valves in the left ventricle (aortic and mitral valve) are certainly more frequently affected than those of the right heart (pulmonary and tricuspid valve). The functional disorder can result in narrowing (stenosis) or inability to close (insufficiency) or a combination of the two (combined cardiac defect).

With all known interventional systems for implantation of heart valve prosthesis, an expandable stent system is moved transarterially to an insufficient heart valve. A stent system of this type consists, for example, of a self-expanding or balloon-expanding anchoring support (also termed "heart valve stent" or "stent" in the following), to which the actual heart valve prosthesis is fastened, preferably at the distal retaining region of the anchoring support.

In the medical devices previously known from the state-of-the-art, however, it has become apparent that the implantation procedure of a stent system to which the heart valve prosthesis is attached is relatively complicated, difficult and expensive. Apart from the complicated implantation of the heart valve prosthesis as a replacement for an insufficient native heart valve, there is the fundamental risk of incorrect positioning of the stent or heart valve prosthesis with the medical devices used up to the present, which cannot be corrected without more extensive operative intervention.

The problem addressed by the present disclosure is the fact that medical technology does not currently offer any insertion system in particular for transarterial or transfemoral implantation of a self- or balloon-expandable heart valve stent with a heart valve prosthesis attached to it in which, on the one hand, the insertion system enables a minimally invasive implantation of the heart valve prosthesis in a predictable manner and, on the other, dispensing with the need to use a heart-lung machine during the operation on the anaesthetized patient. Consequently the operative intervention can be designed to be especially cost-effective and, in particular, to reduce the physical and mental stress on the patient. In particular, there is a lack of a medical device for implantation of heart valve prostheses that can also be used for patients on whom, due to their age, an operation cannot be carried out without the aid of a heart-lung machine.

Because of the increasing number of patients requiring treatment, there is also a growing need for an insertion system with which a minimally invasive intervention can be made on a patient for treatment of a heart valve stenosis and/or heart valve insufficiency in a precisely predictable way, whereby the success of the operation is in particular no longer significantly dependent on the skill and experience of the heart surgeon or radiologist carrying out the treatment.

This situation also applies to operations in which heart valve prostheses with stent systems are implanted with the aid of a so-called balloon catheter system.

It is also regarded as problematic that, when using systems already known from the state-of-the-art by means of which a heart valve prosthesis can be implanted in the body of the patient with minimal invasiveness, incorrect positioning of the heart valve prosthesis or the associated heart valve stent can frequently only be avoided when the heart surgeon or radiologist is especially experienced. It is indeed known, for example, to insert a heart valve stent with a heart valve prosthesis attached to it into the body of a patient as far as the heart via the aorta, whereby self-expansion or balloon-expansion of the heart valve stent is initiated by external manipulation when the implantation location is reached, which should lead to a secure anchorage and precise positioning of the heart valve prosthesis; such heart valve stents cannot usually be removed in a simple way, however, and their position cannot usually be corrected once the stent has expanded.

Accordingly, there is basically a risk with the known systems that if, for example, the self-expansion or balloon-expansion of the heart valve stent with the attached heart valve prosthesis is initiated in a non-optimum position, due to a slip by the doctor carrying out the treatment or other technical circumstances such as stent foreshortening, this position can only be corrected appropriately by means of a major, in particular operative, intervention, which must frequently be carried out on the open heart.

For example, a heart valve stent for heart valve prosthesis is described in document WO 2004/019825 A1. With this heart valve stent, distal-end support arches or hoops and positioning arches or hoops are provided, which can be inserted into the pockets of the native heart valve of a patient so that the heart valve stent can be positioned by means of the support hoops. Additional so-called commissural hoops can also be formed on the known heart valve stent which, together with the support arches, clamp parts of the old heart valve once the stent has unfolded to that the stent can be positioned and anchored as a result of this clamping action.

Although the support arches provided on the anchoring stent enable improved positioning of the heart valve prosthesis to be implanted, there is nevertheless still a risk of incorrect implantation and of the heart valve prosthesis being incapable of functioning correctly or functioning but unsatisfactorily. For example, it may be found during the intervention that the heart valve prosthesis or the heart valve stent is not optimally dimensioned for the patient. In such cases, even if only the respective distal support or positioning arches of the stent are in their expanded state, removal (explantation) or repositioning of the heart valve stent with the heart valve prosthesis is no longer possible and there exists an increased mortality risk for the particular patient.

The aortic arch in the human body represents a further problem for such interventions, since it has to be accessed during insertion through the aorta. When this is done, the catheter tip and the respective catheter must undergo a change of direction of approximately 180° over a relatively small radius, usually about 50 mm, without causing injury or damage to the vessel wall.

The objective of the disclosure is to propose a catheter system for introducing an expandable heart valve stent into the body of a patient and for positioning the stent at a desired implantation site, wherein the catheter system is designed to enable the implantation of a heart valve prosthesis attached to a heart valve stent in the optimum implantation location in a sequence of events defined before the intervention.

Secondly, the objective is to propose a medical device for treatment of a heart valve stenosis and/or heart valve insufficiency, comprising a catheter system and an expandable heart valve stent mounted in the catheter tip of the insertion system and which is designed to reduce the risk to the patient on implantation of the heart valve prosthesis.

In accordance with a preferred embodiment, the present disclosure provides a catheter system for introducing an expandable heart valve stent into the body of a patient, the catheter system comprising a catheter tip and a catheter shaft. The catheter tip of the catheter system has a seat portion for accommodating the stent to be introduced into the patient's body in its collapsed state. The catheter system has further a stent holder for realisably fixing the stent to the catheter tip. The seat portion of the catheter tip is constituted by a first sleeve-shaped member and a second sleeve-shaped member, said sleeve-shaped members being moveable relative to each other as well as relative to the stent holder of the catheter tip. The catheter shaft comprises first force transmitting means, second force transmitting means and guiding means. The distal end section of the first force transmitting means is connected to the first sleeve-shaped member of the catheter tip and the proximal end section of the first force transmitting means is connectable to a first operating means of a handle. The distal end section of the second force transmitting means is connected to the second sleeve-shaped member of the catheter tip and the proximal end section of the second force transmitting means is connectable to a second operating means of the handle.

Preferably, the cross-section of second sleeve-shaped member of the catheter tip is equal to or less than the cross-section of the first sleeve-shaped member of the catheter tip. In case the cross-section of second sleeve-shaped member of the catheter tip is less than the cross-section of the first sleeve-shaped member, the second sleeve-shaped member is at least partly accommodatable within the first sleeve-shaped member in a telescopic manner. This may allow minimizing the cross-section of catheter tip. At the same time, an expandable heart valve stent may be released from the catheter tip of the catheter system in a step-wise manner. In case the cross-section of second sleeve-shaped member of the catheter tip is less than the cross-section of the first sleeve-shaped member, the second sleeve-shaped member and the first sleeve-shaped member—once brought together—can reside on an internal support structure, e.g. a cylindrical insert, resulting in a step and gap free transition.

According to one aspect of the present disclosure, the catheter system comprises guiding means having a guiding tube with a passageway extending there between. The guiding means serves for guiding of the catheter shaft has a distal end, a proximal end and a passageway extending there between. The first and second force transmitting means are at least partly received within this passageway such as to be moveable relative to the guiding means. The guiding tube of the guiding means has a length such that the distal end of the guiding means terminates proximal to the catheter tip of the catheter system. Moreover, guiding tube has a cross-section less than the cross-section of the catheter tip.

According to another aspect of the present disclosure, the catheter system further comprises a guide wire suited for guiding the catheter tip of the catheter system to an implantation site. The guide wire is designed to be advanced into a patient's vasculature independently from the catheter system and, in particular, independently from the catheter tip of the catheter system.

In accordance with another preferred embodiment, an insertion system for inserting an expandable heart valve stent is disclosed.

Whilst the term "vascular" refers to the blood vessels of the patient's body including both veins and arteries, in a preferred embodiment, the insertion system is for transarterial delivery using the arteries, although it is conceivable that in other embodiments transvenous delivery via a vein could be used.

In particular, the vascular insertion system comprises a catheter system with a catheter tip, a catheter shaft and a handle. The catheter tip has a seat portion for accommodating a stent to be inserted in its collapsed state and a stent holder for releasably fixing the stent. The proximal end of the catheter system is attached to the handle and the distal end is attached to the catheter tip. The catheter system comprises the catheter shaft for connecting the catheter tip to the handle of the insertion system, the distal end section of the catheter shaft being flexible enough such that the catheter tip and the distal end section of the catheter shaft may be easily navigated through the anatomy and especially through the aortic arch during insertion through the aorta of the patient.

The handle has at least one first and one second operating means with which the catheter tip of the insertion system may be appropriately manipulated so that an expandable stent housed in the catheter tip may be released from the catheter tip in steps or in a defined or definable sequence of events.

The catheter tip of the catheter system and at least the distal part of the catheter shaft are typically inserted into the femoral artery and moved up the descending thoracic aorta until the catheter tip is positioned in the ascending aorta. The proximal end of the catheter shaft together with the handle attached thereto remains outside of the patient's body.

In accordance with a preferred embodiment, the catheter tip has first and second housing portions termed "sleeve-shaped members" in the following, that may be manipulated with the handle. These sleeve-shaped members are used for accommodating specific portions of the stent. The first sleeve-shaped member is used for accommodating first functional components of the stent, for example retaining hoops of the stent (or alternatively positioning hoops of the stent), while the second sleeve-shaped member is used for accommodating the second functional components of the stent, for example, positioning hoops of the stent (or alternatively for accommodating retaining hoops of the stent).

In relation to the handle provided for the insertion system, it is preferably provided that, on one hand, the first operating means cooperate with the first sleeve-shaped member of the catheter tip so that, on actuation of the first operating means, a previously definable longitudinal displacement of the first sleeve-shaped member may be effected relative to the stent holder and the guiding tube of the catheter shaft. On the other hand, the second operating means cooperates with the second sleeve-shaped member of the catheter tip so that a previously definable longitudinal displacement of the second sleeve-shaped member may be affected relative to the stent holder and the guiding tube of the catheter shaft.

The cross-section of the second sleeve-shaped member is identical to the cross-section of the first sleeve-shaped member such that the sleeve-shaped members can completely enclose a stent accommodated in the catheter tip without a gap between the first and second sleeve-shaped members thereby providing a catheter tip having an atraumatic shape. In addition, the first and second sleeve-shaped members are movable relative to each other and relative to the stent holder.

For this purpose, first force transmitting means with a distal end section connected to the first sleeve-shaped member and a proximal end section connected to first operating means of the handle are provided. In addition, second force transmitting means with a distal end section connected to the second sleeve-shaped member and a proximal end section connected to second operating means of the handle are provided. When manipulating the first and/or second operating means of the handle, the first and/or second sleeve-shaped members may be moved relative to each other and relative to the stent holder.

In accordance with the preferred embodiment, the first force transmitting means is constituted by a first catheter tube defining a first lumen and the second force transmitting means is constituted by a second catheter tube defining a second lumen. The second catheter tube has a cross-section less than the cross-section of the first catheter tube. The first catheter tube is disposed concentrically and coaxially with the second catheter tube and the second catheter tube is received within the first lumen defined by the first catheter tube.

Contrary to the first and second sleeve-shaped members of the catheter tip, however, the stent holder of the catheter tip is not moveable relative to the handle of the insertion system. Rather, the stent holder is connected to the handle by using a stent holder tube having a distal end connected to the stent holder and a proximal end connected to a body of the handle. The stent holder tube has a cross-section less than the cross-section of the first catheter tube. In particular, the first catheter tube is disposed concentrically and coaxially with both, the second catheter tube on the one hand and the stent holder tube on the other hand. Preferably, the stent holder tube has a cross-section less than the cross-section of the first catheter tube and greater than the cross-section of the second catheter tube such that the stent holder tube is received within the first lumen defined by the first catheter tube and the second catheter tube is received within a passageway defined by the stent holder tube. The passageway defined by the stent holder tube has a diameter sufficient to accommodate the second catheter tube such that the second catheter tube is moveable relative to the stent holder tube.

The second lumen defined by the second catheter tube has a diameter sufficient to accommodate a guide wire. The second catheter tube is made from a rigid material including, for example, nitinol, stainless steel or a rigid plastic material. The material of the distal end section of the second catheter tube may have an increased flexibility compared to the material of the proximal end section in order to allow the distal end section of the catheter shaft to pass the aortic arch during insertion of the catheter tip.

The distal end section of the second catheter tube terminates in a soft catheter end tip having an atraumatic shape. The soft catheter end tip is provided with a channel aligned with the second lumen defined by the second catheter tube such that a guide wire accommodated within the second lumen of the second catheter tube may pass through the channel of the soft catheter end tip. The second sleeve-shaped member of the catheter tip is connected to the soft catheter end tip such that the opened end of the second sleeve-shaped member faces in the proximal direction opposite to the direction of the soft catheter end tip and to the second catheter tube.

The stent holder tube is made of a rigid material, for example, a rigid plastic material, stainless steel or nitinol. The distal end of the stent holder tube terminates in the stent holder which is also made of a rigid material, for example, a rigid plastic material or stainless steel. The passageway defined by the stent holder tube is aligned with a channel which passes through the stent holder. In this way, the second catheter tube is accommodated in the passageway of the stent holder tube and the channel of the stent holder such as to be moveable relative to the stent holder tube and the stent holder. The stent holder tube is provided for connecting the stent holder to the handle. For this purpose, the stent holder tube has a distal end connected to the stent holder and a proximal end connected to a body of the handle.

The first catheter tube is made of a bendable but inelastic material. For example, the first catheter tube may be at least partly made of a braided or non-braided catheter tube. Hence, the first catheter tube has a stiff braid reinforced body similar to the catheter body described in U.S. Pat. No. 4,665,604 which is incorporated herein by reference.

The first catheter tube shall be adapted to transfer compression and tension forces from the first operating means of the handle to the first sleeve-shaped member of the catheter tip without overly changing of its total length. The distal end of the first catheter tube terminates at a flared section as the transition to the section defining the first sleeve-shaped member of the catheter tip. The flared section and the first sleeve-shaped member may be formed integrally and may be connected to the distal end section of the first catheter tube. Alternatively, the first sleeve-shaped member and the flared section of the first catheter tube may be all of the same material and originating from the same raw tube prior to a widening process so that the flared section and the first sleeve-shaped member are the same elements.

The insertion system according to the preferred embodiment further comprises a guiding tube having a cross-section greater than the cross-section of the first catheter tube. The guiding tube defines a passageway and is disposed concentrically and coaxially with the first catheter tube, the stent holder tube and the second catheter tube such that the first catheter tube with the stent holder tube and the second catheter tube accommodated therein is at least partly accommodated within the passageway defined by the guiding tube, wherein the first catheter tube is moveable relative to the guiding tube. In particular, the guiding tube terminates proximal to the catheter tip wherein the cross-section of proximal end section of the guiding tube shall be substantially the same as or less than the cross-section of the flared section provided at the proximal end of the first catheter tube. The proximal end section of the guiding tube terminates distal to the handle. The proximal end section of the guiding tube may be detached/disconnected from the handle so that the handle as well as the first and second catheter tubes and the stent holder tube together with catheter tip may be moved relative to the guiding tube.

The distal end of the guiding tube is formed such that the flared section provided at the distal end section of the first catheter tube may abut on the distal end of the guiding tube without abrupt transition. The guiding tube may be of a thin material such as to allow length deformation of the guiding tube upon transfer of compression and tension forces. The guiding tube material, however, shall have sufficient stiffness in order to mechanically avoid kinking of the flexible sections of the distal portion of the catheter shaft during insertion of the catheter tip.

The proximal end of the guiding tube is releasably connectable to the body of the handle. In this way, the guiding tube may have a double-function:

In case, the proximal end of the guiding tube is connected to the handle, the guiding tube serves as a distal extension of the body of the handle relative to which the first and second operating means are moveable for manipulating the first and second sleeve-shaped members of the catheter tip. Hence, position of the stent holder relative to the native heart valve of the patient may be changed by moving the guiding tube connected to the handle.

In case, the proximal end of the guiding tube is not connected to the body of the handle, the guiding tube may serve as a portal for passing the catheter shaft of the catheter system into the patient's body from proximal of the catheter tip.

In any case, the guiding tube has a length and is adapted such that the first catheter tube and the second catheter tube are moveable relative to each other and relative to the stent holder independent from any movement or activation of the guiding tube. In particular, the movement of the sleeve shaped members is independent from the presence or absence of the guiding tube. The length of the guiding tube is such that the sleeved shaped members and hence the first and second catheter tubes are moveable relative to each other and relative to the stent holder without interfering with the distal end of the guiding tube.

An inlet may be provided at a proximal end section of the guiding tube for injection of fluids into the guiding tube. Furthermore, a check valve may be provided at the proximal end section of the guiding tube to prevent fluid from leaking out of the guiding tube.

The guiding tube may have a length sufficient to protect the inner wall of the blood vessel through which the catheter tip passes. In addition, a separate introducer system (not belonging to the catheter system) may be provided. The introducer system then may serve as a portal for passing the complete catheter system from the catheter tip to the catheter shaft into the patient's body and up to the heart.

In addition, the guiding tube reduces the compression force exerted on the first catheter tube that is inserted through the guiding tube. This increases manoeuvrability of the first catheter tube throughout the procedure in which the first catheter tube serves as force transmitting means for manipulating the first sleeve-shaped member of the catheter tip. A consequence thereof is that the frictional force acting on the first catheter tube is reduced compared with a catheter design which is not provided with a guiding tube. Moreover, moving the catheter tip after it has been advanced through the vascular system of a patient, is greatly improved while at the same time lowering the risk of injury of the patient.

In accordance with the preferred embodiment, the guiding tube has a cross-section equal to or less than the cross-section of the catheter tip. In this regard, the guiding tube will have a length shorter than the length of the first and second catheter tubes such that the distal end of the guiding tube terminates proximal to the catheter tip. As will be appreciated, the guiding tube may not be removed from the catheter system in case the proximal end sections of the first and second catheter tube are connected to the respective operating means of a handle.

The length of the guiding tube depends on the length of the first and second catheter tubes and will typically be between about 20 cm and 100-2 cm. Those skilled in the art will appreciate, however, that all dimensions provided herein are intended as examples only, and that the guiding tubes and catheter tubes of different dimensions may be substituted for a particular use. As already indicated, the first and second catheter tubes are moveable relative to each other and relative to the stent holder independent from the guiding tube. The movement of the sleeve shaped members is independent from the presence or absence of the guiding tube. In other words, the guiding tube does not serve for manipulating the sleeve-shaped members of the catheter tip. In particular, the guiding tube does not block the travel of the sleeve-shaped members.

As will be appreciated, the guiding tube will be of a size, i.e. has an outer diameter, which will permit insertion in a patient's blood vessel (artery or vein) which is used for moving the stent transarterially or via a vein to an insufficient heart valve.

The guiding tube may be capable of traversing tortuous pathways in the body of the patient without kinking. The guiding tube may include an inner lubricious liner, an outer polymeric jacket, and a coil reinforcement between the inner and the outer layers. This guiding tube may provide favourable flexibility without kinking or compression. One or more radiopaque bands or markers may be incorporated within the guiding tubes material to allow precise location of the guiding tubes distal end for positioning accuracy. Those skilled in the art will appreciate that other known materials may also be suitable for a particular purpose.

In an embodiment disclosed herein, the catheter tip and the catheter shaft proximally connected to the catheter tip may be inserted into the patient's body by using a guide wire. The guide wire serves for guiding the catheter tip of the catheter system to an implantation site. Once in position above the aortic valve the guide wire may then be removed. Alternatively, the guide wire remains in the patient's body during implantation of a heart valve prosthesis accommodated in the catheter tip. Then, the guide wire is removed together with the catheter from the patient's body.

The guide wire is designed to be advanced into a patient's vasculature independently from the catheter tip and the catheter shaft proximally connected to the catheter tip. In other words, the catheter tip together with at least the distal part of the catheter shaft and the guide wire are advanced as single units through the vasculature of the patient, respectively. Once the guide wire is placed, the catheter tip and the catheter shaft proximally connected to the catheter tip can be advanced over the guide wire directly to the particular site in the patient's cardiovascular system.

In accordance with the present invention, a guide wire is advanced through the patient's vascular system, its direction being controlled and fluoroscopically monitored by the surgeon, until its distal end is at the desired location. Preferably, the guide wire is very small in diameter, thereby not presenting any substantial obstruction to blood flow in the blood vessel. After inserting the guide wire, the catheter tip together with the catheter shaft proximally connected to the catheter tip are advanced over the guide wire with the wire being received in the second lumen which is defined by the second catheter tube of the catheter shaft. The guide wire thus simply and automatically guides the catheter tip of the catheter system directly to the intended region, without requiring difficult, time consuming manipulations.

In a preferred embodiment of the present disclosure, the guide wire has a diameter less than the diameter of the second lumen defined by the second catheter tube. This allows that the guide wire may be at least partly received within the second lumen defined by the second catheter tube for guiding the catheter tip, at least partly disposed about the guide wire, to the implantation site.

In a preferred embodiment of the invention, the second lumen defined by the second catheter tube of the catheter shaft has a minimum dimension which is just slightly greater than the diameter of the guide wire. The maximum cross-sectional dimension of the second lumen is substantially larger than the cross-section of the guide wire. Thus, when the guide wire is disposed within the second lumen there will be substantial voids through the second lumen, on opposite sides of the guide wire through which fluids may be administered to the patient and through which blood pressure measurements may be taken. Such fluids may be administered and pressure measurements may be taken without removing the guide wire at all. By way of example, the cross-section of the guide wire preferably is of the order of no more than about fifty percent of the cross-sectional area of the second lumen.

In order to implant a heart valve prosthesis accommodated in the catheter tip, the catheter tip and the catheter shaft proximally connected to the catheter tip are advanced over the guide wire. As the tip of the guide wire terminates in the left ventricle of the heart, pushing the guide wire may contact the left ventricular apex.

In order to avoid any damage of the left ventricular apex when the guide wire is inserted, and to avoid any injury or damage to the vessel wall when the guide wire is inserted (advanced) through a vessel, the guide wire preferably has a flexible bumper at the leading end of the advancing guide wire, which minimizes the risk of trauma or injury to the delicate internal surfaces of the artery. The bumper is preferably highly flexible and with a smooth leading end. For example, the guide wire may terminate in a smoothly surfaced rounded tip, at the distal end of the guide wire. Alternatively, the distal end of the guide wire may have a j-hook shape or a hockey-stick shape, thereby reducing the risk of trauma.

Since the guide wire and the catheter tip together with the catheter shaft proximally connected to the catheter tip are generally independently advanced into the vasculature, the guide wire must be sufficiently stiff throughout its length to prevent buckling. Furthermore, the guide wire shall have sufficient stiffness to track the delivery system (catheter tip and catheter shaft proximally connected to the catheter tip) around the aortic arch. On the other hand, at least the distal tip of the guide wire shall be soft enough to prevent puncture of the heart tissue.

The guide wire may comprise a distal tip guide section and a proximal pull section. The pull section allowing for the tip guide section to be pulled out after final positioning of the catheter tip and having an optimal cross sectional area and size, is generally smaller than that of the tip guide section so as to assure minimum blood leakage at the insertion site. The tip guide section is capable of guiding the catheter through a patient's vasculature.

The guide wire may, in an exemplary embodiment, be approximately 175 centimeters long so that it may be introduced through the femoral artery and have ample length to reach the patient's coronary region. The guide wire may include a small diameter main wire. This rotationally rigid main wire of the guide wire can be solid or tubular, as long as it is rigid torsionally so that it may transmit fully to the distal end a rotational motion imparted to the proximal end. The main wire has relatively little twist as its proximal end is rotated. Practically all rotation applied to the proximal end will be transmitted quickly to the very distal tip of the guide wire. Alternatively, the guide wire may be formed substantially from elongate helical springs.

As already indicated, the aortic arch in the human body may represent a challenge for transfemoral implantation of a self- or balloon-expandable heart valve stent with a heart valve prosthesis attached to it, since it has to be accessed during insertion through the aorta. When this is done, the catheter tip and the catheter shaft proximally connected to the catheter tip must undergo a change of direction of approximately 180° over a relatively small radius, usually about 50 mm, without causing injury or damage to the vessel wall. For aiding the bending of the catheter tip and the catheter shaft proximally connected to the catheter tip when passing through the aortic arch and for supporting the catheter tip in accessing the ascending aorta, the guide wire may have a specific structure such as to make a U turn in the aortic arch. Hence, the guide wire may be programmed such that the guide wire takes a U-shape bend.

In a preferred embodiment of the present disclosure, at least a distal section of the guide wire has a predefined curved configuration adapted to the curvature of the patient's aortic arch. The predefined curved configuration of at least the distal section of the guide wire is selected such as to push the catheter tip in the direction of the centre of the ascending aorta when the catheter tip is at least partly disposed about the distal section of the guide wire and transfemoral inserted into the patient's body.

In this respect, the guide wire has a double-function: On the one hand, the guide wire serves for guiding the catheter tip of the catheter system to an implantation site. On the other hand, the guide wire serves for positioning the catheter tip in the centre of the ascending aorta when the catheter tip has accessed the ascending aorta. Then, positioning arches or hoops of the stent accommodated in the catheter tip may be easily inserted into the pockets of the native heart valve of a patient so that the heart valve stent can be easily positioned.

In a preferred embodiment, at least the distal section of the guide wire exhibits a first predefinable shape before advancing the guide wire into the patient's vasculature and a second predefinable shape in the advanced state of said guide wire, wherein the second predefinable shape of the distal section of the guide wire corresponds to the predefined curved configuration of the distal section of the guide wire. For achieving this, the guide wire may consist at least partly of a shape memory material such that at least the distal section of the guide wire can transform from a temporary shape into a permanent shape under influence of an external stimulus, wherein the temporary shape of the distal section of the guide wire corresponds to the first shape and the permanent shape of the distal section of the guide wire corresponds to the second shape.

A shape memory material, for example Nitinol, may be used as the material for at least the distal section of the guide wire. Such a shape memory material is preferably designed such that the guide wire can transform from a temporary shape into a permanent shape under the influence of an external stimulus. The temporary shape is thereby the first shape of the guide wire (i.e. the shape of the guide wire before inserting it into the patient's body), while the permanent shape is assumed in the second shape of the guide wire (i.e. in the inserted state of the guide wire). In particular, use of a shape memory material such as Nitinol, i.e. an equiatomic alloy of nickel and titanium, allows for a particularly gentle insertion procedure.

It is conceivable of course that other shape memory materials, for example shape-memory polymers, are used as the material for at least the distal section of the guide wire. At least parts of the guide wire may be formed by using, for example, a polymer composite exhibiting a crystalline or semi-crystalline polymer network having crystalline switching segments. On the other hand, an amorphous polymer network having amorphous switching segments is also conceivable.

When manufacturing the guide wire preferably made from a shape memory material, the permanent shape of the guide wire, i.e. the shape of the guide wire which is assumed in the inserted state of the guide wire, is formed. Once the desired shape has been formed, this shape is "fixed", this process being known as "programming". Programming may be effected by heating the guide wire, forming the guide wire into the desired shape and then cooling the guide wire. Programming may also be effected by forming and shaping the structure of the guide wire at lower temperature, this being known as "cold stretching." The permanent shape is thus saved, enabling the guide wire to be stored and implanted in a temporary, non-formed shape. If an external stimulus then acts on the stent structure, the shape memory effect is activated and the saved, permanent shape restored.

A particularly preferred embodiment provides for the external stimulus to be a definable switching temperature. It is thus conceivable that the material of the guide wire needs to be heated to a higher temperature than the switching temperature in order to activate the shape memory effect and thus regenerate the saved permanent shape of the guide wire. A specific switching temperature can be preset by the relevant selection of the chemical composition of the shape memory material.

It is particularly preferred to set the switching temperature to be in the range of between 10° C. and the patient's body temperature and preferably in the range of between 10° C. and room temperature (22° C.). Doing so is of advantage, especially with regard to the guide wire which needs to be inserted in a patient's body. Accordingly, all that needs to be ensured in this regard when inserting the guide wire is that the guide wire is warmed up to room temperature or the patient's body temperature (37° C.) at the site of implantation to activate the shape memory effect of the stent material.

Alternatively, the guide wire may be made from another material (for example a platinum-tungsten alloy) which allows that the distal region of the guide wire can be bent manually by the surgeon and will retain its bent configuration when relaxed. This enables the guide wire to be controllably steered by rotation of the guide wire to direct the curved distal end selectively into the aortic arch and into the ascending aorta. Rotational control of the guide wire may be enhanced by bending the proximal end of the wire to form somewhat of a handle.

In use, the surgeon may bend the distal region of the guide wire so that it will be biased toward and will assume somewhat of a curve when relaxed. When advanced through the patient's artery the degree of resilience at the distal region of the wire is such that the wire will straighten and follow the path of the artery quite easily. A progressively increased flexibility resulting from, for example, a continuous taper at the distal region of the guide wire may enhance the ability of the guide wire to flex from the pre-bent biased curve and follow the path of the blood vessel.

When the distal end of the pre-bent, biased guide wire is at the descending aorta proximal of the aortic arch, the surgeon can steer it into the aortic arch and thereafter into the ascending arch by rotation of the guide wire by manipulating it from the proximal end.

Alternatively, the guide wire may be inserted into the patient's body by using a guide catheter. The guide catheter may comprise a guide catheter tube defining a lumen for receiving the guide wire. The guide catheter may serve for inserting the guide wire. Once the guide catheter is introduced through the femoral artery and the aortic arch and has reached the patient's aortic valve region, the guide wire is released from the guide catheter by removing the guide catheter whereas the guide wire remains in the patient's body. In this case, the guide wire exhibits its first predefinable shape before releasing the guide wire from the guide catheter and its second predefinable shape after releasing the guide wire from the guide catheter. As already indicated, the second predefinable shape of the distal section of the guide wire is selected such that the distal section of the guide wire pushes the catheter tip in the direction of the centre of the ascending aorta when the catheter tip is at least partly disposed about the distal section of the guide wire and transfemoral inserted into the patient's body.

According to one aspect of the present disclosure, at least the distal region of the guide wire is at least partly formed from a material having a high radiopacity. A relatively high degree of radiopacity of the distal region of the guide wire enhances fluoroscopic imaging of the guide wire as it is advanced through the patient's artery.

The procedure for using the guide wire in accordance with the present invention involves initial placement and location of the guide wire in the femoral artery and the aortic arch. Once the guide wire is in place the catheter tip with the catheter shaft of the catheter system then may be advanced over the guide wire to a point where the stent accommodated in the catheter tip is in the ascending aorta proximal to the native aortic heart valve. This can be verified fluoroscopically because of the highly radiopaque characteristic of the catheter tip and/or guide wire and also by injecting radiopaque dye through, for example, a lumen of the catheter system. For this reason, the catheter tip of the catheter system may be provided with radiopaque markers which also facilitate fluoroscopic monitoring of its progress and position.

In order to treat a heart valve stenosis and/or heart valve insufficiency in a patient, a medical device is disclosed. The medical device comprises an insertion system and an expandable heart valve stent accommodated in the catheter tip of the insertion system. While it is accommodated in the catheter tip of the insertion system, the stent adopts a first previously definable configuration. Outside the catheter tip or in the implanted state, however, the stent exists in a second previously definable configuration. The first configuration of the stent corresponds to the folded-up state, while the stent exists in its expanded state in the second configuration.

A heart valve stent is used with the medical device, as described for example in the European Patent Application No. 07 110 318 or in the European Patent Application No. 08 151 963. In a preferred embodiment of the medical device, a heart valve stent is accordingly used which exhibits the following:

- a first retaining region, to which a heart valve prosthesis can be attached;
- an opposing, second retaining region with at least one retaining element, for example in the form of retaining eyes or in the form of retaining heads, whereby at least one retaining element of the stent can be put in releasable engagement with the stent holder of the catheter tip forming part of the insertion system;

at least one retaining hoop, to which a heart valve prosthesis can be fastened; and at least one and preferably three positioning hoops, which are designed to engage in pockets of the native heart valve in the implanted state of the stent, thus to enable automatic positioning of the stent in the aorta of the patient.

In particular, an insertion system is proposed, with which an expandable heart valve stent with a heart valve prosthesis attached to this stent can be advanced to the implantation site in a particularly simple way, for example via the aorta of a patient being treated (transarterially or transfemorally). Preferably, during transarterial or transfemoral access by the catheter system, the whole free cross-section available within the aorta is not completely filled up, since the catheter tip provided at the distal end region of the catheter system, in which the stent can be accommodated with the heart valve prosthesis, can be made sufficiently small with respect to its external diameter.

The expandable heart valve stent with the heart valve prosthesis attached to it can be accommodated temporarily during implantation in the folded-up state in the catheter tip of the insertion system, which is provided at the distal end region of the catheter system. The catheter system may be of a length sufficient to allow the catheter tip provided at the distal end region of the catheter system to be guided through the aorta to the patient's heart by insertion at the patient's groin.

The insertion system designed for transarterial or transfemoral access is therefore suitable for inserting a heart valve stent with a heart valve prosthesis attached to it, transarterially or transfemorally into the body of the patient; for example, the catheter system of the insertion system is inserted with the catheter tip located at the distal end of the catheter system via puncture of the A. femoris communis (inguinal artery).

In particular, with the insertion system designed for transarterial or transfemoral access, the catheter system may be designed so that it is both kink-resistant and flexible such that a bending radius of up to 4 cm, and preferably up to 3 cm, can be realised, at least at the distal end region of the catheter system.

According to another aspect, the disclosure resides in a handle for manipulating a vascular insertion system, wherein the handle comprises means that prescribe a pre-set sequence of steps such that each subsequent step is inhibited until the preceding step has been completed. Ideally the handle includes means that prescribe or enforce a pre-set sequence of steps for staged release of the stent.

The term "pre-set" refers to steps that have been set of fixed in advance of operation of the vascular insertion system and handle. The steps of operation are pre-conditioned such that one step must be completed before the next step can be effected. A predetermined series of steps reduces the risk of incorrect positioning and requires less skill and expertise on the part of whomsoever performs the procedure. Thus, the sequence of events which can be determined beforehand relates to those events or steps of the operation which depend on and, for example, may be controlled by, the insertion system and handle.

In this way, a catheter tip of the insertion system may be manipulated especially reliably with the handle and a heart valve stent may be introduced in a particularly simple but nevertheless reliable way into the body of a patient and optimally positioned at the implantation site in the heart.

While it will be appreciated that such a handle may be applied to any catheter system for which, for example, delivery, accurate positioning and/or control of medical devices is required, for the purposes of the present disclosure, the handle is used in conjunction with a vascular insertion system for introducing a stent into a patient's body and for positioning the stent at a desired implantation site.

According to one aspect of the present disclosure, the handle has at least one first and one second operating means with which the catheter tip of an insertion system may be appropriately manipulated so that a self-expandable stent housed in the catheter tip may be released from the catheter tip in steps or in a previously defined or definable sequence of events.

According to one aspect, the disclosure resides in a catheter system having first and second force transmission means. These force transmission means are at the distal end region of the catheter system, i.e. at the end region of the catheter system nearest the heart, and can be connected to a catheter tip in which a heart valve stent is mounted or can be mounted. In detail, the force transmission means are designed to manipulate the first and second housing portions of the catheter tip so that a self-expandable stent housed in the catheter tip may be released from the catheter tip in steps or in accordance with a previously defined or definable sequence of events. Then at the proximal end region of the catheter system, i.e. at the end region of the catheter system which is facing away from the heart, the force transmission means may be connected to first and second operating means of a handle of the type referred to above.

According to another aspect, the disclosure resides in an insertion system having a catheter system of the type referred to above, by means of which a cardiac valve stent can be introduced into the body of the patient in its folded-up state. The insertion system further has a catheter tip provided at the distal end region of the catheter system, i.e. adjacent to the heart, with first and second manipulable housing portions. Furthermore, the insertion system has a handle of the type referred to above at the proximal end region of the catheter system, i.e. at the end region of the catheter system which is remote from the heart and the catheter tip. The first and second housing portions of the catheter tip may be manipulated appropriately with the handle so that the self-expandable stent accommodated in the catheter tip may be released from the catheter tip in a previously defined or definable sequence of events.

According to another aspect, the disclosure resides in a medical device having an insertion system of the type referred to above together with a self-expandable cardiac valve stent accommodated in the catheter tip of the insertion system.

An insertion system can be implemented with the present disclosure for inserting a stent into the body of a patient, whereby the insertion system exhibits the following:

a catheter system, by means of which an expandable cardiac valve stent (also simply termed "stent" in the following) can be introduced in its folded-up state into the body of a patient;

a catheter tip provided at the distal end region of the catheter system, in which the stent can be mounted;

a handle at the proximal end region of the catheter system, with which the catheter tip can be manipulated.

Preferably the insertion system according to the disclosure comprises a catheter tip, as is described, for example, in the International Patent Application No. PCT/EP2007/061117. The catheter tip has a region termed "stent holder" in the following, by means of which the stent can be attached to the catheter tip. In detail, the stent holder is used for releasably fixing at least one region of the stent in the catheter tip.

Furthermore it is possible in a preferred embodiment of the catheter tip for this to have first and second housing portions that may be manipulated with the handle. These housing portions are used for accommodating specific portions of the stent. The first housing portion is used for accommodating first functional components of the stent, for example retaining hoops of the stent (or alternatively positioning hoops of the stent), while the second housing portion is used for accommodating the second functional components of the stent, for example, positioning hoops of the stent (or alternatively for accommodating retaining hoops of the stent).

In relation to the handle provided for the insertion system, it is preferably provided that, on one hand, the first operating means cooperate with the first housing portion of the catheter tip so that, on actuation of the first operating means, a previously definable longitudinal displacement of the first housing portion may be effected relative to the stent holder and, on the other hand, the second operating means cooperates with the second housing portion of the catheter tip so that a previously definable longitudinal displacement of the second housing portion may be affected relative to the stent holder.

The present disclosure also resides in an insertion system comprising a handle of the present disclosure, a catheter system of the present disclosure and a catheter tip. In particular, an insertion system is proposed, with which a expandable heart valve stent with a heart valve prosthesis attached to this stent can be advanced to the implantation site in a particularly simple way, for example via the aorta of a patient being treated (transarterially or transfemorally) or from the apex of the heart (transapically). Preferably, during transarterial or transfemoral access by the catheter system, the whole free cross-section available within the aorta is not completely filled up, since the catheter tip provided at the distal end region of the catheter system, in which the stent can be accommodated with the heart valve prosthesis, can be made sufficiently small with respect to its external diameter.

In particular, according to one aspect, the insertion system of the disclosure is not only suitable for a transarterial or transfemoral access, but can also be used transapically, i.e. from the apex of the heart, to insert and position the heart valve stent with the heart valve prosthesis attached to it into the body of the patient and to place it percutaneously, orthotopically in vivo, so that the heart valve prosthesis can assume the function of an insufficient or stenosed native heart valve. As will be explained, an insertion system that is designed for transapical access can have a shorter catheter system compared with that for transarterial access.

To enable the stent accommodated in the catheter tip to be inserted into the body of the patient with the aid of the catheter system and, where required, with the aid of a further insertion wire (guide wire), it is preferably provided that the catheter tip has a mounting (stent holder) for releasably fixing of at least the second retaining region of the stent and mounting regions for accommodating the first retaining region with the positioning hoops and the retaining hoops together with, where required, the heart valve prosthesis fastened to the retaining hoops. Further it is preferable for the handle to be provided at the proximal end the region of the catheter system, so that the catheter tip and, in particular, the respective housing portions of the catheter tip can be manipulated and moved in a directed manner.

In particular, a radial or also lateral movement of the catheter tip and/or the individual housing portions of the catheter tip can be obtained. As a result of this selective movement of the individual components of the catheter tip, individual components (positioning hoops, retaining hoops) of the heart valve stent can be sequentially released in accordance with a predictable sequence of events, so that the implantation of the heart valve prosthesis can take place with the necessary positioning and anchoring.

Specifically, it is provided in the insertion system in accordance with the disclosure that the catheter tip has the housing portions already referred to, whereby the handle has at least a first operating means associated with the first housing portion and a second operating means associated with the second housing portion. The first operating means cooperates with the first housing portion of the catheter tip so that, on actuation of the first operating means, a previously definable longitudinal displacement of the first housing portion can be effected relative to the stent holder of the catheter tip. In an analogous way, the second operating means cooperates with the second housing portion of the catheter tip so that, on actuation of the second operating means, a previously definable longitudinal displacement of the second housing portion can be effected relative to the stent holder of the catheter tip.

The respective co-operation of the operating means forming part of the handle with the associated housing portions of the catheter tip can be achieved, for example, with the aid of suitable force transmission means of the catheter system.

By providing the appropriate operating means in the handle, on the one hand, and the first and second housing portions in the catheter tip on the other, the respective housing portions of the catheter tip can be manipulated selectively and can be moved according to a previously definable sequence of events.

The proposed insertion system is therefore not only suitable to introduce the stent housed in the catheter tip provided at the distal end of the catheter system into the body of the patient at the implantation site with a suitable radial and/or lateral movement, with the aid of the catheter system, but also to obtain a sequential release of the respective functional components (positioning hoops, retaining hoops) of the stent by directed and previously definable movements of the housing portions of the catheter tip, so that the implantation of the heart valve prosthesis with the heart valve stent may take place in a particularly suitable but nevertheless effective manner.

In particular, it is possible that, for example, release of the positioning hoops of the heart valve stent are released by a twisting and/or a lateral movement in the distal or proximal direction of one of the two housing portions of the catheter tip, while the retaining hoops of the stent are still held in the folded-up form by the other housing portion of the catheter tip. The retaining hoops of the stent can then be released by a corresponding manipulation of the other housing region of the catheter tip.

To ensure that a stent mounted in the catheter tip with a heart valve prosthesis attached to the retaining hoops of the stent can be implanted transarterially or transfemorally, in other words coming via the aorta, it is proposed by the insertion system in accordance with the disclosure that the first housing portion of the catheter tip is in the form of a so-called "stent sheath". The stent sheath is a sleeve-like housing portion, whose opening points in the direction of the distal end tip of the catheter tip. When the catheter tip is actually inserted into the body of the patient, the catheter tip is in its so-called "closed state". In this closed state, these stent sheath forms the outer circumferential surface of the catheter tip, while the stent is housed in its folded-up state in the interior of the stent sheath.

When the first operating means of the handle is actuated, with the insertion system designed for transarterial or transfemoral access, the first housing portion of the catheter tip can be moved relative to the stent holder in the longitudinal direction of the catheter tip. In detail, to open the catheter tip or to release a stent housed in the catheter tip, the movement of the first housing portion takes place in the direction of the handle, away from the distal end tip of the catheter tip.

With the insertion system designed for transarterial or transfemoral access, it is further provided that the second housing portion of the catheter tip is in the form of a so-called "stent funnel". The stent funnel is a sleeve-like housing portion, which is connected to the distal end tip of the catheter tip and which has its opening pointing in the direction of the proximal end region of the catheter tip. The retaining hoops of the stent and the heart valve prosthesis, where fastened to the retaining hoops, can be housed in the interior of the stent funnel. The stent funnel fits telescopically into the stent sheath when the catheter tip is in the closed state. The positioning hoops of the stent are then located between the outer circumferential surface of the stent funnel and the inner circumferential surface of the stent sheath.

When the second operating means of the handle is actuated, with the insertion system designed for transarterial or transfemoral access, the second housing portion of the catheter tip can also be moved relative to the stent holder in the longitudinal direction of the catheter tip. In detail, to release a stent housed in the catheter tip, the second housing portion is moved together with the distal end tip of the catheter tip in the distal direction, i.e. away from the handle.

The insertion system designed for transarterial or transfemoral access is therefore suitable for inserting a heart valve stent with a heart valve prosthesis attached to it, transarterially or transfemorally into the body of the patient; for example, the catheter system of the insertion system is inserted with the catheter tip located at the distal end of the catheter system via puncture of the A. femoris communis (inguinal artery).

The catheter tip and, optionally, also the catheter system of the insertion system, are advanced, preferably under angiographic (vessel display) and echocardiographic (ultrasonic) control into the heart valve position. The actual implantation of the heart valve then follows, in which, by means of previously definable manipulations of the associated housing portions of the catheter tip, which can be effected with the respective operating actuating means of the handle, the individual components of the heart valve stent mounted in the catheter tip are released.

Alternatively, however, the insertion system in accordance with the disclosure is also suitable for a transapical access, in which case—approaching from the apex of the heart—the catheter tip of the catheter system is pushed, for example, through the left ventricle to the aortic valve. With an appropriately modified catheter tip, an analogous implantation of the heart valve stent with the heart valve prosthesis is possible here.

In detail, with the insertion system designed for transapical access, it is provided that the first housing portion of the catheter tip is in the form of a stent sheath, which is connected to the distal end tip of the catheter tip and has an opening pointing in the direction of the proximal end region of the catheter tip. As with the insertion system designed for transarterial or transfemoral access, the stent sheath for the insertion system designed for transapical access forms the outer circumferential surface of the catheter tip, when this is in the closed state.

When the first operating means of the handle is actuated, with the insertion system designed for transapical access, the first housing portion of the catheter tip can be moved relative to the stent holder in the longitudinal direction of the catheter tip, whereby the movement of the first housing portion takes place in the distal direction, thus away from the handle, to open the catheter tip or to release a stent housed in the catheter tip.

With the insertion system designed for transapical access, the second housing portion of the catheter tip is in the form of a stent funnel which has its opening pointing in the direction of the distal end tip of the catheter tip. Once again, the retaining hoops of the stent and the heart valve prosthesis, where fastened to the retaining hoops, can be mounted in the interior of the stent funnel, while the stent funnel fits telescopically into the stent sheath when the catheter tip is in the closed state, whereby the positioning hoops of the stent are located between the outer circumferential surface of the stent funnel and the inner circumferential surface of the stent sheath.

When the second operating means of the handle is actuated, with the insertion system designed for transapical access, the second housing portion of the catheter tip can also be moved relative to the stent holder in the longitudinal direction of the catheter tip. Specifically, to release a stent housed in the catheter tip, the second housing portion is moved in the direction of the distal end tip of the catheter tip.

Irrespective of whether the insertion system is designed for a transarterial and transfemoral access or a transapical access, the insertion system of the disclosure exhibits a catheter tip with a first housing portion, for example for housing of the retaining hoops of the stent (as first functional components of the stent) and a second housing portion, for example for housing of the positioning hoops of the stent (as second functional components of the stent), whereby the two housing portions can be manipulated by actuation of operating means provided in the handle, in accordance with a previously definable sequence of events, and as a result the individual components of the heart valve stent can be released.

In relation to the catheter system used with the insertion system, it is preferably provided that this has an outer catheter, in which at least one inner catheter is accommodated. The outer circumferential surface of the outer catheter then forms the outer shell of the catheter system. Preferably the outer catheter and the at least one inner catheter then respectively act as force transmission means. In the insertion system, the force transmission means are connected at the proximal end region of the catheter system with the actuating means of the handle and are connected at the distal end region of the catheter system to the housing portions of the catheter tip. The outer catheter and the at least one inner catheter have the function of transmitting compressive and tensile forces from the corresponding operating means of the handle to the corresponding housing portions of the catheter tip. It is preferable that the outer catheter and the at least one inner catheter are each designed so that their length virtually does not change even under compressive or tensile stress.

In particular, with the insertion system designed for transarterial or transfemoral access, the catheter system should be designed so that it is both kink-resistant and flexible such that a bending radius of up to 4 cm, and preferably up to 3 cm, can be realised, at least at the distal end region of the catheter system.

To enable the catheter tip to be moved radially, in particular for the purpose of precise positioning of a heart valve stent advanced with the insertion system to the implantation location on the heart, it is provided in a preferred embodiment of the insertion system designed for transapical access that the catheter system and the respective couplings of the catheter system to the catheter tip on one side and to the handle on the other side are configured so that it is possible to twist the catheter tip about the longitudinal axis of the of the catheter tip by turning the handle and/or the catheter system. In particular, the catheter system and the respective couplings of the catheter system to the catheter tip and to the handle should exhibit a previously definable, preferably small, delay in reaction, due to a torque introduced by means of the handle.

As already indicated, it is preferably provided for the insertion system according to the present disclosure that the catheter tip has a stent holder with retaining elements. The stent holder with the retaining elements is used to anchor the second retaining region of the stent during the insertion procedure and during positioning of this stent in the implantation location at the catheter tip. It would be possible to configure the retaining elements of the stent holder as projecting elements which can be brought into engagement with corresponding retaining rings having complementary configuration at the second retaining region of the stent for releasably fixing the second retaining region of the stent.

In a particularly preferred embodiment of the stent holder forming part of the catheter tip it is provided, however, that the stent holder has an essentially cylindrical body, whose axis of symmetry lies on the longitudinal axis of the catheter tip. Several uniformly spaced recesses are formed on the cylindrical body at the proximal-side end region of the body in the insertion system designed for transapical access, and at the distal-side end region of the cylindrical body in the insertion system designed for transfemoral or transarterial access. These recesses can be connected via corresponding grooves to the proximal or distal-side end face of the cylindrical body.

The configuration and size of the recesses formed in the material of the cylindrical body are chosen so that a fastening or retaining element of a heart valve stent mounted in the catheter tip of complementary form to the recess can be accommodated, preferably by positive fit, in each of the recesses, so that each retaining element of the stent is in releasable engagement with a recess of the fixing device.

In this connection, it would be possible for the retaining elements of the stent to be formed at the second retaining region of the stent in the form of projecting elements, for example. These retaining elements of the stent, in the form of projecting elements in the example, can each be connected to the positioning hoops of the stent by means of a neck section. When the retaining elements of the stent are mounted in the recesses of the stent holder, preferably by positive fit, at least the end regions of the neck sections are in the grooves that are formed in the material of the cylindrical body of the stent holder.

Irrespective of the particular embodiment of the stent holder, it is a basic requirement that the retaining elements of the stent holder (projecting elements and recesses) are covered during the insertion procedure and during the positioning of the stent at the implantation site, in common with the retaining elements located at the second retaining region of the stent, by the sleeve-shaped first housing portion of the catheter tip. This ensures that the engagement between the retaining elements of the stent and the retaining elements of the stent holder is secure and that the second retaining region of the stent is still held positively in its folded-up state.

In this position it is possible to check the function of the already unfolded heart valve prosthesis. Once a check has been made to ensure that the heart valve prosthesis is functioning correctly—by a further manipulation of the first housing portion (stent sheath) of the catheter tip with the first operating means—the region of the first housing portion previously covering the retaining elements of the stent holder at the proximal part of the stent can be moved farther in the longitudinal direction of the catheter tip relative to the fixing mechanism of the catheter tip so the first housing portion no longer covers the respective retaining elements of the stent holder and the stent. As a result, the engagement between the retaining eyes etc. provided at the proximal end of the stent and the retaining elements of the stent holder can be released, which causes the proximal part of the stent to be released as well and thus completely unfolded.

If, however, the check shows that the already partially implanted heart valve prosthesis is not able to fulfil its function or is not able to do so satisfactorily, the insertion system proposed by the disclosure has the particular advantage of retracting the stent with the heart valve prosthesis back into the catheter tip by moving the respective housing portions of the catheter tip appropriately in the opposite direction and of removing all parts of the insertion system, in other words the catheter tip with the catheter and the stent accommodated in the catheter tip, out of the body of the patient so that the risk of the operation is substantially reduced and a further attempt at implantation can be made on the same patient.

To ensure that, as far as possible, no damage can take place to the vessel wall during insertion of the catheter tip into the body of the patient when, for example, the catheter tip is inserted transarterially, and no injury can occur within the interior of the heart when, for example, the catheter tip is inserted transapically, it is preferable if the catheter tip in particular has a rotationally symmetrical form and preferably a rounded shape.

As the catheter tip is inserted, the catheter tip further should be completely closed, as far as possible, and, to facilitate insertion through the aorta, should have a tip on the distal end that is particularly preferably of a flexible material, for example silicone.

The catheter system used with the insertion system proposed by the disclosure should also be advantageously configured so that a liquid coolant or drug can be circulated through the internal hollow catheter system as far as the catheter tip. With the aid of such a liquid coolant, for example in the form of a saline solution, a heart valve stent accommodated in the catheter tip can be appropriately cooled while the catheter tip is being advanced to the implantation site. This is of particular advantage when a shape memory material is used as the material of the heart valve stent, which is designed so that the stent deforms from a temporary shape to a permanent shape under the action of an external stimulus, whereby the temporary shape exists in a first configuration of the stent (in the folded-up state, when the stent is accommodated in the catheter tip of the insertion system) and the "permanent shape" in a second configuration of the stent (in the expanded state of the stent after release of the stent from the catheter tip).

It should be noted that the "permanent shape" of the expanded stent is totally adapted to the native shape of its surrounding area. This makes allowance for the fact that the native shape of the surrounding area at the implantation site differs from patient to patient. The property of the stent whereby the "permanent shape" of the expanded stent is automatically fully adapted to the surrounding environment consequently ensures that the heart valve prosthesis can always be implanted optimally.

An especially gentle implant procedure is possible when implanting the stent with the heart valve prosthesis mounted on it into the body of a patient with the insertion system of the disclosure, particularly if a shape memory material, for example Nitinol, i.e. an equi-atomic alloy of nickel and titanium, can be used for the stent.

If, as is preferable, the catheter system of the insertion systems proposed by the disclosure is designed so that a suitable coolant can be circulated through it, the stent mountable in the catheter tip can therefore be appropriately cooled while being advanced, to maintain the temperature of the stent material below the critical transition temperature. When the catheter tip with the cooled stent has been advanced to the implantation site, cooling of the stent is interrupted, at the latest when the housing portions of the catheter tip are manipulated, as a result of which the stent is warmed to the body temperature (36° C.) of the patient and the shape memory effect of the stent material is initiated.

Due to the self-expanding property of the individual components of the stent, radial forces are generated which act on the individual components of the stent, particularly the respective positioning hoops and retaining hoops, as well as the first and second retaining regions of the stent. Since the respective components of the stent remain in the respective housing portions of the catheter tip, the radial forces which build up and act on the individual components of the stent after the transition temperature has been exceeded are compensated by the respective housing portions of the catheter tip, so that—in spite of the initiation of the shape memory effect—the stent is retained positively in its first (folded-up) shape.

By an appropriate manipulation of the respective housing portions of the catheter tip, which is defined previously on the basis of the particular embodiment of the insertion system of the disclosure, the positioning hoops are then released from the catheter tip first—by a suitable stepwise release of the stent and the individual components of the stent from the respective housing portions of the catheter tip. Because of the action of the radial forces, the positioning hoops of the stent are opened in a radial direction. The opened stretched positioning hoops can then be positioned in the recesses pockets of the native heart valve.

The remaining components of the stent are then released from the catheter tip. The released remaining components of the stent, in particular the retaining hoops with the heart valve prosthesis attached e.g. with the aid of a thread, then open in a radial direction and consequently the heart valve prosthesis attached to the retaining hoops unfolds like an umbrella.

The radial forces acting on the retaining hoops of the stent but also on the proximal retaining region of the endoprosthesis result in the stent being pressed against the vessel wall in a radial direction. On the one hand, this results in secure anchoring of the stent with the opened heart valve prosthesis at the implantation site and, on the other hand, of reliably sealing the heart valve prosthesis in the second retaining region of the stent.

For flushing or rinsing the catheter system with coolant etc., it is particularly preferred that the handle has at least one syringe adapter for delivering and/or discharging a fluid to or from the catheter system.

To monitor the insertion procedure of the catheter system as well as the manipulation of the bendable region of the deflecting mechanism, which may optionally be provided on the distal end of the catheter system, it is advantageous to provide marking elements on the catheter tip and/or at appropriate points of the catheter system, which are made from a material that absorbs X-ray radiation, for example, so that the respective position of the catheter tip and/or the catheter system can be detected on the X-ray image during the operation.

A screen filter may of course also be used with the insertion system of the disclosure, so that penetration of particles into the bloodstream of the respective patient can be prevented. Such a screen filter may be attached to the insertion system or the catheter system so that it extends completely around it radially. When used, it should be elastically biased so that it lies against the vessel wall in the aorta to thus ensures a particle-tight closure.

The insertion system proposed by the disclosure may additionally be provided with a conventional balloon, which can be disposed in the interior of the catheter system or the catheter tip and carried along with it or also passed through the interior of the catheter system to the expanding heart valve stent. With such a balloon, the volume of which can be which can be increased accordingly e.g. by a fluid under elevated pressure, the expansion of the anchoring support can be further assisted.

As explained above, the stent of the medical device, which can be inserted into the body of the patient with the aid of the insertion system described above, preferably has a one-piece structure cut integrally from a metal tube, in which a retaining hoop is associated with each positioning hoop and in which, at the proximal end of the endoprosthesis, each end portion of the positioning hoop is connected to the end portion of the associated retaining hoop. Thus, on the one hand, it is possible to dispense with plastic hinges or similar connecting devices for the stent. On the other hand, the stent preferably used with the medical device proposed by this disclosure is an endoprosthesis which has a minimum longitudinal extension and offers a positioning function by means of the positioning hoops on the one hand and the function of retaining a heart valve prosthesis by means of retaining hoops on the other hand.

It is clear that, during the transition of the stent form the first pre-definable mode to the second pre-definable mode due to a widening in the cross-section of the entire stent, the retaining hoops on the one hand and the positioning hoops on the other hand are opened in a radial direction. This being the case, the second mode of the stent is advantageously selected so that as the retaining and positioning hoops are being opened, they abut against the vessel wall of the aorta and form a positive connection with it, thereby firmly anchoring the stent and the heart valve prosthesis at the implantation site.

Due to the fact that the structure of the stent results in a particularly short design of the catheter tip of the insertion system, the catheter tip of the insertion system can be manoeuvred in the patient's body particularly easily, which is of particular advantage if the implantation route to the heart valve to be replaced is via the aortic arch. The minimal length of the catheter tip of the insertion system is ensured particularly by the special structure of the stent.

Accordingly, using the insertion system proposed by the disclosure, the positioning and retaining hoops of such an anchoring stent at the implantation site can be disposed and dimensioned with a view to automatically initiating a sequential self-expansion of the stent with the heart valve prosthesis. For this to take place, it is preferably provided that the stent together with the heart valve prosthesis fastened to it, where required, are mounted for the purpose of implantation in the interior of the catheter tip that forms part of the insertion system. This catheter tip is guided via the catheter system of the insertion system through the aorta of the patient, for example, or from the apex of the heart, to the implantation site (to the diseased heart). On reaching the implantation site, the catheter tip of the insertion system is manipulated so that the positioning hoops can be released to permit their self-expansion. Subsequently the catheter tip of the insertion system with the already partially expanded stent is moved and aligned so that the positioning hoops are inserted into the pockets of the native heart valve. This allows the stent to be precisely positioned in relation to the native heart valve.

The catheter tip of the insertion system is further manipulated so that the retaining hoops of the anchoring stent are also released, as a result of which they automatically expand. As this happens, the heart valve flaps of the native heart valve are clamped between respective positioning and retaining hoops and the heart valve prosthesis attached to the distal retaining region of the anchoring stent is opened.

Once the anchoring stent incorporating the heart valve prosthesis has been implanted, the catheter system with the catheter tip is withdrawn from the body of the patient.

Naturally, due to the increased control afforded by the implantation system it is also conceivable, for example, for a heart valve stent to be implanted in a two-part procedure, carried out either during separate procedures or as separate parts of the same procedure. In a first part, for example, an anchoring stent is introduced to an implantation site. In a second part, a secondary stent with a valve prosthesis is introduced to the implantation site. The secondary stent comprises appropriate functional components that can co-operate and engage with the anchoring stent. Thus, the secondary stent accommodates and retains a heart valve prosthesis on the one hand, whilst co-operating with the anchoring stent to anchor and retain the heart valve stent with the valve prosthesis in position on the other.

Since the implantation system both increases control and enhances the ability to accurately position an implant such as a stent, it would also be conceivable to replace a failing valve from a previously implanted heart valve with a new valve prosthesis. The functional components position and secure the new, or secondary, heart valve stent at the implantation site of the previously implanted heart valve stent and accommodate and retain the new, or secondary, heart valve prosthesis. Thus, by way of example, a new heart valve stent with valve prosthesis could be implanted within a previously implanted heart valve stent in the same manner as implantation of a first heart valve stent with prosthesis.

Preferred embodiments will be described with reference to the appended drawings below.

Figure 2:
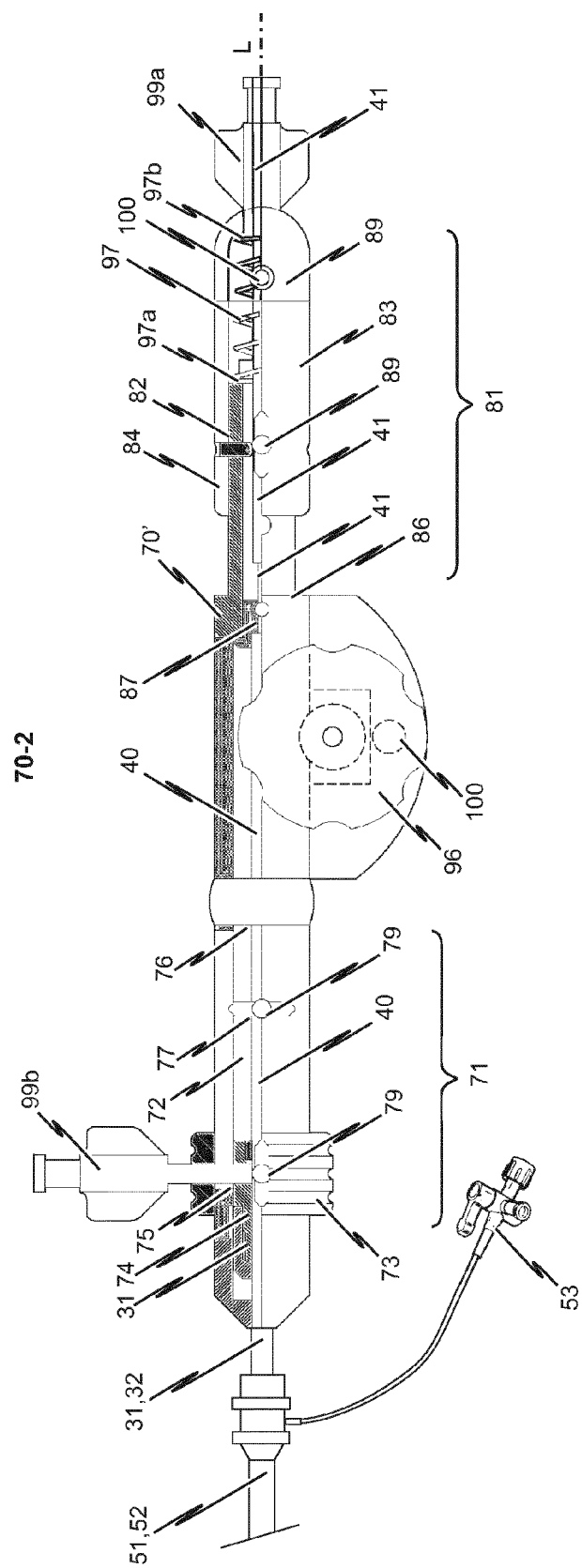
Figure 3A:
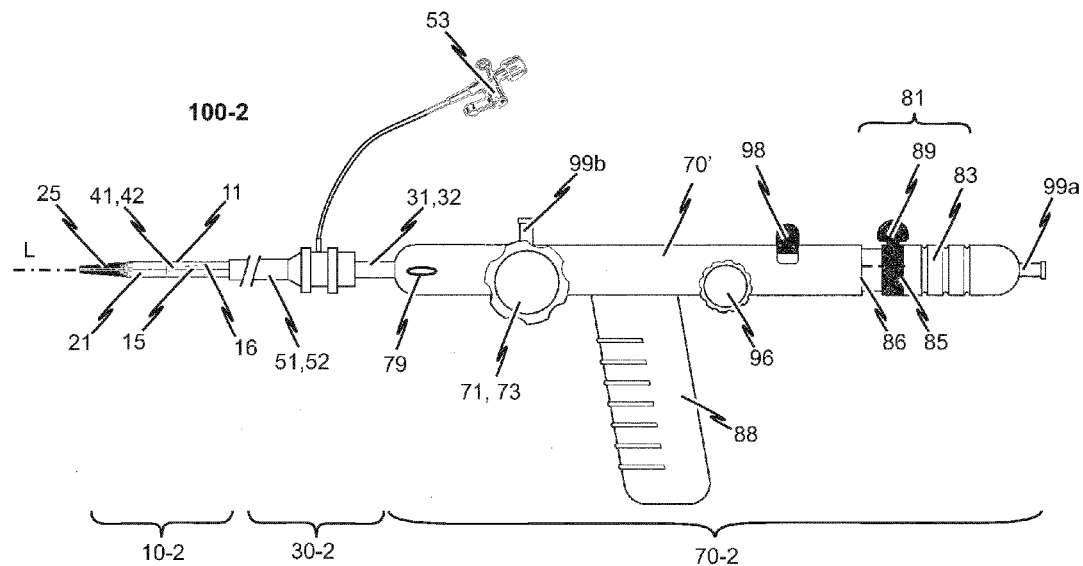
Figure 3B:
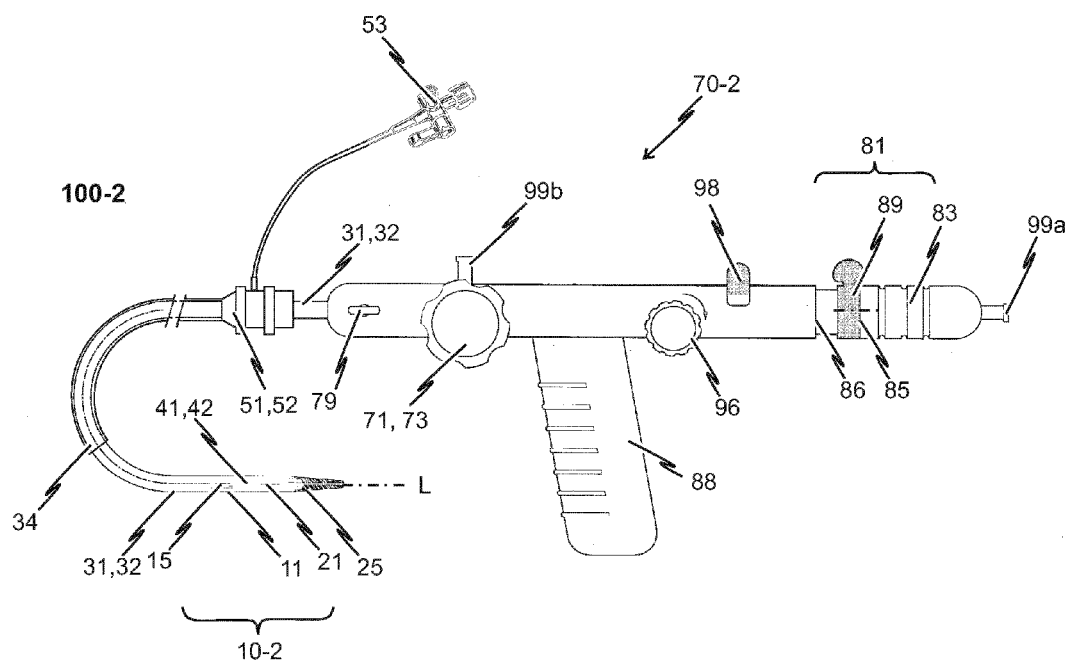
Figure 4:
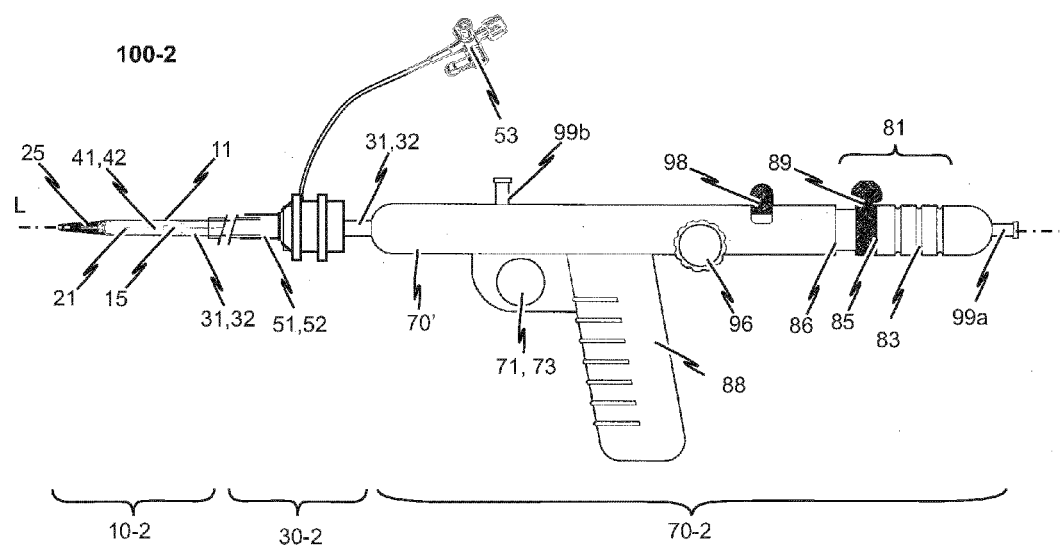
Figure 5:
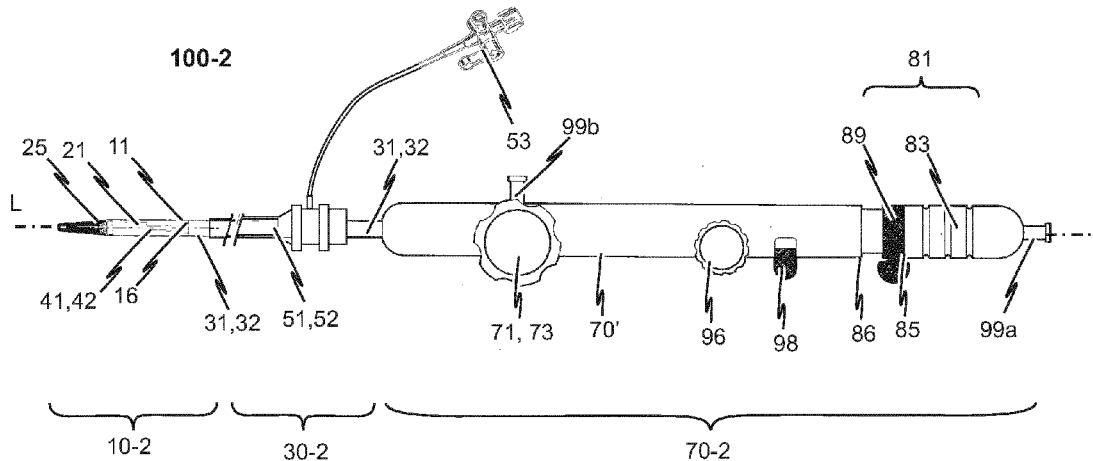
Figure 8:
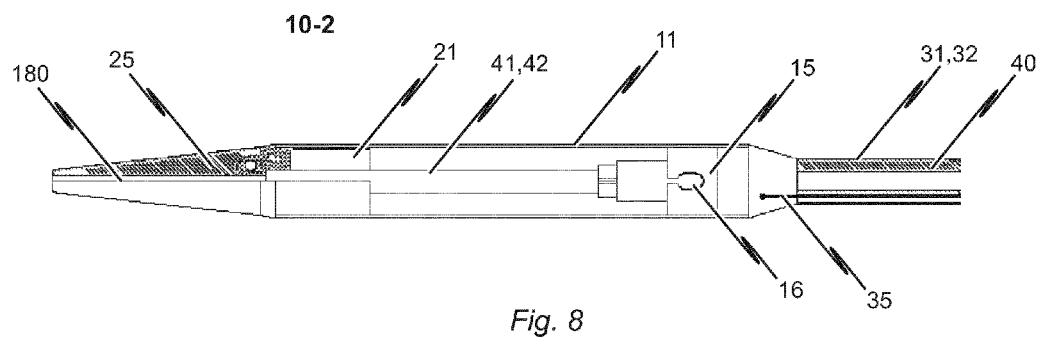
Figure 9:
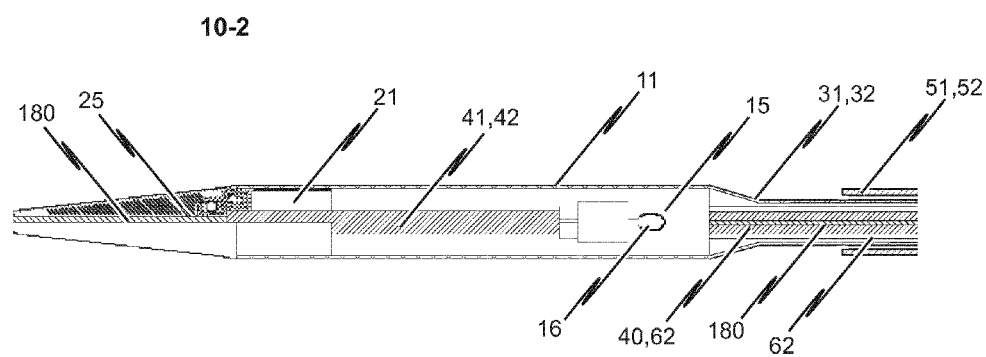
Figure 10:
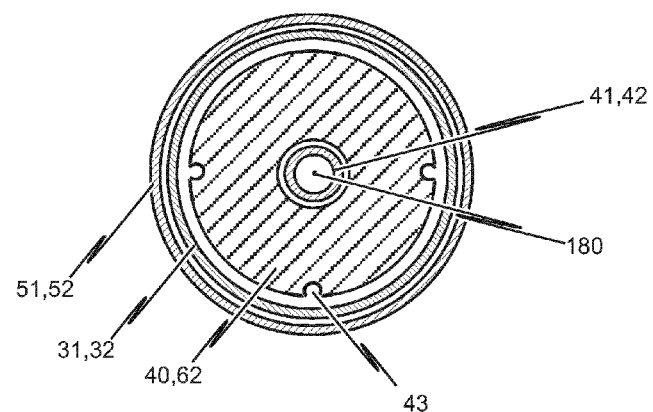
Figure 11:
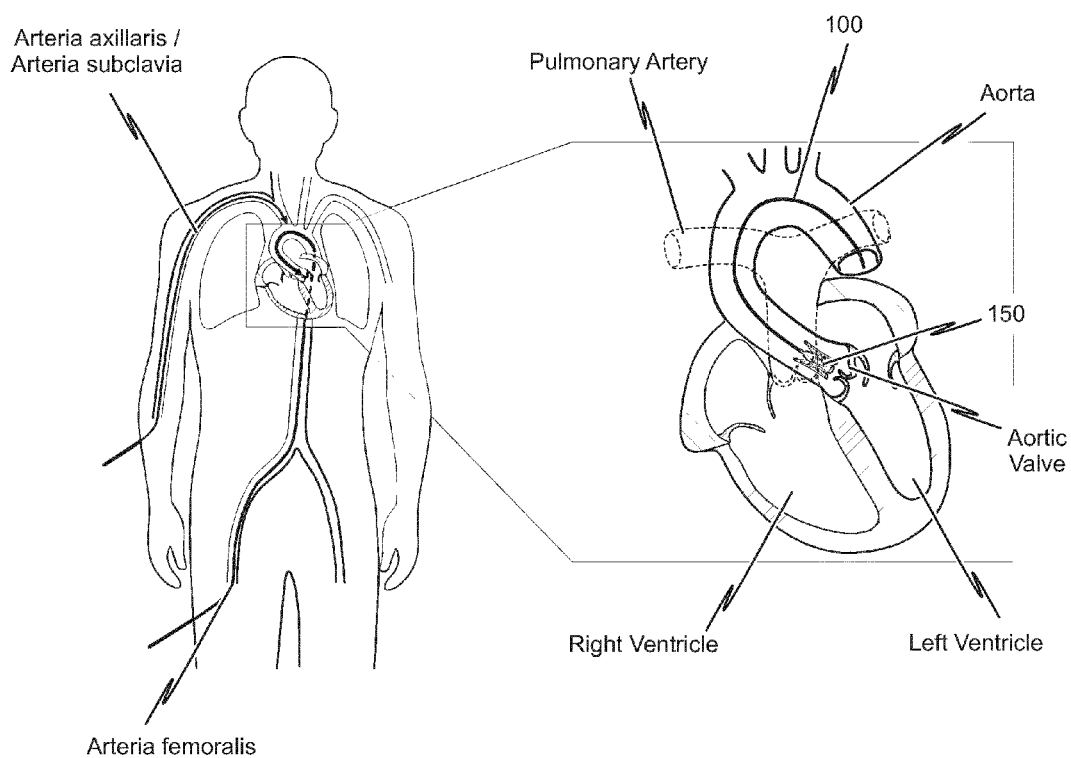
Figure 13A:
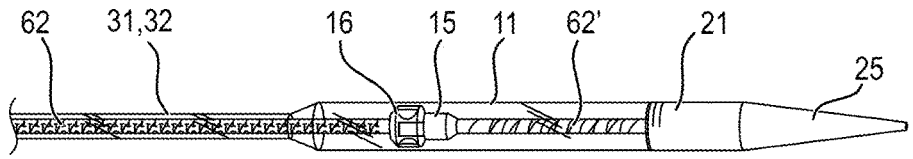
Figure 13B:
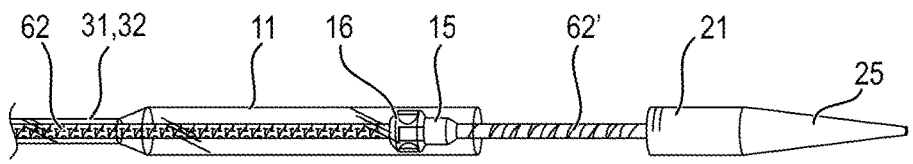
Figure 13C:
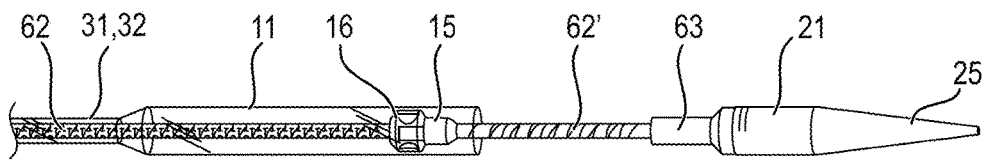
Figure 13D:
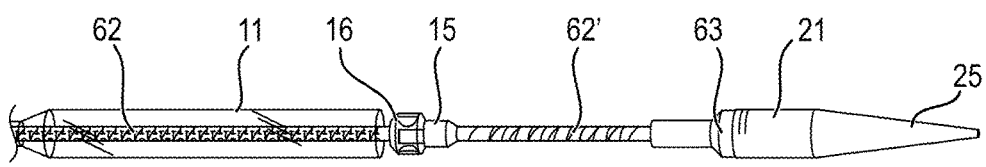
Figure 13E:
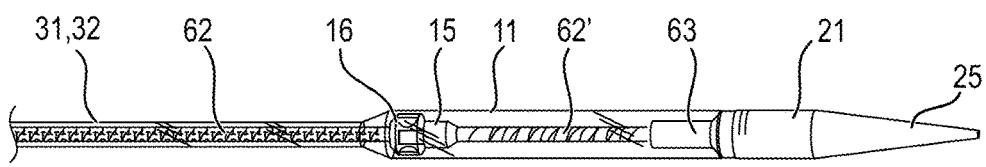
Figure 14:
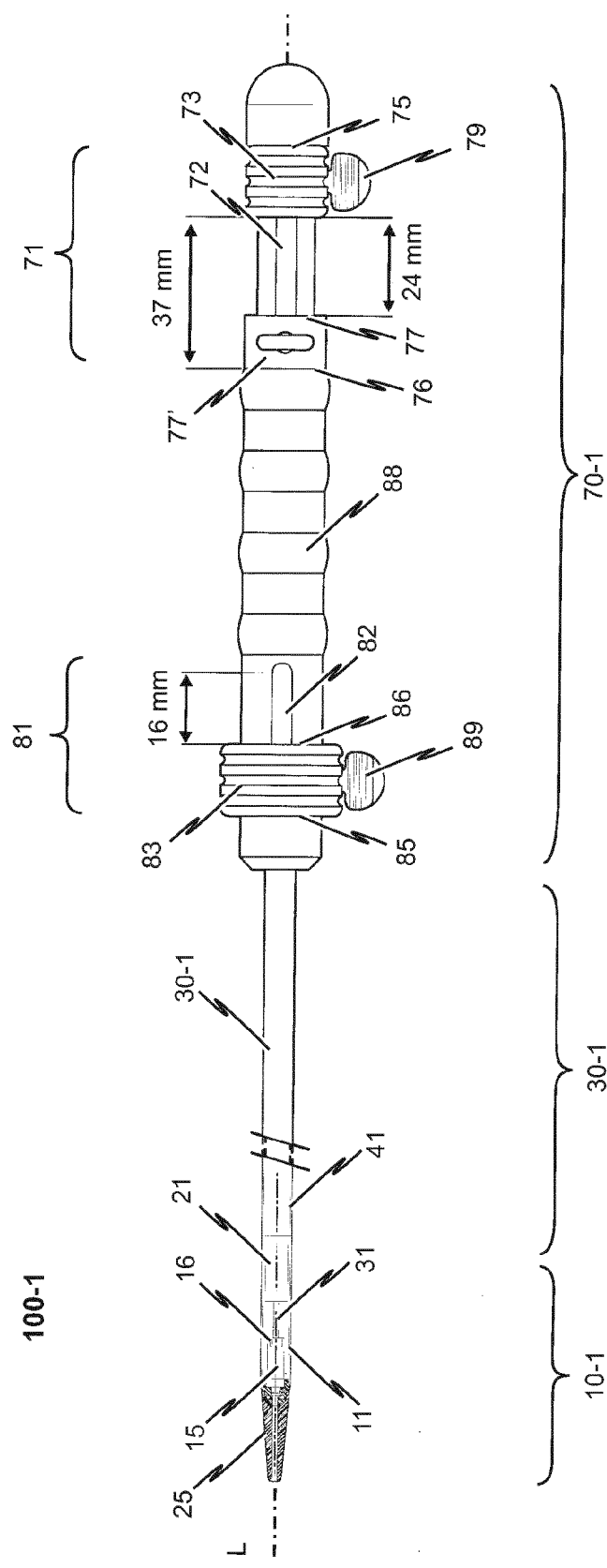
Figure 15:
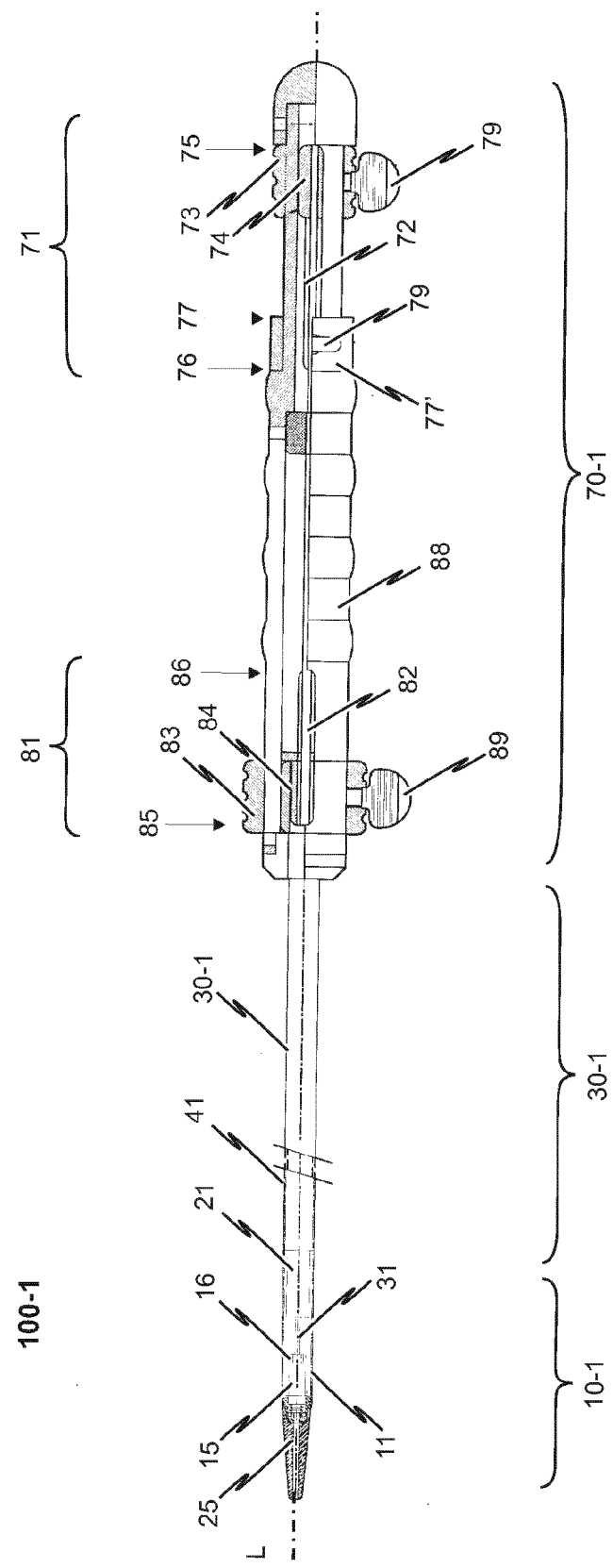
Figure 18:
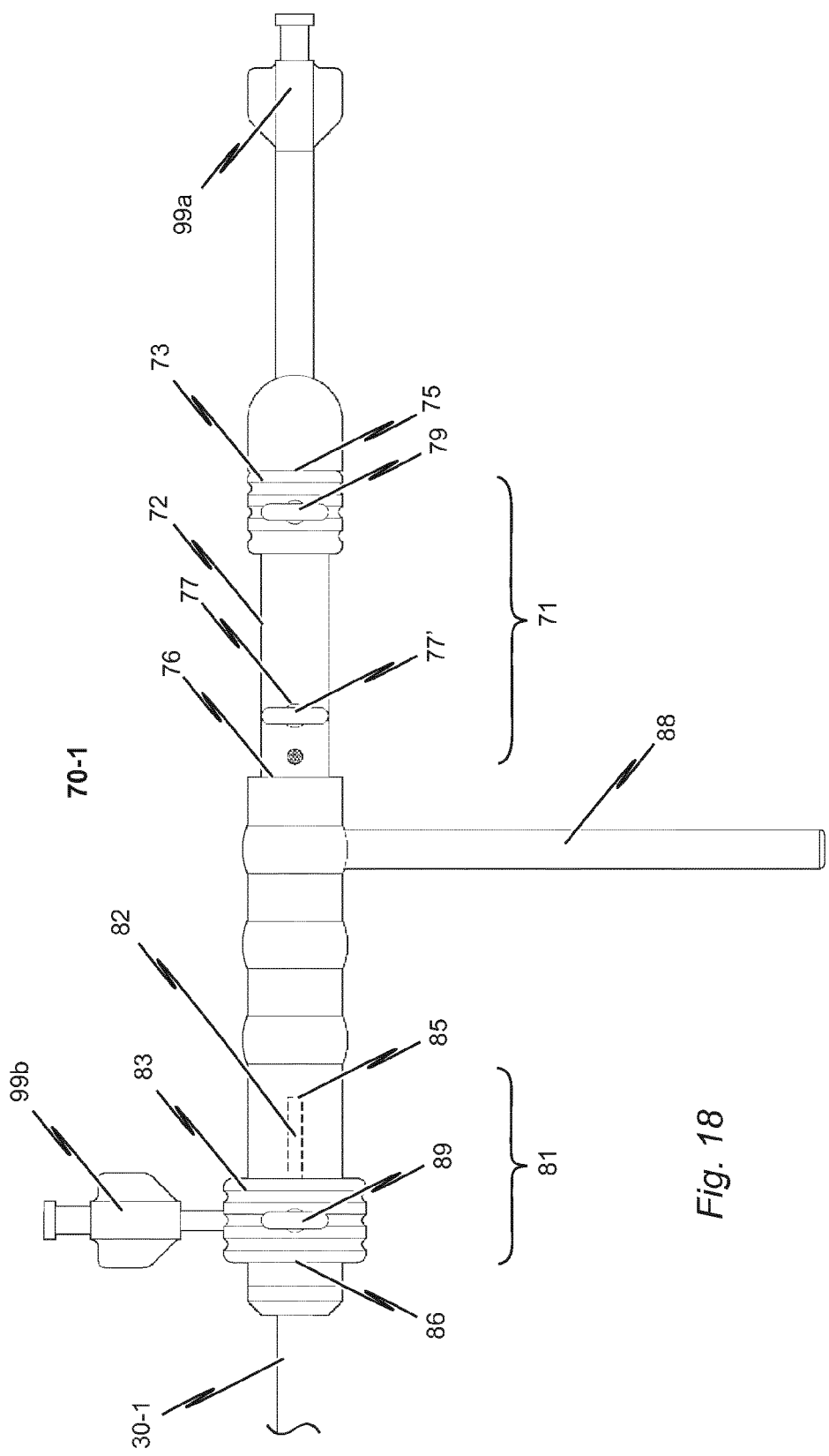
Figure 19:
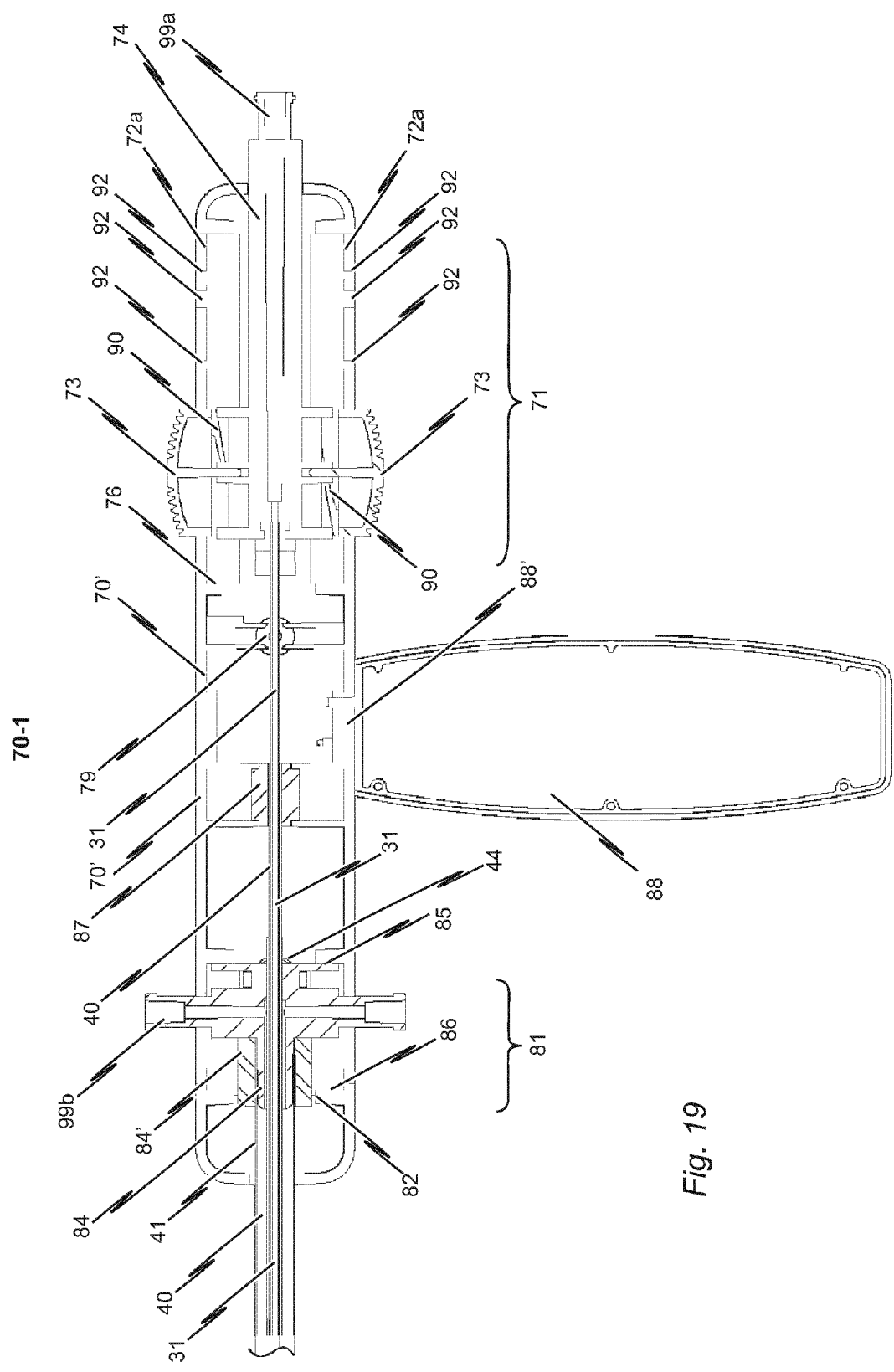
Figure 20:
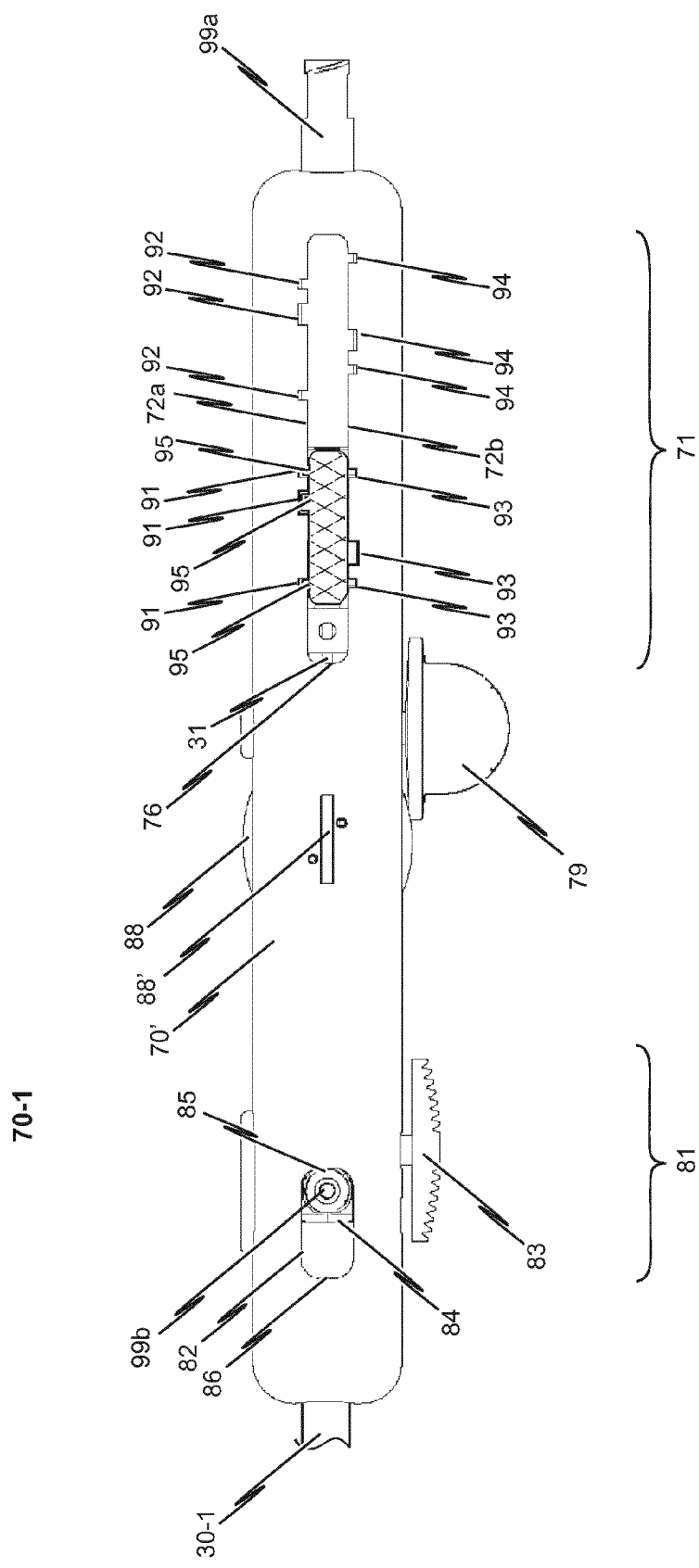
Figure 21:
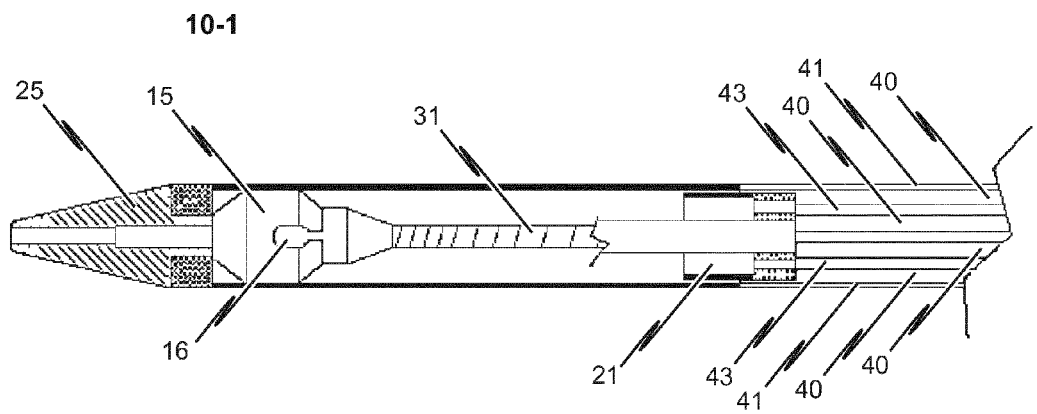
Figure 22:
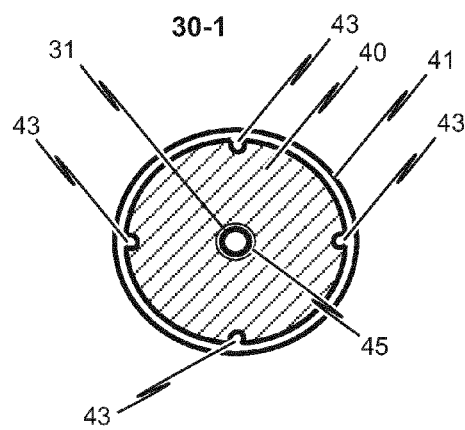
Figure 24A:
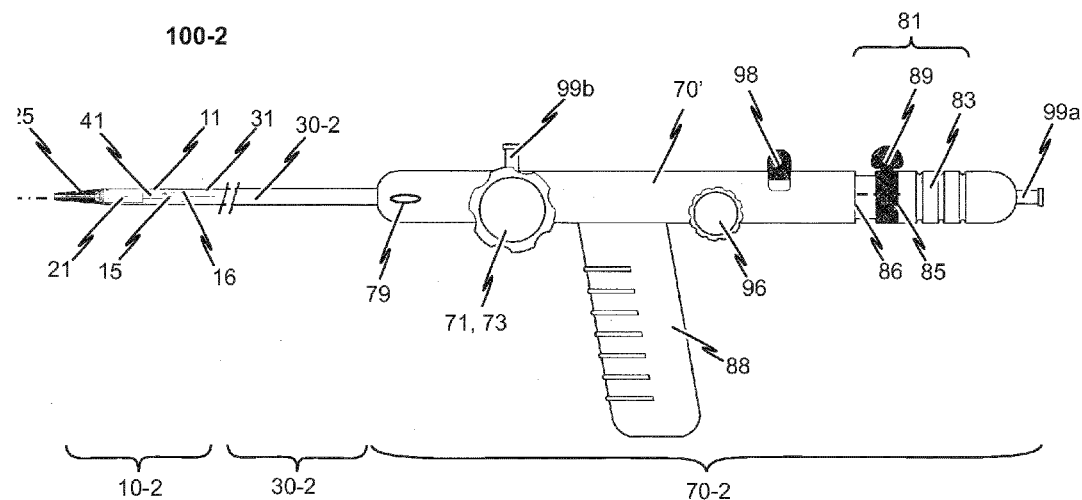
Figure 24B:
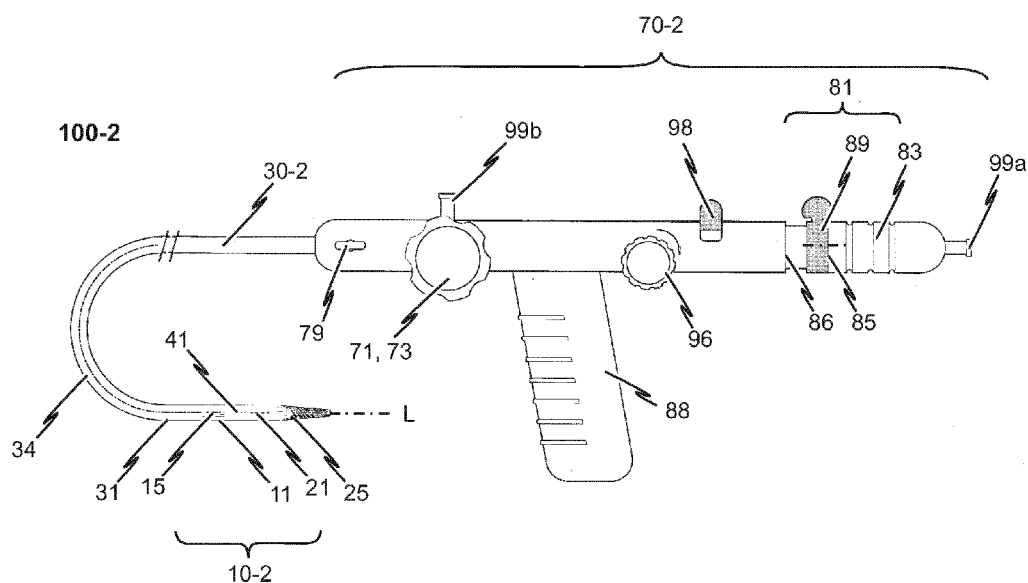
Figure 25:
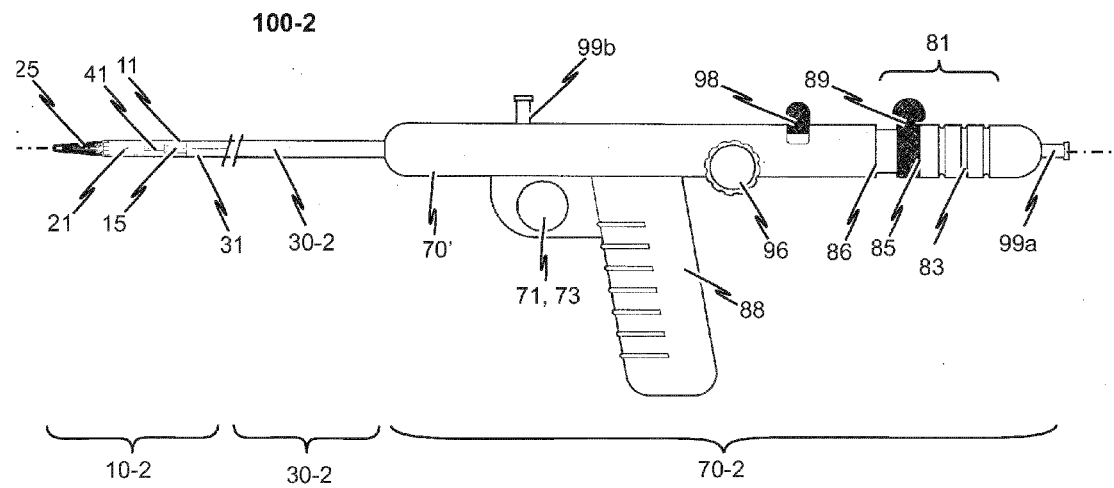
Figure 26:
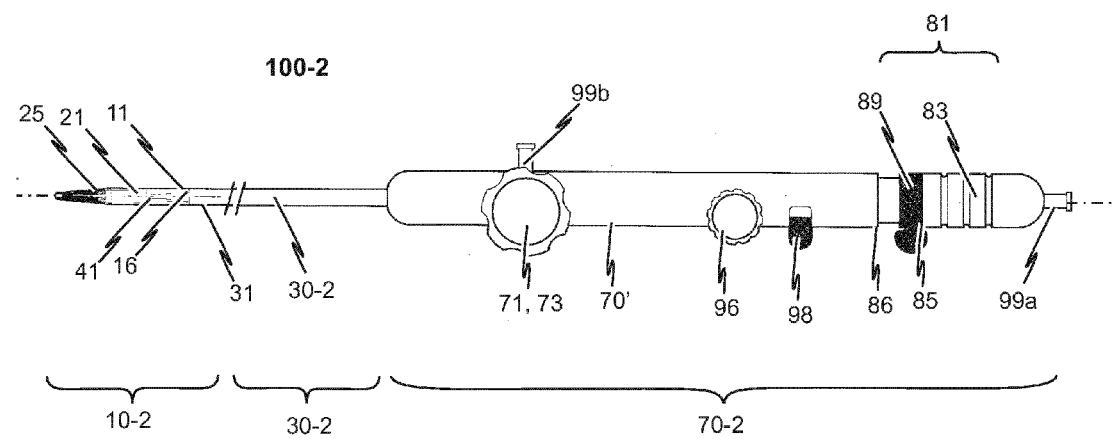
Figure 29:
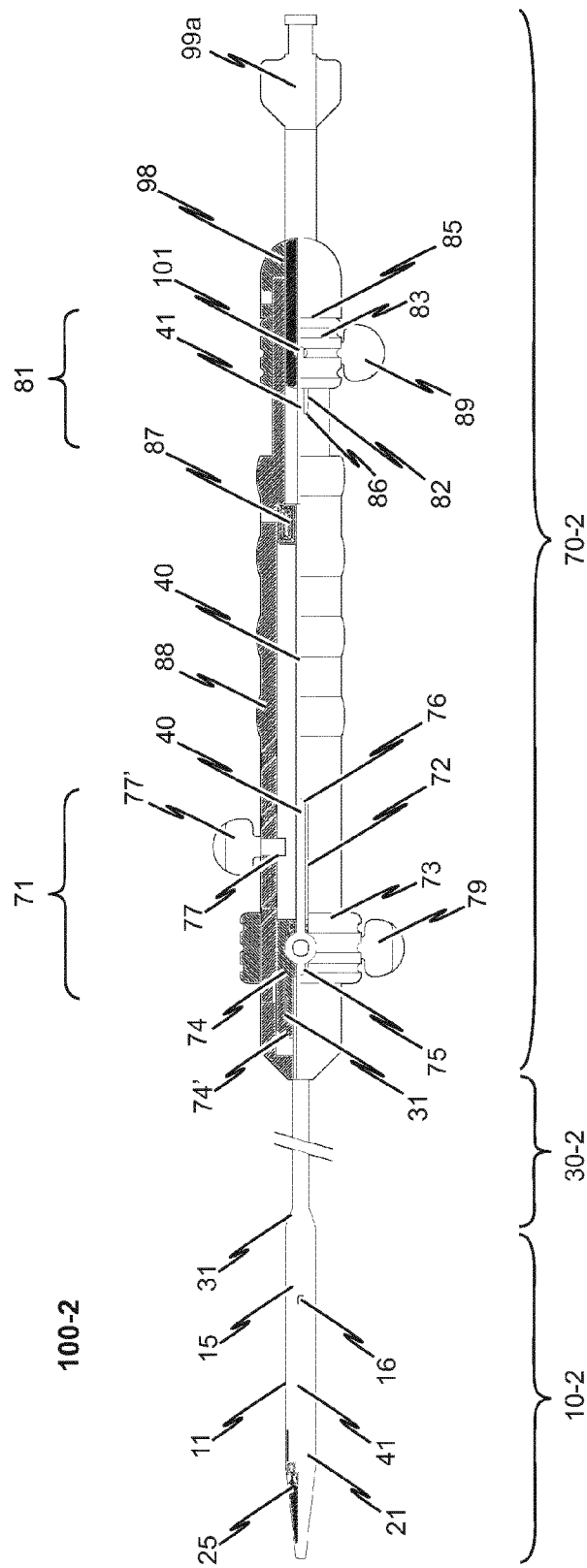
Figure 30:
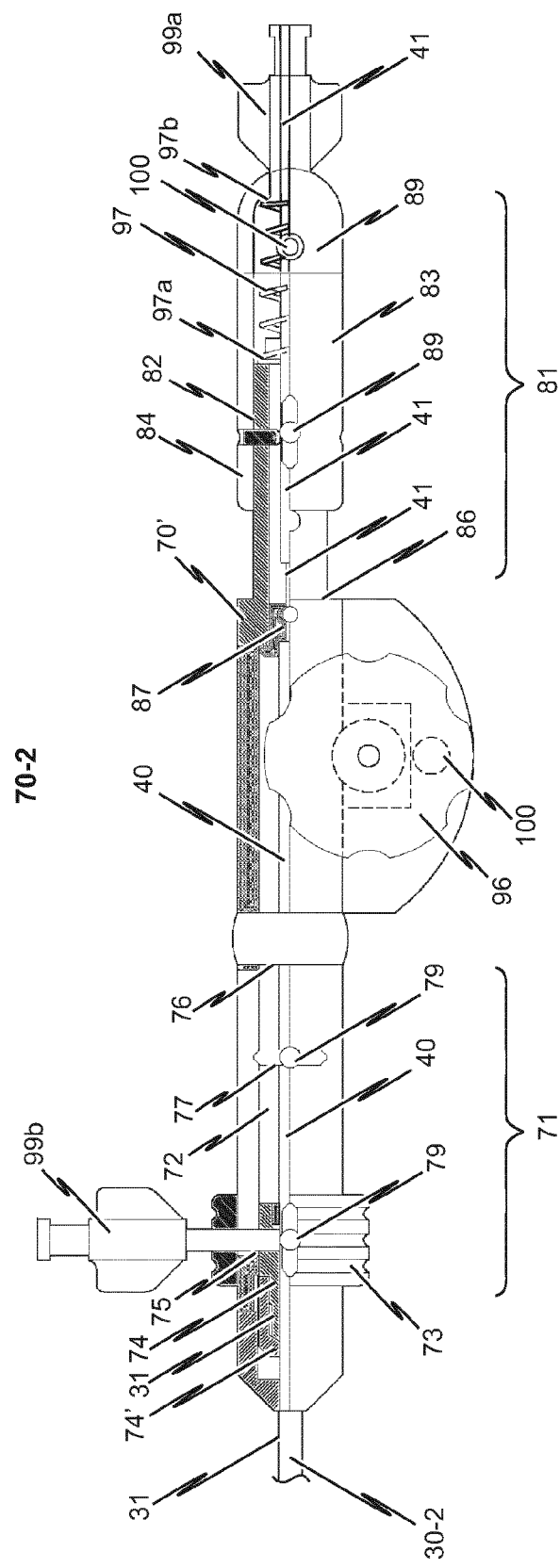
Figure 31A:
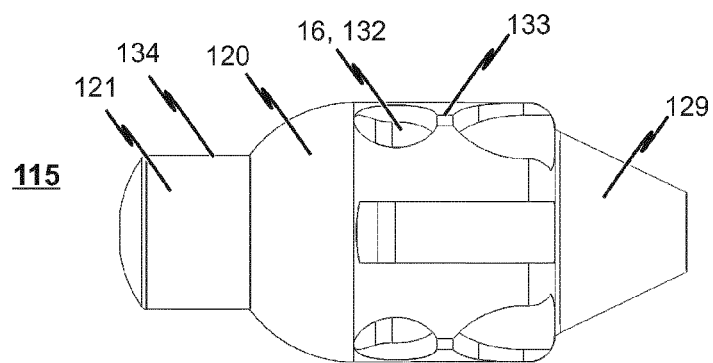
Figure 31B:
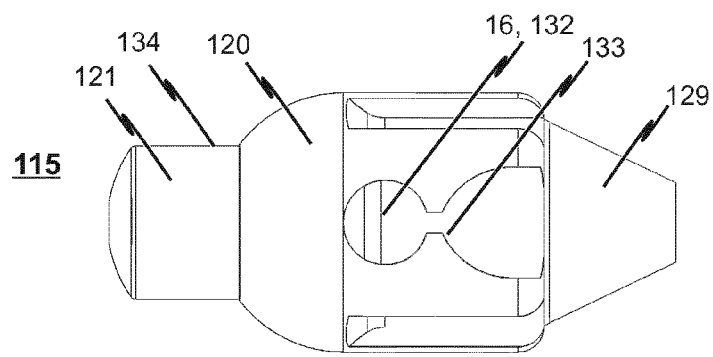
Figure 32:
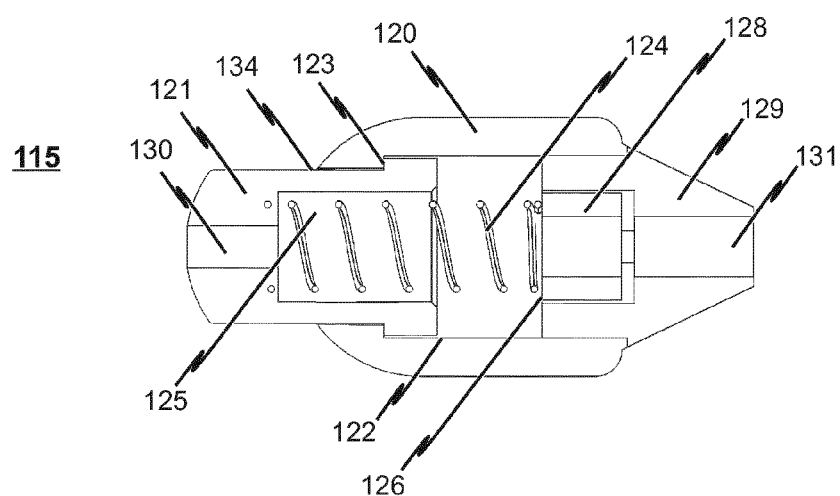
Figure 33:
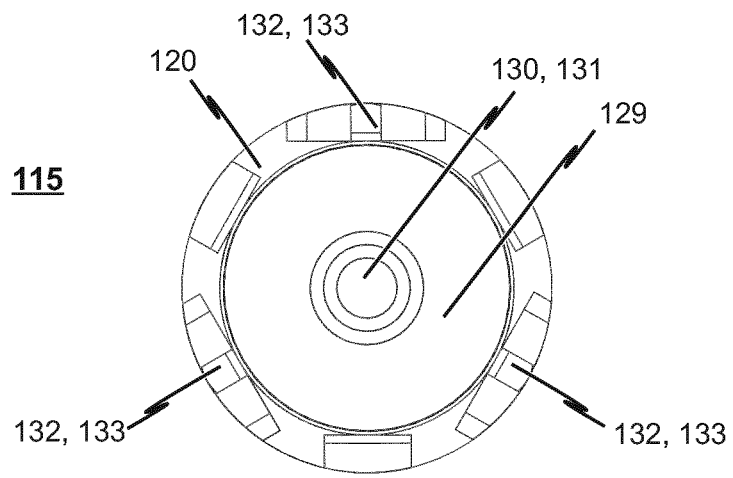
Figure 34:
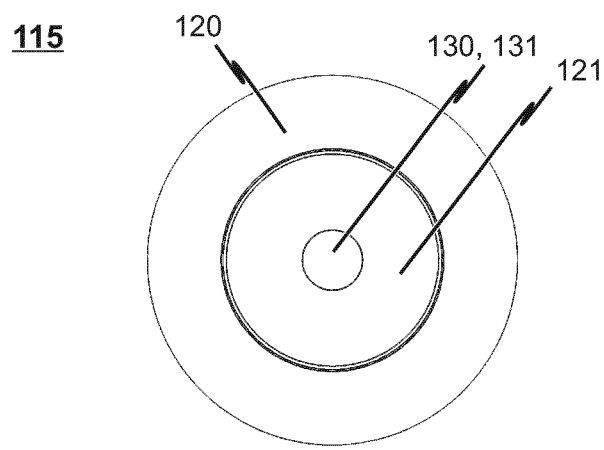
Figure 35:
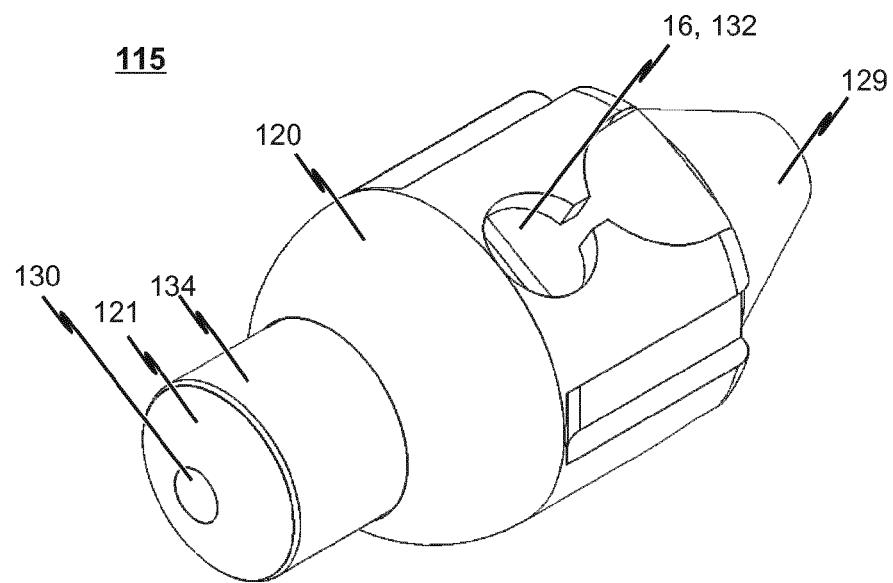
Figure 36:
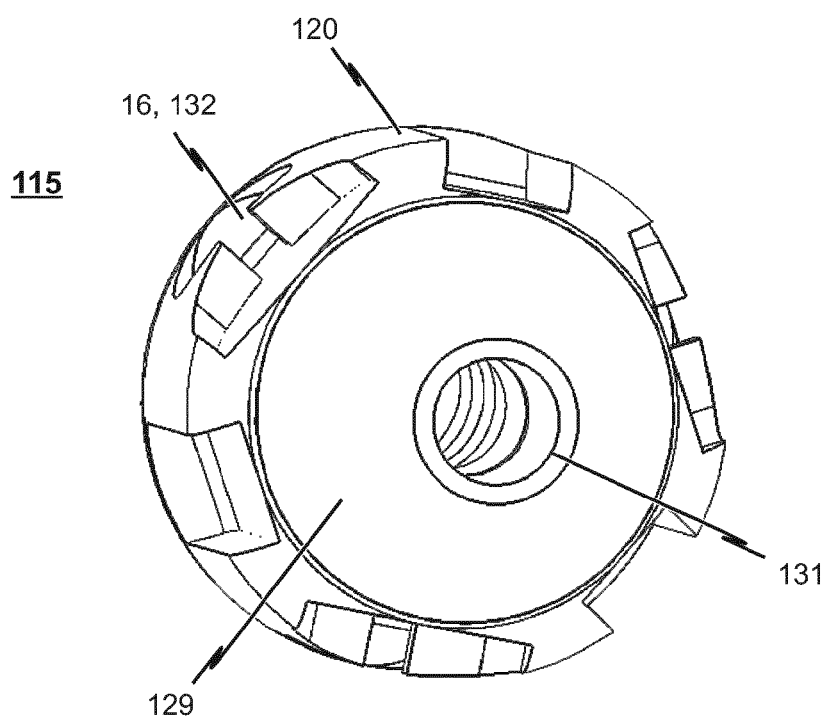
Figure 37:
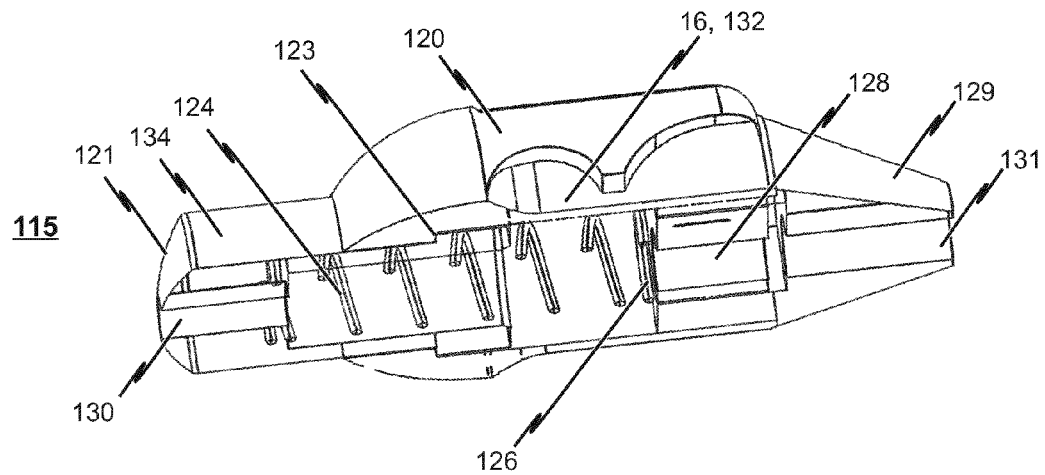
Figure 38:
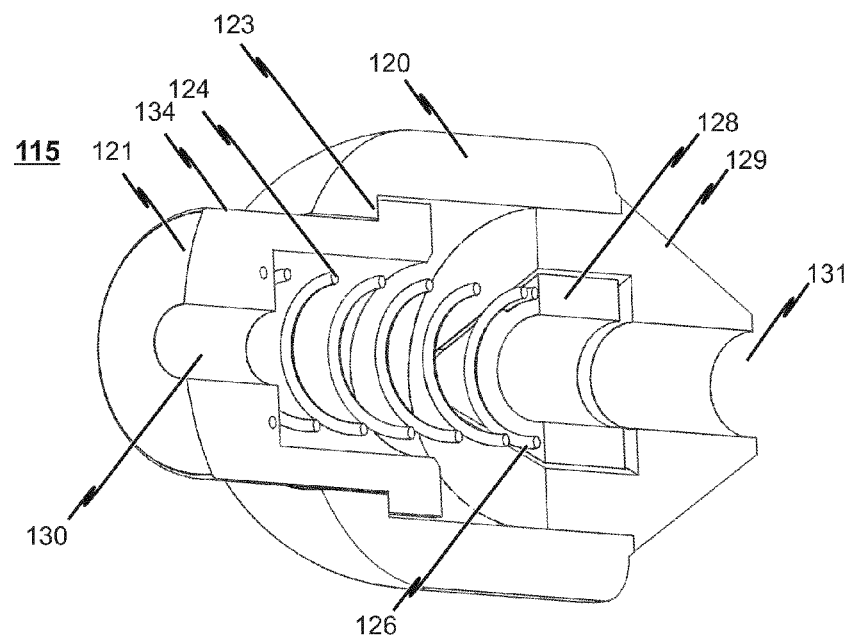
Figure 39:
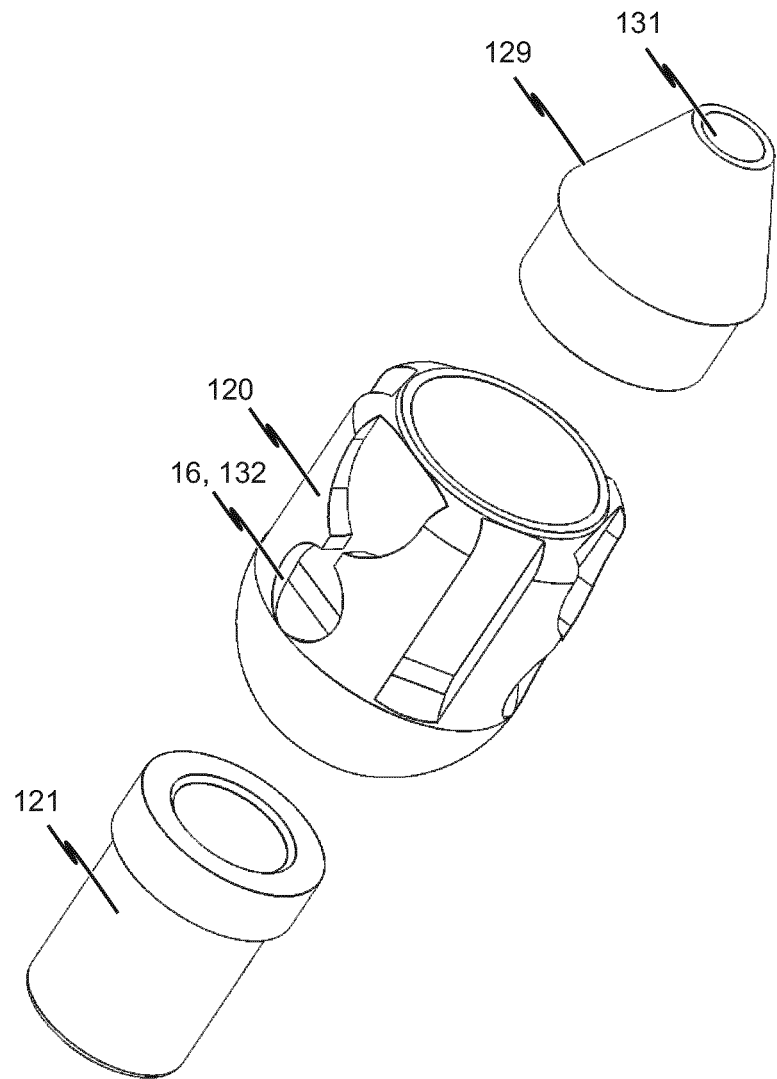
Figure 40A:
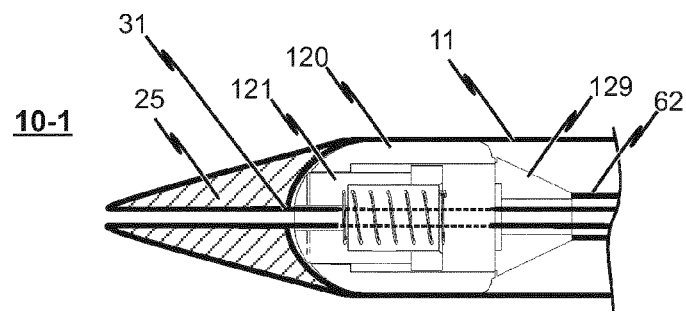
Figure 40B:
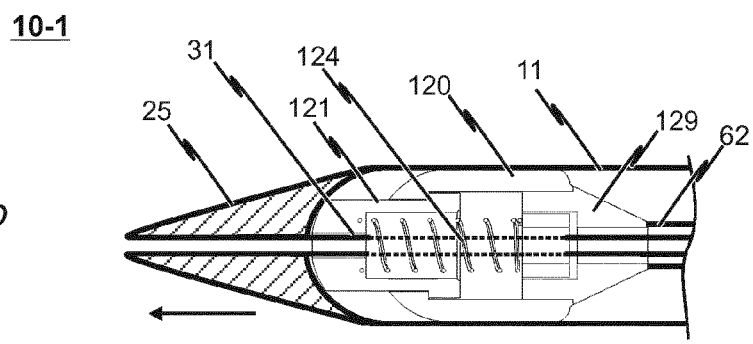
Figure 40C:
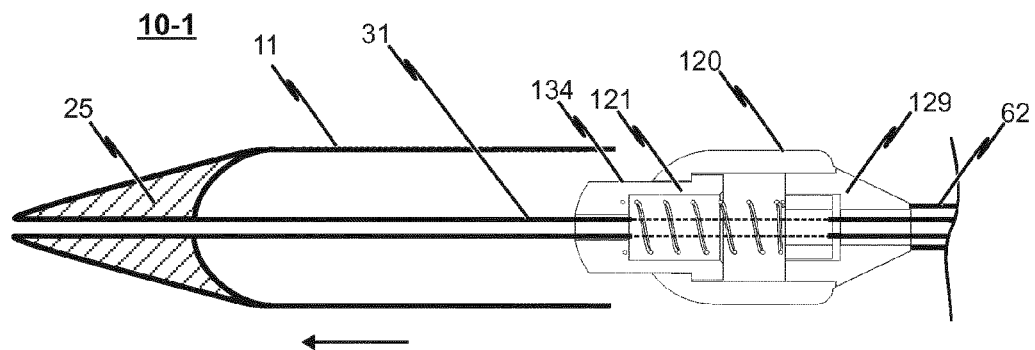
Figure 41A:
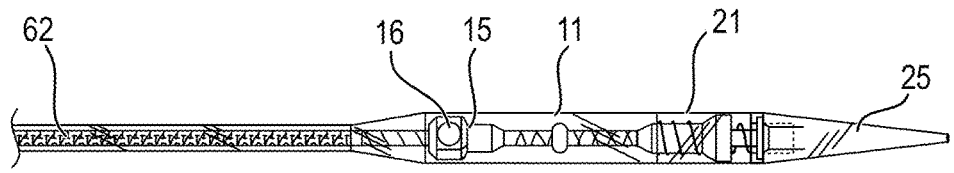
Figure 41B:
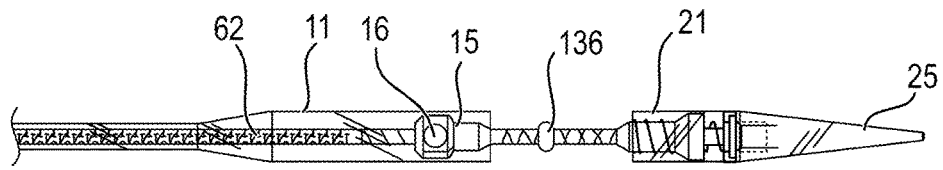
Figure 41C:
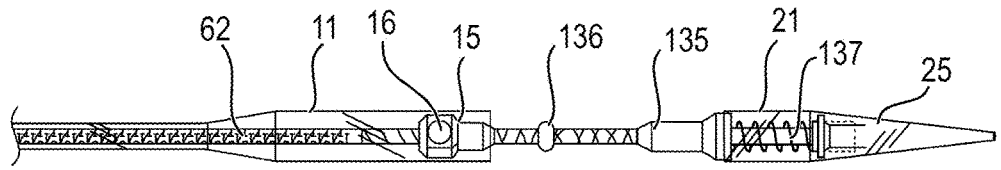
Figure 41D:
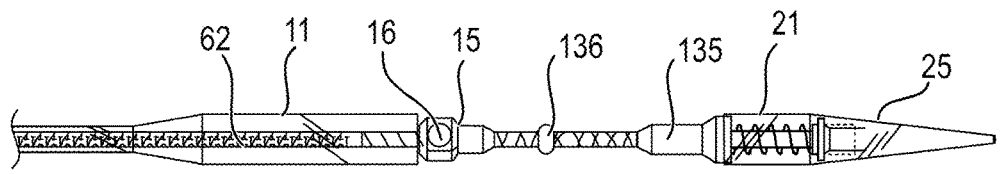
Figure 41E:
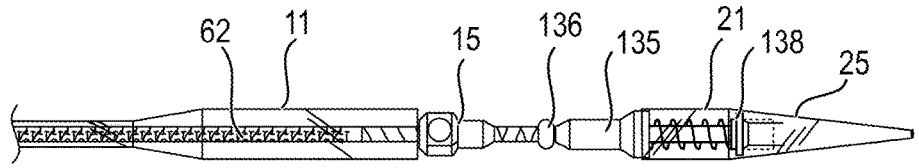
Figure 41F:
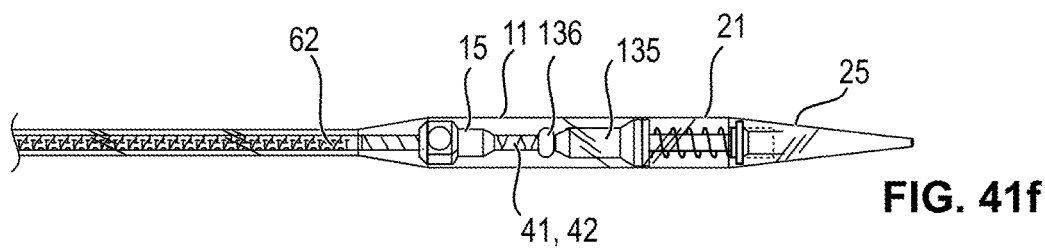

Of these:

FIG. 1: an embodiment of an insertion system for transfemoral/transarterial insertion of an expandable heart valve stent in a part-sectioned side elevation;

FIG. 2: an embodiment of a handle for an insertion system for transfemoral/transarterial insertion of an expandable heart valve stent in a part-sectioned side elevation;

FIG. 3*a*: an embodiment of an insertion system for transfemoral/transarterial insertion of a heart valve stent in a side elevation;

FIG. 3*b*: a side elevation of the transfemoral/transarterial insertion system in accordance with FIG. 3*a* with a deflected catheter system;

FIG. 4: a further embodiment of an insertion system for transfemoral/transarterial insertion of a heart valve stent in a side elevation;

FIG. 5: a further embodiment of an insertion system for transfemoral/transarterial insertion of a heart valve stent in a side elevation;

FIG. 6*a-d*: side elevations of the transfemoral/transarterial insertion system in accordance with FIG. 3*a* in its four previously defined functional states to illustrate the loading procedure of the insertion system FIG. 7*a-d*: side elevations of the transfemoral/transarterial insertion system in accordance with FIG. 3*a* in its four previously defined functional states to illustrate the release procedure of a stent housed in the catheter tip of the insertion system;

FIG. 8: an embodiment of a catheter tip for an insertion system for transfemoral/transarterial insertion of an expandable heart valve stent in a part-sectioned side elevation;

FIG. 9: a further embodiment of a catheter tip for an insertion system for transfemoral/transarterial insertion of an expandable heart valve stent in a part-sectioned side elevation;

FIG. 10: an exemplary embodiment of a catheter shaft for an insertion system for transfemoral/transarterial insertion of an expandable heart valve stent in a cross-sectional elevation;

FIG. 11: a schematic view to illustrate a transfemoral/transarterial implantation procedure of a heart valve stent;

FIG. 12*a-c*: three-dimensional schematic part-sectioned view of the catheter tip of a transfemoral/trans-apical insertion system in different functional states to illustrate the implantation procedure of a heart valve stent mounted in the catheter tip;

FIG. 13*a-d*: side elevations of a further embodiment of a catheter tip for an insertion system for transfemoral/transarterial insertion of an expandable heart valve stent in its four previously defined functional states to illustrate the release procedure of a stent housed in the catheter tip of the insertion system;

FIG. 13*e*: a side elevation of the embodiment of a catheter tip in accordance with FIG. 13*a-d* in its state after releasing a stent housed in the catheter tip and ready to be removed again from the body of the patient;

FIG. 14: an embodiment of an insertion system for transapical insertion of a self-expandable heart valve stent in a side elevation;

FIG. 15: a part-sectioned side elevation of the transapical insertion system in accordance with FIG. 14;

FIG. 16*a-d*: side elevations of the transapical insertion system in accordance with FIG. 14 in its four previously defined functional states to clarify the loading procedure of the insertion system;

FIG. 17*a-d*: side elevations of the transapical insertion system in accordance with FIG. 14 in its four previously defined functional states to clarify the release procedure of a stent housed in the catheter tip of the insertion system;

FIG. 18: an embodiment of a handle for an insertion system for transapical insertion of a self-expandable heart valve stent in a side elevation;

FIG. 19: a further embodiment of a handle for an insertion system for transapical insertion of a self-expandable heart valve stent in a side sectional elevation;

FIG. 20: a plan view of a handle in accordance with FIG. 19;

FIG. 21: an embodiment of a catheter tip for an insertion system for transapical insertion of a self-expandable heart valve stent in a side sectional elevation;

FIG. 22: an embodiment of a catheter shaft for an insertion system for transapical insertion of a self-expandable heart valve stent in a cross-sectional elevation;

FIG. 23a-d: three-dimensional side elevation of an embodiment of a catheter tip for a transapical insertion system in different functional states to illustrate a transapical implantation procedure of a heart valve stent;

FIG. 24a: an embodiment of an insertion system for transfemoral/transarterial insertion of a heart valve stent in a side elevation;

FIG. 24b: a side elevation of the transfemoral/transarterial insertion system in accordance with FIG. 24a with a deflected catheter shaft;

FIG. 25: a further embodiment of an insertion system for transfemoral/transarterial insertion of a heart valve stent in a side elevation;

FIG. 26: a further embodiment of an insertion system for transfemoral/transarterial insertion of a heart valve stent in a side elevation;

FIG. 27a-d: side elevations of the transfemoral/transarterial insertion system in accordance with FIG. 24a in its four previously defined functional states to illustrate the loading procedure of the insertion system FIG. 28a-d: side elevations of the transfemoral/transarterial insertion system in accordance with FIG. 24a in its four previously defined functional states to illustrate the release procedure of a stent housed in the catheter tip of the insertion system;

FIG. 29: a further embodiment of an insertion system for transfemoral/transarterial insertion of a self-expandable heart valve stent in a part-sectioned side elevation;

FIG. 30: an embodiment of a handle for an insertion system for transfemoral/transarterial insertion of a self-expandable heart valve stent in a part-sectioned side elevation;

FIGS. 31a-b: a further embodiment of a stent holder for a transapical insertion system in side elevations;

FIG. 32: the stent holder in accordance with FIG. 31 in a sectioned side elevation;

FIG. 33: a top view of the distal end region of the stent holder in accordance with FIG. 31;

FIG. 34: a top view of the proximal end portion of the stent holder in accordance with FIG. 31;

FIG. 35: the stent holder in accordance with FIG. 31 in a first perspective elevation;

FIG. 36: the stent holder in accordance with FIG. 31 in a second perspective elevation;

FIG. 37: a part-sectioned perspective elevation of the stent holder in accordance with FIG. 31;

FIG. 38: a part-sectioned perspective elevation of the stent holder in accordance with FIG. 31;

FIG. 39: parts of the stent holder in accordance with FIG. 31;

FIGS. 40a-c: side elevations of a catheter-tip for an insertion system for transapical insertion of an expandable heart valve stent in a side sectional elevation with a stent holder in accordance with FIG. 31;

FIGS. 41a-d: side elevations of a further embodiment of a catheter tip for an insertion system for transfemoral/transarterial insertion of an expandable heart valve stent in its four previously defined functional states to illustrate the release procedure of a stent housed in a modified catheter tip of a transfemoral insertion system;

FIG. 41e: a side elevation of the embodiment of a catheter tip in accordance with FIGS. 41a-d in a transitional state between a state after releasing a stent housed in the catheter tip and a state ready to be removed again from the body of the patient; and FIG. 41f: a side elevation of the embodiment of a catheter tip in accordance with FIGS. 41a-d in its state after releasing a stent housed in the catheter tip and ready to be removed again from the body of the patient.

FIG. 11 shows schematically an example of how a transarterial or transfemoral access can be gained to the heart of a patient. In the illustration in accordance with FIG. 11, a heart valve stent 150 is advanced with the aid of a insertion system 100-2 via the femoral artery to the aortic valve. Embodiments of an insertion system 100-2, which is suitable for transarterial or transfemoral access, are described in the following.

In accordance with a preferred embodiment, an insertion system 100-2 has a catheter system 1 and a handle 70-2 connected to the proximal end section of the catheter system 1. As depicted, for example, in FIG. 1, the catheter system 1 of the preferred embodiment comprises a catheter tip 10-2 having a seat portion for accommodating a stent to be inserted in its collapsed state and a stent holder 15 for releasably fixing the stent. The catheter system 1 further comprises a catheter shaft 30-2 for connecting the catheter tip 10-2 to the handle 70-2 of the insertion system 100-2, the distal end section of the catheter shaft 30-2 being flexible enough such that the catheter tip 10-2 and the distal end section of the catheter shaft 30-2 may pass the aortic arch during insertion through the aorta of the patient.

The seat portion of the catheter tip 10-2 comprises a first sleeve-shaped member 11 and a second sleeve-shaped member 21, the cross-section of the second sleeve-shaped member 21 are preferably identical to each other such that the first and second sleeve-shaped member 11, 21 can completely enclosed a stent accommodated in the catheter tip 10-2. In addition, the first and second sleeve-shaped members 11, 21 are movable relative to each other and relative to the stent holder 15.

For this purpose, first force transmitting means 31 with a distal end section connected to the first sleeve-shaped member 11 and a proximal end section connected to first operating means 71 of the handle 70-2 are provided. In addition, second force transmitting means 41 with a distal end section connected to the second sleeve-shaped member 21 and a proximal end section connected to second operating means 81 of the handle 70-2 are provided. When manipulating the first and/or second operating means 71, 81 of the handle 70-2, the first and/or second sleeve-shaped members 11, 21 may be moved relative to each other and relative to the stent holder 15.

As can be seen from FIG. 10, the first force transmitting means 31 may be constituted by a first catheter tube 32 defining a first lumen and the second force transmitting means 41 is constituted by a second catheter tube 42 defining a second lumen. The second catheter tube 42 may have a cross-section less than the cross-section of the first catheter tube 32. The first catheter tube 32 may be disposed concentrically and coaxially with the second catheter tube 42 and the second catheter tube 42 is received within the first lumen defined by the first catheter tube 32.

Contrary to the first and second sleeve-shaped members 11, 21 of the catheter tip 10-2, however, the stent holder 15 of the catheter tip 10-2 is not moveable relative to the handle 70-2 of the insertion system 100-2. Rather, the stent holder 15 is connected to the housing 70-2' of the handle 70-2 by using a stent holder tube 62 having a distal end connected to the stent holder 15 and a proximal end connected to a body 70-2' of the handle 70-2.

Referring to FIG. 10, the stent holder tube 62 may have a cross-section less than the cross-section of the first catheter tube 32. In particular, the first catheter tube 32 may be disposed concentrically and coaxially with both, the second catheter tube 42 on the one hand and the stent holder tube 62 on the other hand. Preferably, the stent holder tube 62 has a cross-section less than the cross-section of the first catheter tube 32 and greater than the cross-section of the second catheter tube 42 such that the stent holder tube 62 is received within the first lumen defined by the first catheter tube 32 and the second catheter tube 42 is received within a passageway defined by the stent holder tube 62. The passageway defined by the stent holder tube 62 has a diameter sufficient to accommodate the second catheter tube 42 such that the second catheter tube 42 is moveable relative to the stent holder tube 62.

The second lumen defined by the second catheter tube 42 has a diameter sufficient to accommodate a guide wire 180. The second catheter tube 42 may be made from a rigid material including, for example, nitinol, stainless steel or a rigid plastic material (see FIG. 10). The material of the distal end section of the second catheter tube 42 may have an increased flexibility compared to the material of the proximal end section in order to allow the distal end section of the catheter shaft 30-2 to pass the aortic arch during insertion of the catheter tip 10-2. For example, the guiding tube 52 may be a 17F-catheter tube and the first catheter tube 32 may be a 12F-catheter tube.

As can been seen, for example, from FIG. 9, the distal end section of the second catheter tube 42 terminates in a soft catheter end tip 25 having an atraumatic shape. The soft catheter end tip 25 is provided with a channel aligned with the second lumen defined by the second catheter tube 42 such that a guide wire 180 accommodated within the second lumen of the second catheter tube 42 may pass through the channel of the soft catheter end tip 25. The second sleeve-shaped member 21 of the catheter tip 10-2 is connected to the soft catheter end tip 25 such that the opened end of the second sleeve-shaped member 21 faces in the proximal direction opposite to the direction of the soft catheter end tip 25 and to the second catheter tube 42.

According to the exemplary embodiment depicted in FIG. 10, the stent holder tube 62 is made of a rigid material, for example, a rigid plastic material, stainless steel or nitinol. The distal end of the stent holder tube 62 terminates in the stent holder 15 which is also made of a rigid material, for example, a rigid plastic material or stainless steel. The passageway defined by the stent holder tube 62 is aligned with a channel which passes through the stent holder 15. In this way, the second catheter tube 42 is accommodated in the passageway of the stent holder tube 62 and the channel of the stent holder 15 such as to be moveable relative to the stent holder tube 62 and the stent holder 15.

The first catheter tube 32 is made of a bendable but inelastic material. For example, the first catheter tube 32 may be at least partly made of a braided or non-braided catheter tube. The first catheter tube 32 shall be adapted to transfer compression and tension forces from the first operating means 71 of the handle 70-2 to the first sleeve-shaped member 11 of the catheter tip 10-2 without overly changing its total length. The distal end of the first catheter tube 32 terminates at a flared section as a transition to the section defining the first sleeve-shaped member 11 of the catheter tip 10-2.

As can be seen from FIG. 9, the flared section and the first sleeve-shaped member 11 may be formed integrally and may be connected to the distal end section of the first catheter tube 31. In addition, the flared section may constitute the first sleeve-shaped member 11 of the catheter tip 10-2. The first sleeve-shaped member 11 and the flared section of the first catheter tube 31 may be all of the same material and originating from the same raw tube prior to a widening process so that the flared section and the first sleeve-shaped member 11 are the same elements.

Referring for example to FIG. 1, the insertion system 100-2 according to the preferred embodiment further comprises a guiding tube 52 having a cross-section greater than the cross-section of the first catheter tube 32. The guiding tube 52 defines a passageway and is disposed concentrically and coaxially with the first catheter tube 32, the stent holder tube 62 and the second catheter tube 42 such that the first catheter tube 32 with the stent holder tube 62 and the second catheter tube 42 accommodated therein is at least partly accommodated within the passageway defined by the guiding tube 52, wherein the first catheter tube 32 is moveable relative to the guiding tube 52. In particular, the guiding tube 52 terminates proximal to the catheter tip 10-2 wherein the cross-section of proximal end section of the guiding tube 52 shall be the same as or less than the cross-section of the flared section provided at the proximal end of the first catheter tube 32 so that a smooth transition from the first sleeve-shaped member 11 of the catheter tip 10-2 to the guiding tube 52 may be achieved (see FIG. 9).

The proximal end section of the guiding tube 52 terminates distal to the handle 70-2. The proximal end section of the guiding tube 52 may be detached/disconnected from the handle 70-2 so that the handle 70-2 as well as the first and second catheter tubes 32, 42 and the stent holder tube 62 together with catheter tip 10-2 may be moved relative to the guiding tube 52.

The distal end of the guiding tube 52 is formed such that the flared section provided at the distal end section of the first catheter tube 32 may abut on the distal end of the guiding tube 52 without abrupt transition. The guiding tube 52 may be of a thin material such as to allow length deformation of the guiding tube 52 upon transfer of compression and tension forces. The material of the guiding tube 52, however, shall have sufficient stiffness in order to mechanically avoid kinking of the flexible sections of the distal portion of the catheter shaft 30-2 during insertion of the catheter tip 10-2.

The proximal end of the guiding tube 52 is releasably connectable to the body 70-2' of the handle 70-2. In this way, the guiding tube 52 may have a double-function:

In case, the proximal end of the guiding tube 52 is connected to the handle 70-2, the guiding tube 52 serves as a distal extension of the body 70-2' of the handle 70-2 relative to which the first and second operating means 71, 81 are moveable for manipulating the first and second sleeve-shaped members 11, 21 of the catheter tip 10-2. Hence, the position of the stent holder 15 relative to the native heart valve of the patient may be changed by moving the guiding tube 52 connected to the handle 70-2.

In case, the proximal end of the guiding tube 52 is not connected to the body 70-2' of the handle 70-2, the guiding tube 52 may serve as an introducer tube, i.e. as a portal for passing the catheter tip 10-2 of the catheter system 1 into the patient's body and up to the heart.

As depicted, for example, in FIG. 1, an inlet port 53 may be provided at a proximal end section of the guiding tube 52 for injection of fluids into the guiding tube 52. Furthermore, a check valve may be provided at the proximal end section of the guiding tube 52 to prevent fluid from leaking out of the guiding tube 52.

A description is given in the following, with reference to FIGS. 1 to 10, of the components of exemplary embodiments of insertion systems 100-2, which are suitable for a transarterial or transfemoral access to the implantation location. During a transarterial or transfemoral access, the catheter tip 10-2 of the insertion system 100-2 is advanced, for example, via the aorta to the implantation site.

FIG. 1 shows a part-sectioned representation of an exemplary embodiment of an insertion system 100-2 designed for transfemoral or transarterial access.

As illustrated in FIG. 1, an insertion system 100-2 according to the present disclosure may comprise a catheter system 1 and a handle 70-2 connected to the proximal end section of the catheter system 1. The catheter system 1 comprises a catheter tip 10-2 and a catheter shaft 30-2 for connecting the catheter tip 10-2 to the handle 70-2. The catheter tip 10-2 has a seat portion for accommodating a stent (see FIGS. 12*a-c*) in its collapsed state as well as a stent holder 15 for releasably fixing the stent.

The seat portion of the catheter tip 10-2 is constituted by a first sleeve-shaped member 11 and a second sleeve-shaped member 21. As will be explained in more detail with reference to FIGS. 6*a-d* and FIGS. 7*a-d*, the sleeve-shaped members 11, 21 of the catheter tip 10-2 are movable relative to each other and relative to the stent holder 15.

The catheter shaft 30-2 comprises first force transmitting means 31, second force transmitting means 41 and guiding means 51. In accordance with the exemplary embodiment depicted in FIG. 1, the first and second force transmitting means 41 31, 41 of the catheter system 1 are realized as flexible, elongated catheter tubes 32, 42. Each of the first and second catheter tubes 32, 42 defines a separate lumen. In addition, the guiding means 51 is realized as guiding tube 52 defining a passageway within which the first and second catheter tubes 32, 42 are received such as to be movable relative to the guiding tube 52.

As can be seen in FIG. 1, the guiding tube 52 has a distal end which terminates proximal to the catheter tip 10-2. On the other hand, the first catheter tube 32 has a length which is the same as, or substantially similar to the length of the second catheter tube 42. The first catheter tube 32 terminates at its distal end in a flared section as a transition to the section with wider cross-section defining the first sleeve-shaped member 11 of the catheter tip 10-2. In particular, and as can be seen from the illustration in FIG. 9, the wider section of the first catheter tube 32 is formed integrally with the distal end section of the first catheter tube 32. The wider section has a length greater than the length of a collapsed stent to be accommodated in the catheter tip 10-2.

As already mentioned, in the exemplary embodiment depicted in FIG. 1, the first force transmitting means 31 of the catheter system 1 is constituted by a first catheter tube 32 defining a first lumen, wherein the second force transmitting means 41 is constituted by a second catheter tube 42 defining a second lumen. The second catheter tube 42 has a cross-section less than the cross-section of the first catheter tube 32, wherein the first catheter tube 32 is disposed concentrically and coaxially with the second catheter tube 42. The cross-section of the catheter tip 10-2, however, is greater than or equal to the cross-section of the guiding tube 52.

On the other hand, the guiding tube 52 has a cross-section which is greater than the cross-section of the part of the first catheter tube 32 which is received within the guiding tube 52. The cross-section of the catheter tip 10-2, however, is greater than the cross-section of the guiding tube 52. Hence, the guiding tube 52 cannot be removed from the insertion system 100-2 without disconnecting the catheter system 1 from the handle 70-2.

At the proximal end section of the guiding tube 52, a check valve may be provided for preventing fluid from leaking out of the guiding tube 52. Furthermore, an inlet port 53 may be provided at the proximal end section of the guiding tube 52 for injection of fluids into the guiding tube 52. Hence, fluids such as saline solution may be injected through the inlet port 52 to flush the interior passageway of the guiding tube 52 and to reduce the incidence of blood clotting. A stopcock may be attached to the inlet port 53 to maintain the port 53 in a closed position when the port 53 is not being accessed to flush the passageway of the guiding tube 52.

The guiding tube 52 is movable relative to the handle 70-2 and the first and second catheter tubes 32, 42. This provides a grip for the user who can hold the catheter shaft 30-2 at its proximal end section during positioning of the catheter tip 10-2 and during manipulation of the sleeve-shaped element 11 of the catheter tip 10-2. The user can hold the guiding tube 52, and in particular the proximal end section of the guiding tube 52 for supporting the movement of the first sleeve-shaped element 11 of the catheter tip 10-2 relative to the handle 70-2 such that the outer sheath of the catheter system 1 need not be held by the user or kinked.

In the exemplary embodiment of the insertion system 100-2 depicted in FIG. 1, a handle 70-2 is utilized, said handle 70-2 comprising first and a second operating means 71, 81, which are connected by means of corresponding first and second force transmission means 31, 41 of the catheter shaft 30-2 to the first and second sleeve-shaped members 11, 21 of the catheter tip 10-2. The first operating means 71 has a first pusher 73 which is functionally connected to the first slide 74. The first slide 74 is guided in a first guide 72 in the longitudinal direction L of the handle 70-2. The distal-side end of the first guide 72 defines the first stop 75 and the proximal-side end of the first guide 72 the second stop 76, which define the overall longitudinal displacement that can be effected with the first operating means 71. A locking element 77' may be positioned between the distal-side and the proximal-side end of the first guide 72, which defines the additional stop 77.

The second operating means 81 of the handle 70-2 shown in FIG. 1 has a second pusher 83, which is functionally connected to a second slide 84. The second slide 84 is guided in a longitudinal guide (second guide 82) between a first stop 85 and a second stop 86. The second slide 84 is connected by means of the second force transmission means 41 with the second sleeve-shaped member 21 of the catheter tip 10-2. On actuation of the second operating means 81, the second slide 84 is moved in the longitudinal direction L of the handle 70-2 from the first stop 85 to the second stop 86. This movement effects a longitudinal displacement of the second sleeve-shaped member 21 of the catheter tip 10-2 connected via the second force transmission means 41 with the second operating means 81.

To prevent an unintended displacement of the second slide 84, the second operating means 81 is equipped with a securing element 89, which may connect the second slide 84 with the body 70-2' of the handle 70-2 when in use. A longitudinal displacement of the second slide 84 to the second stop 86 is possible following removal or deactivation of the securing element 89.

FIG. 2 shows a further embodiment of a handle 70-2 of an insertion system 100-2 designed for transfemoral or transarterial access in a part-sectioned side view. The construction and mode of operation of the first and second operating means 81 71, 81 of the embodiment of the handle 70-2 shown in FIG. 2 is comparable in structural and functional respects to the handle 70-2 as previously described with reference to FIG. 1. Hence, elements in FIG. 2 that are generally similar to previously described elements have the same reference numbers compared with the reference numbers in FIG. 1 previously used for the similar elements.

In distinction to the handle 70-2 described with reference to FIG. 1, however, the handle 70-2 in accordance with FIG. 2 is provided with a third operating means 96 in the form of a wheel, by means of which a flexural link region 34 of the catheter shaft 30-2 can be controlled. It is important to note, however, that the catheter shaft 30-2 is only optionally provided with such flexural link region 34. Rather, the material of the distal end section of the catheter shaft 30-2 may have an increased flexibility compared to the material of the proximal end section in order to allow the distal end section of the catheter shaft to pass 30 the aortic arch during insertion of the catheter tip.

In the exemplary embodiment depicted in FIG. 2, the third operating element 96 preferably has a detent device 100, to allow a set deflection of the flexural link region 34 of the catheter shaft 30-2 to be fixed. For example, it is possible to provide a suitable catch mechanism on the hand wheel of the third operating means 96, which cooperates with the body 70-2' of the handle 70-2. In particular, it is possible for the flexural link region 34 of the catheter shaft 30-2 to be connected to the third operating means 96 by way of a control wire 35 whereby, on an actuation of the third operating means 96 via the control wire 35 a tensile forces is exerted on the flexural link region 34, which produces the deflection of the flexural link region 34 (see FIG. 3*b*).

However it is also possible, of course, to choose another embodiment as the third operating means 96 for deflecting a flexural link region 34 of the catheter shaft 30-2, in case the catheter shaft 30-2 is provided with such a flexural link region 34.

The handle 70-2 of the insertion system 100-2 designed for transarterial or transfemoral access may be provided with a pretensioning device, shown in FIG. 2. With such a pretensioning device, a constant tensile force may be exerted via the second operating means 81 on the second sleeve-shaped member 21 of the catheter tip 10-2. As shown in FIG. 2, the pretensioning device may have a compression spring 97, permanently stressed along its spring axis, which is prestressed between a first stop 97*a* connected to the body 70-2' of the handle 70-2 and a second stop 97*b* connected to the proximal end region of the second operating means 81. In this respect, a permanent, previously defined or definable tensile force is exerted on the second sleeve-shaped member 21 of the catheter tip 10-2.

The pretensioning device implemented with the spring 97 in the embodiment in accordance with FIG. 2 may be advantageous when the catheter shaft 30-2 is bent during the implantation procedure, for example, when the catheter tip 10-2 of the insertion system 100-2 is inserted through the aorta. When the catheter shaft 30-2 is bent, the outer fibres of the catheter shaft 30-2 are shortened. This can be compensated appropriately with the aid of the pretensioning device. In detail, on bending of the flexural link region 34 relative to the neutral fibres of the catheter shaft 30-2 running along the longitudinal axis L, the outer fibres of the catheter shaft 30-2 radially spaced from the neutral fibres are shortened. Since the second force transmission means 41, which connects the second operating means 81 with the second sleeve-shaped member 21 in the insertion system 100-2, normally runs along the neutral fibre of the catheter shaft 30-2, a bending contraction inevitably occurs when the catheter shaft 30-2 is bent, having the result that, despite fixing of the first operating means 71, the first sleeve-shaped member 11 of the catheter tip 10-2 is displaced relative to the stent holder 15 in a proximal direction.

This longitudinal displacement of the first sleeve-shaped member 11 of the catheter tip 10-2 that takes place during the bending procedure is compensated with the aid of the prestressing device (spring 97), since the spring 97 of the prestressing device exerts a constant tensile force on the second force transmission means 41 and therefore on the second sleeve-shaped member 21 of the catheter tip 10-2 and consequently constantly presses the distal-side end tip 25 of the catheter tip 10-2 against the distal-side end of the first sleeve-shaped member 11. This enables the catheter tip 10-2 to remain completely closed even during a deflection of the catheter shaft 30-2 effected, for example, when the catheter tip 10-2 is inserted through the aorta.

On actuation of the second operating means 81 of the handle 70-2, it is necessary to press the second slide 84 against the prestress supplied by the spring 97 of the prestressing device on the second stop 86.

It is important to note, however, that a prestressing device of the kind as described above is not mandatory for the insertion system as disclosed herein.

A further exemplary embodiment of an insertion system 100-2 designed for transarterial/transfemoral access is shown in FIGS. 3*a, b*. Elements in FIGS. 3*a, b* that are generally similar to previously described elements have the same reference numbers compared with the reference numbers in FIGS. 1 and 2 previously used for the similar elements.

The insertion system 100-2 shown in FIGS. 3*a, b* comprises a catheter system 1 of the kind as previously described with reference to FIG. 1, i.e. a catheter system 1 having a catheter tip 10-2 and a catheter shaft 30-2 which is provided with a first catheter tube 32 acting as first force transmitting means 31, a second catheter tube 42 acting as second force transmitting means 41, and a guiding tube 52 acting as guiding means 51. Contrary to the catheter shaft 30-2 utilized in the exemplary embodiment of the insertion system 100-2 depicted in FIG. 1, however, the catheter shaft 30-2 of the insertion system 100-2 shown in FIGS. 3*a, b* is provided with a flexural link region 34 of the kind as previously described with reference to FIG. 2.

As will be described in the following, the insertion system 100-2 shown in FIGS. 3*a, b* is provided with a different embodiment of a handle 70-2 which is used in order to manipulate the first and second sleeve-shaped members 11, 21 of the catheter tip 10-2.

In relation to the handle 70-2 used with the insertion system 100-2 shown in FIG. 3*a*, it can be seen that the end region of the handle 70-2 is in the form of a turning mechanism 98 (rotatable means), with which the second force transmission means 41 of the catheter shaft 30-2 can be twisted with the distal-side end tip 25 and the second sleeve-shaped member 21 of the catheter tip 10-2 fastened to it about the longitudinal axis L of the catheter tip 10-2. The second sleeve-shaped member 21 of the catheter tip 10-2 is connected by means of a loose bearing to the stent holder 15, allowing transmission of a turning moment between the second sleeve-shaped member 21 and the stent holder 15, without allowing transmission of any tensile or compression forces acting in the direction of the longitudinal axis L of the catheter tip 10-2. Thus, when a turning movement of the second sleeve-shaped member 21 is induced with the turning mechanism 98, the stent holder 15 also turns correspondingly about the longitudinal axis L.

The turning mechanism 98 preferably allows the stent holder 15 to twist through approximately 120°. Thus the rotation of a stent housed in the catheter tip 10-2, and particularly the positioning hoops already released in the second functional state of the insertion system 100-2, can be controlled, facilitating precise positioning of the already expanded positioning hoops of the stent in the pockets of the insufficient, native heart valve.

Preferably, the rotation movement of the stent holder 15 about the longitudinal axis L of the catheter tip 10-2 that can be effected with the turning mechanism 98 exhibits a previously definable, preferably small delay in reaction to a turning moment initiated by means of the turning mechanism 98.

Further, the embodiment of the handle 70-2 shown in FIG. 3a is equipped with a third operating means 96 in the form of a wheel, with which a flexural link 34, preferably provided at the distal end region of the catheter shaft 30-2, can be deflected.

The deflection of the distal end region of the catheter shaft 30-2 that can be effected with this flexural link region 34 is shown schematically in FIG. 3b. In detail, a device is provided for force transmission (control wire 35—see FIG. 8) which is connected on one side to the flexural link regions 34 preferably provided at the distal end region of the catheter shaft 30-2 and, on the other side, to the third operating means 96 of the handle 70-2 implemented in the embodiment shown in FIG. 3 as a hand wheel.

It is possible to implement the device for force transmission as a control wire 35, which is passed through the inside of the first transmission means 31 and preferably at the distal end of the flexural link region 34 or at the proximal end of the catheter tip 10-2 (see FIG. 8) to have a directed effect on the curvature of the flexural link region 34. With the tensile forces that can be exerted on the flexural link region 34 with the aid of the control wire 35, it is possible to obtain a defined curvature of the distal end region of the catheter shaft 30-2. This is a particular advantage during transarterial/transfemoral access when navigating the aortic arch.

Further exemplary embodiments of an insertion system 100-2 which is suitable for transarterial/transfemoral access to the implantation location are shown in FIGS. 4 and 5. Elements in FIGS. 4 and 5 that are generally similar to previously described elements have the same reference numbers compared with the reference numbers in FIGS. 1, 2 and 3a, b previously used for the similar elements.

Compared with the exemplary embodiment depicted in FIGS. 1 and 2 as well as FIGS. 3a, b, the embodiments shown in FIGS. 4 and 5 differ first and foremost in relation to the implementation of the corresponding operating means 71, 81 of the handle 70-2.

The insertion system 100-2 in accordance with FIG. 4 has a handle 70-2 with which the first operating means 71, which is used for manipulation of the first sleeve-shaped member 11 of the catheter tip 10-2, is similar to a trigger of a revolver. The user such as a physician who carries out the treatment may hold the handle 70-2 at the grip 88, while the first operating means 71 in the form of a trigger of a revolver is operated with the index finger of the hand holding it.

In the insertion system 100-2 shown in FIG. 5, a handle 70-2 is used which corresponds in structural and functional respects to the handle 70-2 used with the insertion system 100-2 in FIG. 3 with the exception of the grip 88 provided in the embodiment in accordance with FIG. 3.

A description is given in the following, with reference to FIGS. 6a-d and FIGS. 7a-d, of the functional coaction of the components of an insertion system 100-2, which is suitable for a transarterial or transfemoral access to the implantation location. Elements in FIGS. 6a to 6d and FIGS. 7a to 7d that are generally similar to previously described elements have the same reference numbers compared with the reference numbers in FIGS. 1 to 5 previously used for the similar elements.

Reference is made to FIGS. 6a to 6d for illustrating the procedure for loading a stent into the catheter tip 10-2 of the insertion system 100-2. In FIGS. 7a to 7d, the stepwise release of a stent mounted in the catheter tip 10-2 of the insertion system 100-2 is illustrated.

It is important to note, however, that the procedure for loading a stent into the catheter tip 10-2 as depicted in FIGS. 6a to 6d, as well as the procedure for stepwise releasing of a stent mounted in the catheter tip 10-2 as depicted in FIGS. 7a to 7d also apply to the other exemplary embodiments of the transarterial/transfemoral insertion system 100-2 disclosed herein.

The handle 70-2 for the transarterial/transfemoral insertion system 100-2 according to the illustration in FIGS. 6 and 7 has a wheel rotatably mounted in the handle 70-2 which is functionally connected to the first sleeve-shaped member 11 of the catheter tip 10-2 associated with the first operating means 71 via a corresponding first force transmission means 31, so that force can be directly transmitted from the first operating means 71 in the form of the wheel to the first sleeve-shaped member 11 of the catheter tip 10-2.

In detail, it is provided that, with the first operating means 71 of the handle 70-2 in accordance with FIG. 6 and FIG. 7, the first operating means 71 in the form of the wheel can turn between a first stop and a second stop, in order to execute a definable longitudinal displacement stroke on the first sleeve-shaped member 11 of the catheter tip 10-2. The first operating means 71 of the handle 70-2 is provided with a additional stop between the first and second stop which cooperates, on one side with the first stop and on the other up with the second stop so that, on actuation of the first operating means 71, a longitudinal displacement of the first sleeve-shaped member 11 of the catheter tip 10-2 can be effected relative to the stent holder 15 of the catheter tip 10-2, consisting of two defined separate steps.

With the first operating means 71 used in the form of a wheel, the additional stop associated with the first operating means 71 is in the form of a locking element 77' positioned removably in the flow of force between the wheel and the first sleeve-shaped member 11 of the catheter tip 10-2, interrupting direct force transmission from the wheel to the first sleeve-shaped member 11 of the catheter tip 10-2. Alternatively, however, it is possible for the additional stop associated with the first operating means 71 to be in the form of a locking element restricting the free rotation of the wheel between the first and the second stop.

However, it is of course also possible in principle for the first operating means 71 of the handle 70-2 used with the insertion system 100-2 designed for transarterial/transfemoral access not to be a wheel, but to be implemented as a pusher mechanism.

In relation to the handle 70-2 that is used with the embodiment of the insertion system 100-2, for example in accordance with the illustrations in FIGS. 6 and 7, it is provided that the second operating means 81 has a second slide 84 guided in a second guide 82 and functionally connected to a second pusher 83. This second slide 84, which is guided in the interior of the handle 70-2 and therefore cannot be seen in the view of FIGS. 6 and 7, is functionally connected to the second sleeve-shaped member 21 of the catheter tip 10-2 associated with the second operating means 81 by means of a second force transmission means 41 so that, on actuation of the second operating means 81, force is directly transmitted from the second slide 84 to the second sleeve-shaped member 21 of the catheter tip 10-2.

The second operating means 81 can be displaced between a first position (Pos. 1) and a second position (Pos. 2) in the longitudinal direction of the handle 70-2, whereby the longitudinal displacement stroke that can be thus effected via the second force transmission means 41 is transferred directly to the second sleeve-shaped member 21 of the catheter tip 10-2. The first and second positions are each defined with the aid of a first and a second stop 85, 86.

A securing element 89 is provided, associated with the second operating means 81, which is removably located on the second guide 82 and which blocks longitudinal displacement of the (second) slide 84 associated with the second operating means 81 when used.

The handle 70-2 which is used with the transarterial/ transfemoral insertion system 100-2 of the embodiment shown in FIGS. 6 and 7 further exhibits an optional grip 88, which facilitates the operability of the handle 70-2 and in particular the operating conformity of the handle 70-2. The grip 88 is preferably releasably connected to the body 70-2' of the handle 70-2 and can optionally be fixed at different positions on the body 70-2' of the handle 70-2.

In relation to the construction of the catheter tip 10-2 which is used, for example, with the insertion system 100-2 shown in FIGS. 6 and 7 and which allows transarterial/ transfemoral access of a stent housed in the catheter tip 10-2 to the implantation location, it can be seen from FIGS. 6 and 7 that the catheter tip 10-2 has a stent holder 15 for releasably fixing of, for example, the second retaining region of a stent that can be housed in the catheter tip 10-2. The retaining elements 16 of the stent holder 15 in the form of a crown are provided at the proximal end of the stent holder 15.

Further, the catheter tip 10-2 of the insertion system 100-2 designed for transarterial/transfemoral access comprises a mounting device for mounting a heart valve stent, where required, with a heart valve prosthesis fastened to it. In detail, the mounting device of the catheter tip 10-2 consists of a first sleeve-shaped member 11, particularly for accommodating the positioning hoops of a stent, and a second sleeve-shaped member 21, in particular for accommodating the heart valve prosthesis fastened to it, when required.

The first operating means 71 of the handle 70-2 co-operates in the embodiment according to FIGS. 6 and 7 with the first sleeve-shaped member 11 of the catheter tip 10-2 so that, on actuation of the first operating means 71, by transfer of a defined longitudinal displacement stroke, a previously definable longitudinal displacement of the first sleeve-shaped member 11 can be effected relative to the stent holder 15. On the other hand, with the insertion system 100-2 according to FIGS. 6 and 7, the second operating means 81 of the handle 70-2 co-operates with the second sleeve-shaped member 21 of the catheter tip 10-2 so that, on actuation of the second operating means 81, by transfer of a defined longitudinal displacement stroke, a previously definable longitudinal displacement of the second sleeve-shaped member 21 of the catheter tip 10-2 relative to the stent holder 15 can be effected.

The second sleeve-shaped member 21, which is used to house the retaining hoops of the stent with, where required, the heart valve prosthesis fastened to them, is located at the distal end region of the catheter tip 10-2, while the first sleeve-shaped member 11 is located between the second sleeve-shaped member 21 and the handle 70-2.

In the insertion system 100-2 shown in FIGS. 6 and 7, the second force transmission means 41, which connects the second operating means 81 of the handle 70-2 to the second sleeve-shaped member 21 of the catheter tip 10-2, is preferably in the form of an inner catheter running inside the interior of the catheter or tube system. The first force transmission means 31, which connects the first operating means 71 of the handle 70-2 to the first sleeve-shaped member 11 of the catheter tip 10-2, is in the form of an outer catheter, in the interior of which the first force transmission means 31 runs in the form of the inner catheter.

On actuation on the second operating means 81, the second sleeve-shaped member 21 can be moved relative to the stent holder 15 in the longitudinal direction L of the catheter tip 10-2 in a distal direction, thus away from the handle 70-2, while, on actuation of the first operating means 71 of the handle 70-2, the first sleeve-shaped member 11 of the catheter tip 10-2 can be moved relative to the stent holder 15 in the longitudinal direction L of the catheter tip 10-2 in a proximal direction, and thus towards the handle 70-2.

The manipulations of the respective sleeve-shaped members 11, 21 of the catheter tip 10-2 that can be effected on actuation of the respective operating means 71, 81 with the insertion system 100-2 of 100-2 designed for transarterial/ transfemoral access in accordance with FIGS. 6 and 7 are described in detail in the following, with reference in particular to FIGS. 7a to 7d.

An embodiment of a transarterial/transfemoral insertion system 100-2 is shown in its four different functional states in FIGS. 7a to 7d. In detail, the insertion system 100-2 is shown in its first functional state in FIG. 7a, in which the catheter shaft 30-2 with the catheter tip 10-2 and, where required, with the stent accommodated in it can be inserted into the patient transarterially or transfemorally and advanced via the aorta to the implantation site.

Figure 7A:
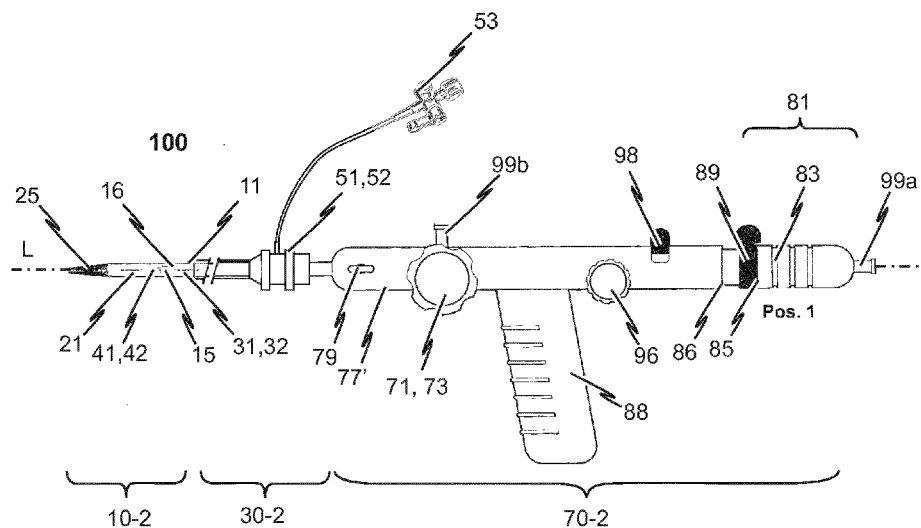

In the first functional state of the insertion system 100-2 in accordance with FIG. 7a, the catheter tip 10-2 is completely closed, whereby the two sleeve-shaped members 11, 21 of the catheter tip 10-2 overlap telescopically. The respective diameters of the sleeve-shaped members 11, 21 are chosen so that the folded-up retaining hoops of a stent, with the heart valve prosthesis fastened to them where required, can be housed in the second sleeve-shaped member 21. The folded-up positioning hoops of the stent housed between the second sleeve-shaped member 21 and the first sleeve-shaped member 11 are held together in their folded form.

The second retaining region of the stent is shown in the first functional state of the insertion system 100-2, as shown in FIG. 7a, with the stent holder 15 fixed at the proximal end of the catheter tip 10-2. For this purpose, the retaining elements (retaining rings etc.) provided at the second retaining region of the stent are engaged with retaining elements 16 of the stent holder 15.

The retaining elements 16 of the stent holder 15 are covered by the first sleeve-shaped member 11 of the catheter tip 10-2 in the first functional state shown in FIG. 7a, so that an engagement between retaining elements provided on the second retaining region of a stent and retaining elements 16 of the stent holder 15 would be possible.

The first functional state of the insertion system 100-2 shown in FIG. 7a is maintained during the transarterial insertion procedure. On reaching the implantation location, the insertion system 100-2 is transferred from the first functional state shown in FIG. 7a to the second functional state shown in FIG. 7b, by transferring the first operating means 71 (shown in the embodiment of the wheel in FIG. 7) from the first position into the second position. The longitudinal displacement stroke transferred by actuation of the first operating means 71 to the first sleeve-shaped member 11 of the catheter tip 10-2 effects a displacement of the first sleeve-shaped member 11 relative to the stent holder 15 in the proximal direction, thus towards the handle 70-2.

The longitudinal displacement stroke executed on the first sleeve-shaped member 11 of the catheter tip 10-2 during the transition from the first functional state (see FIG. 7a) to the second functional state (see FIG. 7b) by the first operating means 71 of the handle 70-2 via a corresponding first force transmission means 31 is previously defined so that the first sleeve-shaped member 11 is displaced relative to the stent holder 15 in the proximal direction just so far that the positioning hoops of a stent housed in the catheter tip 10-2 would be released, though the distal end of the first sleeve-shaped member 11 of the catheter tip 10-2 would still cover the retaining elements 16 of the stent holder 15, so that the engagement between the retaining elements provided at the second retaining region of the stent and the retaining elements 16 of the stent holder 15 would be secure.

Since the second sleeve-shaped member 21 is not manipulated during the transition from the first functional state into the second functional state, the first retaining region of a stent housed in the catheter tip 10-2 with the heart valve prosthesis fastened to it would continue to be housed in its folded together state in the sleeve-shaped element of the second sleeve-shaped member 21.

The positioning hoops of a stent housed in the catheter tip 10-2 released in the second functional state of the insertion system 100-2 are opened as a result of the radial forces acting on them and can thus be positioned in the pockets of the insufficient native heart valve. Following appropriate positioning of the positioning hoops of the stent in the pockets of the native heart valve, the insertion system 100-2 is transferred from the second functional state shown in FIG. 7b into the third functional state shown in FIG. 7c. This is done my manipulation of the second operating means 81, after the securing element 89 associated with the second operating means 81 has been removed.

On actuation of the second operating means 81, the second sleeve-shaped member 21 of the catheter tip 10-2 associated with the second operating means 81 is moved relative to the stent holder 15 by a previously established longitudinal displacement stroke defined with the second operating means 81 in a distal direction, thus away from the handle 70-2. The longitudinal displacement stroke acting on the second sleeve-shaped member 21 is chosen so that the sleeve-shaped member 21 no longer covers the first retaining region of a stent housed in the catheter tip 10-2 with the heart valve prosthesis fastened to it, where required, and thus releases the first retaining region of the stent. Due to the action of the radial forces, the distal retaining region of the stent with the heart valve prosthesis attached to it, where required, unfolds completely.

Figure 7B:
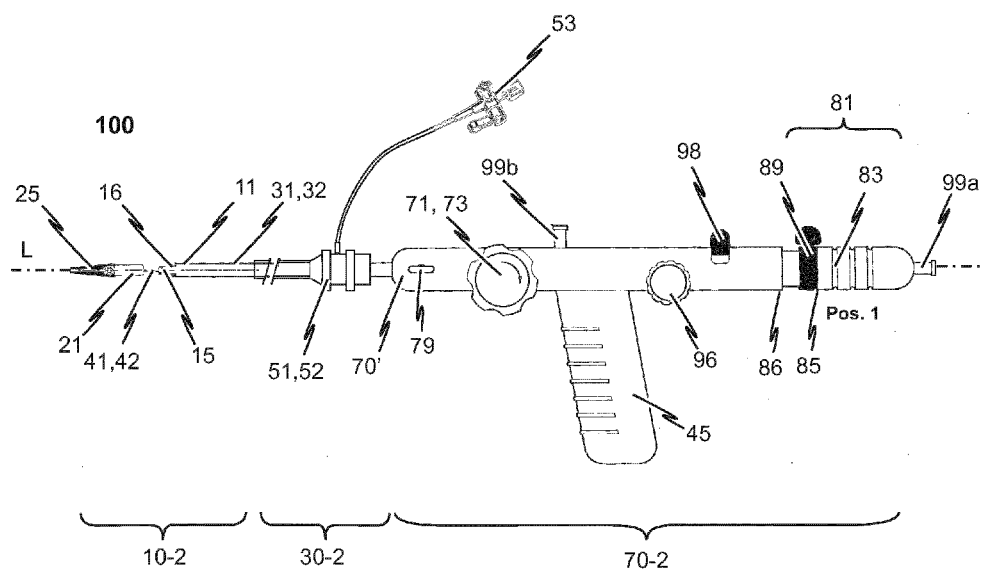
Figure 7C:
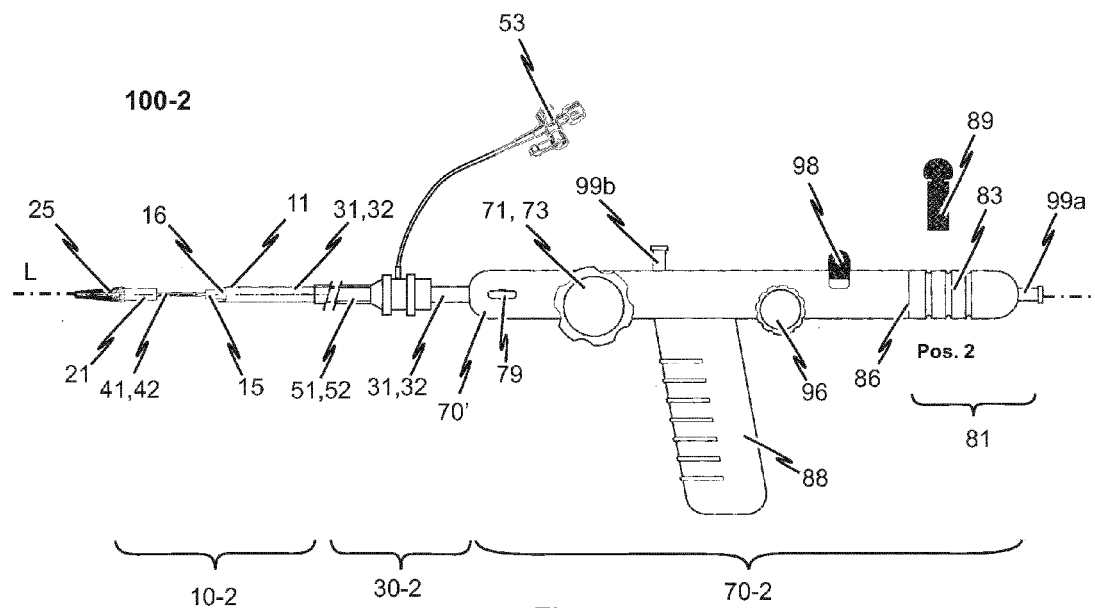

Since the first operating means 71 of the handle 70-2 and the associated first sleeve-shaped member 11 of the catheter tip 10-2 are not manipulated during the transition from the second functional state in accordance with FIG. 7b into the third functional state in accordance with FIG. 7c, the distal end region of the first sleeve-shaped member 11 continues to cover the retaining elements 16 of the stent holder 15, so that the engagement between the retaining elements of a stent housed in the catheter tip 10-2 and the retaining elements 16 of the stent holder 15 is secure and the proximal retaining region of the stent is in its folded-up state. This anchorage of the stent to the catheter tip 10-2 of the insertion system 100-2 allows an explantation of a stent that is already partially unfolded by returning the insertion system 100-2 from the third functional state, by appropriate manipulation of the second operating means 81 of the handle 70-2, to the second functional state and then by suitable actuation of the first operating means 71 transfer to the first functional state.

Figure 7D:
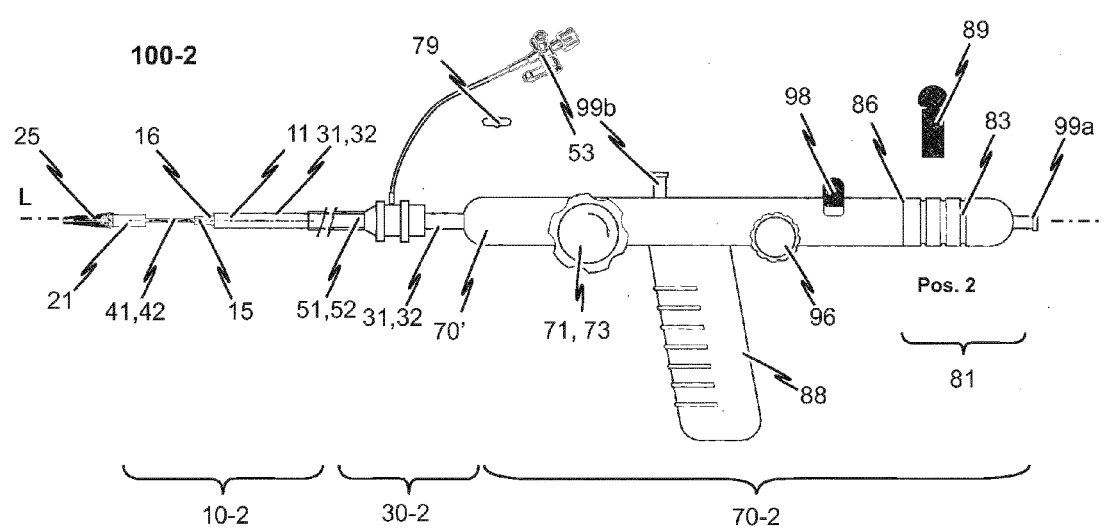

If an explantation of the stent with the heart valve prosthesis attached to it, where required, is unnecessary, the insertion system 100-2 is transferred from the third functional state shown in FIG. 7c into the fourth functional state shown in FIG. 7d, by turning the first operating means 71 of the handle 70-2 further from the second position to the third position after removal of the securing element 79 (locking element). This manipulation of the first operating means 71 that can be effected after removal of the securing element 79 results in a further defined movement of the first sleeve-shaped member 11 relative to the stent holder 15 of the catheter tip 10-2 in a proximal direction, thus towards the handle 70-2. The longitudinal displacement stroke executed on the first sleeve-shaped member 11 is chosen so that the distal end of the first sleeve-shaped member 11 no longer covers the retaining elements 16 of the stent holder 15, as a result of which an engagement between the retaining elements of a stent housed in the catheter tip 10-2 and the retaining elements 16 of the stent holder 15 can be released, which would also lead to a complete release of the second retaining region of the stent and a complete separation of the stent from the catheter tip 10-2 and correspondingly to a complete unfolding of the stent.

Figure 6A:
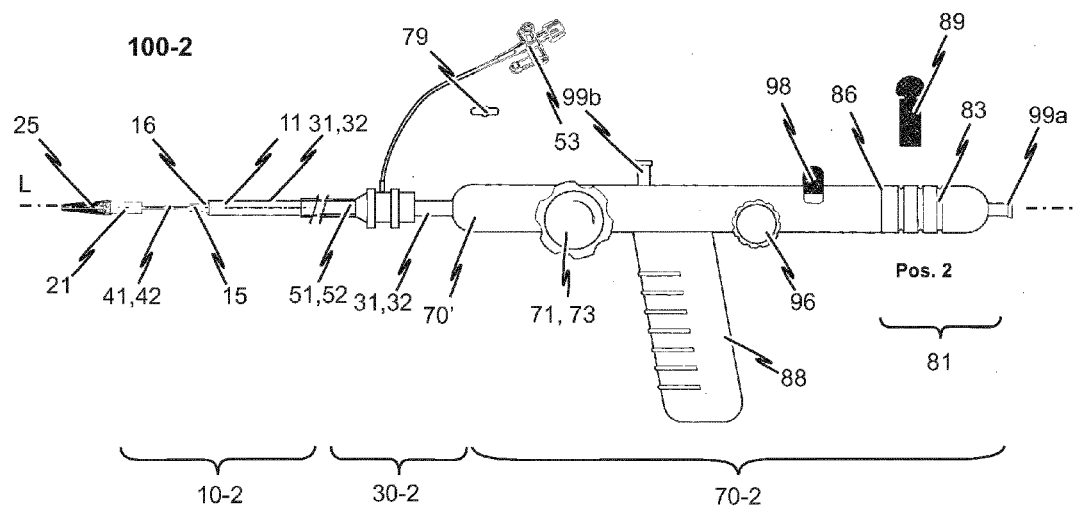
Figure 6B:
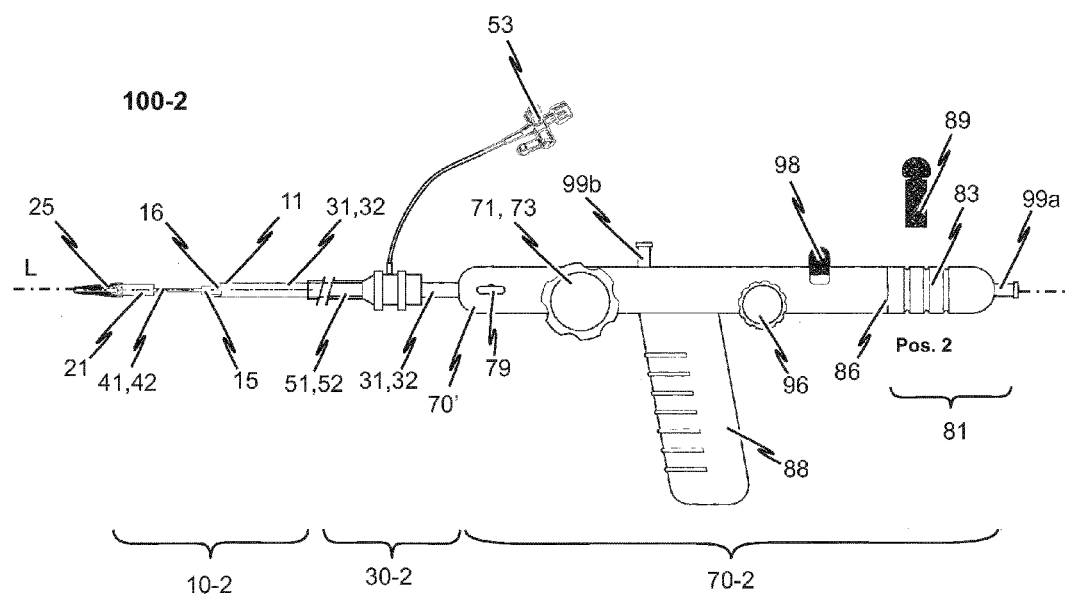
Figure 6C:
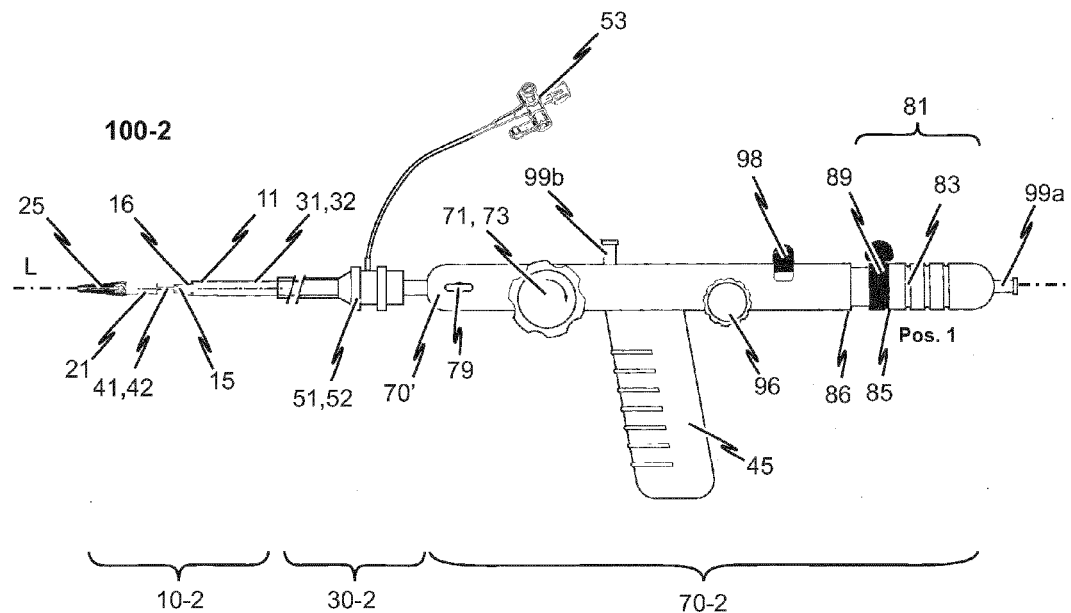
Figure 6D:
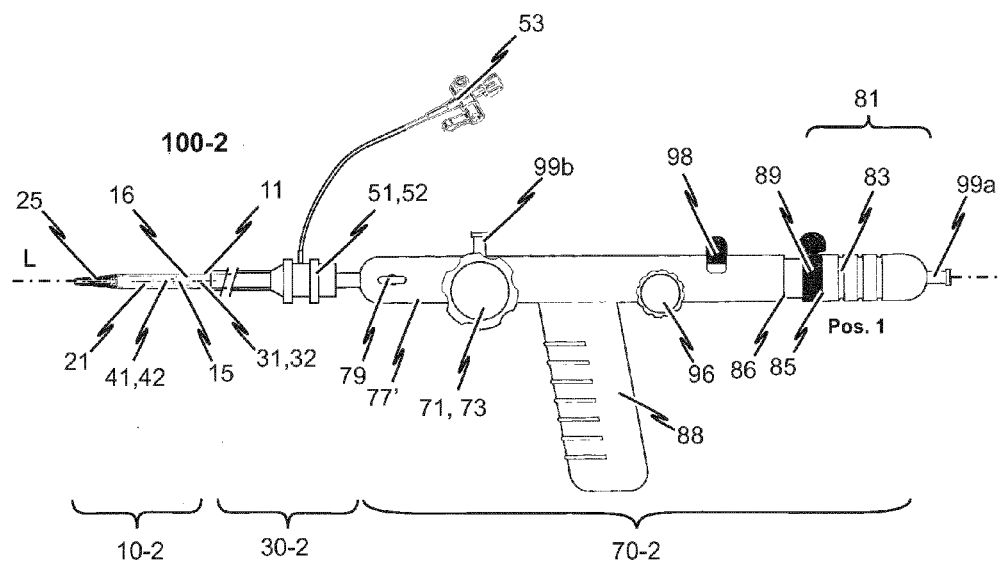

The four functional states of the insertion system 100-2 designed for transarterial/transfemoral access, previously described with reference to FIGS. 7a to 7d, are shown in reverse order in FIGS. 6a to 6d to clarify the procedure for loading a stent into the catheter tip 10-2 of the insertion system 100-2. Comparison between FIGS. 6a to 6d and FIGS. 7a to 7d show that the insertion system 100-2 can be loaded with a heart valve stent by transferring the insertion system 100-2, starting from its fourth functional state in accordance with FIG. 6a (see FIG. 7d), into its third functional state in accordance with FIG. 6b (see FIG. 7c) after a stent has been positioned between the stent holder 15 on the second sleeve-shaped member 21 with its first retaining region in the direction of the second sleeve-shaped member 21. Then the remaining functional states of the insertion system 100-2 are taken up in steps until the insertion system 100-2 shown in FIG. 6d is finally in its first functional state with the closed catheter tip 10-2.

Reference is made to FIG. 9 for describing an exemplary embodiment of the catheter tip 10-2. Elements in FIG. 9 that are generally similar to previously described elements have the same reference numbers compared with the reference numbers in FIGS. 1 to 7 previously used for the similar elements.

An exemplary embodiment of a catheter shaft 30-2 is described in the following, with reference to the illustration in FIG. 9. This catheter shaft 30-2 can be used with an insertion system 100-2 designed for transarterial or transfemoral access.

In detail, FIG. 9 shows an exemplary embodiment of a shaft for an insertion system 100-2 in a cross-sectional elevation.

The catheter shaft 30-2 exhibits a first force transmission means 31 in the form of a first catheter tube 32, whereby this first catheter tube 32 is used to connect the first operating means 71 of the handle 70-2 to the first sleeve-shaped member 11 of the catheter tip 10-2. As can be seen in particular from the illustration in FIG. 1, the first force transmission means 31 implemented as a first catheter tube 32 may be clamped between a screw cap 74' and the first slide 74 of the first operating means 71 and consequently is permanently connected to the first slide 74. The distal-side end region of the first catheter tube 32 merges into the first sleeve-shaped member 11 of the catheter tip 10-2 in the form of the stent sheath.

The second force transmission means 41 of the catheter shaft 30-2 used with an insertion system 100-2 designed for transarterial or transfemoral access is preferably implemented as a second catheter tube 42. The proximal-side end region of the second catheter tube 42 is connected to the second operating means 81 of the handle 70-2. The distal-side end region of the second catheter tube 42 is connected to the catheter end tip 25 of the catheter tip 10-2. The second sleeve-shaped member 21 of the catheter tip 10-2 is permanently connected by means of its distal-side end to the end tip 25 of the catheter tip 10-2 so that, on actuation of the second operating means 81 via the force transmission means 41 in the form of the second catheter tube 42, a tensile or compressive force can be transmitted to the second sleeve-shaped member 21 of the catheter tip 10-2.

The exemplary embodiment of the catheter tip 10-2 further comprises a stent holder 15 at the proximal end section of the catheter tip 10-2. The stent holder 15 has a passageway extending there through. The distal end section of the second force transmitting means 41 (second catheter tube 42) passes through the passageway of the stent holder 15 and terminates at the second sleeve-shaped member 21.

The respective sleeve-shaped members 11, 21 of the catheter tip 10-2 can be manipulated by corresponding operating means 71, 81 of a handle 70-2 (not shown in FIG. 9). In detail, the first sleeve-shaped member 11 of the catheter tip 10-2 is connected with a first operating means 71 of a handle 70-2 by using a first force transmitting means 31. On the other hand, the second sleeve-shaped member 21 of the catheter tip 10-2 is connected to a second operating means 81 of the handle 70-2 by using a second force transmitting means 41. In a preferred embodiment of the catheter shaft 30-2, the first force transmitting means 31 is constituted by a first catheter tube 32 defining a first lumen, wherein the second force transmitting means 41 is constituted by a second catheter tube 42 defining a second lumen. The second catheter tube 42 has a cross-section less than the cross-section of the first catheter tube 32, wherein the first catheter tube 32 is disposed concentrically and coaxially with the second catheter tube 42.

As shown in FIG. 9, the distal end section of the second catheter tube 42 passes through the opened front face of the second sleeve-shaped member 21 and terminates in a cone-shaped end tip 25 of the catheter system 1, wherein the base of this cone-shaped end tip 25 defines the distal front face of the second sleeve-shaped member 21.

The end tip 25 of the catheter system 1 is preferably a soft catheter end tip, for example a soft polymeric catheter end tip.

At its distal end, the first catheter tube 32 terminates after an intermediate flared section in a section with wider cross-section defining the first sleeve-shaped member 11 of the catheter tip 10-2. As can be seen from FIG. 9, the flared section is formed integrally with the distal end section of the first catheter tube 32. The flared section has a length greater than the length of a collapsed stent to be accommodated in the catheter tip 10-2, wherein the difference in the length between the flared section and the stent in its collapsed state represents the length of the stent holder 15.

The catheter shaft 30-2, which is connected to the catheter tip 10-2 depicted in FIG. 9, also comprises a guiding tube 52 of the kind as previously described with reference to the exemplary embodiment depicted in FIG. 1.

The distal end of the guiding tube 52 terminates proximal to the catheter tip 10-2. The guiding tube 52 defines a passageway within which the first and second catheter tube 42 32, 42 are received such as to be movable relative to the guiding tube 52.

The distal end of the guiding tube 52 may be tapered such that it abuts the first catheter tube 32 in one of its possible positions on the catheter shaft 30-2.

Reference is made to FIG. 10, which is a cross-sectional view of a catheter shaft 30-2 according to an exemplary embodiment.

As can be seen from the illustration in FIG. 10, the second force transmission means 41 in the form of the second catheter tube 42 runs along the neutral fibre of the catheter shaft 30-2 inside the first catheter tube 32. The space between the first catheter tube 32 and the second catheter tube 42 may be filled with a filler material, so that a filler body 40 is formed. The filler material is preferably a relatively elastic plastic material to allow the catheter shaft 30-2 to bend overall. The filler body 40 is used for connecting the stent holder 15 of the catheter tip 10-2 to the body 70-2' of the handle 70-2.

Alternatively, a stent holder tube 62 may be used for connecting the stent holder 15 of the catheter tip 10-2 to the body 70-2' of the handle 70-2. The stent holder tube 62 may have a distal end connected to the stent holder 15, a proximal end connected to the body 70-2' of the handle 70-2 and a passageway extending through the stent holder tube 62. Preferably, the stent holder tube 62 has a cross-section less than the cross-section of the first catheter tube 32 and greater than the cross-section of the second catheter tube 42, wherein the first catheter tube 32 is disposed concentrically and coaxially with the stent holder tube 62 thereby accommodating the stent holder tube 62 such that the first catheter tube 32 is moveable relative to the stent holder tube 62. The passageway of the stent holder tube 62 shall have a diameter sufficient to accommodate the second catheter tube 42 such that the second catheter tube 42 is moveable relative to the stent holder tube 62.

As depicted in FIG. 1, the filler body 40 (or the stent holder tube 62) may be connected by means of a fixing 87 to the body 70-2' of the handle 70-2. The proximal-side end region of the stent holder 15 attaches at the distal-side end region of the filler body 40 (see FIG. 8). The connection between the stent holder 15 and the filler body 40 is preferably chosen so that it allows rotation of the stent holder 15 relative to the filler body 40. This is especially necessary for control of the rotation of the positioning hoops of the already partially released stent during the implantation procedure (see FIG. 12a).

As an alternative, the complete catheter system 1 can be rotated for appropriate positioning of a stent connected with the catheter tip 10-2 and, in particular the positioning hoops of an already partially released stent during the implantation procedure. This is possible due to an appropriate transmission of torque and the flexibility of the catheter system 1.

In case, a stent holder tube 62 is used for connecting the stent holder 15 of the catheter tip 10-2 to the body 70-2' of the handle 70-2, the stent holder tube 62 may be rotatable relatively to the first and second catheter tubes 32, 42 about the longitudinal axis L of the catheter system 1. This will be described later in more detail with reference to the exemplary embodiment depicted in FIG. 10.

On the other hand, the second force transmission means 41 in the form of the second catheter tube 42 can be turned about the longitudinal direction L, for example, by means of a rotatable cap 98 which may be provided at the proximal end region of the handle 70-2. This rotary movement is transferred from the second catheter tube 42 direct to the end tip 25 of the catheter tip 10-2 and thus to the second sleeve-shaped member 21 of the catheter tip 10-2.

It is particularly preferred that the second catheter tube 42 runs through the body of the stent holder 15 and cooperates with the stent holder 15 with the aid of a suitable toothing, to transmit a turning moment exerted by means of the rotary cap of the handle 70-2 on the second catheter tube 42 to the stent holder 15, while tensile or compression forces acting in the longitudinal direction L of the catheter tip 10-2 are not transmitted from the second catheter tube 42 to the stent holder 15.

As can also be seen in the illustration in FIG. 10, a least one fluid channel 43 may be provided in the filler body 40 of the catheter shaft 30-2, connected at its proximal-side end to an injection adapter 99*b* (see FIG. 2) and at its distal-side end correspondingly to the catheter tip 10-2, consequently ensuring supply of fluid to the catheter tip 10-2 and draining of fluid from the catheter tip 10-2.

Furthermore, a channel may be provided in the filler body 40 for accommodating a control wire (control wire 35—see FIG. 8), with an operating means may cooperate with a flexural link region, in case the catheter shaft 30-2 is provided with such a flexural link region (see FIG. 3 and FIG. 2). In the illustration in FIG. 8, the distal-side end of a control wire 35 is fixed to the proximal-side end region of the stent holder 15.

Reference is made to FIG. 10, which is a cross-sectional view of a catheter shaft 30-2 according to an exemplary embodiment.

According to the embodiment depicted in FIG. 10, the first force transmitting means 31 may be constituted by a first catheter tube 32 defining a first lumen and the second force transmitting means 41 is constituted by a second catheter tube 42 defining a second lumen. The second catheter tube 42 may have a cross-section less than the cross-section of the first catheter tube 32. The first catheter tube 32 may be disposed concentrically and coaxially with the second catheter tube 42 and the second catheter tube 42 is received within the first lumen defined by the first catheter tube 32.

A stent holder tube 62 is provided for connecting the stent holder 15 to the handle 70-2, said stent holder tube 62 having a distal end connected to the stent holder 15 and a proximal end connected to a body 70-2' of the handle 70-2.

As can be seen from FIG. 10, the stent holder tube 62 may have a cross-section less than the cross-section of the first catheter tube 32. In particular, the first catheter tube 32 may be disposed concentrically and coaxially with both, the second catheter tube 42 on the one hand and the stent holder tube 62 on the other hand. Preferably, the stent holder tube 62 has a cross-section less than the cross-section of the first catheter tube 32 and greater than the cross-section of the second catheter tube 42 such that the stent holder tube 62 is received within the first lumen defined by the first catheter tube 32 and the second catheter tube 42 is received within a passageway defined by the stent holder tube 62. The passageway defined by the stent holder tube 62 has a diameter sufficient to accommodate the second catheter tube 42 such that the second catheter tube 42 is moveable relative to the stent holder tube 62.

The second lumen defined by the second catheter tube 42 has a diameter sufficient to accommodate a guide wire 180. The second catheter tube 42 may be made from a rigid material including, for example, nitinol, stainless steel or a rigid plastic material. The material of the distal end section of the second catheter tube 42 may have an increased flexibility compared to the material of the proximal end section in order to allow the distal end section of the catheter shaft 30-2 to pass the aortic arch during insertion of the catheter tip 10-2. For example, the guiding tube 52 may be a 17F-catheter tube and the first catheter tube 32 may be a 12F-catheter tube.

According to the exemplary embodiment depicted in FIG. 10, the stent holder tube 62 is made of a rigid material, for example, a rigid plastic material, stainless steel or nitinol. The distal end of the stent holder tube 62 terminates in the stent holder 15 which is also made of a rigid material, for example, a rigid plastic material or stainless steel. The passageway defined by the stent holder tube 62 is aligned with a channel which passes through the stent holder 15. In this way, the second catheter tube 42 is accommodated in the passageway of the stent holder tube 62 and the channel of the stent holder 15 such as to be moveable relative to the stent holder tube 62 and the stent holder 15.

The embodiments of the insertion system 100-2 designed for transarterial/transfemoral access may have a first injection adapter 99*a* at the proximal end of the handle 70-2. This first injection adapter 99*a* is used for flushing the insertion system 100-2 and as outlet of a guide wire 180, with the aid of which the actual introduction of the catheter shaft 30-2 with the catheter tip 10-2 provided at the distal end of the catheter shaft 30-2 into the body of the patient is simplified. The catheter shaft 30-2, the catheter tip 10-2 and the handle 70-2 are thereby threaded into the guide wire 180 and pushed along it, for example into the aorta and to the heart of the patient.

In the embodiments of the insertion system 100-2 designed for transarterial/transfemoral access, a second injection adapter 99*b* may further be provided, by means of which a liquid coolant etc. can be passed, for example, via the fluid channels 43 (see FIG. 10) formed in the interior of the catheter shaft 30-2 to the catheter tip 10-2. With the aid of such a liquid coolant, a stent accommodated in the catheter tip 10-2 can be appropriately cooled while the catheter tip 10-2 is being advanced to the implantation location, as long as the insertion system 100-2 is in its first functional state, in which the catheter tip 10-2 is completely enclosed by the telescopically arranged sleeve-shaped members 11 and 21.

The provision of cooling that can be produced with the second injection adapter 99*b* for the stent accommodated in the catheter tip 10-2 is a particular advantage when a shape memory material is used as stent material and when the stent can deform under the effect of an external stimulus from a temporary form to a permanent form, whereby the temporary form exists in the first configuration of the stent (in the folded-up state, when the stent is accommodated in the catheter tip 10-2) and the permanent form exists in the second configuration of the stent (in the expanded state of the stent after release of the stent from the catheter tip 10-2).

In the embodiments of the insertion system 100-2 previously described, the guiding tube 52 is preferably made from a material allowing the guiding tube 52 to be capable of traversing a tortuous pathway in the body of the patient without kinking. For example, the guiding tube 52 may include an inner lubricious liner, an outer polymeric jacket, and a coil reinforcement between the inner and outer layers. In addition, it is preferred when at least on radiopaque band or member is incorporated within the guiding tube's material to allow precise location of the distal end of the guiding tube 52 for positioning accuracy.

On the other hand, the first and second catheter tubes 32, 42 of the catheter shaft 30-2 are preferably made from flexible, sterilizable materials. These materials may include, for example, polyurethane, silicone, polyvinyl chloride (PVC) nylon and/or polyether block amide, e.g. Pebax®. Furthermore, the first catheter tube 32 and/or second catheter tube 42 are/is at least partly made from a less rigid material than the guiding tube 52. In an exemplary embodiment, the first catheter tube 32 and/or the second catheter tube 42 are/is at least partly made of a braided wire construction. In addition, the stent holder tube 62 may also be at least partly made of a braided wire construction.

Individual features of different embodiments of this disclosure may be combined in any suitable manner.

A preferred embodiment of a medical device for treatment of a heart valve stenosis and/or heart valve insufficiency in a patient is described in the following with reference to FIGS. 12a to 12c. As depicted, the medical device exhibits an insertion system 100-2 designed for transarterial/transfemoral access, as has been described in detail previously, for example, with reference to FIGS. 1 to 10.

In addition to the insertion system 100-2, the medical device has an expandable heart valve stent 150 mounted in the catheter tip 10-2 of the insertion system 100-2, to which a heart valve prosthesis 160 to be implanted is fastened. In the first functional state, not shown, the stent 150 exhibits a first, previously definable configuration, in which it is in its folded-together state. On the other hand, the stent 150 is designed to adopt a second previously definable configuration in the implanted state, in which it exists in its expanded state.

Through the use of the insertion system 100-2 described above, during the implantation procedure, the stent 150 is transferred sequentially, following a previously definable sequence of events in steps from its first previously defined configuration into its second previously defined configuration.

In detail, the stent 150 that is used with the medical device in accordance with the depiction in FIGS. 12a to 12c exhibits a first retaining region, to which the heart valve prosthesis 160 is attached. Further, the stent 150 comprises a second retaining region with three retaining elements 151, each in the configuration of retaining rings, which can be brought in to a releasable engagement with the retaining elements 16 of the stent holder 15 provided in the catheter tip 10-2.

In addition, the stent 150 has three retaining hoops 153 to accommodate the heart valve prosthesis 160 and three positioning hoops 154 for automatic positioning of the stent 150 at the implantation site, whereby the respective positioning hoops 154 of the stent 150 are designed in functional and structural respects to engage the pockets 170 of the native heart valve during the implantation procedure and in the implanted state of the stent 150, in particular from the second functional state of the insertion system 100-2. In detail, each positioning hoop 154 and its associated retaining hoop 153 has an essentially U or V-shaped structure, which is closed towards the distal end of the stent 150.

The stent 150, which together with the insertion system 100-2 forms the basis of the medical device, is especially suitable for insertion into the body of a patient with the aid of the insertion system 100-2 with minimal invasiveness. The distinctive feature of the stent 150 is that the three positioning hoops 154 of the stent 150 undertake the function of automatic positioning of the stent 150 with the heart valve prosthesis 160 attached to it in the aorta of the patient. The positioning hoops 154 have radiused head sections, which engage in the pockets 170 of the insufficient heart valve to be replaced by the heart valve prosthesis during positioning of the stent 150 at the implantation site. The provision of a total of three positioning hoops 154 takes care of the necessary positioning accuracy in the rotary direction.

In this state shown in 12a, the catheter tip 10-2 and the catheter shaft 30-2 of the transarterial or transfemoral insertion system 100-2 has been inserted by a puncture of the groin artery of the patient and the catheter tip 10-2 has been advanced to the implantation site with the aid of a guide wire 180. In detail, the insertion system 100-2 to be used is shown already in its second functional state in FIG. 12a. The second functional state of the insertion system 100-2 designed for transarterial or transfemoral access has been described previously, for example with reference to FIG. 7b.

In the second functional state, the first sleeve-shaped member 11 of the catheter tip 10-2 has already moved by a first predetermined amount of movement in a proximal direction, and thus towards the handle 70-2, leading to a release of the positioning hoops 154 of the stent 150. These already expanded positioning hoops 154 of the stent 150 shown in FIG. 12a are positioned—where necessary by a suitable rotation of the stent holder 15 of the catheter tip 10-2—in the pockets 170 of the native heart valve position. After positioning of the positioning hoops 154 in the pockets 170 of the native heart valve is complete, the insertion system 100-2 is transferred from its second functional state (see FIG. 7b) into its third functional state (see FIG. 7c).

The manner in which the insertion system 100-2 is transferred into its third functional state has been described previously, for example with reference to FIG. 7c. FIG. 12b shows the insertion system 100-2 in accordance with FIG. 12a, in which the second sleeve-shaped member 21 has been displaced in a distal direction so that the first retaining region of the stent 150 with the retaining hoops 153 and the heart valve prosthesis 160 attached to them are released. These components are opened as a result of the radial forces attacking them, whereby the old heart valves are clamped between the positioning hoops 154 and the retaining hoops 153.

After the functioning of the heart valve prosthesis 160 has been checked, the insertion system 100-2 is then transferred from its third functional state into its fourth functional state, as has previously been described, for example with reference to FIG. 7d. FIG. 12 shows the effect of the transfer of the insertion system 100-2 into its fourth functional state on the heart valve prosthesis 160 and the stent 150.

In detail, it can be seen that, in the fourth functional state of the insertion system 100-2, the first sleeve-shaped member 11 of the catheter tip 10-2 has been displaced further in a proximal direction, as a result of which the anchorage of the retaining elements 151 on the second retaining region of the stent 150 is released. This has the result that that the second retaining region of the stent 150 can also expand and press against the vessel wall.

Finally, the catheter tip 10-2 and the catheter shaft 30-2 of the insertion system 100-2 are removed again from the body of the patient.

When the heart valve stent 150 is implanted, the old (insufficient) heart valve is pressed against the vessel wall at the same time due to the self-expanding characteristic of the stent 150, as can be seen in particular in FIG. 12*c*. In particular, the semilunar heart valves of the insufficient, native heart valve are clamped between the positioning hoops 154 and the retaining hoops 153 because of the expansion of the stent 150, in addition to which the heart valve prosthesis 160 located on the first retaining region of the stent 150 is optimally positioned and is stably anchored.

The disclosed solutions provide an improved insertion system 100-2 with the stent mountable in the catheter tip 10-2 of the insertion system 100-2. The stent may be inserted transarterially by the special insertion system 100-2 and can be optimally positioned, so that a heart valve prosthesis sewn on the first retaining region of the stent can undertake the function of the insufficient or stenosed native heart valve. The radial forces developed due to the self-expanding characteristic of the stent ensure a secure anchoring in the area of the aorta. The catheter system 1 of the insertion system 100-2 is preferably an 18 to 21F introducer, which is compatible with 21F-insertion tubes and a 0.035" guide wire 180. The length of the catheter system 1 for transarterial access should be at least 100-2 cm. The optionally provided flexural link region at the distal region of the catheter system 1 is preferably approximately 30 cm.

A further embodiment of a catheter tip 10-2 for an insertion system for transfemoral/transarterial insertion of an expandable heart valve stent is shown in its four different functional states in FIGS. 13*a* to 13*d*. In detail, the catheter tip 10-2 is shown in its first functional state in FIG. 13*a*, in which the catheter shaft with the catheter tip 10-2 and, where required, with the stent accommodated in it can be inserted into the patient transarterially or transfemorally and advanced via the aorta to the implantation site.

In the first functional state of the catheter tip 10-2 in accordance with FIG. 13*a*, the catheter tip 10-2 is completely closed, whereby the two sleeve-shaped members 11, 21 of the catheter tip 10-2 abut. In this embodiment, the two sleeve-shaped members 11, 21 of the catheter tip 10-2 have an equal outer cross-section diameter, thereby not forming a step in the state depicted in FIG. 13*a*. The respective inner diameters of the sleeve-shaped members 11, 21 are chosen so that the folded-up retaining hoops of a stent, with the heart valve prosthesis fastened to them where required, can be housed in the second sleeve-shaped member 21. The folded-up positioning hoops of the stent housed between the second sleeve-shaped member 21 and the first sleeve-shaped member 11 are held together in their folded form.

In the first functional state of the catheter tip 10-2, as shown in FIG. 13*a*, the second retaining region of the stent is fixed with the stent holder 15 at the proximal end of the catheter tip 10-2. For this purpose, the retaining elements (retaining rings etc.) provided at the second retaining region of the stent are engaged with retaining elements 16 of the stent holder 15.

The retaining elements 16 of the stent holder 15 are covered by the first sleeve-shaped member 11 of the catheter tip 10-2 in the first functional state shown in FIG. 13*a*, so that an engagement between retaining elements provided on the second retaining region of a stent and retaining elements 16 of the stent holder 15 would be possible.

The first functional state of the catheter tip 10-2 shown in FIG. 13*a* is maintained during the transarterial insertion procedure. On reaching the implantation location, the catheter tip 10-2 is transferred from the first functional state shown in FIG. 13*a* to the second functional state shown in FIG. 13*b*, by transferring the first operating means of the handle (first operating means 71 shown in the embodiment of the wheel in FIG. 7) from the first position into the second position. The longitudinal displacement stroke transferred by actuation of the first operating means 71 to the first sleeve-shaped member 11 of the catheter tip 10-2 effects a displacement of the first sleeve-shaped member 11 relative to the stent holder 15 in the proximal direction, thus towards the handle 70-2.

The longitudinal displacement stroke executed on the first sleeve-shaped member 11 of the catheter tip 10-2 during the transition from the first functional state (see FIG. 13*a*) to the second functional state (see FIG. 13*b*) by the first operating means 71 of the handle 70-2 via a corresponding first force transmission means 31 is previously defined so that the first sleeve-shaped member 11 is displaced relative to the stent holder 15 in the proximal direction just so far that the positioning hoops of a stent housed in the catheter tip 10-2 would be released, though the distal end of the first sleeve-shaped member 11 of the catheter tip 10-2 would still cover the retaining elements 16 of the stent holder 15, so that the engagement between the retaining elements provided at the second retaining region of the stent and the retaining elements 16 of the stent holder 15 would be secure.

Since the second sleeve-shaped member 21 is not manipulated during the transition from the first functional state into the second functional state, the first retaining region of a stent housed in the catheter tip 10-2 with the heart valve prosthesis fastened to it would continue to be housed in its folded together state in the sleeve-shaped element of the second sleeve-shaped member 21.

The positioning hoops of a stent housed in the catheter tip 10-2 released in the second functional state of the catheter tip 10-2 are opened as a result of the radial forces acting on them and can thus be positioned in the pockets of the insufficient native heart valve. Following appropriate positioning of the positioning hoops of the stent in the pockets of the native heart valve, the catheter tip 10-2 is transferred from the second functional state shown in FIG. 13*b* into the third functional state shown in FIG. 13*c*. This is done my manipulation of the second operating means 81 of the handle, after the securing element 89 associated with the second operating means 81 has been removed.

On actuation of the second operating means 81 of the handle, the second sleeve-shaped member 21 of the catheter tip 10-2 associated with the second operating means 81 is moved relative to the stent holder 15 by a previously established longitudinal displacement stroke defined with the second operating means 81 in a distal direction, thus away from the handle 70-2. The longitudinal displacement stroke acting on the second sleeve-shaped member 21 is chosen so that the sleeve-shaped member 21 no longer covers the first retaining region of a stent housed in the catheter tip 10-2 with the heart valve prosthesis fastened to it, where required, and thus releases the first retaining region of the stent. Due to the action of the radial forces, the distal retaining region of the stent with the heart valve prosthesis attached to it, where required, unfolds completely.

Since the first operating means 71 of the handle 70-2 and the associated first sleeve-shaped member 11 of the catheter tip 10-2 are not manipulated during the transition from the second functional state in accordance with FIG. 13*b* into the third functional state in accordance with FIG. 13*c*, the distal end region of the first sleeve-shaped member 11 continues to cover the retaining elements 16 of the stent holder 15, so that the engagement between the retaining elements of a stent housed in the catheter tip 10-2 and the retaining elements 16 of the stent holder 15 is secure and the proximal retaining region of the stent is in its folded-up state. This anchorage of the stent to the catheter tip 10-2 of the insertion system 100-2 allows an explantation of a stent that is already partially unfolded by returning the catheter tip 10-2 from the third functional state, by appropriate manipulation of the second operating means 81 of the handle 70-2, to the second functional state and then by suitable actuation of the first operating means 71 transfer to the first functional state.

If an explantation of the stent with the heart valve prosthesis attached to it, where required, is unnecessary, the catheter tip 10-2 is transferred from the third functional state shown in FIG. 13c into the fourth functional state shown in FIG. 13d, by turning the first operating means 71 of the handle 70-2 further from the second position to the third position after removal of the securing element 79 (locking element). This manipulation of the first operating means 71 that can be effected after removal of the securing element 79 results in a further defined movement of the first sleeve-shaped member 11 relative to the stent holder 15 of the catheter tip 10-2 in a proximal direction, thus towards the handle 70-2. The longitudinal displacement stroke executed on the first sleeve-shaped member 11 is chosen so that the distal end of the first sleeve-shaped member 11 no longer covers the retaining elements 16 of the stent holder 15, as a result of which an engagement between the retaining elements of a stent housed in the catheter tip 10-2 and the retaining elements 16 of the stent holder 15 can be released, which would also lead to a complete release of the second retaining region of the stent and a complete separation of the stent from the catheter tip 10-2 and correspondingly to a complete unfolding of the stent.

In the embodiment of the catheter tip 10-2 depicted in FIGS. 13a-e, a stent holder tube 62 is used for connecting the stent holder 15 of the catheter tip 10-2 to the body 70-2' of the handle 70-2. The stent holder tube 62 has a distal end connected to the stent holder 15, a proximal end connected to the body 70-2' of the handle 70-2 and a passageway extending through the stent holder tube 62. In addition, an extension portion 62' of the stent holder tube 62 is provided, said extension portion extending from the distal end of the stent holder 15 to a support section 63. The support section 63 may be a tapered portion which is completely accommodated in the second sleeve-shaped member 21 when the catheter tip 10-2 is in its first and second functional state (cf. FIGS. 13a, b).

Preferably, the stent holder tube 62 and its extension 62' have a cross-section less than the cross-section of the first catheter tube 32 and greater than the cross-section of the second catheter tube 42 (not shown in FIGS. 13a-e), wherein the first catheter tube 32 is disposed concentrically and coaxially with the stent holder tube 62 thereby accommodating the stent holder tube 62 such that the first catheter tube 32 is moveable relative to the stent holder tube 62. The passageway of the stent holder tube 62 shall have a diameter sufficient to accommodate the second catheter tube 42 such that the second catheter tube 42 is moveable relative to the stent holder tube 62.

FIG. 13e shows a side elevation of the embodiment of the catheter tip 10-2 in accordance with FIG. 13a-d, whereby the catheter tip 10-2 is in its state after releasing a stent housed in the catheter tip 10-2 and ready to be removed again from the body of the patient. In this state of the catheter tip 10-2, the first sleeve-shaped member 11 is pushed by manipulation of the first operating means 71 of the handle 70-2 such that the first sleeve-shaped member 11 is in its most distal position, in which the distal end of the first sleeve-shaped member 11 abuts against the proximal end of the second sleeve-shaped member 21 without any gap or step there between. For securing this gap and step free state, the distal end of the first sleeve-shaped members 11 is supported by the already mentioned support section 63.

An embodiment of an insertion system 100-1 for transapical insertion of a self-expandable cardiac valve stent into the body of a patient is described in the following with reference to FIGS. 14 to 17. FIGS. 16a-d and FIGS. 17a-d show the insertion system 100-1 of this embodiment in its four different previously definable functional states, while FIGS. 14 and 15 show the insertion system 100-1 in a side elevation and partly sectioned side elevation.

The insertion system 100-1 shown in FIGS. 14 to 17 is suitable for a transapical access to a heart valve requiring treatment, for example an aortic valve. With the insertion system 100-1, it is possible to implant a self-expandable heart valve stent transapically, thus approaching from the apex of the heart, in the body of a patient. To this end, the insertion system 100-1 has a catheter shaft 30-1, by means of which the heart valve stent not shown explicitly in FIGS. 14 to 17 can be introduced in its folded-up state into the body of the patient.

In the insertion system 100-1 according to FIGS. 14 to 17, a catheter tip 10-1 is provided at the distal end region of the catheter shaft 30-1, in which the heart valve stent to be implanted into the body of the patient can be housed. At the proximal end region of the catheter shaft 30-1, a handle 70-1 is provided, with which the catheter tip 10-1 can be manipulated.

In detail, the catheter tip 10-1 of the transapical insertion system has a stent holder 15 by means of which the second retaining region of the stent to be implanted into the body of the patient with the catheter tip 10-1 can be releasably fixed. Further, the catheter tip 10-1 comprises a housing portion for accommodating at least the first retaining region of the stent. In detail, the housing portion consists of a first housing portion 11 and a second housing portion 21.

In the insertion system 100-1 designed for transapical access, it is provided that the first housing portion 11 of the catheter tip 10-1 is in the form of a stent sheath, which is connected to the distal end of tip 25 of the catheter tip 10-1, with its opening pointing in the direction of the proximal end region of the catheter tip 10-1. The first housing portion 11, in the form of a stent sheath, forms the outer circumferential surface of the catheter tip 10-1 when this—as shown, for example, in FIG. 17a—is in its closed state.

In the insertion system 100-1 designed for a transapical access, the second housing portion 21 of the catheter tip 10-1 is in the form of a stent funnel, whose opening points in the direction of the distal end tip 25 of the catheter tip 10-1. The retaining hoops of the stent and the heart valve prosthesis, where required, fastened to the retaining hoops, can be mounted in the interior of the second housing portion 21 in the form of the stent funnel. The second housing portion 21 in the form of the stent funnel can be telescopically accommodated by the first housing portion 11 in the form of the stent sheath, when the catheter tip 10-1 (see FIG. 17a) is in the closed state. In this way, the positioning hoops of the stent are located between the outer circumferential surface of the stent funnel and the inner circumferential surface of the stent sheath when a heart valve stent is mounted in the catheter tip 10-1.

In relation to the handle 70-1 of the transapical insertion system 100-1, it is provided that this has a first operating means 71 associated with the first housing portion 11 and a second operating means 81 associated with the second housing portion 21. The first operating means 71 cooperates with the first housing portion 11 of the catheter tip 10-1 so that, on actuation of the first operating means 71, a previously definable longitudinal displacement of the first housing portion 11 can be effected relative to the stent holder 15. In addition, the second housing portion 81 of the handle 30-1 cooperates with the second housing portion 21 of the catheter tip 10-1 so that, on actuation of the second operating means 81, a previously definable longitudinal displacement of the second housing portion 21 of the catheter tip 10-1 can be effected relative to the stent holder 15.

Figure 17A:
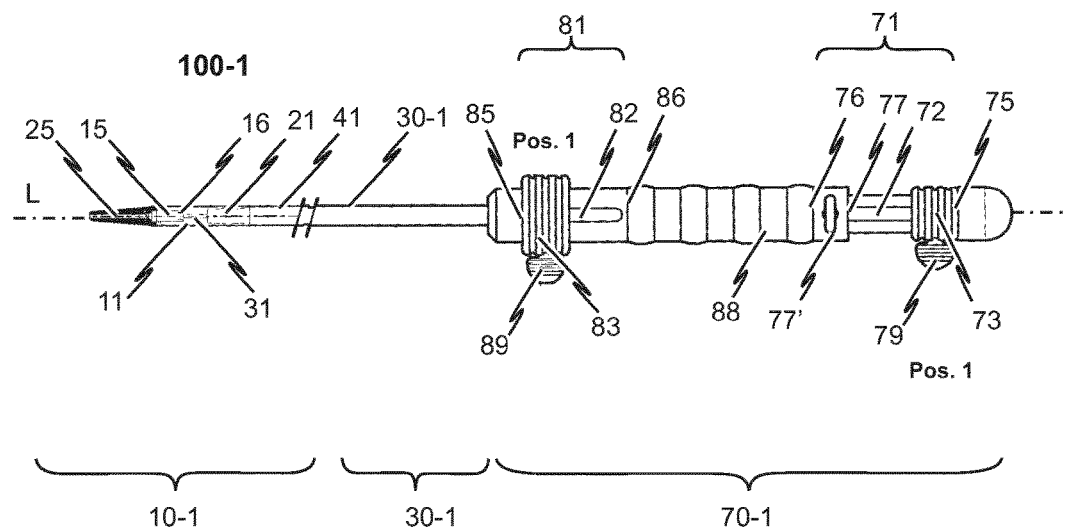
Figure 17B:
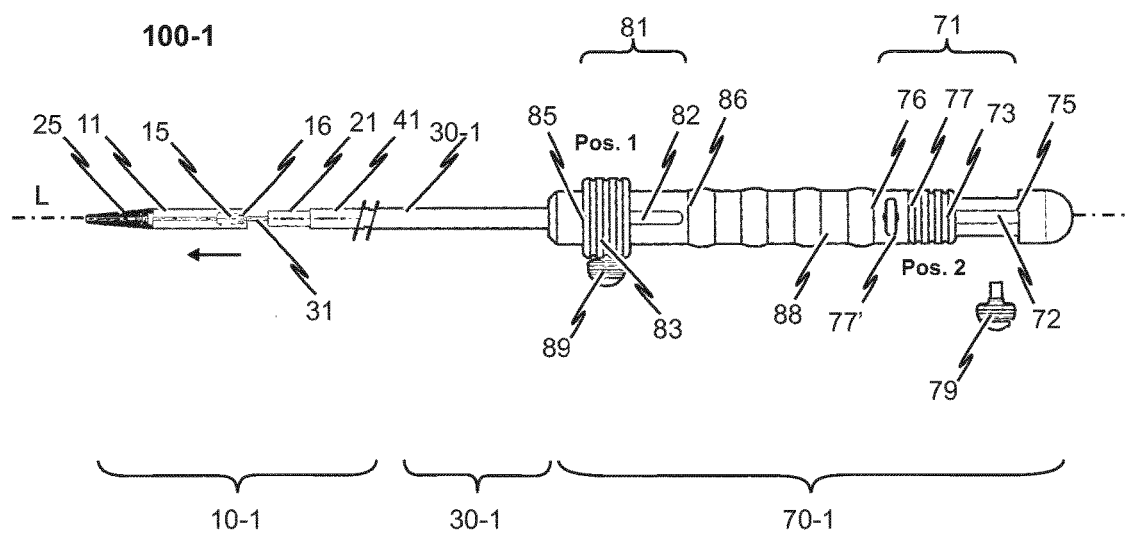
Figure 17C:
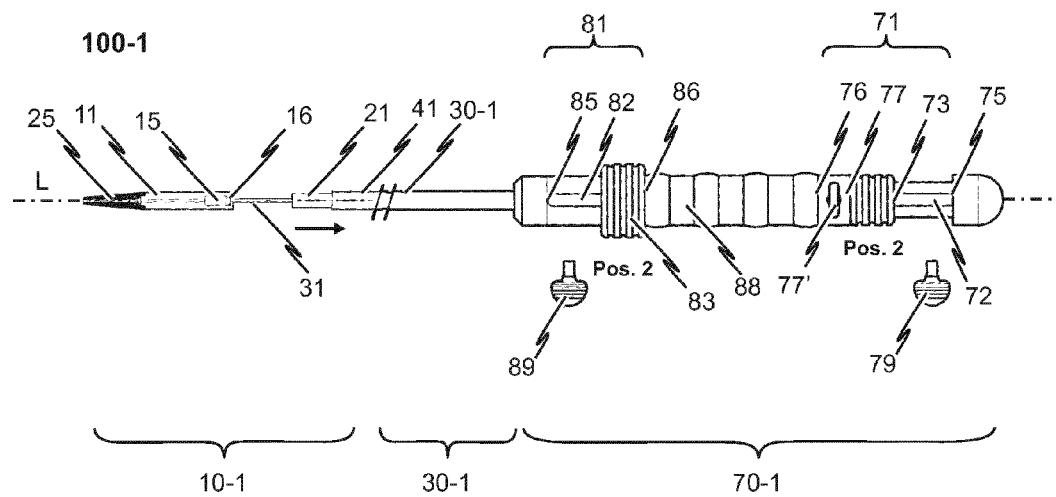
Figure 17D:
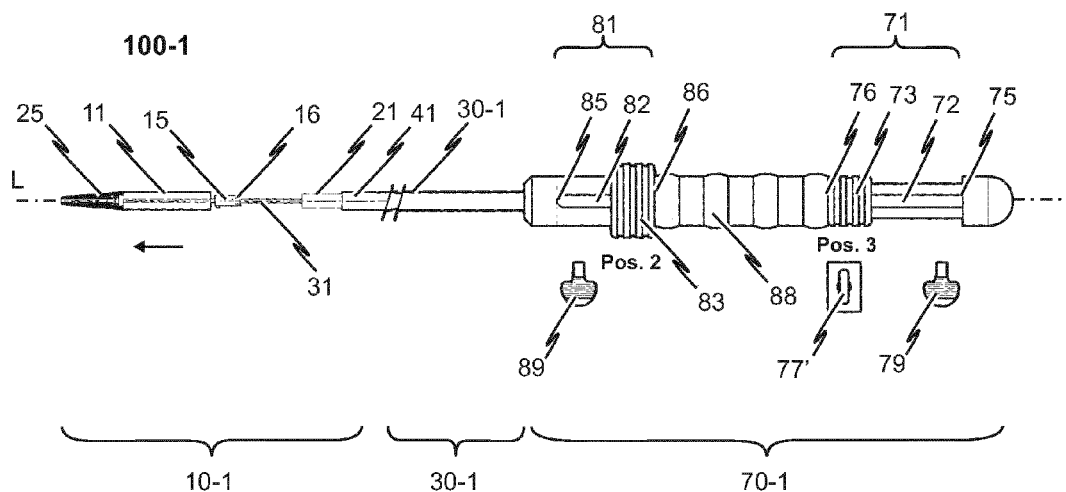

With the insertion system 100-1 designed for transapical access, on actuation of the first operating means 71 of the handle 70-1, the first housing portion 11 of the catheter tip 10-1 can be moved in the longitudinal direction L of the catheter tip 10-1 relative to the stent holder 15, whereby the movement of the first housing portion 11 takes place in a distal direction, thus away from the handle, to open the catheter tip 10-1 or to release a stent mounted in the catheter tip 10-1 (see FIGS. 17*b* and 17*d*).

With the insertion system designed for transapical access, on actuation of the second operating means 81 of the handle 70-1, the second housing portion 21 of the catheter tip 10-1 can likewise be moved in the longitudinal direction L of the catheter tip 10-1 relative to the stent holder 15. In particular, the second housing portion 21 is moved in the direction of the distal end tip 25 of the catheter tip 10-1 to release a stent mounted in the catheter tip 10-1 (see FIG. 17*c*).

In relation to the stent holder 15 forming part of the catheter tip 10-1, it is provided in the embodiment of the transapical insertion system 100-1 shown in FIGS. 14 to 17 that the stent holder 15 is in the form of a crown with a total of three projecting elements 16. The projecting elements 16 of the crown are complementary to retaining elements, for example implemented as retaining rings, which are implemented on a retaining region of a stent mounted or mountable in the catheter tip 10-1. Thus it is possible for the projecting elements 16 of the crown to form a releasable engagement with the retaining elements of the stent, therefore, in order to fasten the stent releasably to the stent holder 15 of the catheter tip 10.

As already explained, with the transapical insertion system 100-1 it is provided that the first housing portion 11 of the catheter tip 10-1 is designed as a tubular or sleeve-shaped element, which acts as stent sheath and which is connected permanently to the end tip 25 of the catheter tip 10-1. The distal-side end tip 25 of the catheter tip 10-1 is formed from the most inelastic material possible, such as a relatively strong plastic material or metal. A bonded and/or positive locking connection is particularly suitable for the joint between the end tip 25 and the first housing portion 11 in the form of the stent sheath.

On the other hand, the distal-side end tip 25 of the catheter tip 10-1 is connected to the first operating means 71 of the handle 70-1 by means of a first force transmission means 31 in the form of an inner catheter. This has the result that, on actuation of the first operating means 71, the distal-side end tip 25 of the catheter tip 10-1 can be displaced together with the first housing portion 11 permanently attached to it relative to the stent holder 15 in the longitudinal direction L of the catheter tip 10-1.

As can be seen particularly in the illustration in FIG. 15, in the transapical insertion system 100-1 an inner catheter in the form of a cannula tube acts as first force transmission means 31, which allows the transmission of tensile and shear forces from the first operating means 71 of the handle 70-1 to the distal-side end tip 25 and consequently to the first housing portion 11 of the catheter tip 10-1. In detail, the inner catheter in the form of a cannula tube (first force transmission means 31) extends from a first injection adapter 99*a* provided at the proximal end of the handle 70-1 in the direction of the longitudinal axis L of the insertion system 100-1 to the distal-side end tip 25 and is used to receive and guide a guide wire not explicitly shown in FIGS. 14 to 17, as well as for draining and supplying fluid from or to the catheter tip 10-1, as can be necessary where applicable during insertion of the catheter tip 10-1 into the body of the patient.

In the transapical insertion system 100-1, the second housing portion 21 of the catheter tip 10-1 is in the form of a stent funnel configured as a tubular or sleeve-shaped element. The stent funnel (second housing portion 21) is connected by means of a second force transmission means 41 to the second operating means 81 of the handle 70-1 so that, on actuation of the second operating means 81, tensile or shear forces can be transmitted to the second housing portion 21 of the catheter tip 10-1. This allows the second housing portion 21 in the form of a stent funnel to be displaced relative to the stent holder 15 on one side and the first housing portion 11 on the other side in the longitudinal direction L of the catheter tip 10-1.

As already indicated, with the transapical insertion system 100-1, it is preferred that the first housing portion 11 of the catheter tip 10-1 is in the form of a stent sheath, for example a long extended capillary. The second housing portion 21 is preferably implemented as a stent funnel, also in the form of a long extended capillary, for example. The inside diameter of the tubular or sleeve-shaped first housing portion 11 should be chosen to be larger than the outside diameter of the similarly tubular or sleeve-shaped second housing portion 21, so that the second housing portion 21 can be accommodated telescopically inside the first housing portion 11.

In the embodiment of the transapical insertion system 100-1 shown in FIGS. 14 to 17, the stent holder 15 is in the form of a cylindrical element, which is equipped with suitable retaining elements 16. The retaining elements 16 are used to form a releasable connection with a retaining region of a heart valve stent not shown in the representations in FIGS. 14 to 17, when this heart valve stent is mounted in the catheter tip 10-1. It is also possible to configure the retaining elements 16 of the stent holder 15 so that these can form a releasable engagement with the retaining elements of the stent.

In the representations in FIGS. 14 to 17, the retaining elements 16 on the stent holder 15 are designed as projecting elements which can be brought into engagement with corresponding retaining rings of complementary form. However, it would also be possible to form the retaining elements 16 of the stent holder 15 as depressions or recesses which are introduced into the cylindrical body of the stent holder 15 and which are designed to accommodate corresponding retaining elements of complementary form of the heart valve stent.

In the transapical insertion system 100-1 in accordance with the embodiment shown in FIGS. 14 to 17, the stent holder 15 is permanently located relative to the handle 70-1 so that, for example, when the handle 70-1 is rotated about the longitudinal axis L of the insertion system 100-1, the stent holder 15 participates in this rotary movement. It is possible here for the stent holder 15 to be connected with the handle 70-1 by means of a connecting means permanently attached to the body 70' of the handle 70-1.

More detail is given in the following of an embodiment of a catheter shaft 30-1 for a transapical insertion system 100-1 with reference to FIGS. 15, 19, 21 and 22.

The catheter shaft 30-1 is used to introduce an expandable heart valve stent in its folded-up state into the body of the patient. At the distal end region 39 of the catheter shaft 30-1 is the catheter tip 10-1, in which the heart valve stent is or can be accommodated with the aid of the first and second manipulable housing portion 11, 21. At the proximal end region 49 of the catheter shaft 30-1 is a handle 70-1, yet to be described in more detail, which is used for appropriate manipulation of the manipulable housing portions 11, 21 of the catheter tip 10-1, to allow a stepwise release of the heart valve stent from the catheter tip 10-1.

In detail, the catheter shaft 30-1 exhibits at least one first force transmission means 31 and at least one second force transmission means 41, whereby the first force transmission means 71 of the handle 70-1 connects to the first housing portion 11 of the catheter tip 10-1. The second operating means 81 of the handle 70-1 is connected by means of the second force transmission means 41 with the second housing portion 21 of the catheter tip 10-1.

In the embodiment of the catheter shaft 30-1 shown in FIGS. 15, 19, 21 and 22, the second force transmission means 41 is configured as a tubular element, the proximal end of which is connected to the second operating means 81 of a handle 70-1. The distal end of the second force transmission means 41 in the form of an outer catheter merges into the second housing portion 21 of the catheter tip 10-1 in the form of the stent funnel in a region between the catheter shaft 30-1 and the catheter tip 10-1. It is possible to configure the second housing portion 21 in the form of the stent funnel and the second force transmission means 41 in the form of the outer catheter in one piece.

However, there is also of course the possibility of joining the proximal end of the second housing portion 21 in the form of the stent funnel to the distal end of the second force transmission means 41 in the form of the outer catheter, for example by bonding them using an adhesive.

So that there is no step or edge in the transition region between the catheter shaft 30-1 in the catheter tip 10-1 which can lead to an injury to the tissue of the apex of the heart during the insertion of the catheter shaft 30-1 (i.e. with the catheter tip 10-1 in the closed state), it is preferable that the outside diameter of the second force transmission means 41 in the form of the outer catheter is essentially identical to the outside diameter of the first housing portion 11 in the form of the stent sheath. This can be achieved by providing at least one step between the second housing portion 21 in the form of the stent funnel and the second force transmission means 41 in the form of the outer catheter.

In the embodiment of the catheter shaft 30-1 shown in FIGS. 15, 19, 21 and 22 for the transapical insertion system 100-1, a catheter in the form of a cannula tube is used as first force transmission means 31, extending in the implementation, for example according to the illustrations in FIGS. 14 to 17, from the proximal end region of the handle 70-1 to the distal-side end tip 25 of the catheter tip 10-1.

The first force transmission means 31 implemented as a cannula tube can be connected at the proximal end of the insertion system 100-1 to a (first) injection adapter 99*a*; it would be possible, for example, to form the proximal end of the first force transmission means 31 as the injection adapter 99*a*.

When the insertion system 100-1 is used for implanting an expandable heart valve stent accommodated in the catheter tip 10-1 at the implantation location in the heart, it is preferable that a guide wire (not explicitly shown in the drawings) is passed through the first force transmission means 31 implemented as a cannula capillary.

As already indicated, it is provided with the transapical insertion system 100-1 that the stent to hold 15 of the catheter tip 10-1 is preferably permanently attached to the handle 70-1 or the body 70' of the handle 70-1 so that, in relation to the stent holder 15, in particular the degree of freedom of rotational movement about the longitudinal axis L of the insertion system 100-1 and a degree of freedom of movement in the direction of the longitudinal axis L of the insertion system 100-1 are frozen. Thus the stent holder 15 cannot be moved at least in the longitudinal direction L of the insertion system 100-1 relative to the body 70' of the handle 70-1. Likewise, a rotational movement of the stent holder 15 about the longitudinal axis L of the handle 70-1 is excluded.

The stent holder 15 is fixed relative to the handle 70-1, for example, by means of a connecting means 42 permanently attached to the body 70' of the handle.

In a preferred implementation of the catheter shaft 30-1 used with the transapical insertion system 100-1, it is provided that the second force transmission means 41, which connects the second operating means 82 of the handle 70-1 to the second housing portion 21 in the form of the stent funnel, is implemented as an outer catheter, while the first force transmission means 41 implemented as a cannula capillary is passed through the interior of the outer catheter (second force transmission means 41). A further cannula capillary, for example, can be considered as connecting means 42 to fix the stent holder 15 relative to the handle 70-1, running through the interior of the second force transmission means 41 in the form of the outer catheter. The first force transmission means 31 implemented as a cannula capillary is then passed through the interior of the connecting means 42 in the form of a cannula capillary. Alternatively, as connecting means, it is possible to use a further cannula capillary which runs both through the outer catheter capillary and through the first force transmission means 41 implemented as cannula capillary.

Thus the first housing portion 11 of the catheter tip 10-1 of the transapical insertion system 100-1 is designed to accommodate the second housing portion 21 of the catheter tip 10-1 with the functional components of the stent mounted in it, for example with retaining hoops of the stent.

In relation to the embodiment of a handle 70-1 for the transapical insertion system 100-1 in accordance with FIGS. 14 to 20, it is preferably provided that the first operating means 71, which cooperates with the first housing portion 11 of the catheter tip 10 by means of the first force transmission means 31, has a first slide 74 guided in a first guide 72 and functionally connected to a first pusher 73. This first slide 74 cooperates with the first housing portion 11 of the catheter tip 10-1 associated with the first operating means 71 by means of the first force transmission means 31 so that, on actuation of the first operating means 71, tensile and shear forces can be transmitted from the first slide to the first housing portion 11 (stent sheath) of the catheter tip 10-1.

With the handle 70-1 for the transapical insertion system 100-1, a second operating means 81 is further provided, which is functionally connected by means of the second force transmission means 41 to the second housing portion 21 of the catheter tip 10-1. The second actuating means 81 has a second slide 84 guided in a second guide 82 and functionally connected to a second pusher 83, whereby this second slide 84 is functionally connected with the second housing portion 21 of the catheter tip 10-1 associated with the second operating means 81 by means of the second force transmission means 41 so that, on actuation of the second operating means 81 and, in particular, on actuation of the second slide 84, force can be directly transmitted from the second slide 84 to the second housing portion 21 (stent funnel) of the catheter tip 10.

In relation to the second actuating means 81 of the handle 70-1 used with the insertion system 100-1 shown in FIGS. 14 to 17, it is further provided that the handle 70-1 has a first and a second stop 85, 86, each associated with the second operating means 81 and designed to define the longitudinal displacement stroke of the second housing portion 21 (stent funnel) of the catheter tip 10-1 that can be effected by actuation of the second operating means 81. In particular, the displacement distance (displacement stroke) that can be realised with the second pusher 83 of the second operating means 81 is correspondingly defined.

It is further provided with the transapical insertion system 100-1 in accordance with the first embodiment that the handle 70-1 has a first and a second stop 75, 76, which are each associated with the first operating means 71 and which define the overall longitudinal displacement stroke of the first housing portion 11 (stent sheath) of the catheter tip 10-1 that can be effected on actuation of the first operating means 71.

In addition to the first and second stops 75, 76 associated with the first operating means 71, the handle 70-1 in the embodiment of the transapical insertion system 100-1 shown in FIGS. 14 to 17 comprises a further, third stop 77 associated with the first operating means 71, which cooperates with the first stop 75 on one side and the second stop 76 on the other so that, on actuation of the first operating means 71, a stepwise longitudinal displacement of the first slide 74 on the first guide 72 can be effected, consisting of two separate steps, and consequently a stepwise longitudinal displacement, consisting of two separate steps, of the first housing portion (stent sheath) of the catheter tip 10-1 relative to the stent holder 15 and crown of the catheter tip 10-1.

While the third stop 77 associated with the first operating means 71 is suitably positioned on the first guide 72 between the first and second stop 75, 76 associated with the first operating element 71, the first and third stop 75, 76 on one side and the second and third stop 76, 77 on the other define the longitudinal displacement stroke of the first housing portion 11 (stent sheath) of the catheter tip 10-1 on each separate step that is effected on actuation of the first operating means 71.

In the embodiment of the trans-apical insertion system 100-1 shown in FIGS. 14 to 17, it is provided that the third stop of the handle 70-1, specified previously, which is associated with the first operating means 71, is in the form of a stop element 77' releasably fastened on the first guide 72 of the first slide 74.

Finally, it is further provided for the handle 70-1 of the transapical insertion system 100-1 shown in FIGS. 14 to 17 that the first operating means 71 and the second operating means 81 are each associated with at least one securing element 79, 89. In particular, the first securing element 79 associated with the first operating means 71 of the handle 70-1 is implemented as an element that can be removed from the first slide 74 or from the first pusher 72 of the first operating means 71. This securing element 79 cooperates with the first slide 74 so that the longitudinal displacement of the first housing portion 11 (stent sheath) of the catheter tip 10-1 that can be effected with the first operating means 71 can be blocked.

The second securing element 89, which is associated with this second operating means 84, is similarly implemented as an element that can be removed from the second slide 84 or from the second pusher 83 of the second operating means 81 which cooperates with the second operating means 81 so that a longitudinal displacement of the second housing portion 21 (stent funnel) of the catheter tip 10-1 that can be effected with the second operating means 80 can be blocked.

The four different functional states realisable with a transapical insertion system 100-1 are described in the following, initially with reference to the drawings in FIGS. 17a to 17d.

FIG. 17a shows an embodiment of a transapical insertion system 100-1 in its first functional state, in which the catheter tip 10-1 is completely closed. As already indicated, a self-expandable heart valve stent (not shown in FIG. 17a) can be housed in the catheter tip 10-1 in the corresponding housing portion 11, 12 of the catheter tip 10-1.

In the first functional state in accordance with FIG. 17a, the respective pushers 73 and 83 and the respective slides 74 and 84 of the operating means 71 and 81 are located in their first position (Pos. 1). In particular, the second pusher 83 of the second operating means 81 abuts the first stop 85 provided on the catheter tip-side end of the second guide 82. In this first position, the second pusher 83 is fixed by the securing element 83 so that a longitudinal displacement of the second pusher 83 and the slide 84 of the second operating means 21 on the second guide 82 in the direction of the second stop 86 associated with the second operating means 21 is blocked.

In the first functional state in accordance with FIG. 17a, the first pusher 73 and the first slide 74 of the first operating means 71 are also in the first position (Pos. 1) at the first stop 75 of the first operating means 71. The first stop 75 of the first operating means 71 is located at the proximal end of the first guide 72. In this first position, the first pusher 74 and the first slide 74 of the first operating means 71 is anchored with the aid of the second securing element 89, to block a longitudinal displacement of the first pusher 73 and the first slide 74 along the first guide 72 in the direction of the catheter tip 10.

As already indicated, the catheter tip 10-1 of the insertion system 100-1 is in a completely closed state in the first functional state of the transapical insertion system 100-1 (see FIG. 17a). In this state, the first and second housing portion 11, 12 of the catheter tip 10-1, in the form of sleeve-shaped elements interlock telescopically. The respective inside and outside diameters of these sleeve-shaped elements are appropriately coordinated with one another. As is described in detail in the following, the sleeve-like first and second housing portion 11, 21 of the catheter tip 10-1 are coordinated with one another in relation to their respective inside and outside diameters so that the folded-up retaining hoops of the stent mounted or to be mounted in the catheter tip 10 with the heart valve prosthesis fastened to them can be held in the second housing portion 21 in the form of the stent funnel. The folded-up positioning hoops of the stent are housed between the second housing portion 21 in the form of the stent funnel and the first housing portion 11 in the form of the stent sheath and are held in their folded form.

The catheter tip 10-1 can be inserted into the body of the patient in the first functional state of the insertion system 100-1 (see FIG. 17a) and can be advanced to the desired implantation location. With the transapical insertion system 100-1 in accordance with the first embodiment, access to the implantation location, i.e. to the diseased heart, can be carried out transapically, thus approaching from the apex of the heart, since the stent holder 15 is located at the distal region of the catheter tip 10-1, while proximal from this is the second housing portion 21 (stent funnel) of the catheter tip 10-1.

FIG. 17b shows the insertion system 100-1 in accordance with FIG. 17a in its second functional state. This second functional state is discontinued as soon as the catheter tip 10-1 has reached the implantation location in the body of the patient. As is explained in detail in the following, with reference to FIGS. 17b to 17d, when the catheter tip 10-1 has reached the implantation location, the appropriate manipulations of the individual housing portion 11, 21 of the catheter tip 10-1 are carried out. These manipulations are necessary to release the stent housed in the catheter tip 10-1 in the steps in accordance with a previously defined sequence of events. How this stepwise release of the stent mountable or mounted in the catheter tip 10 can be implemented with the aid of the insertion system 100-1 through directed movements of the individual housing portion 21, 11 of the catheter tip 10-1 is described in detail in the following.

After the catheter tip 10-1 has reached the implantation location, the insertion system 100-1 is transferred from the first functional state shown in FIG. 17a to the second functional state shown in FIG. 17b by actuation of the first operating means 71. In particular, the securing element 79 associated with the first operating means 71 is removed, as a result of which blocking of the capacity of the first pusher 73 and the first slide 74 for longitudinal displacement is removed.

After removal of the securing element 79 from the first operating means 71 and after the removal of the block on the first pusher 73 and the first slide 74, the first pusher 73 and the first slide 74 are moved along the first guide 72 in the direction of the catheter tip 10-1 from the first position (Pos. 1) to the second position (Pos. 2). The second position (Pos. 2) is determined by the third stop 77 located between the first stop 75 (Pos. 1) and the second stop 76.

The first housing portion 11 (stent sheath) of the catheter tip 10-1 associated with the first operating means 71 is moved by an actuation of this type of the first operating means 71 in a distal direction relative to the stent holder 15. The amount of movement, i.e. the degree of longitudinal displacement of the first housing portion 11 (stent sheath) of the catheter tip 10-1 relative to the stent holder 15, is determined by the longitudinal displacement stroke between the first position (Pos. 1) and the second position (Pos. 2) that can be effected with the first pusher 73 and the first slide 74.

The resulting movement of the first mounting area 11 (stent sheath) of the catheter tip 10-1 relative to the stent holder 15 has the result that the telescopic-like overlapping between the two sleeve-shaped first and second housing portion 11, 21 is removed. For this purpose, the amount of movement of the first housing portion 11 relative to the stent holder 15 and relative to the second housing portion 21 and, consequently, the longitudinal displacement stroke that can be effected with the first pusher 73 and the first slide 74 is chosen so that the sleeve-shaped first housing portion 11 (stent sheath) no longer surrounds the second housing portion (stent funnel) telescopically but nevertheless covers the stent holder 15 and particularly the fixing elements 16 of the stent holder. As a result, in this second functional state of the insertion system 100-1 (see FIG. 17b), the heart valve stent mounted or mountable in the catheter tip 10-1 is kept anchored to the stent holder 15 of the catheter tip 10-1.

As is described in detail in the following with reference to the drawings of FIGS. 23a to 23d, in the second functional state of the insertion system 100-1 (see FIG. 17b) the retaining hoops 153 of a stent 150 mounted in the catheter tip 10-1 with a heart valve prosthesis fastened to them are held by the second housing portion 21 (stent funnel) of the catheter tip 10-1, still in their folded-up form, since these components of the stent 153 are accommodated unchanged from the first functional state in accordance with FIG. 17a in their folded-up form in the second housing portion 21 (stent funnel) of the catheter tip 10-1.

Likewise, the engagement between the retaining elements 151 provided on the stent 150 and the corresponding retaining elements 16 of the stent holder 15 in a complementary configuration is secured by means of the proximal end of the first housing portion 11, so that the second retaining region of the stent 150, on which its retaining elements 151 are provided, is also (still) in its folded-up state with the aid of the first housing portion 11. As already explained, this is made possible since the proximal end of the first housing portion 11 still covers the stent holder 15 with the retaining elements 16.

On the other hand, however, the first housing portion 11 (stent sheath) of the catheter tip 10-1 has been moved by manipulation of the first operating means 71 away from the handle 70 in the distal direction relative to the stent holder 15 and the second housing portion 21 (stent funnel), so that the positioning hoops 154 of the stent 150 mounted or mountable in the catheter tip are no longer covered by the first housing portion 11 (stent sheath). Expressed in another way, this means that, by the longitudinal displacement of the first housing portion 11 (stent sheath) effected in the second functional state of the insertion system 100-1, the telescopic-like housing of the positioning hoops 154 of the stent 150 between the first and second housing portion 11, 21 of the catheter tip 10-1 in the first functional state (see FIG. 17a) is ended. Thus in the second functional state of the insertion system 100-1 (see FIG. 17b) the first housing portion 11 (stent sheath) no longer undertakes the function of retaining the positioning hoops 154 of the stent 150 in their folded-up form, so that these are released and correspondingly can unfold.

As can be seen in detail in the illustrations in FIGS. 23a to 23d, the positioning hoops 154 of the stent 150 are opened after having been released because of the radial forces acting in a radial direction. These opened positioning hoops 154 can be positioned in the pockets of the native heart valve.

After the positioning hoops 154 of the stent 150 have been positioned in the pockets of the native heart valve, the insertion system 100-1 is transferred from the second functional state shown in FIG. 17b to the third functional state shown in FIG. 17c. This is done by removing the securing element 89 associated with the second operating means 81 of the handle 70-1 and consequently the longitudinal displaceability of the second push 83 and the second slide 84 is restored.

After the securing element 89 has been removed, the second pusher 83 and the second slide 84 are displaced along the second guide 82 from the first position (Pos. 1) to the second position (Pos. 2). The longitudinal displacement stroke that can be effected is defined by the second stop 86 of the second operating means 81, which is located at the proximal end of the second guide 82.

As a result of the manipulation of the second operating means 21, the second housing portion 21 (stent funnel) of the catheter tip 10-1 associated with the second operating means 21 is moved relative to the stent holder 15 of the catheter tip 10-1 and also relative to the first housing portion 11 (stent sheath) in the proximal direction towards the handle 70. The movement stroke of the second housing portion 21 thus corresponds to the longitudinal displacement stroke effected between the second pusher 83 and the second slide 84. This movement of the second housing portion 21

(stent funnel) relative to the stent holder 15, on the one hand, and the first housing portion 11 on the other—by a suitable choice of the longitudinal displacement stroke that can be realised with the second operating means 81—has the result that the second housing portion 21 no longer covers the first retaining region of the stent 150 with the retaining elements 151 and consequently the retaining hoops 153 of the stent 150 with the heart valve prosthesis fastened to them are released. Due to the radial forces acting on the retaining region, release of the retaining elements 151 of the stent 150 leads to a complete unfolding of the retaining region of the stent 150 (see FIG. 23*d*).

Since the proximal end of the first housing portion 11 (stent sheath) of the catheter tip 10-1 still covers the stent holder 15 in the third functional state of the insertion system 100-1 (see FIG. 17*c* or FIG. 23*c*), though, the engagement between the retaining elements 16 of the stent holder 15 and the retaining elements 151 of the stent 150 remains secure, so that the stent 150, in spite of the unfolding of its retaining hoops 153, remains functionally connected to the catheter tip 10-1 of the insertion system 100-1 and an explantation of the stent 150 with the heart valve prosthesis attached to it is still possible. They explantation would take place according to a corresponding reverse sequence, whereby the first the insertion system 100-1 is transferred from the third functional state to the second functional state and then into the first functional state.

After the complete release of the retaining hoops 153 of the stent 150 and after a check of the function of the unfolded heart valve prosthesis, if there are no abnormalities during the check, the stent 150 is fully released. This is done by transferring the insertion system 100-1 from its third functional state shown in FIG. 17*c* to the fourth functional state shown in FIG. 17*d*.

In the fourth functional state, the stop element 77' provided between the first stop 75 and the second stop 76 on the first guide 72 of the first operating means 71, which defines the third stop 77 in the second functional state in accordance with FIG. 17*b*, has been removed. As a consequence, the first pusher 73 and the first slide 74 of the first operating means 71 can be moved further in the direction of the catheter tip 10-1 on the first guide 72 from the second position (Pos. 2) to the third position (Pos. 3). This third position (Pos. 3) is defined by the second stop 7*b* at the distal end of the first guide 72. Thus a previously defined (further) displacement of the first slide 74 takes place, as a result of which the first housing portion 21 (stent sheath) associated with the first operating means 71 is moved by the longitudinal displacement stroke effected with the further manipulation of the first operating means 71 relative to the stent holder 15 in the distal direction further away from the handle 70-1.

The longitudinal displacement stroke effected with the further manipulation of the first operating means 71 is chosen appropriately so that, with the movement of the first housing portion 11 (stent sheath) relative to the stent holder 15, cover of at least the retaining elements 16 of the stent holder 15 with the proximal end region of the first housing portion 11 is eliminated. Removal of the cover of the retaining elements 16 of the stent holder 15 with the first housing portion 11 has the consequence that the engagement between the retaining elements 151 provided on the stent 150 and the retaining elements 16 of the stent holder 15 is lost, leading to a now complete release of the stent 150 as well (see FIG. 23*d*) and correspondingly to a complete unfolding of the heart valve prosthesis attached to the stent 150.

FIGS. 3*a* to 3*d* show the transapical insertion system 100-1 for different functional states previously defined with reference to FIGS. 17*a* to 17*d*, whereby the depiction now starts with the fourth functional state (see FIG. 3*a*) and ends via the third functional state (see FIG. 3*b*) and the second functional state (see FIG. 3*c*) with the first functional state (see FIG. 3*d*). The sequence shown in FIG. 3 is used to make clear a procedure with which a stent 150 shown for example in FIG. 23 in the catheter tip 10-1 of the transapical insertion system 100-1 is used.

The loading process, as is shown in steps in FIGS. 3*a* to 3*d*, corresponds in reverse to the procedure shown in FIGS. 17*a* to 17*d* for releasing a stent 150 accommodated in the catheter tip 10-1 of the transapical insertion system 100-1. To avoid repetition, reference will be made to the details in FIGS. 17*a* to 17*d*.

Figure 16A:
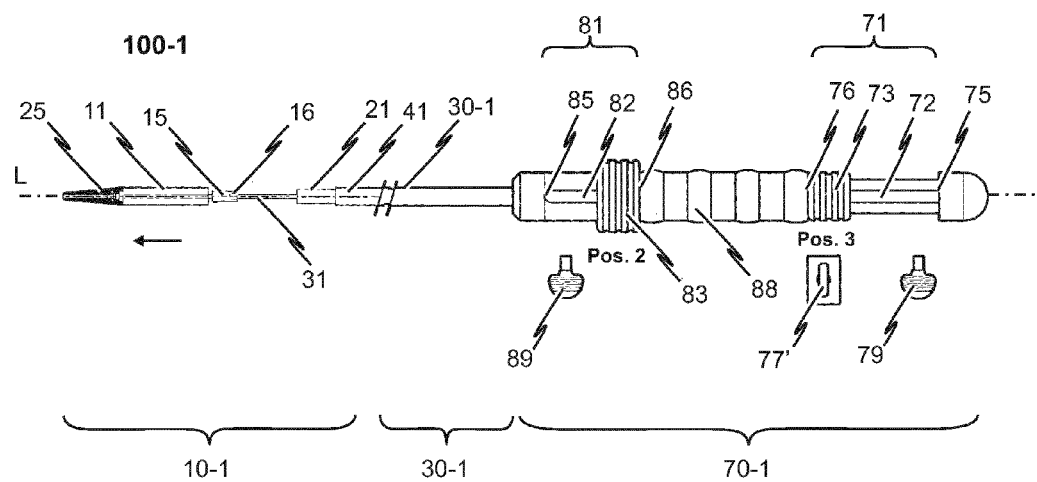
Figure 16B:
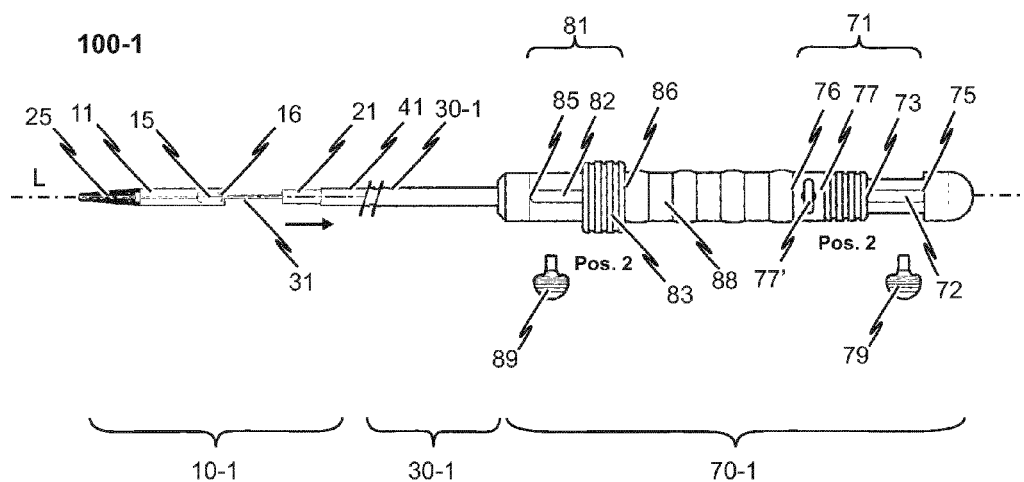
Figure 16C:
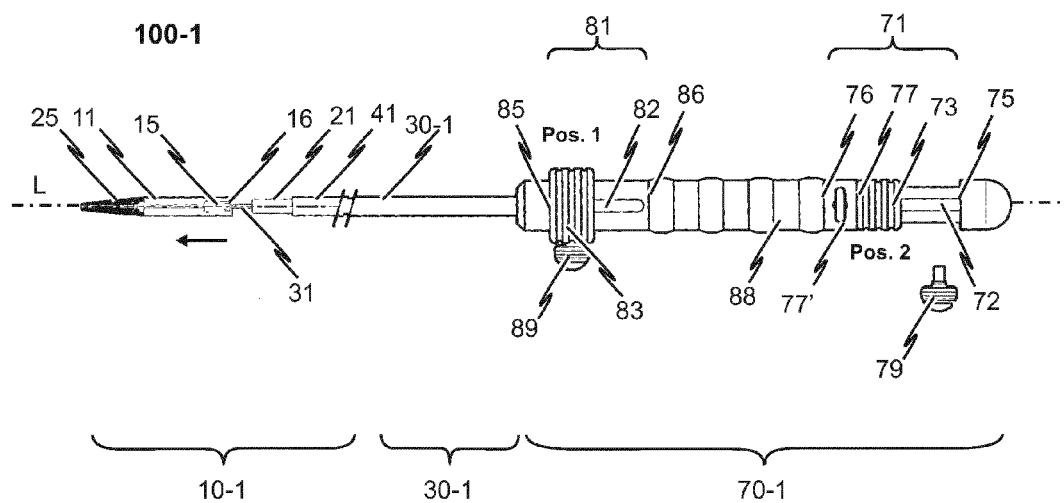
Figure 16D:
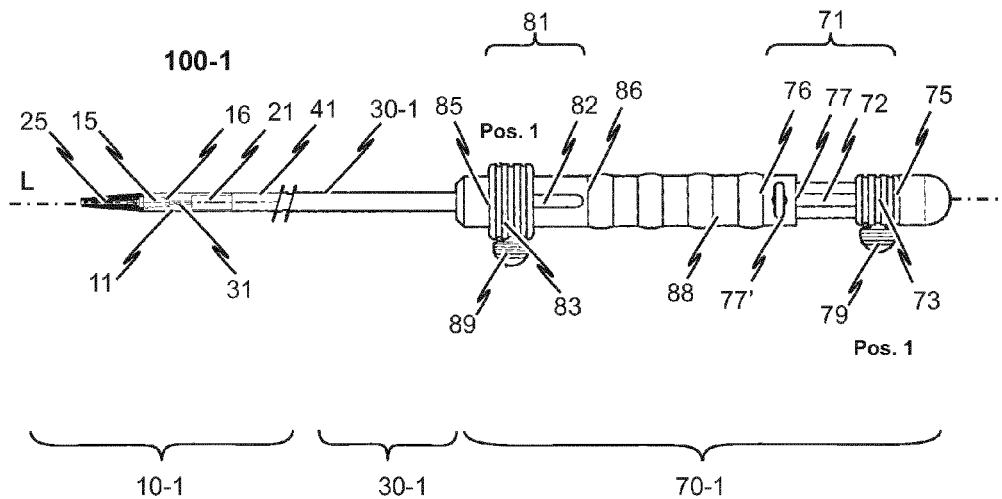

FIG. 14 shows an embodiment of a transapical insertion system 10-1 in an enlarged representation in its first functional state in accordance with FIG. 16*d* and FIG. 17*a*. In particular, separate longitudinal displacement strokes that can be effected with the first and second operating means 71 and 81 are indicated in FIG. 14. It can be seen that the longitudinal displacement stroke of the second operating means 81 between the first stop 85 and the second stop 86 is a total of approx. 16 mm for the embodiment shown. It can be further seen the total longitudinal displacement stroke that can be effected with the first operating means 71 is approx. 37 mm. The overall longitudinal displacement stroke is divided by the stop element 77' provided removably on the first guide 72 into two separate displacement strokes. For the insertion system 100-1, a longitudinal displacement of 24 mm of the first housing portion 11 (stent sheath) relative to the stent holder 15 is provided for the transition from the first functional state into the second functional state. On transition from the third functional state into the fourth functional state of the insertion system 100-1, i.e. after removal of the stop element 77' from the first operating means 71, a subsequent (further) longitudinal displacement of a total of approx. 13 mm of the first housing portion 11 is provided relative to the stent holder 15.

Because of the fact that, with the transapical insertion system 100-1, the handle 70-1 has on the one hand a first and a second stop 85, 86, which are each associated with the second operating means 81 and are designed to define the total longitudinal displacement stroke of the second housing portion 21 (stent funnel) of the catheter tip 10-1 that can be effected on actuation of the second operating means 81 and, on the other hand, has a first, second and third stop 75, 76 and 77 which are each associated with the first operating means 71 and are designed to define the total longitudinal displacement stroke of the first housing portion 11 (stent sheath) of the catheter tip 10-1 that can be effected on actuation of the first operating means 71, the insertion system 100-1 is implemented so that the respective housing portion 11, 21 of the catheter tip 10-1 can be manipulated according to a previously definable sequence of events, for example to allow the release of a stent mounted or mountable in the catheter tip 10-1 at the implantation location to be carried out almost "automatically" without the doctor carrying out the treatment having to have a special skill for, in particular, positioning and fixing the stent at the implantation site.

The previously definable sequence of events for release of the stent mountable in the catheter tip 10-1 at the implantation location is obtained with the embodiment of the transapical insertion system, for example, in FIGS. 14 to 17, in particular by provision of the third stop 77 associated with the first operating means 71 in the form of a stop 77' releasably fastened on the first guide 72 of the first slide 74 forming part of the first operating means 34. This third stop 77 cooperates with the first stop 75 on one side and with the second stop 76 on the other side so that, on actuation of the second operating means 71, a stepwise longitudinal displacement of the first housing portion 11 of the catheter tip 20, consisting of two defined individual steps, can be effected relative to the stent holder 15 in the catheter tip 10-1. In particular, the first and third stop 75, 77 on one side and the second and third stop 76, 77 on the other side define the longitudinal displacement stroke of the first housing portion 11 of the catheter tip 20 that can be effected on actuation of the first operating means 71.

The longitudinal displacement strokes specified in FIG. 14 are indicative examples, which can of course be altered depending on the individual case and are particularly dependent on the size of the stent to be accommodated in the catheter tip 10-1 of the insertion system 100-1.

FIG. 15 shows the transapical insertion system 100-1 in accordance with FIG. 14 in a part-sectioned representation, to allow the mechanics of the respective operating means 71 and 81 to be explained more clearly. As is shown, the first operating means 71 exhibits the first slide 74 guided in the first guide 72 and functionally connected with the first pusher 73. This first slide 74 is functionally connected to the first housing portion 11 (stent sheath) of the catheter tip 10-1 associated with the first operating means 71 by means of the first force transmission means 31 of the catheter shaft 30-1 so that, on actuation of the first operating means, and in particular the first slide 74, it is possible to transmit a force directly from the first slide 74 to the first housing portion 11 (stent sheath) of the catheter tip 10-1.

Further, it can be seen from the representation in FIG. 15, that the third stop 77 associated with the first operating means 77 is in the form of a stop element 44 releasably fastened on the first guide of the first slide 74.

In relation to the second operating means 81, in the embodiment of the transapical insertion system 10-1 according to FIGS. 14 to 17 it is provided that the second operating means 81 has a second slide 84 guided in a second guide 82 and functionally connected to the second pusher 83. This second slide 84 is functionally connected with the second housing portion 21 (stent funnel) of the catheter tip 10-1 associated with the second operating means 81 by means of the second force transmission means 41 already mentioned so that, on actuation of the second operating means 81, and in particular of the second slide 84, force can be directly transmitted from the second slide 84 to the second housing portion 21 of the catheter tip 10-1.

The securing element 79, 89 associated with the respective operating means 71 and 81 co-operate with the respective pushers 73, 83 of the operating means 71, 81 so that, on the one hand, a longitudinal displacement of the associated second slide 84 that can be effected with the second operating means 81, consequently producing a longitudinal displacement of the second housing portion 21 of the catheter tip 10-1 and, on the other hand, a longitudinal displacement of the associated first slide 74 that can be effected with the first operating means 71, consequently producing a longitudinal displacement of the first housing portion 11 of the catheter tip 20, can be blocked. The respective securing elements 79 and 89 can each be removed from the associated operating means 71 and 81 where required, to transfer the insertion system 100-1 from one functional state into another functional state.

The catheter shaft 30-1 used with the insertion system 100-1 designed for transapical access and depicted in FIGS. 14 to 17 is described later with reference to FIGS. 19, 8 and 22.

A procedure for implanting a stent 101 carried out transapically is described in more detail in the following with reference to FIGS. 23a to 23d. A transapical insertion system 100-1 of the type described previously is used.

Figure 23A:
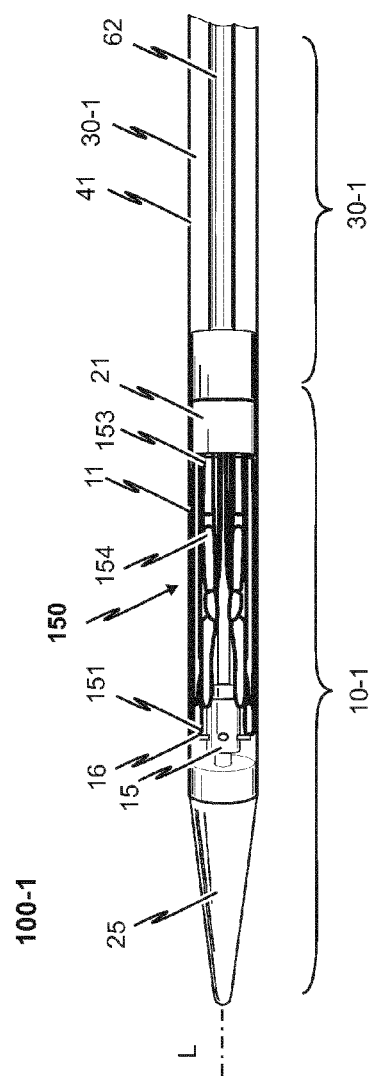

The distal end region 39 of the catheter shaft 30-1 with the catheter tip 10-1 is shown in detail in the representation in FIG. 23a, whereby the insertion system 100-1 is in its first functional state (see FIG. 17a). A self-expandable heart valve stent is housed in the catheter tip 10-1. An endoprosthesis, for example, can be used as heart valve stent 150, as shown in FIGS. 22a to 22c and is described in European Patent Application No. 08 151 963.

As described previously in relation to FIG. 17a, for example, the insertion system 100-1 in the representation of FIG. 23a is in its first functional state, in which retaining elements 151 (here retaining rings) of this stent 150 are in engagement with retaining elements 16 (here projecting elements) of the stent holder 15, while the retaining hoops 153 of the stent 150 with the heart valve prosthesis which can be attached to them and not explicitly shown in the representation of FIG. 23 are housed in the sleeve-shaped second housing portion 21 (stent funnel) of the catheter tip 10-1.

The positioning hoops 154 of the stent 150 in the first functional state of the insertion system 100-1 are between the sleeve-shaped second housing portion 21 and the similarly sleeve-shaped first housing portion 11 of the catheter tip 10-1, whereby the two housing portions 11 and 21 are arranged to overlap telescopically. In particular, the first housing portion 11 of the catheter tip 10-1 covers the following components: the second retaining region of the stent 150, on which the retaining elements 151 are provided; the positioning hoops 154 of the stent 150; and the sleeve-shaped second housing portion 21 of the catheter tip 10-1.

The (first) retaining region of the stent 150 remote from the retaining elements 151 of the stent 150 is housed in the second housing portion 21 with the retaining hoops 153 and the heart valve prosthesis (not shown in the illustration in FIG. 23).

A shape memory material is preferably used as stent material, whereby the shape memory effect and with it the permanent configuration of the stent 150 is initiated through the effect of an external stimulus. It is particularly preferred that this external stimulus is a definable critical temperature, so that the stent material must be heated to a temperature higher than the critical temperature in the range to initiate the shape memory effect and thus to recover the stored permanent configuration of the stent 150. In relation to the area of use of the insertion system 100-1 described here, it is preferred that the critical temperature is in the range between room temperature and the body temperature of the patient. Thus, when implanting the stent 150, care must be taken that the stent 150 is appropriately cooled, for example by flushing the catheter shaft 30-1 and the catheter tip 10-1 of the insertion system 100-1 with a suitable coolant, possibly with a saline solution, using an injection adapter 99a provided in the handle 70-1.

The catheter tip 10-1, in the state shown in FIG. 23a, is advanced to the insufficient native heart transapically, i.e. approaching from the apex of the heart. Trans-arterial access is also possible, of course, when, instead of the insertion system 100-1 shown in FIG. 23, a transfemoral or transarterial insertion system 100-2, which is yet to be described with reference to FIGS. 11 to 19, is used.

When the catheter tip 10-1 with the stent 150 accommodated in the catheter tip 10-1 has been advanced to the desired implantation location, cooling is interrupted, with the result that the stent 150 heats up to the body temperature of the patient (36° C.) and consequently the shape memory effect of the stent material is initiated.

Due to the self-expanding characteristic of the stent that is thus initiated, radial forces develop, which act on the individual components of the stent 150 and particularly on the respective positioning hoops 154 and the retaining hoops 153. Since the retaining hoops 153 of the stent 150 are still housed in the sleeve-shaped second housing portion 21 of the catheter tip 10-1, the retaining hoops 153 are held in the folded-up configurations despite initiation of the shape memory effect. The positioning hoops 154 of the stent 150 together with the (first) retaining region of the stent facing the distal-side end tip 25 of the catheter tip 10-1 are positively held by the sleeve-shaped first housing portion 11 in their folded-up configuration.

Figure 23B:
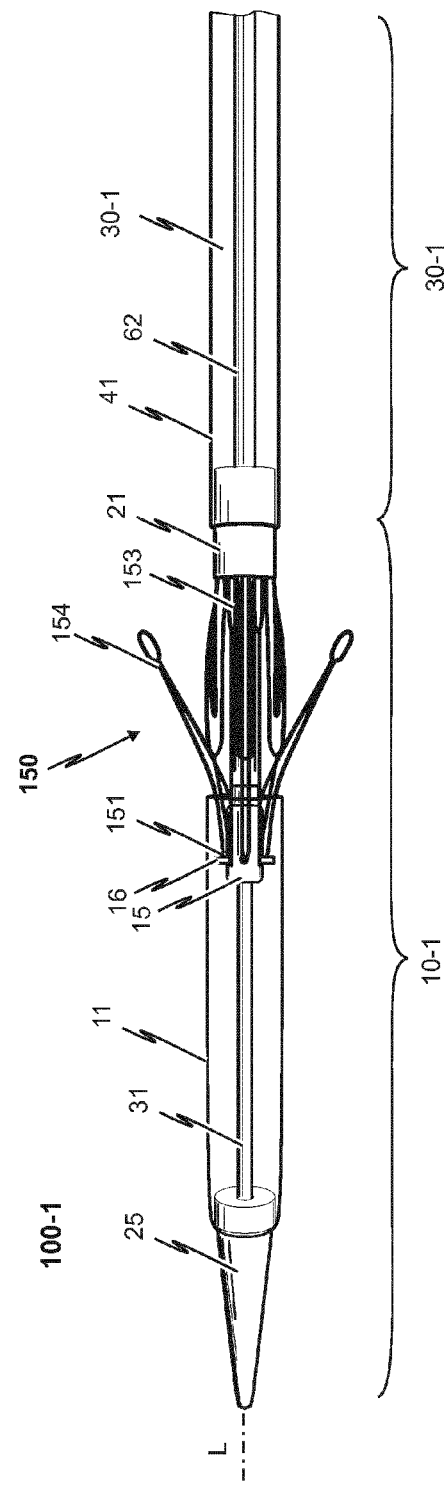

After the implantation location has been reached, the positioning hoops 154 of the stent 150 are released, following a suitable stepwise release of the stent from the insertion system 10-1. This is achieved by transferring the insertion system 10-1 from its first functional state (see FIG. 23*a*) to its second functional state (see FIG. 23*b*), as has previously been described in detail with reference, for example, to FIG. 17*a* and FIG. 17*b* and is shown in FIG. 23*b*. The first housing portion 11 of the catheter tip 10-1 is moved relative to the stent holder 15 in the distal direction, and thus away from the handle, by manipulation of the first operating means 71 of the handle 70-1 forming part of the insertion system 100-1. The longitudinal displacement stroke of the sleeve-shaped first housing portion 11 that is effected relative to the stent holder 15 has the result that the positioning hoops 154 of the stent 150 are no longer surrounded and held by the sleeve-shaped first housing portion 11 of the catheter tip 10-1. As a consequence of the self-expanding characteristic of the positioning hoops 15 of the stent, these are opened because of the radial forces acting on them in a radial direction. The opened positioning hoops 154 then positioned in the pockets of the native heart valve.

As already indicated, the catheter tip 10-1 can turn together with the insertion system 100-1 about the longitudinal axis L of the catheter tip 10-1, facilitating the positioning of the unfolded positioning hoops 154 of the stent 150 in the pockets of the native heart valve.

Figure 23C:
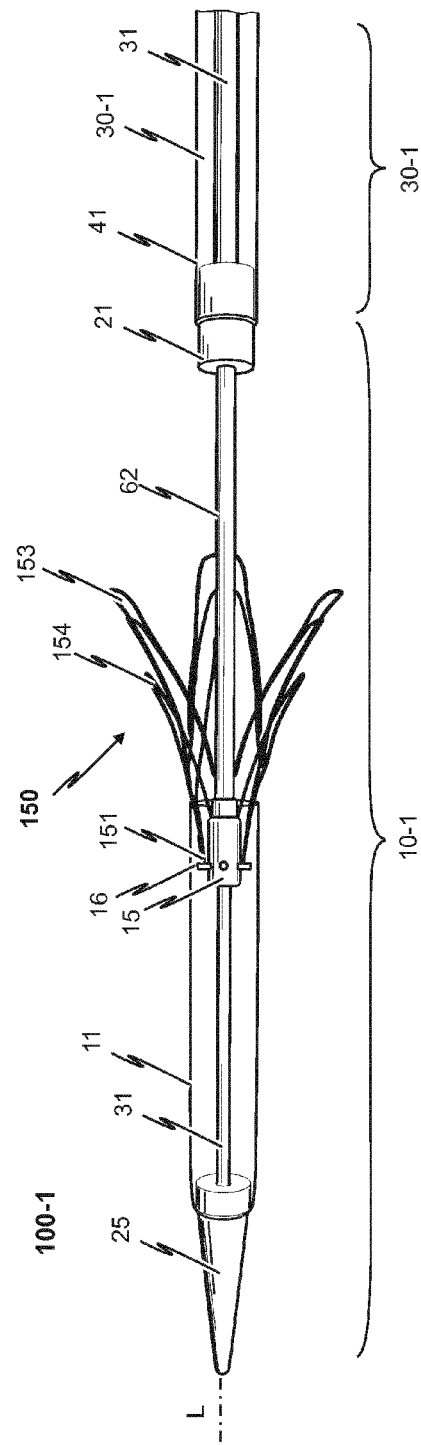

After positioning of the partially expanded stent in the pockets of the native heart valve, the insertion system 100-1 is transferred from its second functional state in accordance with FIG. 23*b* into its third functional state in accordance with FIG. 23*c*. The way in which the insertion system 100-1 is transferred from the second functional state into the third functional state has previously been described in detail with reference to FIG. 17*c*. FIG. 23*c* shows how the (second) retaining region of the stent 150 remote from the end tip 25 of the catheter tip 10-1 in the third functional state of the insertion system 100-1 is released from the second housing portion 21 of the catheter tip 10-1. The retaining hoops 153 of the stent 150 and the associated first retaining region of the stent 150 released in the third functional state of the insertion system are stressed because of the radial forces acting on them in the radial direction and consequently a heart valve prosthesis attached to the retaining hoops 153, for example with the aid of a thread etc., unfolds like an umbrella. An example of a heart valve prosthesis 160 attached to the retaining hoops 153 of a stent is shown in FIG. 34.

The function of the already unfolded heart valve prosthesis can be checked in the state shown in FIG. 23*c*. After the functioning of the heart valve prosthesis has been demonstrated, the insertion system 100-1 can then be transferred—by means of a further manipulation of the first operating means 71 of the handle 70-1—from its third functional state (see FIG. 23*c*) into its fourth functional state (see FIG. 23*d*). The way in which the insertion system 100-1 is transferred into the fourth functional state has been previously described with reference to FIG. 17*d*. The effect of the transfer of the insertion system 100-1 into the fourth functional state is shown in FIG. 10*d*.

By further displacement of the first housing portion 11 of the catheter tip 10-1 in the distal direction, and thus away from the handle 70-1, the proximal end region of the sleeve-shaped first housing portion 11 of the catheter tip 10-1 is moved is moved further in the distal direction so that this proximal part of the first housing portion 11 no longer covers the retaining elements 16 (here projecting elements) of the stent holder 15. Thus the (second) retaining region of the stent facing the end tip 25 of the catheter tip 10-1 is released from the catheter tip 10-1, so that the second retaining region of the stent 150 also expands, consequently leading to a complete unfolding of the stent 150.

In contrast, if it is found that the implanted heart valve prosthesis cannot or can only inadequately fulfil its function during the check of function of the already unfolded heart valve prosthesis in the third functional state of the insertion system 100-1, in accordance with FIG. 23*c*, or if the stent 150 is not optimally positioned or cannot be optimally positioned in the implantation site, there is the possibility of retracting the insertion system 100-1 back into the second and then into the first functional state, by moving the corresponding housing portion 11, 21 of the catheter tip 10-1 in the appropriate opposite direction (see depictions in FIGS. 3*b* to 3*d* for this). This allows the already released and expanded components of the stent 150 to be retracted back again into the respective sleeve-shaped housing portion of the catheter tip 10-1, so that the stent 150 housed in the catheter tip 10-1 can be removed from the body of the patient.

Figure 23D:
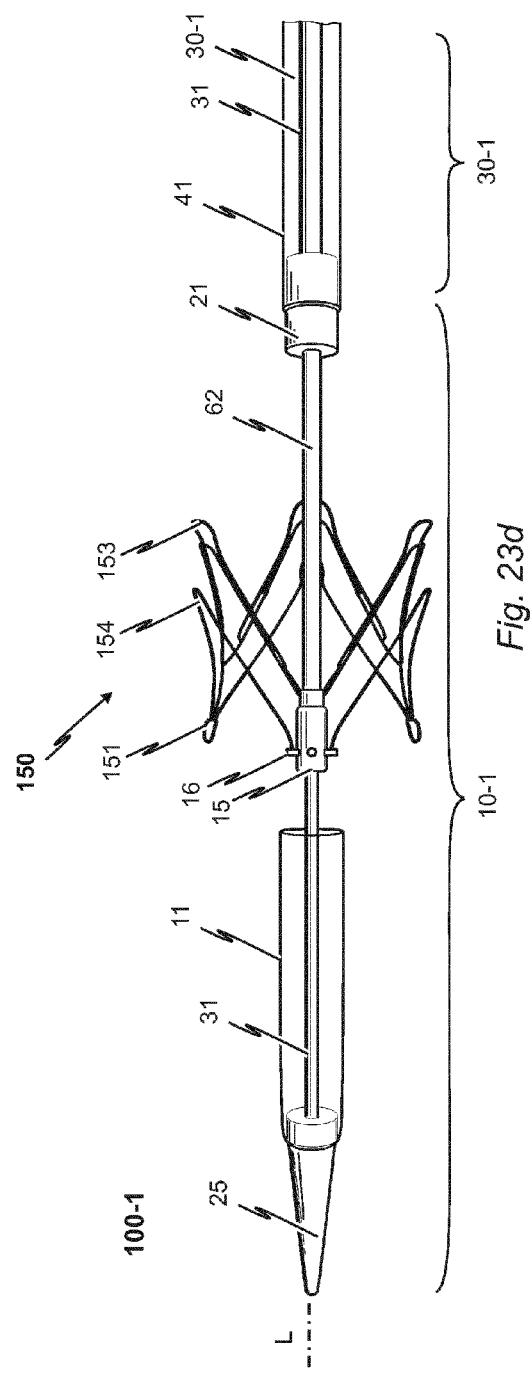

As shown in FIG. 23*d*, the retaining hoops 153 of the stent 150 open in their radial direction on implantation of the stent 150, whereby the radial forces acting on the retaining hoops 153 and also on the second retaining region of the stent 150 result in the stent being pressed against the vessel wall, on the one hand ensuring that the stent 150 with the heart valve prosthesis attached to the first retaining region is securely anchored at the implantation site and, on the other hand, that the heart valve prosthesis is reliably sealed in the first retaining region.

FIG. 18 shows a side elevation of an embodiment of a handle 70-1 for an insertion system 100-1 designed for a transapical access. As regards function, the handle 70-1 shown in FIG. 18 is identical to the handle described with reference to FIGS. 14 to 17. The handle shown in FIG. 18 differs from the embodiment of the handle according to FIGS. 14 to 17 in that it has an additional grip 88, which projects from the body 70' of the handle 70-1, so with that the doctor carrying out the treatment can hold the handle 70-1 like a pistol.

Preferably, the grip 88 can be connected at different positions with the body 70' of the handle 70-1. Thus it is possible for the grip 88 not to be joined to the underside of the body 70' of the handle 70-1, as indicated in FIG. 18, but to be fastened coming from the above onto the body 70'.

Two injection adapters 99a, 99b are provided for the handle 70-1 shown in FIG. 18. The first injection adapter 99a is located on the longitudinal axis L of the handle 70-1 and is connected to the first pusher of the first operating means 71. The second injection adapter 99b is perpendicular to the longitudinal axis and is connected to the second pusher of the second operating means 71. Where required, a guide wire can be passed to the first injection adapter 99a. The second injection adapter 99b—as is described in more detail subsequently with reference to the illustration in FIG. 19—is connected to the second slide 84 of the second operating means 81 and is used to supply and drain fluid which can flow via the catheter shaft 30-1 to the catheter tip 10-1.

FIG. 19 shows a side sectional view of a further embodiment of a handle 70-1 of an insertion system 100-1 which is designed for transapical access. The mechanism in the handle 70-1 used in the transapical insertion system 101 is described in detail in the following, with reference to the depiction in FIG. 19. The details in the following refer to all handles for a transapical insertion system 100-1 described herein.

As shown in FIG. 19, the handle 70-1 has a first and a second operating means 71, 81, which are connected by means of first and second force transmission means 31, 41 of the catheter shaft 30-1 with the first and second housing portion 11, 21 of the catheter tip 10-1. The first operating means 71 has a first slide 74 guided in a first guide 72 and functionally connected to a pusher knob 73.

In detail, the first pusher knob 73 for the embodiment shown in FIG. 19 comprises a detent spring mechanism with spring elements 90 and catches 91, 92, 93, 94 formed in the first guide 72. As can be seen, particularly in the representation in FIG. 20, which shows a planned view on the handle 70-1 in accordance with FIG. 19, the first pusher knob 73 further comprises at least one engaging element 95, which is complementary to the catches 91, 92, 93, 94 formed in the first guide 72. The spring elements 90 of the detent spring mechanism designed and co-operate with the first pusher knob 73 on one side and with the first slide 74 on the other so that, in a state when the first operating means 71 is not actuated, the first pusher knob 73 is spaced from the first slide 74 under spring action and engages at least engaging element 95 in one of the catches 91, 92, 93, 94.

In a state when the first operating means 71 is actuated, the first pusher knob 73 is pressed against the spring force of the spring element 90 in the direction of the first slide 74 so that the engagement between the engaging elements 95 and the catches 92, 93, 94 formed complementary to it is released. In this state, the block on longitudinal displacement of the first slide 74 is removed, so that this can be displaced in the direction of the longitudinal axis L of the handle, so that the first of housing portion 11 of the catheter tip 10-1 can be manipulated.

As can be seen in particular in the illustration in FIG. 20, the detent spring mechanism used with the handle 70-1 has first catches 91 and second catches 92, which are each formed complementary to the engaging elements 95 formed on the first slide 74 and arranged at positions spaced from each other in the longitudinal direction of the first guide 72. In this embodiment, in a functional respect the second catches 92 form the first stop 75 used, for example, with the embodiment in accordance with FIG. 14. The first catches 91 formed in the first guide 72 correspond in a functional respect to the third stop 77 in the embodiment of the handle 70-1 shown, for example, in FIG. 14. Thus the distance between the first catches 91 and the second catches 92 defines the longitudinal displacement stroke of the first housing portion 11 of the catheter tip 10-1 that can be affected on actuation of the first operating means 71.

It is particularly preferred that the first and second catches are provided in a first guide surface 72 of the first guide 72, while the detent spring mechanism further has third and fourth catches 93, 94, which are respectively formed complementary to the engaging element 95 formed on the first slide 74. As shown in FIG. 20, the third and fourth catches 93, 94 are formed in a second guide surface 72b, which is opposite to the first guide surface 72a. As with the first and second catches 91, 92, the third and fourth catches 93, 94 are arranged at positions spaced from one another in the longitudinal direction L of the first guide 72. In particular, it is provided that the distance between the third and fourth catches 93, 94 is chosen to be different from the distance between the first and second catches 91, 92. In this way, it is possible to realise different longitudinal displacement strokes of the first housing portion 11 of the catheter tip 10-1 with one and the same first operating means 71. For this, it is only necessary to use the first slide 74 when turned through 180° in the first guide 72. The provision of different longitudinal displacement strokes that can be realised with the first operating means 71 has the advantage that cardiac valve stents of different length can be implanted with the insertion system 100-1.

The second operating means 81 of the handle 70-1 shown, for example, in FIG. 19 has a second pusher knob 83, which can also be provided with a detent spring mechanism.

The second pusher knob 83 is guided in a second guide 82 and is functionally connected to a second slide 84. The second slide 84 is connected by means of the second force transmission means 41 to the second housing portion 21 of the catheter tip 10-1 so that, on actuation of the second operating means 81, force can be transmitted from the second slide 84 to the housing portion 21 of the catheter tip 10-1.

As also previously explained with the handle described, for example, with reference to FIGS. 14 to 17, the second slide 84 of the second operating means 81 can be moved between a first stop 85 and a second stop 86. When—as with the first operating means 71—a detent spring mechanism is also used with the second operating means 81, it is possible to do without the stops 85 and 86.

A grip 88 is further connected to the body 70' of the handle 70-1 with the handle 70-1 described in FIG. 19. This grip 88 is releasably fastened to the body 70' and in particular can also be connected to the body 70' from the upper side of the handle 70-1. Corresponding brackets 88' are provided for the purpose in the body 70' (see also the illustration in FIG. 20).

An embodiment of a catheter shaft is 30-1 used in an insertion system 100-1 designed for transapical access is described in more detail in the following, with reference to the illustrations in FIGS. 19, 8 and 9.

As can be seen in particular in the FIG. 9, which shows the catheter shaft 30-1 of the insertion system 100-1 designed for transapical access in a cross-sectional view, the catheter shaft 30-1 comprises a first force transmission means 31, which can be connected at its proximal end region to the first operating means 71 of the handle 70-1 and that its distal end region with the first housing portion of the catheter tip 10-1. The first force transmission means 31 is designed to transfer a tensile or shear force to the first housing portion 11 of the catheter tip 10 on actuation of the first operating means 71.

In detail, with the catheter shaft 30-1 of the insertion system 100-1 designed for a transapical access, it is provided that the first force transmission means 31 is formed by a capillary extending from the distal end region to the proximal end region of the catheter shaft 30-1, through which a guide wire can be passed.

As can be seen in particular in the depiction in FIG. 19, the first force transmission means 31 is in the form of an inner catheter, which is permanently attached to the first slide 74 of the first operating means 71. The first force transmission means 31 merges into the first injection adapter 99*a* in the proximal direction from the first slide 74. This first injection adapter 99*a* is also permanently connected to the first slide 74 of the first operating means 71 and can be displaced in the longitudinal direction L of the handle 70-1 relative to the body 70' of the handle 70-1 on actuation of the first operating means 71.

The catheter shaft 30-1 used with the insertion system 100-1 designed for transapical access further exhibits the second force transmission means 41 already mentioned, which is connected on one side to the second slide 84 of the second operating means 81 and on the other side to the second housing portion 21 of the catheter tip 10-1 and is used for transmission of tensile and compressive forces. It can be seen in particular in the illustration in FIG. 19 that, with the catheter shaft 30-1 for the transapical insertion system 100-1, the second force transmission is 41 is implemented as an outer catheter, within which the first transmission means 31, which has already been mentioned, runs in the form of the inner catheter. In detail, the proximal end region of the second operating means 41 in the form of the outer catheter is mounted in a positive and force-locking connection between a screw cap 84' screwed on the second slide 84, ensuring a secure fixing of the proximal end region of the second force transmission means 41 on the second slide 84.

It can be seen, particularly in the illustration in FIG. 9, that the space between the second force transmission means 41 in the form of the outer catheter and the first force transmission means 31 in the form of the inner catheter is occupied by a filler material, in order to form a filler body. The first transmission means 31 in the form of the inner catheter is passed through this filler body so that, on actuation of the first operating means 71, the first force transmission means 31 in the form of the inner catheter is displaced relative to the filler body 40 in the longitudinal direction L of the catheter shaft 30-1.

The filler body is preferably made of a plastic filler material that ensures that the of the catheter shaft 30-1 has the rigidity that is necessary for the transapical insertion system 100-1.

Furthermore, it can be seen from the illustration in FIG. 9 that several fluid channels 43 can be formed in the filler body 40. These fluid channels are connected on one side to the second injection adapter 99*b* (see FIG. 19) and on the other side to the catheter tip 10-1 (see FIG. 21), to ensure that the catheter shaft 30-1 and catheter tip 10-1 can be flushed through and that fluid can be supplied and drained.

FIG. 19 shows that the filler body 40 is permanently connected to the body 70' of the handle 70-1. The opposing distal-side end of the filler body 40 is connected permanently to the proximal end of the catheter tip 10-1 (see FIG. 21).

The catheter shaft 30-1 of the transapical insertion system 100-1 further comprises a cannula capillary 45, the proximal-side end region of which is connected by means of a fixing 87 to the body 70' of the handle 70-1 and the distal-side end region of which is connected to the stent holder 15, and consequently the stent holder 15 is basically held at a non-variable distance relative to the body 70' of the handle 70-1. The first force transmission means in the form of the inner catheter runs through the inside of this cannula capillary 45.

As the illustration in FIG. 8 shows, the first force transmission means 31 in the form of the inner catheter has a spiral-shaped notch at its distal side end region, with which only the catheter tip 10-1 has a certain degree of flexibility. The distal-side end region of the first force transmission means 31 in the form of the inner catheter is permanently connected to the distal-side end tip 25 of the catheter tip 10-1. As already described previously, the distal-side end tip 25 is connected at its proximal end to the housing portion 11 of the catheter tip 10-1 in the form of the stent sheath. When the first operating means 71 is actuated, the first force transmission means is consequently moved relative to the cannula capillary 45 and the filler body 40 as well as relative to the stent holder 15, through which the first housing portion 11 (stent sheath) can be moved in the longitudinal direction L of the catheter tip 10-1.

The second force transmission means 41 is permanently connected to the second housing portion 21 of the catheter tip in the form of the stent funnel at the transition between the catheter tip 10-1 and the second force transmission means 41 in the form of the outer catheter. The second housing portion 21 (stent funnel) and the filler body 40 are also joined together. Through holes are provided at the connection between the stent funnel (second housing portion 21) and the filler body 40, through which fluid inserted into the fluid channels 43 formed in the filler body 40 using the second injection adapter 99*b* can be passed into the catheter tip 10-1. A corresponding seal 44 is provided for the fluid channels 43 at the distal-side end of the filler body 40.

It can be further seen from the illustration in FIG. 21 that the stent holder 15 has a distal configuration in atraumatic form, which reduces the risk of an injury when the catheter tip 10-1 is removed after release of the stent housed in the catheter tip 10-1.

All previously described components can be used with each embodiment of a transapical insertion system 100-1.

A description is given in the following, with reference to FIGS. 24 to 34, of the components of an insertion system 100-2, which is suitable for a transarterial or transfemoral access to the implantation location. During a transarterial or transfemoral access, the catheter tip 10-2 of the insertion system 100-2 is advanced, for example, via the aorta to the implantation site.

FIG. 33 shows schematically an example of how a transarterial or transfemoral access can be gained to the heart of a patient. In the illustration in accordance with FIG. 33, a heart valve stent is advanced with the aid of a special insertion system via the femoral artery to the aortic valve. Embodiments of the special insertion system, which is suitable for transarterial or transfemoral access are described in the following.

The four different functional states of a transfemoral insertion system 100-2 are shown in detail in FIGS. 27*a* to 27*d*, to illustrate the procedure for loading a stent into the catheter tip 10-2 of the insertion system 100-2. The respective functional states of the transfemoral insertion system 100-2 are shown in FIGS. 28a to 28d to illustrate the release of a stent mounted in the catheter tip 10-2 of the insertion system 100-2.

The embodiment of the insertion system 100-2 suitable for transarterial or transfemoral access differs from the transapical insertion system 100-1 previously described with reference to the depictions in FIGS. 14 to 17 through a modified construction of the catheter tip 10-2 to enable transarterial access to the implantation site. Further, in comparison with the transapical insertion system 100-1, the stent insertion system 100-2 designed for transarterial or transfemoral access has both a different handle 70-2 and a different catheter shaft 30-2.

The handle 70-2 used for the insertion system 100-2 designed for transarterial or transfemoral access essentially differs from the handle 70-1 used for the transapical insertion system 100-1 only in its structural layout.

In distinction to the handle 70-1 for the transapical insertion system 100-1, the handle 70-2 for the transarterial/transfemoral insertion system 100-2 according to the illustration in FIGS. 27 and 28 has a wheel rotatably mounted in the handle 70-2 which is functionally connected to the first housing portion 13 (stent sheath) of the catheter tip 10-2 associated with the first operating means 71 via a corresponding first force transmission means 31, so that force can be directly transmitted from the first operating means 71 in the form of the wheel to the first housing portion 11 of the catheter tip 10-2.

In detail, it is provided that, with the first operating means 71 of the handle 70-2 in accordance with FIG. 27 and FIG. 28, the first operating means 71 in the form of the wheel can turn between a first stop and a second stop, in order to execute a definable longitudinal displacement stroke on the first housing portion 11 of the catheter tip 10-2. As with the first operating means of the handle 70-1 used with the transapical insertion system 100-1, the first operating means 71 of the handle 70-2 used with the insertion system 100-2 designed for transarterial/transfemoral access is provided with a third stop between the first and second stop which cooperates, on one side with the first stop and on the other up with the second stop so that, on actuation of the first operating means 71, a longitudinal displacement of the first housing portion 11 of the catheter tip 10-2 can be effected relative to the stent holder 15 of the catheter tip 10-2, consisting of two defined separate steps.

With the first operating means 71 used in the form of a wheel, the third stop associated with the first operating means 71 is in the form of a locking element 77' positioned removably in the flow of force between the wheel and the first housing portion 11 of the catheter tip 10-2, interrupting direct force transmission from the wheel to the first housing portion 11 of the catheter tip 10-2. Alternatively, however, it is possible for the third stop associated with the first operating means 71 to be in the form of a locking element restricting the free rotation of the wheel between the first and the fourth stop.

However, it is of course also possible in principle for the first operating means 71 of the handle 70-2 used with the insertion system 100-2 designed for transarterial/trans femoral access not to be a wheel, but—as with the handle 70-1 of the transapical insertion system 100-1—to be implemented as a pusher mechanism.

In relation to the handle 30-2 that is used with the embodiment of the insertion system 100-2, for example in accordance with the illustrations in FIGS. 27 and 28, it is provided that—as also with the transapical embodiment of the insertion system 100-1—the second operating means 81 has a second slide 84 guided in a second guide 82 and functionally connected to a second pusher 83. This second slide 84, which is guided in the interior of the handle 70-2 and therefore cannot be seen in the view of FIGS. 27 and 28, is functionally connected to the second housing portion 21 (stent funnel) of the catheter tip 10-2 associated with the second operating means 81 by means of a second force transmission means 41 so that, on actuation of the second operating means 81, force is directly transmitted from the second slide 84 to the second housing portion 21 (stent funnel) of the catheter tip 10-2.

The second operating means 81 can be displaced between a first position (Pos. 1) and a second position (Pos. 2) in the longitudinal direction of the handle 70-2, whereby the longitudinal displacement stroke that can be thus effected via the second force transmission means 41 is transferred directly to the second housing portion 21 of the catheter tip 10-2. The first and second positions are each defined with the aid of a first and a second stop 85, 86.

A securing element 89 is provided, associated with the second operating means 81, which is removably located on the second guide 82 and which blocks longitudinal displacement of the (second) slide 84 associated with the second operating means 82 when used.

The handle 70-2 which is used with the transarterial/transfemoral insertion system 100-2 of the embodiment shown in FIGS. 27 and 28 further exhibits a grip 88, which facilitates the operability of the handle 70-2 and in particular the operating conformity of the handle 70-2. A grip 88 of this type can of course also be used with the handle 70-1 which is used with the transapical insertion system shown in FIGS. 14 to 17.

The handle 88 is preferably releasably connected to the body 70' of the handle 70-2 and can optionally be fixed at different positions on the body 70' of the handle 70-2.

In relation to the construction of the catheter tip 10-2 which is used, for example, with the insertion system 100-2 shown in FIGS. 27 and 28 and which allows transarterial/transfemoral access of a stent housed in the catheter tip 10-2 to the implantation location, it can be seen from FIGS. 27 and 28 that the catheter tip 10-2—as also the catheter tip 10-1 for the transapical insertion system 100-1—has a stent holder 15 for releasably fixing of, for example, the second retaining region of a stent that can be housed in the catheter tip 10-2. In comparison with the catheter tip 10-1 of the insertion system 100-1 designed for transapical access, the retaining elements 16 of the stent holder in the form of a crown are now provided at the proximal end of the stent holder 15.

Further, the catheter tip 10-2 of the insertion system 100-2 designed for transarterial/transfemoral access comprises a mounting device for mounting a heart valve stent, where required, with a heart valve prosthesis fastened to it. In detail, the mounting device of the catheter tip 10-2 consists of a first housing portion 11, particularly for accommodating the positioning hoops of a stent, and a second housing portion 21, in particular for accommodating the heart valve prosthesis fastened to it, when required.

As also with the previously described embodiment of the transapical insertion system 100-1, for example, with reference to FIGS. 14 to 17, the first operating means 71 of the handle 70-2 co-operates in the embodiment according to FIGS. 27 and 28 with the first housing portion 11 of the catheter tip 10-2 so that, on actuation of the first operating means 11, by transfer of a defined longitudinal displacement stroke, a previously definable longitudinal displacement of the first housing portion 11 can be effected relative to the stent holder 15. On the other hand, with the insertion system according to FIGS. 27 and 28, the second operating means 81 of the handle 70-2 co-operates with the second housing portion 21 of the catheter tip 10-2 so that, on actuation of the second operating means 81, by transfer of a defined longitudinal displacement stroke, a previously definable longitudinal displacement of the second housing portion 21 of the catheter tip 10-2 relative to the stent holder 15 can be effected.

In distinction to the transapical insertion system 100-1 described with reference to FIGS. 14 to 17, the second housing portion 21 (stent funnel), which is used to house the retaining hoops of the stent with, where required, the heart valve prosthesis fastened to them, is located at the distal end region of the catheter tip 10 to in the transarterial/transfemoral insertion system 100-2, for example in accordance with FIGS. 27 and 28, while the first housing portion 11 (stent sheath) is located between the second housing portion 21 and the handle 70-2.

In the insertion system 100-2 shown in FIGS. 27 and 28, which is designed for transarterial access to the insufficient or stenosed native heart valve, the second force transmission means 41, which connects the second operating means 81 of the handle 70-2 to the second housing portion 21 (stent funnel) of the catheter tip 10-2, is preferably in the form of an inner catheter running inside the interior of the catheter or tube system. The first force transmission means 31, which connects the first operating means 71 of the handle 70-2 to the first housing portion 11 (stent sheath) of the catheter tip 10-2, is in the form of an outer catheter, in the interior of which the first force transmission means 31 runs in the form of the inner catheter.

On actuation on the second operating means 81, the second housing portion 21 (stent funnel) can be moved relative to the stent holder 15 in the longitudinal direction L of the catheter tip 10-2 in a distal direction, thus away from the handle 70-2, while, on actuation of the first operating means 71 of the handle 70-2, the first housing portion 11 of the catheter tip 10-2 can be moved relative to the stent holder 15 in the longitudinal direction L of the catheter tip 10-2 in a proximal direction, and thus towards the handle 70-2.

The manipulations of the respective housing portions 11, 21 of the catheter tip 10-2 that can be effected on actuation of the respective operating means 71, 81 with the insertion system of 100-2 designed for transarterial/transfemoral access in accordance with FIGS. 27 and 28 are described in detail in the following, with reference in particular to FIGS. 28a to 28d.

An embodiment of a transarterial/transfemoral insertion system 100-2 is shown in its four different functional states in FIGS. 15a to 15d. In detail, the insertion system 100-2 is shown in its first functional state in FIG. 28a, in which the catheter shaft 30-2 with the catheter tip 10-2 and, where required, with the stent accommodated in it can be inserted into the patient transarterially or transfemorally and advanced via the aorta to the implantation site.

Figure 28A:
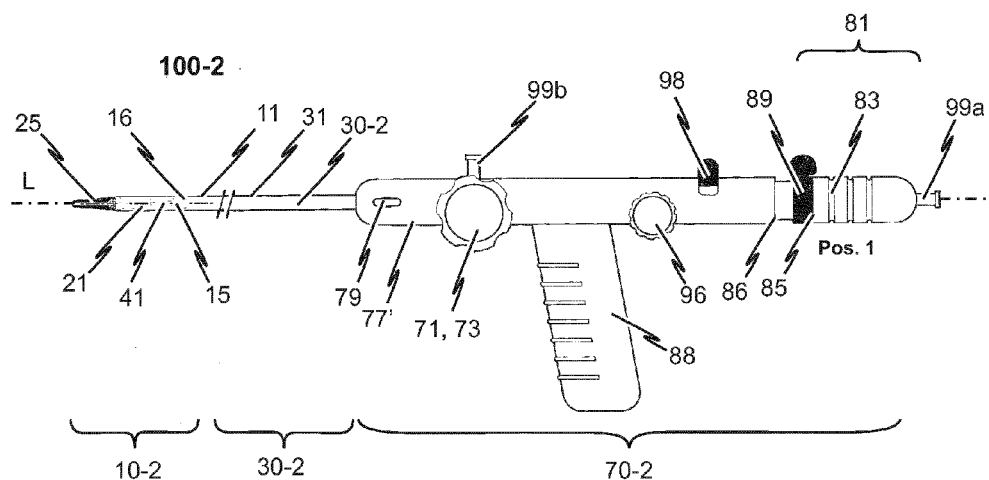

In the first functional state of the insertion system 100-2 in accordance with FIG. 28a, the catheter tip 10-2 is completely closed, whereby the two sleeve-like housing portions 11, 21 of the catheter tip 10-2 overlap telescopically. The respective diameters of the sleeve-like housing portions 11, 21 are chosen so that the folded-up retaining hoops of a stent, with the heart valve prosthesis fastened to them where required, can be housed in the second housing portion 21. The folded-up positioning hoops of the stent housed between the sleeve-shaped element of the second housing portion 21 and the sleeve-shaped element of the first housing portion 11 and are held together in their folded form.

The second retaining region of the stent is shown in the first functional state of the insertion system 100-2, as shown in FIG. 28a, with the stent holder 15 fixed at the proximal end of the catheter tip 10-2. For this purpose, the retaining elements (retaining rings etc.) provided at the second retaining region of the stent are engaged with retaining elements 16 of the stent holder 15.

The retaining elements 16 of the stent holder 15 are covered by the sleeve-shaped element of the first housing portion 11 of the catheter tip 10-2 in the first functional state shown in FIG. 28a, so that an engagement between retaining elements provided on the second retaining region of a stent and retaining elements 16 of the stent holder 15 would be possible.

The first functional state of the insertion system 100-2 shown in FIG. 28a is maintained during the transarterial insertion procedure. On reaching the implantation location, the insertion system 100-2 is transferred from the first functional state shown in FIG. 28a to the second functional state shown in FIG. 28b, by transferring the first operating means (shown in the embodiment of the wheel in FIG. 28) from the first position into the second position. The longitudinal displacement stroke transferred by actuation of the first operating means 71 to the first housing portion 11 of the catheter tip 10-2 effects a displacement of the sleeve-like first housing portion 11 relative to the stent holder 15 in the proximal direction, thus towards the handle 70-2.

The longitudinal displacement stroke executed on the first housing portion 11 of the catheter tip 10-2 during the transition from the first functional state (see FIG. 28a) to the second functional state (see FIG. 28b) by the first operating means 71 of the handle 70-2 via a corresponding first force transmission means 31 is previously defined so that the sleeve-shaped first housing portion 11 is displaced relative to the stent holder 15 in the proximal direction just so far that the positioning hoops of a stent housed in the catheter tip 10-2 would be released, though the distal end of the first housing portion 11 of the catheter tip 10-2 would still cover the retaining elements 16 of the stent holder 15, so that the engagement between the retaining elements provided at the second retaining region of the stent and the retaining elements 16 of the stent holder 15 would be secure.

Since the second housing portion 21 is not manipulated during the transition from the first functional state into the second functional state, the first retaining region of a stent housed in the catheter tip 10-2 with the heart valve prosthesis fastened to it would continue to be housed in its folded together state in the sleeve-shaped element of the second housing portion 21.

The positioning hoops of a stent housed in the catheter tip 10-2 released in the second functional state of the insertion system 100-2 are opened as a result of the radial forces acting on them and can thus be positioned in the pockets of the insufficient native heart valve. Following appropriate positioning of the positioning hoops of the stent in the pockets of the native heart valve, the insertion system 100-2 is transferred from the second functional state shown in FIG. 28b into the third functional state shown in FIG. 28c. This is done my manipulation of the second operating means 81, after the securing element 89 associated with the second operating means 81 has been removed.

On actuation of the second operating means 81, the second housing portion 21 of the catheter tip 10-2 associated with the second operating means 81 is moved relative to the stent holder by a previously established longitudinal displacement stroke defined with the second operating means 81 in a distal direction, thus away from the handle 70-2. The longitudinal displacement stroke acting on the second housing portion 21 is chosen so that the sleeve-like second housing portion 21 no longer covers the first retaining region of a stent housed in the catheter tip 10-2 with the heart valve prosthesis fastened to it, where required, and thus releases the first retaining region of the stent. Due to the action of the radial forces, the distal retaining region of the stent with the heart valve prosthesis attached to it, where required, unfolds completely.

Figure 28B:
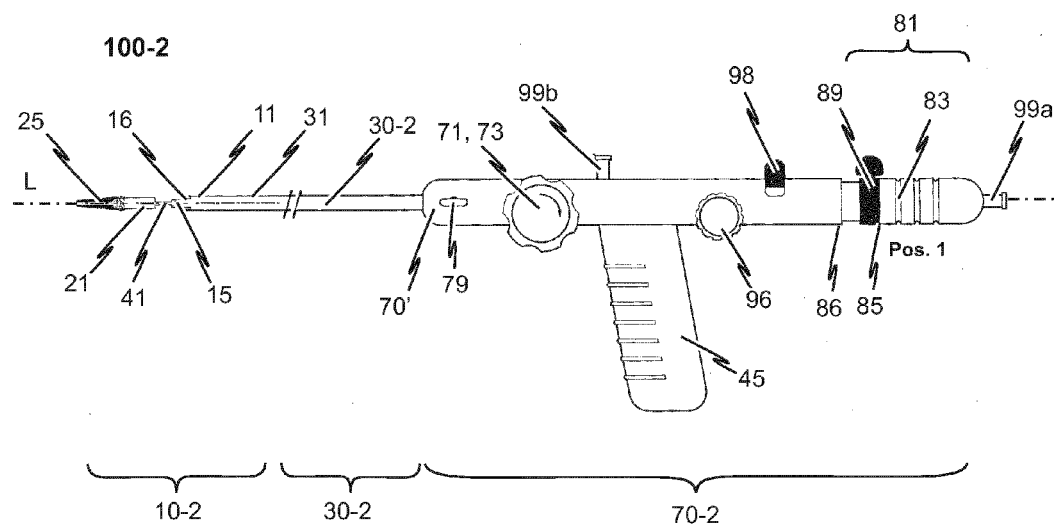
Figure 28C:
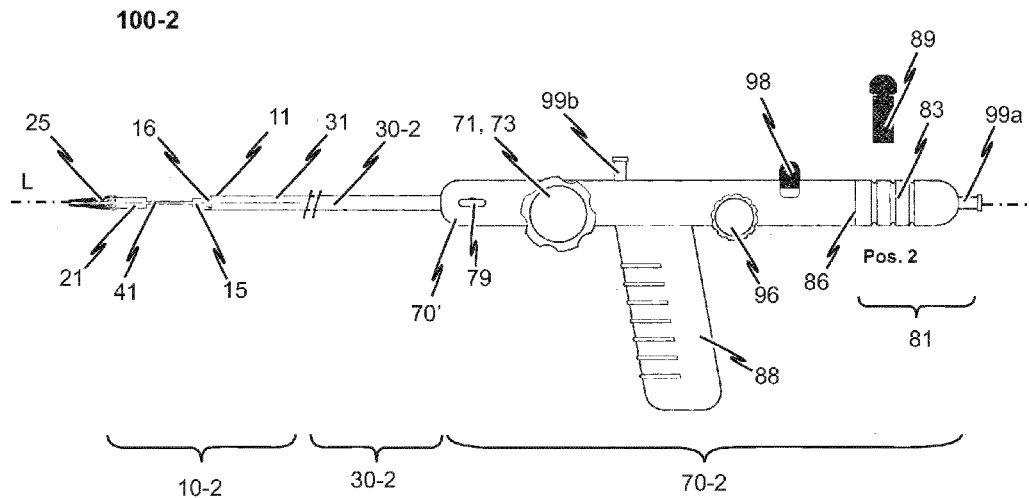

Since the first operating means 71 of the handle 70-2 and the associated first housing portion 11 of the catheter tip 10-2 are not manipulated during the transition from the second functional state in accordance with FIG. 28b into the third functional state in accordance with FIG. 28c, the distal end region of the sleeve-shaped first housing portion 11 continues to cover the retaining elements 16 of the stent holder 15, so that the engagement between the retaining elements of a stent housed in the catheter tip 10-2 and the retaining elements 16 of the stent holder is secure and the proximal retaining region of the stent is in its folded-up state. This anchorage of the stent to the catheter tip 10-2 of the insertion system allows an explantation of a stent that is already partially unfolded by returning the insertion system 100-2 from the third functional state, by appropriate manipulation of the second operating means 81 of the handle 70-2, to the second functional state and then by suitable actuation of the first operating means 71 transfer to the first functional state.

Figure 28D:
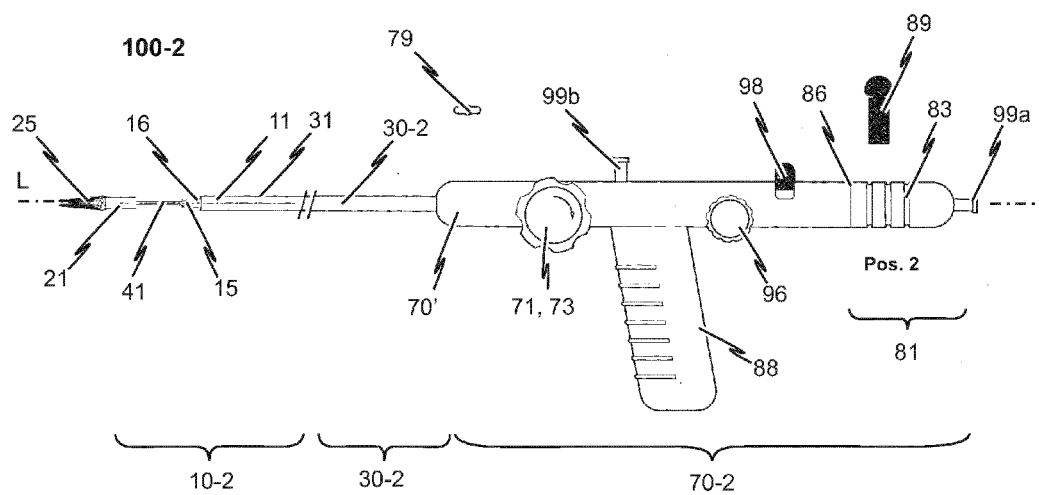

If an explantation of the stent with the heart valve prosthesis attached to it, where required, it is unnecessary, the insertion system 100-2 is transferred from the third functional state shown in FIG. 28c into the fourth functional state shown in FIG. 28d, by turning the first operating means 71 of the handle 70-2 further from the second position to the third position after removal of the securing element 79 (locking element). This manipulation of the first operating means 71 that can be effected after removal of the securing element 79 results in a further defined movement of the first housing portion 11 relative to the stent holder 15 of the catheter tip 10-2 in a proximal direction, thus towards the handle 70-2. The longitudinal displacement stroke executed on the first housing portion 11 is chosen so that the distal end of the sleeve-shaped first housing portion 11 no longer covers the retaining elements 16 of the stent holder 15, as a result of which an engagement between the retaining elements of a stent housed in the catheter tip 10-2 and the retaining elements 16 of the stent holder 15 can be released, which would also lead to a complete release of the second retaining region of the stent and correspondingly to a complete unfolding of the stent.

Figure 27A:
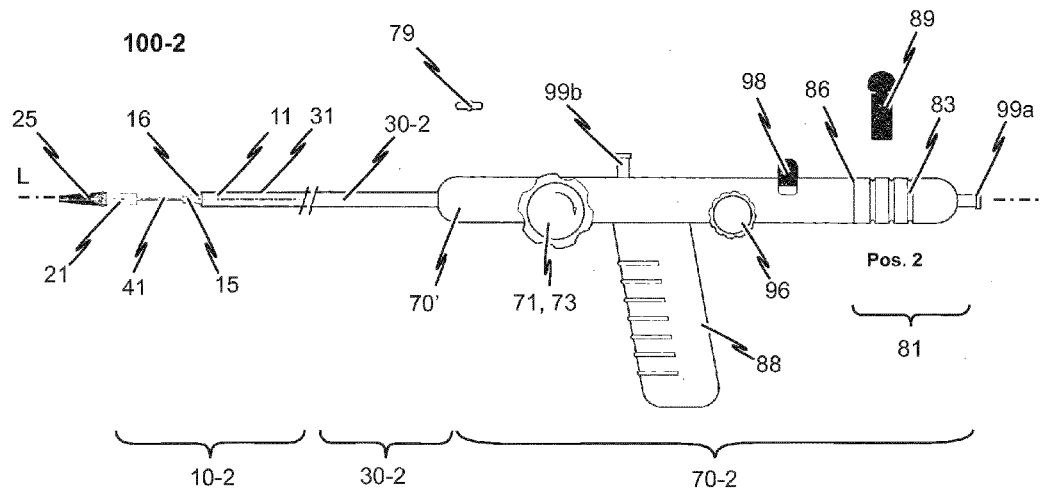
Figure 27B:
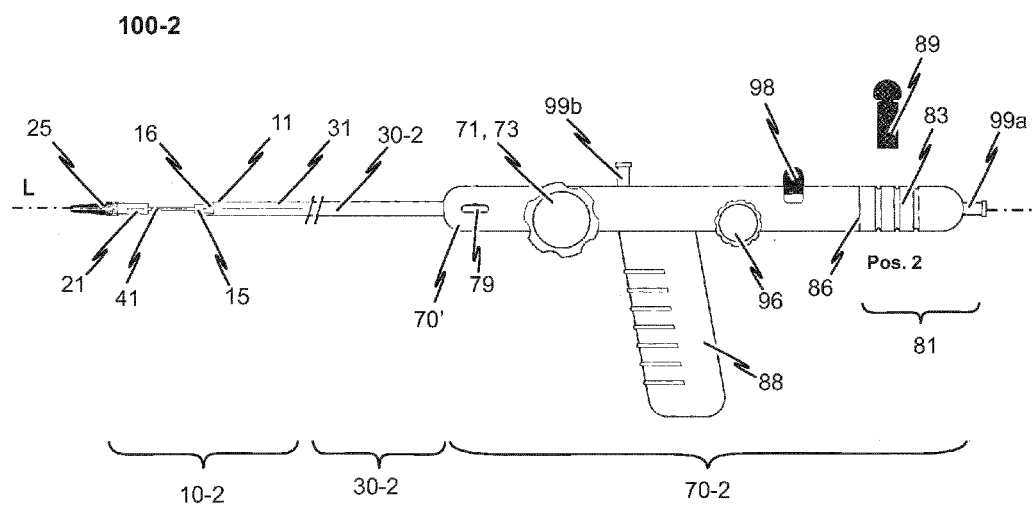
Figure 27C:
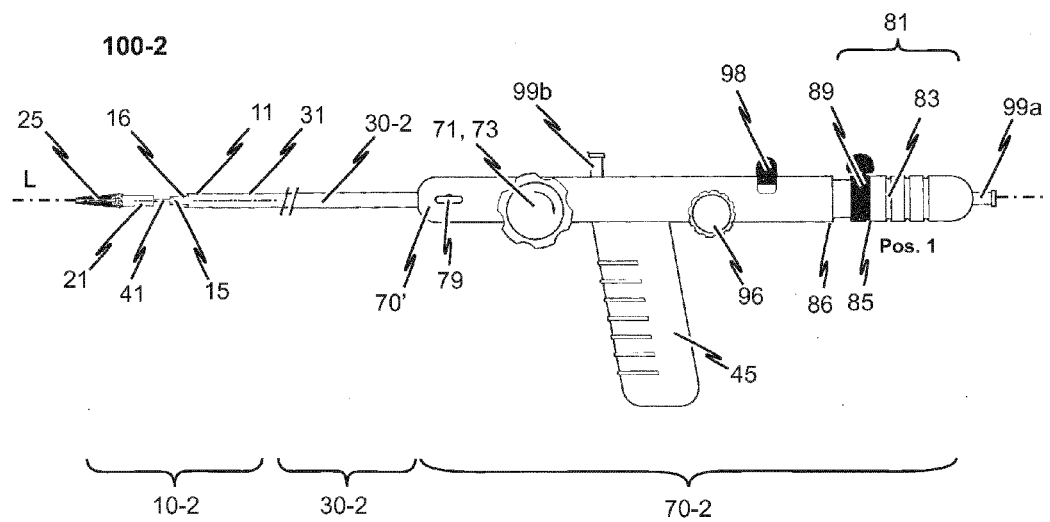
Figure 27D:
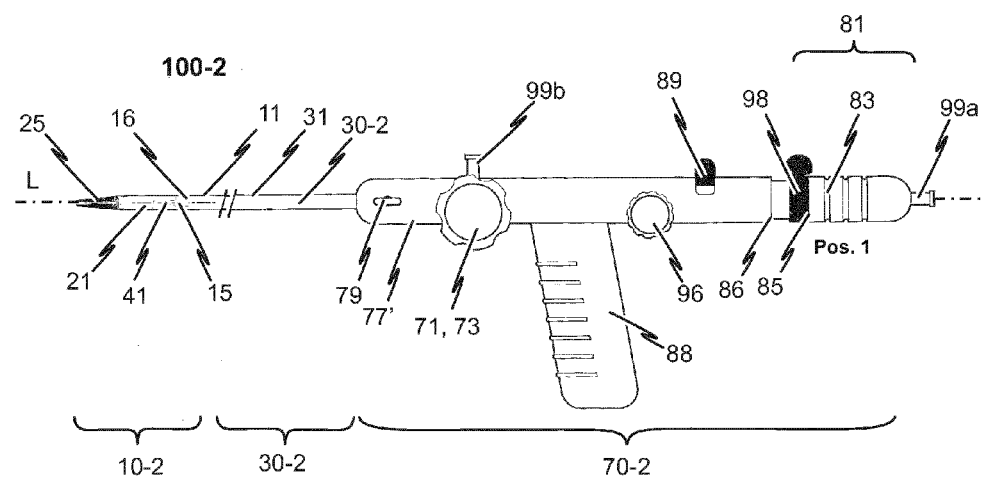

The four functional states of the insertion system 100-2 designed for transarterial/transfemoral access, previously described with reference to FIGS. 28a to 28d, are shown in reverse order in FIGS. 27a to 27d to clarify the procedure for loading a stent into the catheter tip 10-2 of the insertion system 100-2. Comparison between FIGS. 14a to 14d and FIGS. 28a to 28d show that the insertion system 100-2 can be loaded with a heart valve stent by transferring the insertion system 100-2, starting from its fourth functional state in accordance with FIG. 27a (see FIG. 28d), into its third functional state in accordance with FIG. 27b (see FIG. 28c) after a stent has been positioned between the stent holder 15 on the second housing portion 21 with its first retaining region in the direction of the second housing portion 21. Then the remaining functional states of the insertion system 100-2 are taken up in steps until the insertion system 100-2 shown in FIG. 27d is finally in its first functional state with the closed catheter tip 10-2.

A further embodiment of an insertion system 100-2 designed for transarterial/transfemoral access is shown in its first functional state in FIG. 24a. In principle, this embodiment is identical in structural and functional respects to the embodiment shown in FIGS. 27 and 28. In relation to the handle 70-2 of the insertion system 100-2 shown in FIG. 24a, it can be seen that the end region of the handle 70-2 is in the form of a turning mechanism 98 (rotatable means), with which the second force transmission means 41 of the catheter shaft 30-2 can be twisted with the distal-side end tip 25 and the second housing portion 21 (stent funnel) of the catheter tip 10-2 fastened to it about the longitudinal axis L of the catheter tip 10-2. The second housing portion 21 (stent funnel) of the catheter tip 10-2 is connected by means of a loose bearing to the stent holder 15, allowing transmission of a turning moment between the second housing portion 21 and the stent holder 15, without allowing transmission of any tensile or compression forces acting in the direction of the longitudinal axis L of the catheter tip 10-2. Thus, when a turning movement of the second housing portion 21 is induced with the turning mechanism 98, the stent holder 15 also turns correspondingly about the longitudinal axis L.

The turning mechanism 98 preferably allows the stent holder 15 to twist through approx. 120°. Thus the rotation of a stent housed in the catheter tip 10-2, and particularly the positioning hoops already released in the second functional state of the insertion system 100-2, can be controlled, facilitating precise positioning of the already expanded positioning hoops of the stent in the pockets of the insufficient, native heart valve.

Preferably, the rotation movement of the stent holder 15 about the longitudinal access L of the catheter tip 10-2 that can be effected with the turning mechanism 98 exhibits a previously definable, preferably small delay in reaction to a turning moment initiated by means of the turning mechanism 98.

Further, the embodiment of the handle 70-2 shown in FIG. 24a is equipped with a third operating means 96 in the form of a wheel, with which a flexural link 34, preferably provided at the distal end region of the catheter shaft 30-2, can be deflected.

The deflection of the distal end region of the catheter shaft 30-2 that can be effected with this flexural link region 34 is shown schematically in FIG. 24b. In detail, a device is provided for force transmission (control wire 35—see FIG. 32) which is connected on one side to the flexural link regions 34 preferably provided at the distal end region of the catheter shaft 30-2 and, on the other side, to the third operating means 96 of the handle 70-2 implemented in the embodiment shown in FIG. 24 as a hand wheel.

As can be seen in the illustration in FIG. 32, it is possible to implement the device for force transmission as a control wire 35, which is passed through the inside of the first transmission means 31 in the form of the outer catheter and preferably at the distal end of the flexural link region 34 or at the proximal end of the catheter tip 10-2 (see FIG. 31) to have a directed effect on the curvature of the flexural link region 34. With the tensile forces that can be exerted on the flexural link region 34 with the aid of the control wire 35, it is possible to obtain a defined curvature of the distal end region of the catheter shaft 30-2. This is a particular advantage during transarterial/transfemoral access when navigating the aortic arch.

All embodiments of the insertion system 100-2 designed for transarterial/transfemoral access have a first injection adapter 99*a* at the proximal end of the handle 70-2. As also in the insertion system 100-1 designed for transapical access, this first injection adapter 99*a* is used for flushing the insertion system and as outlet of a guide wire, with the aid of which the actual introduction of the catheter shaft 30-2 with the catheter tip 10-2 provided at the distal end of the catheter shaft 30-2 into the body of the patient is simplified. The catheter shaft 30-2, the catheter tip 10-2 and the handle 70-2 are thereby threaded into the guide wire and pushed along it, for example into the aorta and to the heart of the patient.

In the embodiments of the insertion system 100-2 designed for transarterial/transfemoral access, a second injection adapter 99*b* is further provided, by means of which a liquid coolant etc. can be passed via the fluid channels 43 (see FIG. 32) formed in the interior of the catheter shaft 30-2 to the catheter tip 10-2. With the aid of such a liquid coolant, a stent accommodated in the catheter tip 10-2 can be appropriately cooled while the catheter tip 10-2 is being advanced to the implantation location, as long as the insertion system 100-2 is in its first functional state, in which the catheter tip 10-2 is completely enclosed by the telescopically arranged sleeve-shaped housing portion 11 and 21.

The provision of cooling that can be produced with the second injection adapter 99*b* for the stent accommodated in the catheter tip 10-2 is a particular advantage when a shape memory material is used as stent material and when the stent can deform under the effect of an external stimulus from a temporary form to a permanent form, whereby the temporary form exists in the first configuration of the stent (in the folded-up state, when the stent is accommodated in the catheter tip 10-2) and the permanent form exists in the second configuration of the stent (in the expanded state of the stent after release of the stent from the catheter tip 10-2).

Further embodiments of an insertion system 100-2 which are suitable for transarterial/transfemoral access to the implantation location are shown in FIGS. 25 and 13. The respective catheter shaft is 30-2 and catheter tips 10-2 of the insertion systems 100-2 shown in FIGS. 25 and 26 are identical in functional and structural respects to systems which have been described previously with reference to FIGS. 24, 27 and 28.

The embodiment shown in FIGS. 25 and 26 differs first and foremost in relation to the implementation of the corresponding operating means 71, 81. The handle 70-2, which is used in the insertion system 100-2 shown in FIG. 24, has been described in detail previously with reference to FIGS. 27 and 28, so that it will not be explained again, to avoid repetition.

The insertion system 100-2 in accordance with FIG. 25 has a handle 70-2 with which the first operating means 71, which is used for manipulation of the first housing portion 11 of the catheter tip 10-2, is similar to a trigger of a revolver. The doctor carrying out the treatment holds the handle at the grip 88, while the first operating means 71 in the form of a trigger of a revolver is operated with the index finger of the hand holding it.

In the insertion system 100-2 shown in FIG. 26, a handle 70-2 is used which corresponds in structural and functional respects to the handle 70-2 used with the insertion system in FIG. 24 with the exception of the grip 88 provided in the embodiment in accordance with FIG. 24.

FIG. 29 shows a part-sectioned representation of a further embodiment of an insertion system 100-2 designed for transfemoral or transarterial access. In particular, the mechanism used in the handle 70-2 of the insertion system 100-2 can be seen with the aid of this illustration. In detail, the handle 70-2 in accordance with the representation in FIG. 29 comprises first and a second operating means 71, 82, which are connected by means of corresponding first and second force transmission means 31, 41 of the catheter shaft 30-2 yet to be described in detail to the first and second housing portion 11, 21 of the catheter tip 10-2. The first operating means 71 has a first pusher 73 which is functionally connected to the first slide 74. The first slide 74 is guided in a first guide 72 in the longitudinal direction L of the handle 70-2. The distal-side end of the first guide 72 defines the first stop 75 and the proximal-side end of the first guide 72 the second stop 76, which define the overall longitudinal displacement that can be effected with the first operating means 71. A stop element 77' can be positioned between the distal-side and the proximal-side end of the first guide 72, which defines the third stop 77. In principle it is also possible, though, to provide the first operating means 71 with a detent spring mechanism, as has been described previously with reference to FIGS. 19 and 20.

The second operating means 81 of the handle 70-2 shown in FIG. 29 has a second pusher 83, which is functionally connected to a second slide 84. The second slide 84 is guided in a longitudinal guide (second guide 82) between a first stop 85 and a second stop 86. The second slide 84 is connected by means of a second force transmission means 41 with the second housing portion 21 of the catheter tip 10-2. On actuation of the second operating means 81, the second slide 84 is moved in the longitudinal direction L of the handle 70-2 from the first stop 85 to the second stop 86. This movement effects a longitudinal displacement of the second housing portion 21 of the catheter tip 10-2 connected via the second force transmission means 41 with the second operating means 81.

To prevent an unintended displacement of the second slide 84, the second operating means is equipped with a removable securing element 89, which connects the second slide 84 with the body is 70' of the handle 70-2 when in use. A longitudinal displacement of the second slide 84 to the second stop 86 is only possible following removal of the securing element 89. In principle, it is also possible to equip the second operating means 81 with a detent spring mechanism instead of the securing element 89, as has been previously described with reference to FIGS. 19 and 20.

FIG. 30 shows a further embodiment of a handle 70-2 of an insertion system 100-2 designed for transfemoral or transarterial access in a part-sectioned side view. The construction and mode of operation of the first and second operating means 71, 81 of the embodiment of the handle 70-2 shown in FIG. 30 is comparable in structural and functional respects to the handle is previously described for the transarterial or transfemoral insertion system 100-2. In distinction to the handle described with reference to FIG. 29, however, the handle in accordance with FIG. 30 is provided with a third operating means 96 in the form of a wheel, by means of which a flexural link region 34 of the catheter shaft 30-2 can be controlled.

The third operating element 96 preferably has a detent device 100, to allow a set deflection of the flexural link region 34 of the catheter shaft 30-2 to be fixed. For example, in relation to the detent device 100, it is possible to provide a suitable catch mechanism on the hand wheel of the third operating means 96, which cooperates with the body 70' of the handle 70-2. In particular, it is possible for the flexural link region 34 of the catheter tip 30-2 to be connected to the third operating means 96 by way of a control wire 35 whereby, on an actuation of the third operating means 96 via the control wire 35 a tensile forces is exerted on the flexural link region 34, which produces the deflection of the flexural link region 34 (see FIG. 24b).

However it is also possible, of course, to choose another embodiment as the third operating means 96 for deflecting the flexural link region.

It is particularly preferred that the handle 70-2 of the insertion system 100-2 designed for transarterial or transfemoral access is provided with a pretensioning device, shown in FIG. 30, with which a constant tensile force is exerted via the second operating means 81 on the second housing portion 21 of the catheter tip 10-2. In detail, the pretensioning device shown in FIG. 30 has a compression spring 97, permanently stressed along its spring axis, which is prestressed between a first stop 97a connected to the body 70' of the handle 70-2 and a second stop 97b connected to the proximal end region of the second operating means 81, so that a permanent, previously defined or definable tensile force is exerted on the second housing portion 21 of the catheter tip 10.

The pretensioning device implemented with the spring 97 in the embodiment in accordance with FIG. 30 is especially advantageous when the catheter shaft 30-2 is provided with a flexural link region 34 (see FIG. 24). When the flexural link region 34 is bent, the outer fibres of the catheter shaft 30-2 are shortened and this can be compensated for appropriately with the aid of the pretensioning device. In detail, on bending of the flexural link region 34 relative to the neutral fibres of the catheter shaft 30-2 running along the longitudinal axis L, the outer fibres of the catheter shaft 30-2 radially spaced from the neutral fibres are shortened. Since the second force transmission means 41, which connects the second operating means 81 with the second housing portion 21 in the insertion system 100-2 designed for transarterial or transfemoral access, normally runs along the neutral fibre of the catheter shaft 30-2, a bending contraction inevitably occurs when the catheter shaft 30-2 is bent, having the result that, despite fixing of the first operating means 71, the first housing portion 11 of the catheter tip 10-2 is displaced relative to the stent holder 15 in a proximal direction.

This longitudinal displacement of the first housing portion 11 of the catheter tip 10-2 that takes place during the bending procedure is compensated with the aid of the prestressing device (spring 97), since the spring 97 of the prestressing device exerts a constant tensile force on the second force transmission means 41 and therefore on the second housing portion 21 of the catheter tip 10-2 and consequently constantly presses the distal-side end tip 25 of the catheter tip 10-2 against the distal-side end of the first housing portion 11. This ensures that the catheter tip 10-2 in the first functional state of the insertion system 100-2 (see FIG. 28a) remains completely closed even during a deflection of the catheter shaft 30-2 effected with the flexural link region 34.

On actuation of the second operating means 81, i.e. when the insertion system 100-2 transfers from its second functional state shown, for example, in FIG. 28b into its third functional state shown, for example, in FIG. 28c, it is necessary to press the second slide 84 against the prestress supplied by the spring 97 of the prestressing device on the second stop 86.

A catheter shaft 30-2 is described in the following, with reference to the illustrations in FIGS. 30, 31 and 32, which can be used with an insertion system designed for transarterial or transfemoral access.

The catheter shaft 30-2 exhibits a first force transmission means 31 in the form of an outer catheter, whereby this first force transmission 31 is used to connect the first operating means 71 of the handle 70-2 to the first housing portion 11 (stent sheath) of the catheter tip 10-2. As can be seen in particular from the illustration in FIG. 30, the first force transmission means 31 implemented as an outer catheter is clamped between a screw cap 71' and the first slide of the first operating means 71 and consequently is permanently connected to the first slide 74. The distal-side end region of the first force transmission means 31 in the form of the outer catheter merges into the first housing portion 11 of the catheter tip 10-2 in the form of the stent sheath and is connected to the first housing portion 11 in the form of the stent sheath.

The second force transmission means 41 of the catheter shaft 30-2 used with an insertion system 100-2 designed for transarterial or transfemoral access is implemented as an inner catheter. The proximal-side end region of the second force transmission means 41 implemented as an inner catheter is permanently connected to the second slide 84 of the second operating means 81. The distal-side end region of the second force transmission means 41 in the form of the inner catheter is connected to the end tip 25 of the catheter tip 10-2. The second housing portion 21 of the catheter tip 10-2 is permanently connected by means of its distal-side end to the end tip of the catheter tip 10-2 so that, on actuation of the second operating means 81 via the force transmission means 41 in the form of the inner catheter, a tensile or compressive force can be transmitted to the second housing portion 21 of the catheter tip 10-2 in the form of the stent funnel.

As can be seen particularly from the illustration in FIG. 32, the second force transmission means 41 in the form of the inner catheter runs along the neutral fibre of the catheter shaft 30-2 inside the first force transmission means 31 in the form of the outer catheter. The space between the first force transmission means 31 in the form of the outer catheter and the second force transmission means 41 in the form of the inner catheter is filled with a filler material, so that a filler body 40 is formed. The filler material and is preferably a relatively elastic plastic material to allow the catheter shaft 30-2 to bend overall and in particular at the flexural link region 34 (see FIG. 24).

FIG. 30 shows that the filler body 40 is connected by means of a fixing 87 to the body 70' of the handle 70-2. The proximal-side end region of the stent holder 15 attaches at the distal-side end region of the filler body 40 (see FIG. 31). The connection between the stent holder 15 and the filler body 40 is preferably chosen so that it allows rotation of the stent holder 15 relative to the filler body 40. This is especially necessary for control of the rotation of the positioning hoops of the already partially released stent during the implantation procedure (see FIG. 34a). On the other hand, the second force transmission means 41 in the form of the inner catheter 41 can be turned about the longitudinal direction L by means of a rotatable cap 98 provided at the proximal end region of the handle 70-2. This rotary movement is transferred from the second force transmission means 41 direct to the end tip 25 of the catheter tip 10-2 and thus to the second housing portion 21 in the form of the stent funnel.

It is particularly preferred that the second force transmission means in the form of the inner catheter runs through the body of the stent holder 15 and cooperates with the stent holder 15 with the aid of a suitable toothing, to transmit a turning moment exerted by means of the rotary cap of the handle 70-2 on the second force transmission means 41 to the stent holder 15, while tensile or compression forces acting in the longitudinal direction L of the catheter tip 10-2 are not transmitted from the second force transmission means 41 in the form of the inner catheter to the stent holder 15.

As can also be seen in the illustration in FIG. 32, a least one fluid channel 43 is provided in the filler body 40 of the catheter shaft 30-2, connected at its proximal-side end to the second injection adapter 99b (see FIG. 30) and at its distal-side end correspondingly to the catheter tip 10-2, consequently ensuring supply of fluid to the catheter tip 10-2 and draining of fluid from the catheter tip 10-2.

Furthermore, a channel 36 to accommodate a control wire 35 is provided in the filler body 40, with which the third operating means 96 cooperates with the flexural link region 34 of the catheter shaft 30-2 (see FIG. 24 and FIG. 30). In the illustration in FIG. 31, the distal-side end of the control wire 35 is fixed to the proximal-side end region of the stent holder 15.

As already indicated it is possible in principle for the previously described handles 70-1, 70-2, which are suitable either for a transapical insertion system 100-1 or for a transfemoral or transarterial insertion system 100-2, to be provided with operating means 71, 81, with which a detent spring mechanism is used, as has previously been described with reference to illustrations in FIGS. 19 and 20. Externally provided securing elements 79, 89 are then unnecessary.

Furthermore, it is possible in principle to connect one or several grips 88 to the body 70' of the handle 70-1 or 70-2, which are releasably connected to the body 70' and can be plugged in and unplugged as required. It is also possible for the third operating means with the handle 70-2 of the transfemoral or transarterial insertion system 100-2 (see FIG. 30) to be implemented, not as a wheel, but as a pusher.

It is obvious that all the individual features that have been described in connection with the respective handles 70-1 and 70-2 can be combined with one another.

A preferred embodiment of a medical device for treatment of a heart valve stenosis and/or heart valve insufficiency in a patient is described in the following with reference to FIGS. 21a to 21c. As depicted, the medical device exhibits an insertion system 100-to design for transarterial/transfemoral access, as has been described in detail previously, for example, with reference to FIGS. 24 to 31. However, it is also possible for the medical device to exhibit an insertion system 100-1 which it is designed for a transapical access, as has been described previously, for example with reference to FIGS. 14 to 23.

In addition to the insertion system 100-2, the medical device has a self-expandable heart valve stent 150 mounted in the catheter tip 10-2 of the insertion system 100-2, to which a heart valve prosthesis 160 to be implanted is fastened. In the first functional state, not shown, the stent to 150 exhibits a first, previously definable configuration, in which it is in its folded-together state. On the other hand, the stent 150 is designed to adopt a second previously definable configuration in the implanted state, in which it exists in its expanded state.

Through the use of the insertion system 100-2 described above, during the implantation procedure, the stent 150 is transferred sequentially, following a previously definable sequence of events in steps from its first previously defined configuration into its second previously defined configuration.

In detail, the stent 150 that is used with the medical device in accordance with the depiction in FIGS. 34a to 34c exhibits a first retaining region, to which the heart valve prosthesis 160 is attached. Further, the stent comprises a second retaining region with three retaining elements 151, each in the configuration of retaining rings, which can be brought in to a releasable engagement with the retaining elements 16 of the stent holder 15 provided in the catheter tip 10-2.

In addition, the stent 150 has three retaining hoops 153 to accommodate the heart valve prosthesis 160 and three positioning hoops 154 for automatic positioning of the stent 150 at the implantation site, whereby the respective positioning hoops 154 of the stent 150 are designed in functional and structural respects to engage the pockets 170 of the native heart valve during the implantation procedure and in the implanted state of the stent 150, in particular from the second functional state of the insertion system 100-2. In detail, each positioning hoop 154 and its associated retaining hoop 153 has an essentially U or V-shaped structure, which is closed towards the distal end of the stent 150.

The stent 150, which together with the insertion system 100-2 forms the basis of the medical device, is especially suitable for insertion into the body of a patient with the aid of the insertion system 100-2 with minimal invasiveness. The distinctive feature of the stent 150 is that the three positioning hoops 154 of the stent 150 undertake the function of automatic positioning of the stent 150 with the heart valve prosthesis 160 attached to it in the aorta of the patient. The positioning hoops 154 have radiused head sections, which engage in the pockets 170 of the insufficient heart valve to be replaced by the heart valve prosthesis during positioning of the stent 150 at the implantation site. The provision of a total of three positioning hoops 154 takes care of the necessary positioning accuracy in the rotary direction.

In this state shown in 34a, the catheter tip 10-2 and the catheter shaft 30-2 of the transarterial or transfemoral insertion system 100-2 has been inserted by a puncture of the groin artery of the patient and the catheter tip 10-2 has been advanced to the implantation site with the aid of a guide to wire 180. In detail, the insertion system 100-2 to be used is shown already in its second functional state in FIG. 34a. The second functional state of the insertion system 100-2 designed for transarterial or transfemoral access has been described previously, for example with reference to FIG. 28b.

In the second functional state, the sleeve-like first housing portion 11 of the catheter tip 10-2 has already moved by a first predetermined amount of movement in a proximal direction, and thus towards the handle, leading to a release of the positioning hoops 154 of the stent 150. These already expanded positioning hoops 154 of the stent shown in FIG. 34a are positioned—where necessary by a suitable rotation of the catheter tip 10-2—in the pockets 170 of the native heart valve position. After positioning of the positioning hoops 154 in the pockets 170 of the native heart valve is complete, the insertion system 100-2 is transferred from its second functional state (see FIG. 28b) into its third functional state (see FIG. 28c).

The manner in which the insertion system 100-2 is transferred into its third functional state has been described previously, for example with reference to FIG. 28c. FIG. 34b shows the insertion system 100-2 in accordance with FIG. 34a, in which the second sleeve-like housing portion 21 has been displaced in a distal direction so that the first retaining region of the stent with the retaining hoops 153 and the heart valve prosthesis 160 attached to them are released. These components are opened as a result of the radial forces attacking them, whereby the old heart valves are clamped between the positioning hoops 154 and the retaining hoops 153.

After the functioning of the heart valve prosthesis 160 has been checked, the insertion system 100-2 is then transferred from its third functional state into its fourth functional state, as has previously been described, for example with reference to FIG. 28*d*. FIG. 34 shows the effect of the transfer of the insertion system 100-2 in to its fourth functional state on the heart valve prosthesis 160 and the stent 150.

In detail, it can be seen that, in the fourth functional state of the insertion system 100-2, the first housing portion 11 of the catheter tip 10-2 has been displaced further in a proximal direction, as a result of which the anchorage of the retaining elements 151 on the second retaining region of the stent 150 is released. This has the result that that the second retaining region of the stent 150 can also expand and press against the vessel wall.

Finally, the catheter tip 10-2 and the catheter shaft 30-2 of the insertion system 100-2 are removed again from the body of the patient.

When the heart valve stent 150 is implanted, the old (insufficient) heart valve is pressed against the vessel wall at the same time due to the self-expanding characteristic of the stent on 50, as can be seen in particular in FIG. 34*c*. In particular, the semilunar heart valves of the insufficient, native heart valve are clamped between the positioning hoops 154 and the retaining hoops 153 because of the expansion of the stent 150, in addition to which the heart valve prosthesis 160 located on the first retaining region of the stent 150 is optimally positioned and is stably anchored.

In summary, it remains to be said that the solution in accordance with the disclosure is distinguished by the improved insertion system with the stent mountable in the catheter tip of the insertion system. The stent may be inserted transarterially or transapically by the special insertion system and can be optimally positioned, so that a heart valve prosthesis sewn on the first retaining region of the stent can undertake the function of the insufficient or stenosed native heart valve. The radial forces developed due to the self-expanding characteristic of the stent ensure a secure anchoring in the area of the aorta. The catheter shaft of the insertion system is preferably an 18 to 21F introducer, which is compatible with 21F-insertion tubes and a 0.035" guide wire. The length of the catheter shaft for transarterial access should be at least 100 cm. The optionally provided flexural link region at the distal region of the catheter shaft is preferably approx. 30 cm.

A description is given in the following, with reference to FIGS. 31 to 40, of a modified stent holder 115. The modified stent holder 115 may be used in the catheter tip 10-1 of an insertion system 100-1 designed for transapical access.

The modified stent holder 115 comprises a hollow cylindrical body 120 and a guiding element 121 which is at least partly accommodated in the hollow cylindrical body 120. In detail, the guiding element 121 is inserted in the hollow cylindrical body 120 such as to be movable relative to the cylindrical body 120 in the longitudinal direction of the stent holder 115. In this regard, the guiding element 121 forms the distal end section of the stent holder 115.

As can be seen from FIG. 32, the hollow cylindrical body 120 is provided with an inner sidewall 122 which serves as a guiding surface for guiding the guiding element 121 during its movement relative to the hollow cylindrical body 120. Moreover, the hollow cylindrical body 120 is provided with a stop 123 for restricting the movement of the guiding element 121 relative to the cylindrical body 120 in the longitudinal direction of the stent holder 115. In the embodiment of the modified stent holder 115 depicted in FIGS. 31 to 40, the stop 123 is formed as a step in the inner sidewall 122 of the hollow cylindrical body 120.

The embodiment of the modified stent holder 115 depicted in FIGS. 31 to 40 is also provided with a spring element 124. The spring element 124 is accommodated partly in the hollow cylindrical body 120 on the one hand and the guiding element 121 on the other hand. For this reason, the guiding element 121 is provided with a recessed portion 125, the opening of said recess portion 125 facing the interior of the hollow cylindrical body 120.

As can be seen, for example, from FIG. 32, the distal end section of the spring element 124 is accommodated in the recessed portion 125 of the guiding element 121. The proximal end section of the spring element 124 abuts on a counter bearing 126 connected with the proximal end section of the hollow cylindrical body 120.

Preferably, the spring element 124 is designed as a compression spring which applies a compressive force to the guiding element 121 such that the guiding element 121 is pushed away from the counter bearing 126 provided at the proximal end section of the cylindrical body 120. In this way, the distal end of the guiding element 121 protrudes from the hollow cylindrical body 120.

On the other hand, however, the guiding element 121 may be moved relatively to the cylindrical body 120 in the proximal direction when a force is applied on the distal end of the guiding element 121. Then, the spring element 124 becomes shorter.

At the proximal end section of the hollow cylindrical body 120 a further stop 127 is provided in order to restrict the longitudinal movement of the guiding element 121 relative to the cylindrical body 120 in the proximal direction. In the embodiment depicted in FIGS. 31 to 40, the additional stop member 127 is formed by an element inserted in the proximal end section of the cylindrical body 120. This element 128 has a conical kept end 129 which tapers in the proximal direction.

A through hole 130 is formed in the guiding element 121 on its longitudinal axis. Another through-hole 131 is provided in the element 128 such as to be aligned with the through-hole 130 of the guiding element 121. These through holes 130, 131 define a passage way for at least partly accommodating the first catheter tube 31 of the catheter tip 10-1 (see FIGS. 40*a-c*).

The cylindrical body 120 of the modified stent holder 115 is also provided with retaining means 16 which are adapted for accommodating appropriate retaining elements provided on an outflow end of a heart valve prosthesis (not depicted in FIGS. 31 to 40). The engagement between the retaining means 16 of the stent holder 115 on the one hand and the at least one retaining element on the outflow end of the heart valve prosthesis on the other hand can be released by means of an external manipulation in order to release the stent at the implantation side, thereby ensuring that the stent expands and is thus reliably anchored. It will be appreciated that the at least one retaining element of the stent may be of any suitable shape or configuration such as eyes, loops, fingers or imperforate heads.

The use of such at least one retaining element enables the stent to remain in contact with the stent holder 115 prior to full release of the stent. By maintaining contact with a stent prior to its full release, location and implantation position of the stent can be controlled more accurately by a physician. The functioning of the stent and heart valve prosthesis attached to the stent may also be checked and, if one or neither is functioning correctly, the physician can withdraw and removes the stent by virtue of the at least one retaining element of the stent remaining in contact with the remaining means 16 of the stent holder 115.

As illustrated, the retaining means 16 provided at the cylindrical body 120 of the modified stent holder 115 are formed as cut-outs or pockets (in the illustrated embodiment three in total) which are spaced uniformly apart from one another in the material of the cylindrical body 120. These pockets 132 are connected to the proximal-end surface of the cylindrical body 120 by grooves 133.

The shape and size of the pockets 132 in the material of the cylindrical body 120 are selected so that a retaining element of the stent complementing the pocket 132 can be accommodated, preferably positively, in each of the pockets 132. Thus, each retaining element of the stent establishes a releasable engagement with one pocket 132 formed in the cylindrical body 120 of the stent holder 115.

It is preferable in this respect if the retaining elements of the stent are provided in the form of projecting elements or projecting heads (retaining heads) at the end region of the stent. These retaining elements of the stent in the form of projecting elements may each connected to positioning arches (and retaining arches) of the stent via a neck portion or connecting web. When the retaining elements of the stent are positively held in the pockets 132 of the cylindrical body 120, at least the ends of the neck portions lie in the grooves 133.

Referring, for example, to FIGS. 31a-b, each of the pockets 132 formed in the cylindrical body 120 has a shape adapted for substantially accommodating the retaining element provided on the end region of the stent such that there are no parts of the end region of the stent protruding from the superficial surface of the cylindrical body 120.

In addition, the stent holder 115 may comprise snap-on means arranged on the at least one pocket 132 formed in the cylindrical body 120 for releasable fixing the retaining element provided on the end region of the stent in the at least one pocket 132.

The two different functional states realizable with the modified stent holder 115 are described in the following, initially with reference to the drawings in FIGS. 40a to 40c.

FIG. 40a shows a sectional side view of a catheter tip for a transapical insertion system 100-1 in its first functional state, in which the catheter tip 10-1 is completely closed. As already indicated, an expandable heart valve stent (not shown in FIG. 40a) can be housed in the catheter tip 10-1 in the corresponding housing portions 11, 12 of the catheter tip 10-1.

As already indicated, the catheter tip 10-1 partly illustrated in FIG. 40a is in a completely closed state in the first functional state of the transapical insertion system 10-1. In this state, the first and second housing portions 11, 12 of the catheter tip 10-1 in the form of sleeve-shaped elements interlock telescopically. It is important to note that the second housing portion 12 of the catheter tip 10-1 is not illustrated in the partial side view depicted in FIG. 40a.

In the first functional state of the insertion system 100-1, the catheter tip 10-1 can be inserted into the body of the patient and can be advanced to the desired implantation location. With a transapical insertion system 100-1 in accordance with the present disclosure, access to the implantation location, i.e. to the diseased heart, can be carried out transapically, thus approaching from the apex of the heart, since the stent holder 115 is located at the distal region of the catheter tip 10-1, while proximal from this is the second housing portion 21 (stent funnel) of the catheter tip 10-1.

In the first functional state of the transapical insertion system 100-1, i.e. when the catheter tip 10-1 is in a completely closed state (see FIG. 40a), the catheter end tip 25 of the catheter tip 10-1 is hold (by means of the first catheter tube 31) in its most proximal position such that the proximal end section of the catheter end tip 25 presses against the distal end section of the guiding element 121. Accordingly, the guiding element 121 is moved relatively to the cylindrical body 120 in the proximal direction. As can be seen from FIG. 40a, the proximal end section of the guiding element 121 abuts against the stop 123 provided at the proximal end portion of the cylindrical body 120.

FIG. 40c shows the catheter tip 10-1 in accordance with FIG. 40a in its fourth functional state. Hence, compared with the first functional state of the catheter tip 10-1 depicted in FIG. 40a, the first housing portion 11 (stent sheath) is moved relative to the stent holder 115 such that cover of the retaining means provided in the cylindrical body 120 with the proximal end region of the first housing portion 11 is eliminated. Removal of the cover of the retaining means 16 of the stent holder 115 with the first housing potion 11 has a consequence that the engagement between the retaining elements provided on a stent accommodated in the catheter tip 10-1 and the retaining means 16 of the stent holder 115 is lost, leading to a now complete release of the stent as well and correspondingly to a complete unfolding of the heart valve prosthesis attached to the stent.

As can be seen from FIG. 40c and also from FIG. 40b, which shows the catheter tip 10-1 in a transitional state between the first functional state (cf. 40a) and the fourth functional state (cf. FIG. 40c), the pushing fourth applied by the catheter end tip 25 on the distal end section of the guiding element 121 is cancelled when the catheter end tip 25 together with the first sleeve-shaped member 11 of the catheter tip 10-1 is moved relatively to the stent holder 115 in the distal direction. Accordingly, the spring element 124 accommodated in the hollow cylindrical body 120 of the stent holder 115 pushes the guiding element 121 in the distal direction relatively to the cylindrical body 120. Thus, the distal end section of the guiding element 121 protrudes from the distal end of the hollow cylindrical body 120. In this way, the total length of the stent holder 115 is increased. The surface area 134 of the distal end section of the guiding element 121 protruding from the distal end of the cylindrical body 120 serves as a guiding surface for the first sleeve-shaped member 11 of the catheter tip 10-1 when the catheter tip 10-1 is transferred from the fourth functional state shown in FIG. 40c to the first functional state shown in FIG. 40a after releasing a stent accommodated in the catheter tip 10-1 and connected with the catheter tip 10-1 via the stent holder 115.

In this connection, it is important to note—prior to removing the catheter tip 10-1 from the body of the patient after releasing the stent accommodated in the catheter tip 10-1 the catheter tip 10-1 must be transferred again to its first functional state shown in FIG. 40a in order to avoid that the stent or the heart valve prosthesis attached to the stent may be damaged by the catheter tip 10-1 and in order to minimize the risk of trauma. This is due to the fact that the catheter tip 10-1 does not comprise any back tapered sections or corners when the catheter tip 10-1 is in its first functional state depicted in FIG. 40a.

By having guiding means formed by the surface area 134 of the distal end section of the guiding element 121 protruding from the distal end of the cylindrical body 120, the risk is minimized that the first sleeve-shaped member 11 of the catheter tip 10-1 and the stent holder 115 become batched together when the first sleeve-shaped member 11 is moved relatively to the stent holder 115 in the proximal direction.

At the same time, the total length of the stent holder 115, and thus the total length of the catheter tip 10-1 is not increased in the first functional state of the catheter tip 10-1 in which the catheter tip 10-1 is completely closed. A reduced length of the catheter tip 10-1 is of advantage when the catheter tip 10-1 is inserted into the body of the patient and advanced to the desired implantation location.

A modified catheter tip 10-2 of a transfemoral insertion system 100-2 will be described in the following with reference to FIGS. 41*a-f*. In detail, the modified catheter tip 10-2 is shown in its first functional state in FIG. 41*a*, in which the catheter tip 10-2 and, where required, with a stent accommodated in it can be inserted in the patient transarterially or transfemorally and advanced via the aorta to the implantation side.

In the first functional state of the catheter tip 10-2 depicted in FIG. 41*a*, the catheter tip 10-2 is completely closed, whereby the two sleeve-shaped members 11, 21 of the catheter tip may overlap telescopically. Alternatively, the two sleeve-shaped members 11, 21 of the catheter tip 10-2 may abut against each other in the first functional state of the catheter tip 10-2 thereby forming a closed housing portion for accommodating a stent in a compressed state. In any case, the respective diameters of the sleeve-shaped members 11, 21 are chosen for that the folded-up retaining hubs of a stent, with a heart valve prosthesis fastened to them where required, can be housed in the second sleeve-shaped member 21. The folded-up positioning hoops of the stent housed between the second sleeve-shaped member 21 and the first sleeve-shaped member 11 are held together in their folded form.

In the first functional state of the catheter tip 10-2, the at least one retaining element provided at the stent is engaged with the retaining means (pockets 132) of the stent holder 15.

The retaining means (pockets 132) of the stent holder 15 are covered by the first sleeve-shaped member 11 of the catheter tip 10-2 in the first functional state shown in FIG. 41*a*, so that an engagement between retaining elements provided on a stent accommodated in the catheter tip 10-2 and retaining means of the stent holder 15 would be possible.

The first functional state of the catheter tip 10-2 shown in FIG. 41*a* is maintained during the transarterial insertion procedure. On reaching the implantation location, the catheter tip 10-2 is transferred from the first functional state shown in FIG. 41*a* to the second functional state shown in FIG. 41*b* by moving the first sleeve-shaped member 11 of the catheter tip 10-2 relative to the stent holder 15 in the proximal direction, thus towards the handle 70 (not shown in FIG. 41).

The longitudinal displacement stroke executed on the first sleeve-shaped member 11 of the catheter tip 10-2 during the transition of the first functional state (see FIG. 41*a*) to the second functional state (see FIG. 41*b*) is previously defined so that the first sleeve-shaped member 11 is displaced relative to the stent holder 15 in the proximal direction just so far that the positioning hoops of a stent housed in the catheter tip 10-2 would be released, so the distal end of the first sleeve-shaped member 11 of the catheter tip 10-2 would still cover the retaining means 16 of the stent holder 15, so that the engagement between the retaining elements provided at the stent and the retaining means 16 of the stent holder 15 would be secure.

Since the second sleeve-shaped member 21 is not manipulated during the transition for the first functional state into the second functional state, the retaining region of a stent housed in the catheter tip 10-2 with the heart valve prosthesis fastened to it would continue to be housed in its folded together state in the sleeve-shaped element of the second sleeve-shaped member 21.

The positioning hoops of a stent housed in the catheter tip 10-2 released in the second functional state of the catheter tip 10-2 are opened as a result of the radial forces acting on them and can thus be positioned in the pockets of the insufficient native heart valve. Following appropriate positioning of the positioning hoops of the stent in the pockets of the native heart valve, the catheter tip 10-2 is transferred from the second functional state shown in FIG. 41*b* into the third functional state shown in FIG. 41*c*. This is done by moving the second sleeve-shaped member 21 of the catheter tip 10-2 relative to the stent holder 15 in a distal direction, thus away from the handle 70 (not depicted in FIG. 41). The longitudinal displacement stroke on the second sleeve-shaped member 21 is chosen so that the sleeve-shaped member 21 no longer covers the retaining region of a stent housed in the catheter tip 10-2 with the heart valve prosthesis fastened to it, where required, and thus releases the retaining region of the stent. Due to the action of the radial forces, the retaining regional stent with the heart valve prosthesis attached to it, where required unfolds completely.

Since the first sleeve-shaped member 11 of the catheter tip 10-2 is not manipulated during the transition from the second functional state in accordance with FIG. 41*b* into the third functional state in accordance with FIG. 41*c*, the distal end region of the first sleeve-shaped member 11 continues to cover the retaining means 16 of the stent holder 15, so that the engagement between the retaining elements of a stent housed in the catheter tip 10-2 and the retaining means 16 of the stent holder 15 is secured.

This anchorage of the stent to the catheter tip 10-2 allows an explantation of a stent that is already partially unfolded by returning the catheter tip 10-2 from the third functional state via the second functional state to the first functional state.

If an explantation of the stent with the heart valve prosthesis attached to it, where required, is unnecessary, the catheter tip 10-2 is transferred from the third functional state showing in FIG. 41*c* into the fourth functional state shown in FIG. 41*d* by moving the first sleeve-shaped member 11 relative to the stent holder 15 of the catheter tip 10-2 in a proximal direction, thus towards the handle of the insertion system 100-2. The longitudinal displacement stroke executed on the first sleeve-shaped member 11 is chosen so that the distal end of the first sleeve-shaped member 11 no longer covers the retaining means 16 of the stent holder 15, as a result of which an engagement between the retaining elements of a stent housed in the catheter tip 10-2 and the retaining means 16 of the stent holder 15 can be released, which would also lead to a complete release of the stent and to a complete separation of the stent from the catheter tip 10-2 and correspondingly to a complete unfolding of the stent.

After completely separating the stent from the catheter tip 10-2 (cf. the fourth functional state of the catheter tip 10-2 depicted in FIG. 41*d*), the catheter tip 10-2 is again transferred from its fourth functional state via the third and second functional states to the first functional state, in which the catheter tip 10-2 is completely closed. Thereafter, the catheter tip 10-2 may be removed from the body of the patient. Closing the catheter tip 10-2 prior to extracting the catheter tip 10-2 is necessary in order to minimize the risk that the heart valve prosthesis may be damaged or the wall the vessel through which the catheter tip 10-2 is introduced into the body of the patient is ensured.

The modified catheter tip 10-2 depicted in FIGS. 41a to 41f comprises a spring mechanism which is designed such that the proximal end section of the first sleeve-shaped member 11 of the catheter tip 10-2 may not damage parts of the heart valve prosthesis when the catheter tip is not in its completely closed state.

In detail, a plug element 135 is provided for closing the proximal end section of the first sleeve-shaped member when the catheter tip 10-2 is not in its closed state (i.e. in its first functional state depicted, for example, in FIG. 41a). The plug element 135 is slidably attached to the second catheter tube 42, i.e. the second force transmitting means for manipulating the second sleeve-shaped member 21. For this reason, the plug element 135 is provided with a through hole through which the second catheter tube 42 passes. In detail, the distal end section of the second catheter tube 42 passes through the through hole provided in the plug element 135 and also through an opened front face of the second sleeve-shaped member 21 and terminates in a cone-shaped end tip 25 of the catheter tip 10-2, wherein the base of this cone-shaped end tip 25 defines the distal front face of the second sleeve-shaped member 21.

Proximal to the plug element 135, a stop 136 is fixed to the second catheter tube 42 in order to restrict the movement of the plug element 135 in the proximal direction relative to the second catheter tube 42.

Furthermore, a spring element 137 is provided. The spring element 137 is formed as a compression spring and arranged between the distal end face of the plug element 135 and a counter bearing 138 provided at the proximal end of the catheter end tip 25. The spring element 137 is designed such that the distal end section of the plug element 135 closes the proximal opening of the second sleeve-shaped member 21 of the catheter tip 10-2 when the catheter tip 10-2 is not in its closed state and when a stent fixed to the catheter tip 10-2 by means of the stent holder 15 is not covered anymore by the second sleeve-shaped element (i.e. in the third and fourth functional state depicted, for example, in FIGS. 41c and 41d). Accordingly, in these functional states of the catheter tip 10-2 the open end of the second sleeve-shaped member 21 is closed by the plug element 135 thereby avoiding corners, edges or other geometrical discontinuities which could damage the heart valve prosthesis.

After the end with a heart valve prosthesis attached thereto is completely released from the catheter tip 10-2, the catheter tip 10-2 is again transferred from its fourth functional state to its first functional state, i.e. to its closed state. For this purpose, the second sleeve-shaped member 21 together with the catheter end tip 25 is moved relatively to the stent holder 15 in the proximal direction by manipulating the second catheter tube 21. With the movement of the second sleeve-shaped member 21 in the proximal direction, the plug element 135 is also moved in the proximal direction due to the spring element 137 arranged between the plug element 135 and the catheter end tip 25. The movement of the plug element 135, however, is restricted by the stop 136 fixed to the second catheter tube (cf. FIG. 41e).

Thereafter, the first sleeve-shaped member 11 is moved in the distal direction relative to the stent holder 15 thereby transferring the catheter tip 10-2 in its closed state as depicted in FIG. 41f.

The disclosed solution is not limited to the preferred embodiment described in the attached drawings. On the contrary, combinations of the individual features described in detail are also possible.

The invention claimed is:

1. A catheter system for introducing a heart valve stent into a body of a patient, the catheter system comprising:
a catheter tip comprising a first sleeve-shaped member, a second sleeve-shaped member, and a stent holder, wherein the first and second sleeve-shaped members are moveable relative to each other and relative to the stent holder;
a handle; and
a catheter shaft extending between the catheter tip and the handle, the catheter shaft comprising:
a first tubular member having a distal end section connected to the first sleeve-shaped member and a proximal end section connected to the handle; and
a second tubular member having a distal end section connected to the second sleeve-shaped member and a proximal end section connected to the handle,
wherein the stent holder comprises a cylindrical body and a guiding element at least partly accommodated in the cylindrical body, the guiding element forming an end section of the stent holder, and wherein the guiding element is movable relative to the cylindrical body in a longitudinal direction of the stent holder.

2. The catheter system according to claim 1, wherein the cylindrical body includes an inner sidewall for guiding the movement of the guiding element relative to the cylindrical body.

3. The catheter system according to claim 1, wherein the cylindrical body includes a first stop for restricting the movement of the guiding element in a first direction relative to the cylindrical body.

4. The catheter system according to claim 3, wherein the cylindrical body includes a second stop to restrict the movement of the guiding element in a second direction relative to the cylindrical body opposite the first direction.

5. The catheter system according to claim 4, wherein the second stop includes an element inserted into an end of the cylindrical body.

6. The catheter system according to claim 3, wherein the first stop includes a step in an inner sidewall of the cylindrical body.

7. The catheter system according to claim 1, wherein the stent holder includes a spring element, wherein a first portion of the spring element is accommodated in the cylindrical body, and a second portion of the spring element is accommodated in the guiding element.

8. The catheter system according to claim 7, wherein the guiding element includes a recessed portion, an opening of the recessed portion facing an interior of the cylindrical body, wherein the second portion of the spring element is accommodated in the recessed portion of the guiding element, and the first portion of the spring element abuts a surface of the cylindrical body.

9. The catheter system according to claim 8, wherein the spring element includes a compression spring configured to apply a force to the guiding element to move the guiding element away from the surface of the cylindrical body.

10. The catheter system according to claim 1, wherein the cylindrical body of the stent holder includes at least one surface feature configured to receive at least one corresponding retaining element of the heart valve stent.

11. The catheter system according to claim 10, wherein the at least one surface feature includes a plurality of pockets spaced uniformly apart around an outermost surface of the cylindrical body, each pocket connected to an end surface of the cylindrical body by a groove.

12. The catheter system according to claim 11, wherein each pocket is formed in the outermost surface of the cylindrical body and has a shape adapted for accommodating a corresponding retaining element.

13. A catheter system for introducing a heart valve stent into a body of a patient, the catheter system comprising:
- a tip comprising a first sleeve, a second sleeve, and a stent holder, wherein the first and second sleeves are moveable relative to each other and relative to the stent holder;
- a handle; and
- a shaft extending between the catheter tip and the handle, wherein the shaft comprises:
  - a first tube having a distal end coupled to the first sleeve and a proximal end coupled to the handle; and
  - a second tube having a distal end coupled to the second sleeve and a proximal end coupled to the handle;
- wherein the stent holder comprises an elongate body and a guiding element at least partially accommodated in the elongate body, the guiding element movable relative to the elongate body along a longitudinal axis of the stent holder; and
- wherein the guiding element and the elongate body of the stent holder define a lumen for passage of the second tube therethrough.

14. The catheter system according to claim 13, further comprising a third tube having a distal end attached to the stent holder and a proximal end attached to the handle, wherein the second and third tubes are coaxial.

15. A catheter system for introducing a heart valve stent into a body of a patient, the catheter system comprising:
- a tip comprising a first sleeve, a second sleeve, and a stent holder, wherein the first and second sleeves are moveable relative to each other and relative to the stent holder;
- a handle; and
- a shaft extending between the tip and the handle, the shaft comprising:
  - a first tube having a distal end coupled to the first sleeve and a proximal end coupled to the handle; and
  - a second tube having a distal end coupled to the second sleeve and a proximal end coupled to the handle;
- wherein the stent holder comprises an elongate body, a spring element, and a guiding element, each of the spring element and the guiding element being at least partially accommodated in the elongate body and movable relative to the elongate body along a longitudinal axis of the stent holder.

16. The catheter system of claim 15, wherein the spring element includes a compression spring configured to apply a force to the guiding element to move the guiding element away from the elongate body.

17. The catheter system of claim 16, wherein a tension of the compression spring is adjustable by moving the first sleeve along a longitudinal axis of the tip.

18. The catheter system of claim 15, wherein the elongate body of the stent holder includes a plurality of pockets, each pocket configured to receive a corresponding retaining element of the heart valve stent.

* * * * *

UNITED STATES PATENT AND TRADEMARK OFFICE
CERTIFICATE OF CORRECTION

PATENT NO. : 9,510,947 B2  Page 1 of 1
APPLICATION NO. : 14/352117
DATED : December 6, 2016
INVENTOR(S) : Helmut Straubinger et al.

It is certified that error appears in the above-identified patent and that said Letters Patent is hereby corrected as shown below:

On the Title Page

In item (30) Foreign Application Priority Data, the European Application No. should read --11186156.3--.

In item (57) Abstract, second to last line, "first and second force trans mining means" should read --first and second force transmitting means (31, 41)--.

Signed and Sealed this
Thirtieth Day of May, 2017

Michelle K. Lee
*Director of the United States Patent and Trademark Office*